United States Patent
Bisbee, III et al.

(10) Patent No.: US 7,198,071 B2
(45) Date of Patent: Apr. 3, 2007

(54) SYSTEMS AND METHODS OF LOADING FLUID IN A PROSTHETIC KNEE

(75) Inventors: Charles R. Bisbee, III, Mission Viejo, CA (US); Henry H. Hsu, Aliso Viejo, CA (US)

(73) Assignee: Össur Engineering, Inc., Albion, MI (US)

( * ) Notice: Subject to any disclaimer, the term of this patent is extended or adjusted under 35 U.S.C. 154(b) by 21 days.

(21) Appl. No.: 11/124,610

(22) Filed: May 6, 2005

(65) Prior Publication Data

US 2006/0074493 A1 Apr. 6, 2006

Related U.S. Application Data

(63) Continuation-in-part of application No. 10/722,313, filed on Nov. 25, 2003, now Pat. No. 7,101,487.

(60) Provisional application No. 60/624,986, filed on Nov. 3, 2004, provisional application No. 60/569,512, filed on May 7, 2004, provisional application No. 60/467,722, filed on May 2, 2003.

(51) Int. Cl.
  *B65B 1/04* (2006.01)
(52) U.S. Cl. .............. 141/8; 141/65; 141/67; 252/62.52
(58) Field of Classification Search .......... 141/4, 141/7, 8, 65, 39, 67; 128/DIG. 12; 252/62.52; 623/24, 26, 39
See application file for complete search history.

(56) References Cited

U.S. PATENT DOCUMENTS

| | | | |
|---|---|---|---|
| 3,417,409 A | | 12/1968 | Prahl |
| 3,659,294 A | | 5/1972 | Glabiszewski |
| 3,701,368 A | * | 10/1972 | Stern .................. 141/1 |
| 3,820,168 A | | 6/1974 | Horvath |
| 3,995,324 A | | 12/1976 | Burch |
| 4,005,496 A | | 2/1977 | Wilkes |
| 4,023,215 A | | 5/1977 | Moore |
| 4,064,569 A | | 12/1977 | Campbell |
| 4,065,815 A | | 1/1978 | Sen-Jung |
| 4,100,918 A | | 7/1978 | Glancy |

(Continued)

FOREIGN PATENT DOCUMENTS

| | | |
|---|---|---|
| DE | 35 43 291 A1 | 6/1987 |
| DE | 43 05 213 A1 | 8/1993 |
| DE | 43 18 901 A1 | 1/1994 |

(Continued)

OTHER PUBLICATIONS

Advanced Materials & Processes, vol. 161, No. 9, Sep. 2003, pp. 29-30, 3 pages.

(Continued)

*Primary Examiner*—Steven O Douglas
(74) *Attorney, Agent, or Firm*—Knobbe, Martens, Olson & Bear, LLP

(57) ABSTRACT

The invention in some embodiments relates to systems and methods of loading fluid in a prosthetic knee. A vacuum fill technique is utilized in one embodiment to load magnetorheological fluid within small gaps in a chamber of a prosthetic knee. Advantageously, this allows for an efficient loading scheme thereby desirably allowing for faster manufacturing speed. Another advantage is that the magnetorheological fluid is substantially uniformly distributed within the small gaps thereby desirably providing consistent production.

18 Claims, 103 Drawing Sheets

U.S. PATENT DOCUMENTS

| | | |
|---|---|---|
| 4,209,860 A | 7/1980 | Graupe |
| 4,212,087 A | 7/1980 | Mortensen |
| 4,310,932 A | 1/1982 | Näder et al. |
| 4,363,498 A | 12/1982 | Biermann et al. |
| 4,370,977 A | 2/1983 | Mauldin et al. |
| 4,386,891 A | 6/1983 | Riefel et al. |
| 4,433,679 A | 2/1984 | Mauldin et al. |
| 4,458,367 A | 7/1984 | May |
| 4,569,352 A | 2/1986 | Petrofsky et al. |
| 4,578,083 A | 3/1986 | Williams |
| 4,602,619 A | 7/1986 | Wolf et al. |
| 4,657,000 A | 4/1987 | Hepburn |
| 4,685,926 A | 8/1987 | Haupt |
| 4,685,927 A | 8/1987 | Haupt |
| 4,711,242 A | 12/1987 | Petrofsky |
| 4,711,450 A | 12/1987 | McArthur |
| 4,726,404 A * | 2/1988 | Haber et al. .................. 141/59 |
| 4,760,850 A | 8/1988 | Phillips et al. |
| 4,776,326 A | 10/1988 | Young et al. |
| 4,790,522 A | 12/1988 | Drutchas |
| 4,795,474 A | 1/1989 | Horvath |
| 4,838,251 A | 6/1989 | Chignon et al. |
| 4,854,428 A | 8/1989 | Horvath |
| 4,876,944 A | 10/1989 | Wilson et al. |
| 4,893,648 A | 1/1990 | Horvath |
| 4,919,418 A | 4/1990 | Miller |
| 4,928,676 A | 5/1990 | Pansiera |
| 4,958,705 A | 9/1990 | Horvath |
| 5,020,790 A | 6/1991 | Beard et al. |
| 5,062,856 A | 11/1991 | Sawamura et al. |
| 5,092,902 A | 3/1992 | Adams et al. |
| 5,133,774 A | 7/1992 | Sawamura et al. |
| 5,181,931 A | 1/1993 | van de Veen |
| 5,197,488 A | 3/1993 | Kovacevic |
| 5,201,772 A | 4/1993 | Maxwell |
| 5,230,672 A | 7/1993 | Brown et al. |
| 5,277,281 A | 1/1994 | Carlson et al. |
| 5,284,330 A | 2/1994 | Carlson et al. |
| 5,336,269 A | 8/1994 | Smits |
| 5,376,137 A | 12/1994 | Shorter et al. |
| 5,383,939 A | 1/1995 | James |
| 5,397,287 A | 3/1995 | Lindfors |
| 5,398,917 A | 3/1995 | Carlson et al. |
| 5,405,407 A | 4/1995 | Kodama et al. |
| 5,405,409 A | 4/1995 | Knoth |
| 5,413,611 A | 5/1995 | Haslam, II et al. |
| 5,437,611 A | 8/1995 | Stern |
| 5,443,521 A | 8/1995 | Knoth et al. |
| 5,443,524 A | 8/1995 | Sawamura et al. |
| 5,472,412 A | 12/1995 | Knoth |
| 5,476,441 A | 12/1995 | Durfee et al. |
| D372,536 S | 8/1996 | Grifka |
| 5,545,232 A | 8/1996 | Van de Veen |
| 5,571,205 A | 11/1996 | James |
| 5,624,389 A | 4/1997 | Zepf |
| 5,645,590 A | 7/1997 | van de Veen |
| 5,645,752 A | 7/1997 | Weiss et al. |
| D383,542 S | 9/1997 | Wellershaus et al. |
| 5,670,077 A | 9/1997 | Carlson et al. |
| 5,683,615 A | 11/1997 | Munoz |
| 5,704,945 A | 1/1998 | Wagner et al. |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |
| 5,749,533 A | 5/1998 | Daniels |
| 5,755,812 A | 5/1998 | Becker et al. |
| 5,755,813 A | 5/1998 | Krukenberg |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,236 A | 3/1999 | van de Veen |
| 5,893,891 A | 4/1999 | Zahedi |
| 5,899,869 A | 5/1999 | Barrack, Jr. et al. |
| 5,900,184 A | 5/1999 | Weiss et al. |
| 5,906,767 A | 5/1999 | Karol et al. |
| 5,947,238 A | 9/1999 | Jolly et al. |
| 5,948,021 A | 9/1999 | Radcliffe |
| 5,955,667 A | 9/1999 | Fyfe |
| 5,957,981 A | 9/1999 | Gramnäs |
| 5,960,918 A | 10/1999 | Moser et al. |
| 5,967,273 A | 10/1999 | Hampton |
| RE36,521 E | 1/2000 | Hiemisch |
| 6,027,664 A | 2/2000 | Weiss et al. |
| 6,039,091 A * | 3/2000 | Rodgers et al. ................ 141/83 |
| 6,080,123 A | 6/2000 | Pansiera |
| 6,086,616 A | 7/2000 | Okuda et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,690 A | 10/2000 | Hamlin et al. |
| 6,139,586 A | 10/2000 | Wagner et al. |
| 6,165,226 A | 12/2000 | Wagner |
| 6,168,634 B1 | 1/2001 | Schmitz |
| D439,339 S | 3/2001 | Sawatzki |
| D446,304 S | 8/2001 | Sawatzki et al. |
| 6,301,964 B1 | 10/2001 | Fyfe et al. |
| 6,352,144 B1 | 3/2002 | Brooks |
| 6,395,193 B1 | 5/2002 | Kintz et al. |
| 6,423,098 B1 | 7/2002 | Biedermann |
| 6,443,993 B1 | 9/2002 | Koniuk |
| 6,485,519 B2 | 11/2002 | Meyers et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,599,439 B2 | 7/2003 | Iyengar et al. |
| 6,610,101 B2 | 8/2003 | Herr et al. |
| 6,679,920 B2 | 1/2004 | Biedermann et al. |
| 6,719,806 B1 | 4/2004 | Zahedi et al. |
| 6,733,180 B2 * | 5/2004 | Nakamura .................. 384/100 |
| 6,740,123 B2 | 5/2004 | Davalli et al. |
| 6,740,125 B2 | 5/2004 | Mosler |
| 6,755,870 B1 | 6/2004 | Biedermann et al. |
| 6,764,520 B2 | 7/2004 | Deffenbaugh et al. |
| 7,029,500 B2 | 4/2006 | Martin |
| 7,101,487 B2 | 9/2006 | Hsu et al. |
| 2002/0103541 A1 | 8/2002 | Meyers et al. |
| 2003/0019700 A1 | 1/2003 | Wittig |
| 2004/0049290 A1 | 3/2004 | Bedard |
| 2004/0064195 A1 | 4/2004 | Herr |
| 2004/0088057 A1 | 5/2004 | Bedard |
| 2004/0111163 A1 | 6/2004 | Bedard et al. |
| 2004/0181289 A1 | 9/2004 | Bedard et al. |
| 2004/0217324 A1 | 11/2004 | Hsu et al. |
| 2004/0267379 A1 | 12/2004 | Pasolini |
| 2005/0107889 A1 | 5/2005 | Bedard et al. |
| 2005/0192677 A1 | 9/2005 | Ragnarsdottir et al. |
| 2005/0197717 A1 | 9/2005 | Ragnarsdottir et al. |
| 2005/0283257 A1 | 12/2005 | Bisbee, III et al. |
| 2006/0069449 A1 | 3/2006 | Bisbee, III et al. |
| 2006/0085082 A1 | 4/2006 | Asgeirsson et al. |
| 2006/0135883 A1 | 6/2006 | Jónsson et al. |
| 2006/0136072 A1 | 6/2006 | Bisbee, III et al. |
| 2006/0173552 A1 | 8/2006 | Roy |

FOREIGN PATENT DOCUMENTS

| | | |
|---|---|---|
| DE | 42 29 330 A1 | 3/1994 |
| DE | 195 21 464 A1 | 3/1997 |

| | | |
|---|---|---|
| EP | 0 503 775 A1 | 9/1992 |
| EP | 0 628 296 A2 | 12/1994 |
| EP | 0 549 855 B1 | 3/1996 |
| EP | 0 957 838 B1 | 8/2000 |
| EP | 1 066 793 A2 | 1/2001 |
| EP | 1 125 825 A2 | 8/2001 |
| EP | 1 125 825 A3 | 4/2002 |
| FR | 2 623 086 A1 | 5/1989 |
| GB | 2 201 260 A | 8/1988 |
| GB | 2 244 006 A | 11/1991 |
| GB | 2 328 160 A | 2/1999 |
| GB | 2 334 891 A | 9/1999 |
| GB | 2 338 653 A | 12/1999 |
| JP | 60-81530 A | 5/1985 |
| JP | 3-181633 A | 8/1991 |
| JP | 4-78337 A | 3/1992 |
| WO | WO 96/39110 A1 | 12/1996 |
| WO | WO 96/41599 A1 | 12/1996 |
| WO | WO 99/05991 A2 | 2/1999 |
| WO | WO 99/08621 A2 | 2/1999 |
| WO | WO 99/11206 A1 | 3/1999 |
| WO | WO 99/05991 A3 | 6/1999 |
| WO | WO 99/29272 A1 | 6/1999 |
| WO | WO 99/44547 A1 | 9/1999 |
| WO | WO 00/38599 A1 | 7/2000 |
| WO | WO 02/080825 A2 | 10/2002 |

OTHER PUBLICATIONS

Ari J. Wilkenfeld, *Biologically inspired autoadaptive control of a knee prosthesis*, Ph.D. Dissertation Abstract, MIT, Cambridge, Massachusetts, Sep. 2000, 1 page.

Ari J. Wilkenfeld, *Biologically Inspired Autoadaptive Control of a Knee Prosthesis*, Ph.D. Dissertation, Massachusetts Institute of Technology, 2000, 106 pages.

Ari Wilkenfeld & Hugh Herr, *An Auto-Adaptive External Knee Prosthesis*, Artificial Intelligence Laboratory, MIT, Cambridge, Massachusetts, Sep. 2000, 3 pages.

Donald L. Grimes, *An Active Multi-Mode Above-Knee Prosthesis Controller*, Ph.D. Dissertation, Massachusetts Institute of Technology, 1979, 158 pages.

J. David Carlson et al., *Smart Prosthetics Based on Magnetorheological Fluids*, Society of Photo-Optical Instrumnetation Engineeris (SPIE), Mar. 2001, 9 pages.

Otto Bock Orthopadische Industrie GMBH & Co., *C-Leg Fitting Statistics (Abstract)*, Mar. 2000, 4 pages.

Otto Bock Orthopadische Industrie, *C-LEG A new dimension in amputee mobility*, 1997, 4 pages.

Otto Bock® Quality for Life, *Software C-Soft, Menu-driven setting of the C-Leg®*, 2004, 1 page.

Otto Bock® Quality for Life, *The Electronic C-Leg® Compact Leg Prosthesis System, Instructions for Use*, 2002, 28 pages.

Otto Bock® , *The Electronic C-Leg® Knee Joint System, Instructions for Use*, 2002, 32 pages.

*State-Of-The-Art Prosthetic Leg Incorporates Magneto-Rheological Technology*, Medical Product Manufacturing News, Nov. 2000, p. 42, 4 pages.

D. Popovic et al., *Optimal Control for an Above-Knee Prosthesis with Two Degrees of Freedom*, J. Biomechanics, vol. 28, No. 1, 1995, pp. 89-98.

Hugh Herr et al., *User-Adaptive Control of a Magnetorheological Prosthetic Knee*, Industrial Robot: An International Journal, vol. 30, No. 1, 2003, pp. 42-55.

Invitation to Pay Additional Fees and Partial International Search Report mailed Jul. 24, 2006 in counterpart International application No. PCT/US2005/015802, 9 pages.

J. David Carlson, *What Makes a Good MR Fluid?* 8$^{th}$ International Conference on Electrorheological (ER) Fluids and Magnetorheological (MR) Suspensions, Nice, Jul. 9-13, 2001, 7 pages.

D. Carlson et al., *Commercial Magneto-Rheological Fluid Devices*, Lord Corporation, 8 pages.

Jennifer L. Lelas et al., *Hydraulic Versus Magnetorheological-Based Electronic Knee Prostheses: A Clinical Comparison*, 16 pages.

Judith Otto, *Prosthetic Knees: What's on the Way?*, The O&P Edge, http://www.oandp.com/edge/issues/articles/2003-10_02.asp, Oct. 2003, 5 pages.

Judith Otto, *Prosthetic Knees: What's Currently New and Impressive?*, The O&P Edge, http://www.oandp.com/edge/issues/articles/2003-10_03.asp, Oct. 2003, 4 pages.

Nicholas Zamiska, *Bionic Knee 'Learns' How to Walk*, The Wall Street Journal, Jul. 6, 2004, 1 page.

Otto Bock, *Modular Knee Joints*, http://www.healthcare.ottobock.com/technical_orthopedics/beinprothesen/sites/knee.htm , printed from the internet on Jul. 10, 2002, 4 pages.

Össur Academy, *2004 Course Descriptions*, OSSUR North America, 16 pages.

Scott B. Elliot, *Rheo Knee, MR Microprocessor-Controlled Swing and Stance*, Presentation to American Academy of Orthotists & Prosthetists, Feb. 4, 2004, 81 pages.

Siegmer Blumentritt et al., *Design Principles, Biomechanical Data and Clinical Experience with a Polycentric Knee Offering Controlled Stance Phase Knee Flexion: A Preliminary Report*, Journal of Prosthetics and Orthotics, vol. 9, No. 1, 1997, pp. 18-24, http://www.oandp.org/ipo/library/199701_018.asp , 11 pages.

Sneha Thakkar, *Energy Economy Gait Analysis of an Autoadaptive Prosthetic Knee*, Master of Engineering Dissertation, Department of Electrical Engineering and Computer Science, Massachusetts Institute of Technology, 2002, 58 pages.

T. Schmalz et al., *Energy Efficiency of Trans-Femoral Amputees Walking on Computer-Controlled Prosthetic Knee Joint "C-LEG"*, Otto Bock et al., 3 pages.

* cited by examiner

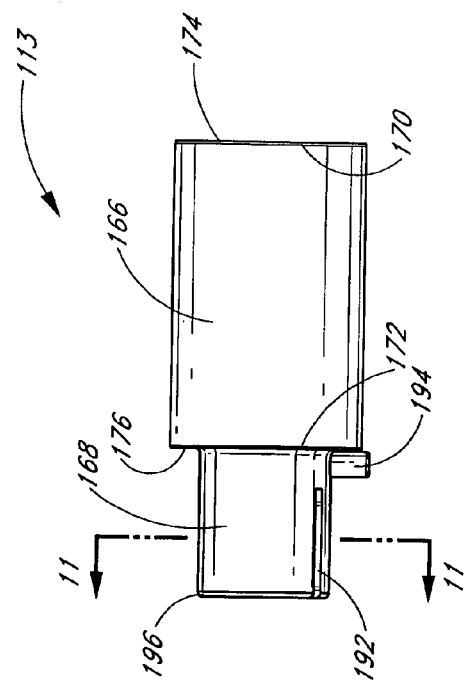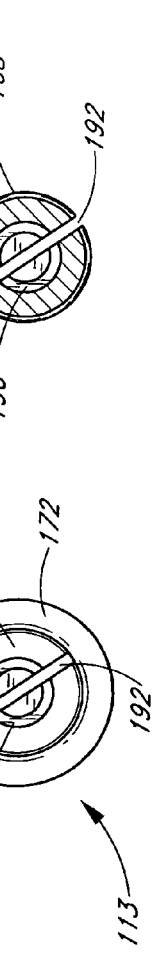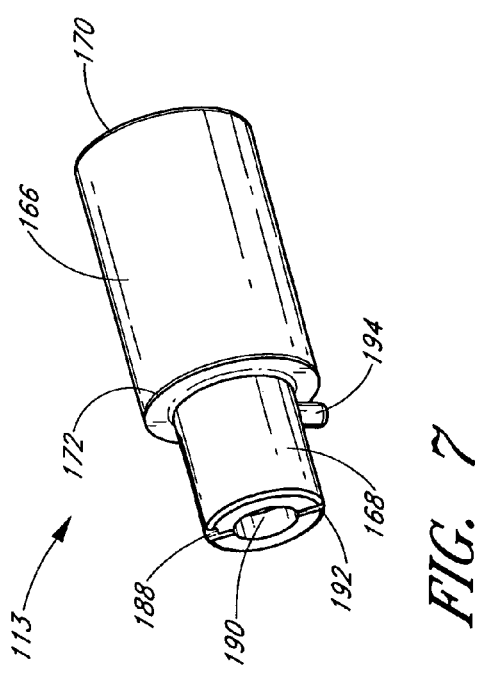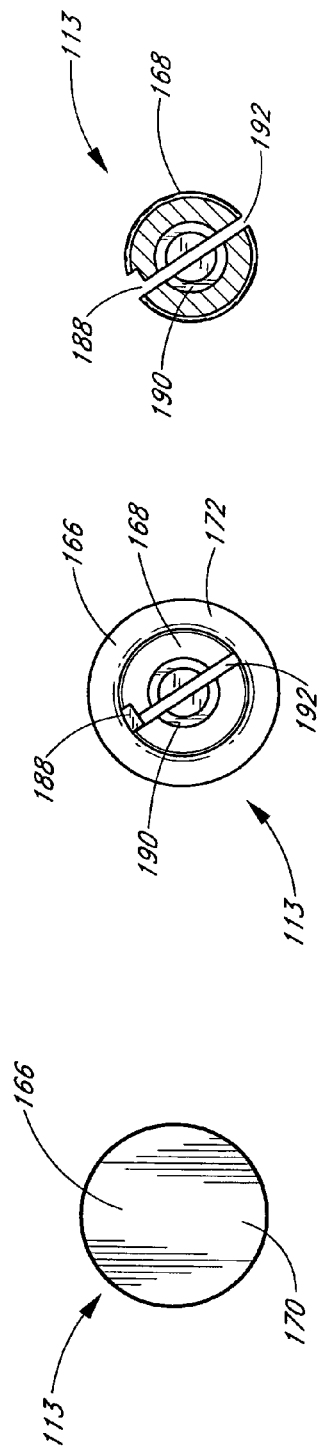

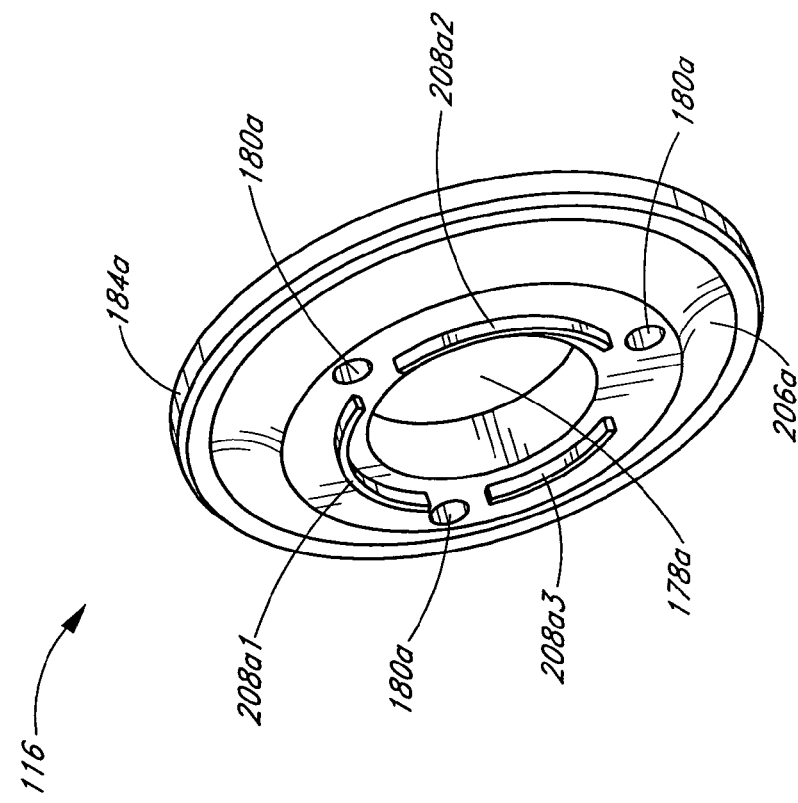
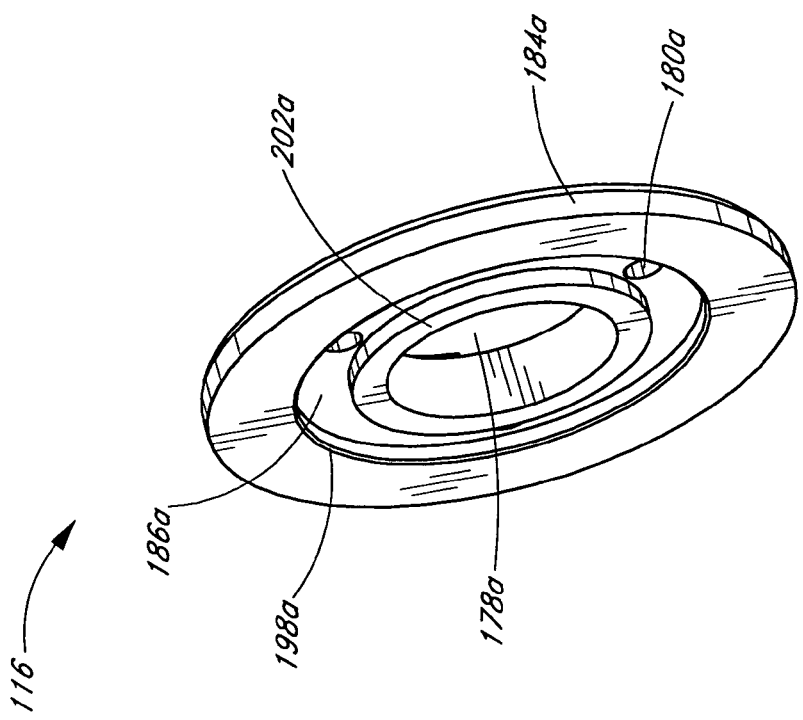

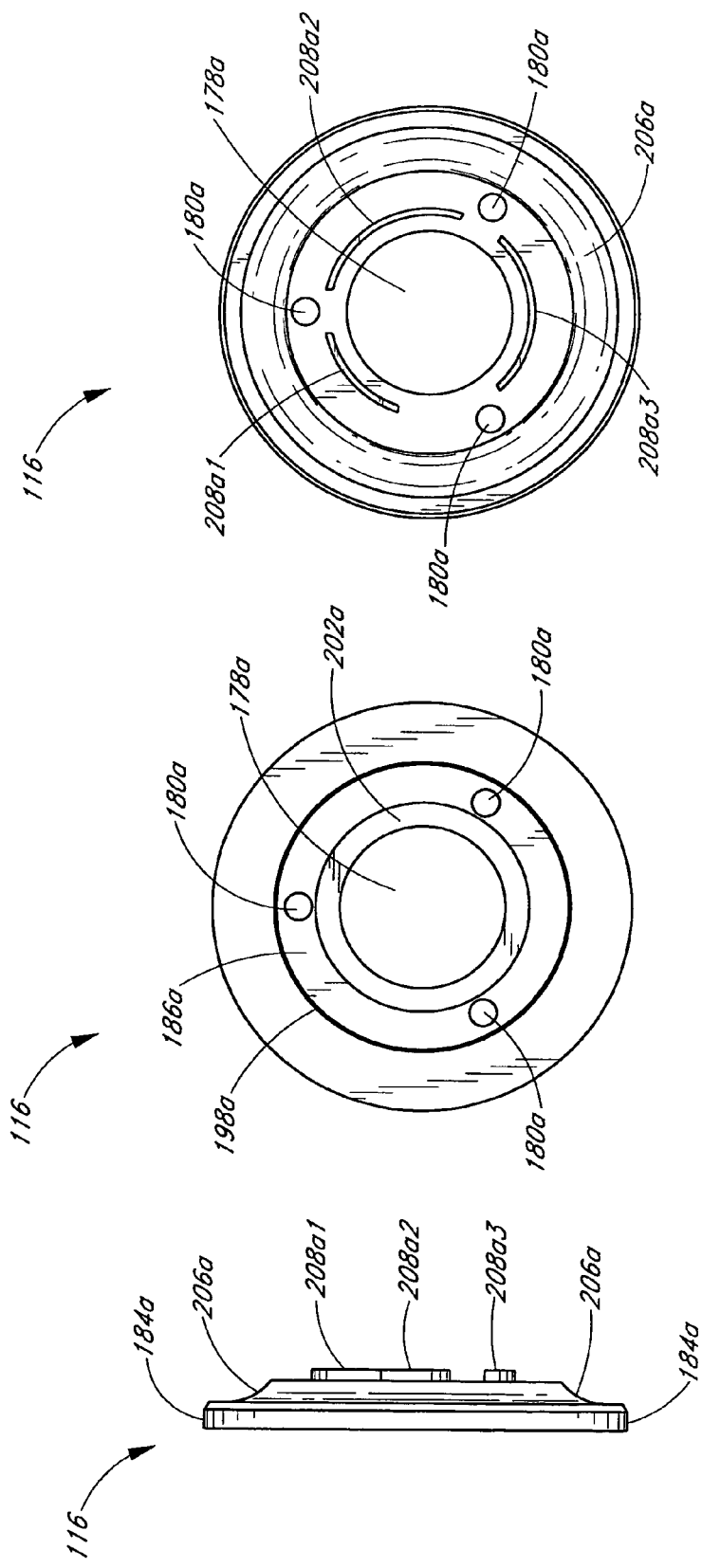

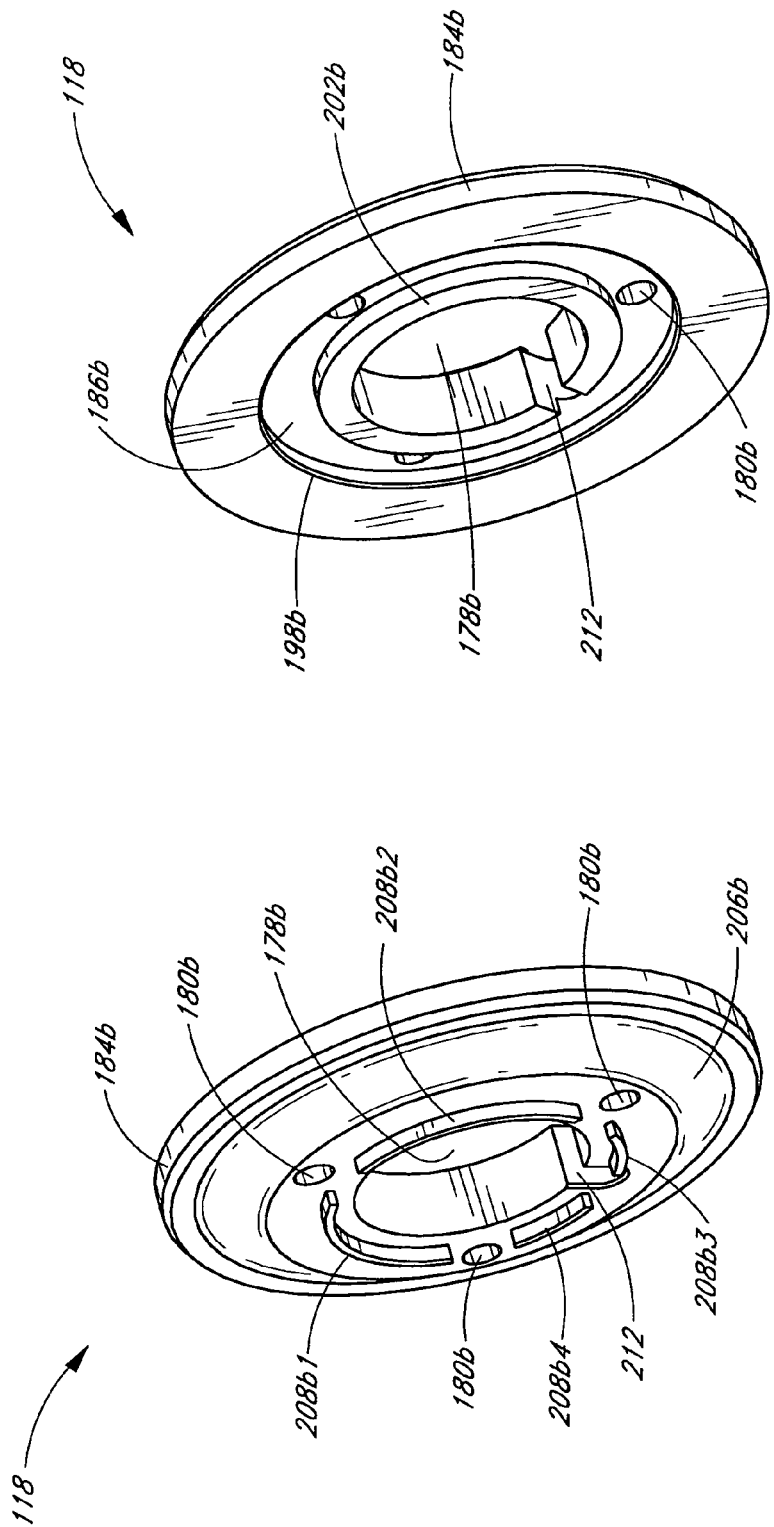

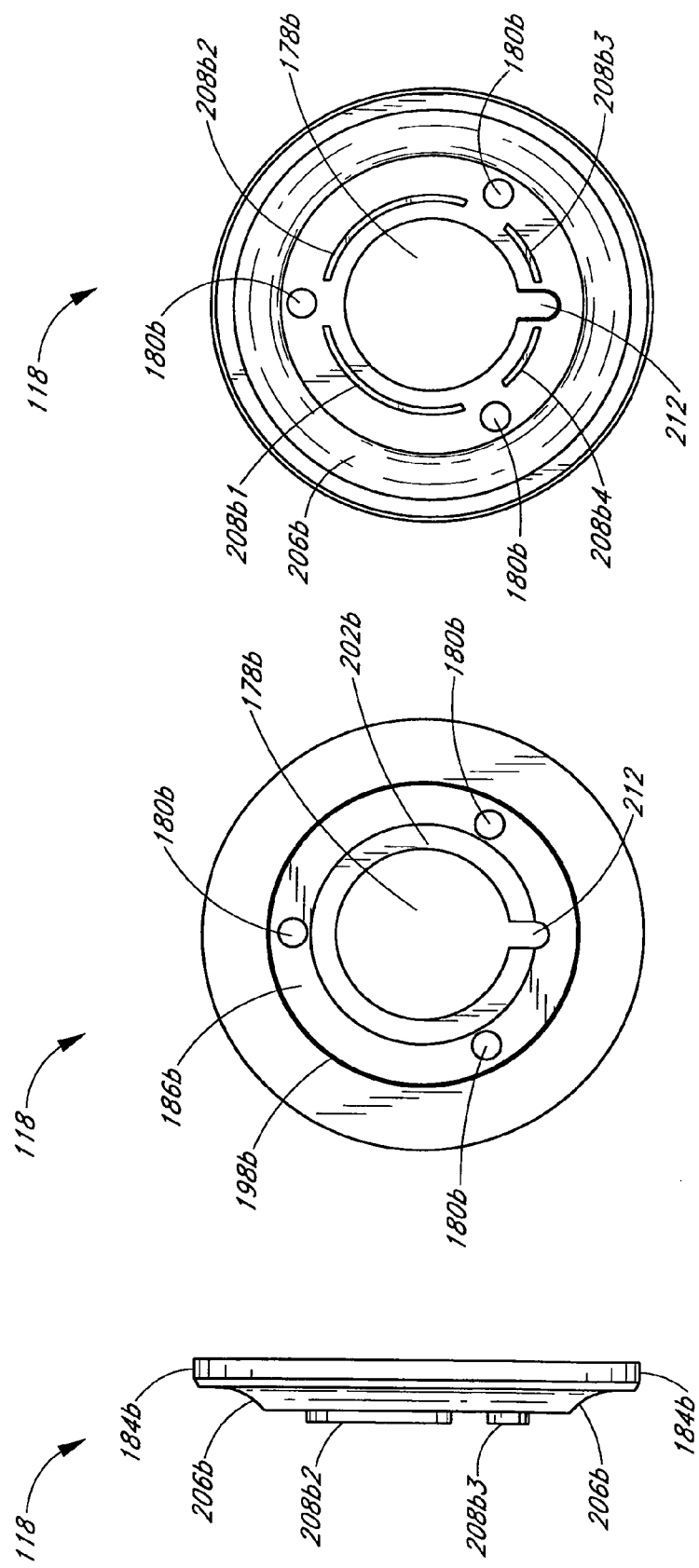

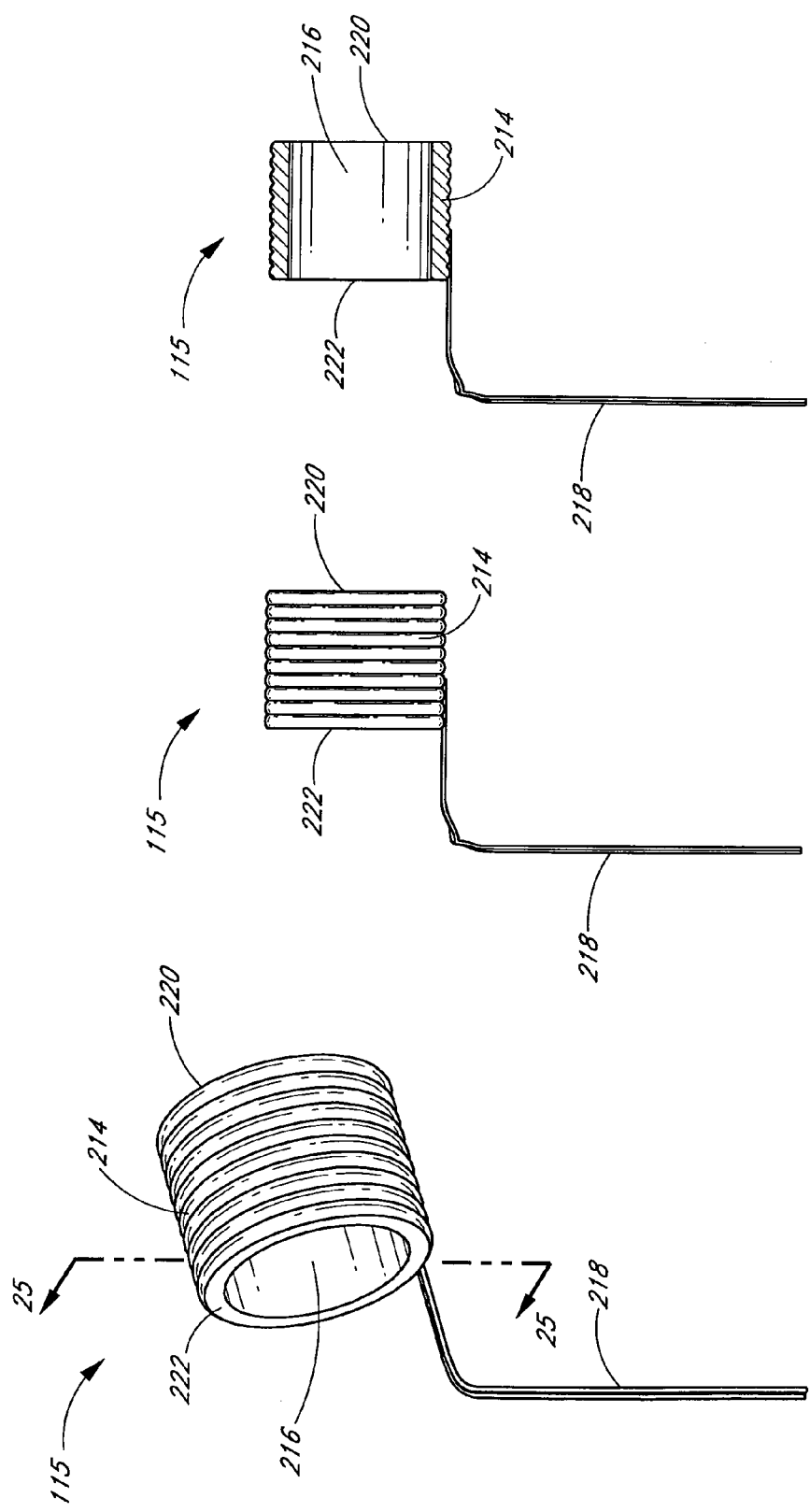

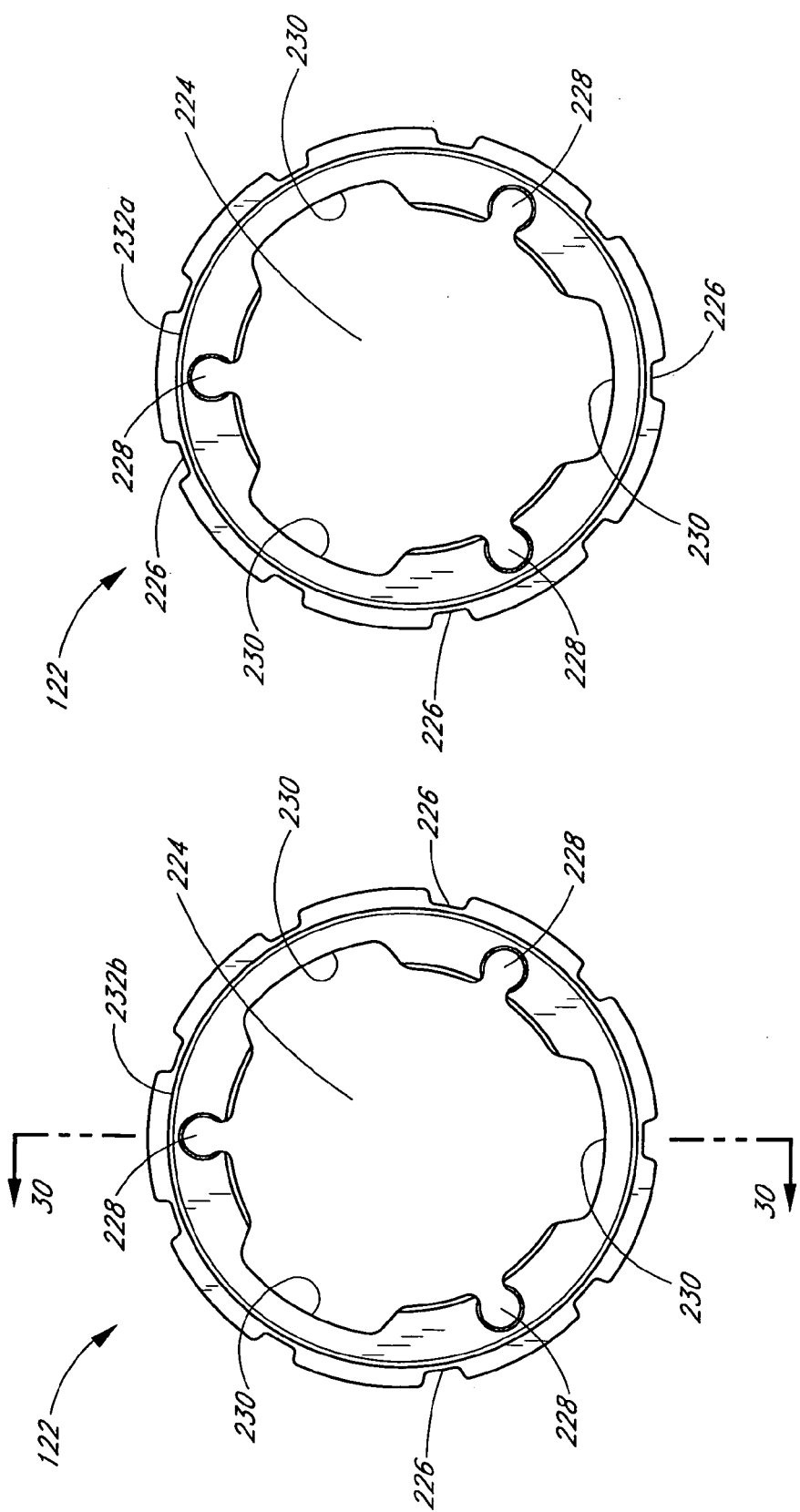

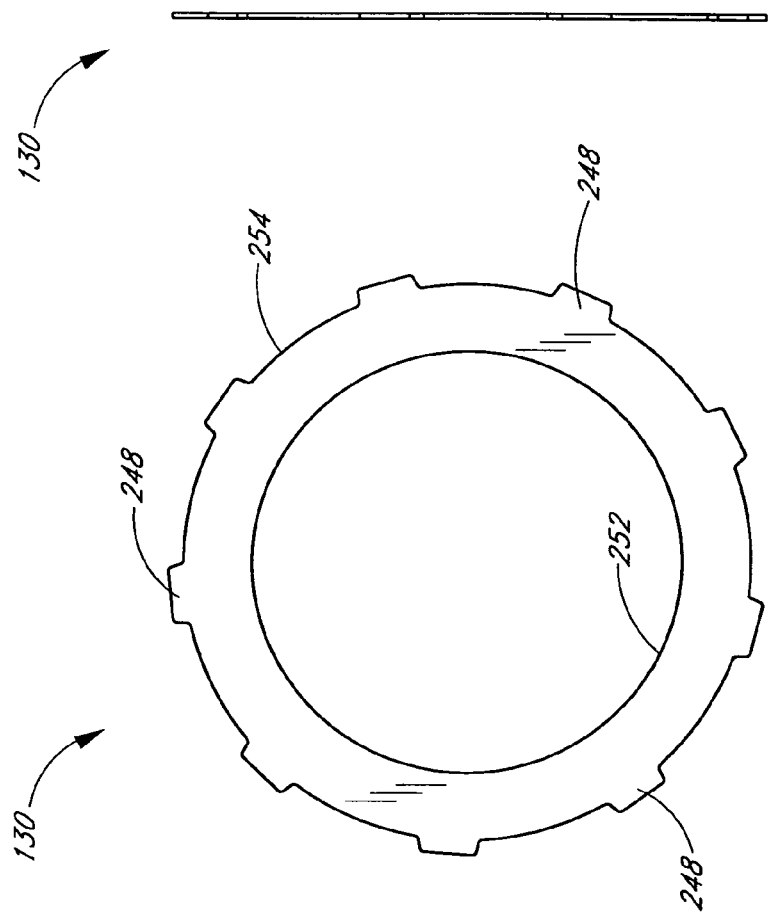
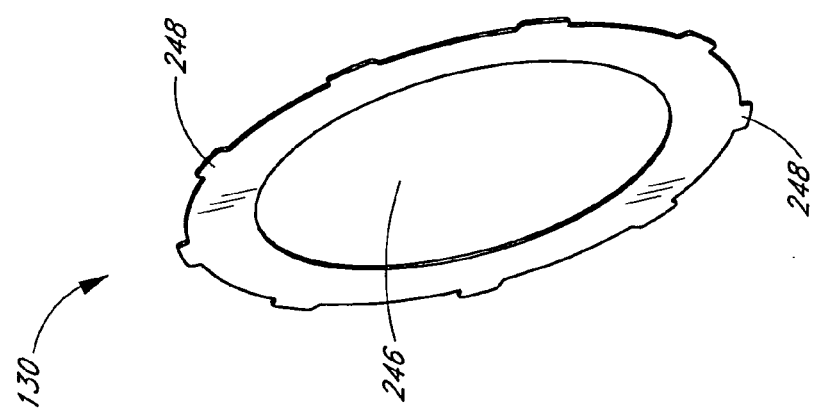
FIG. 39
FIG. 38
FIG. 37

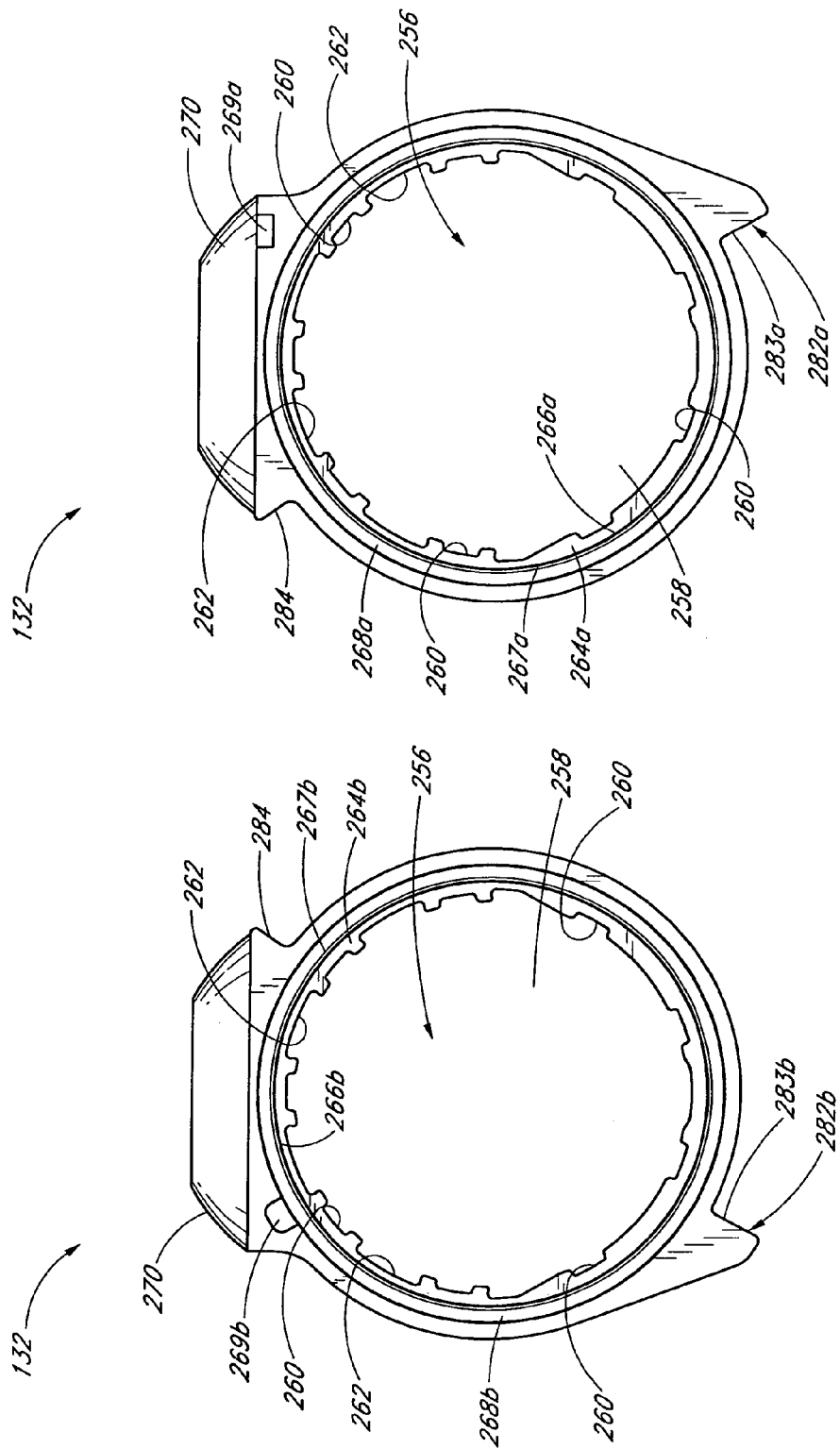

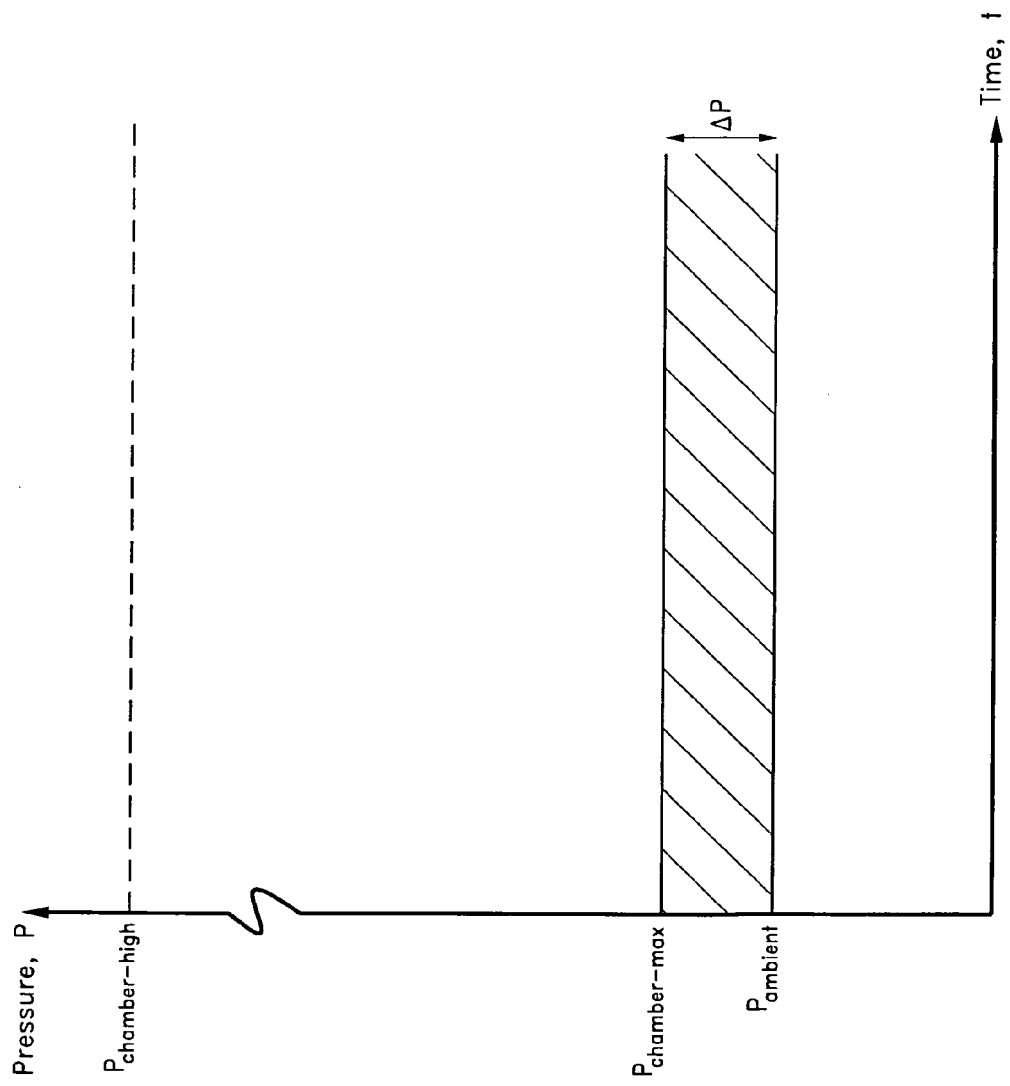

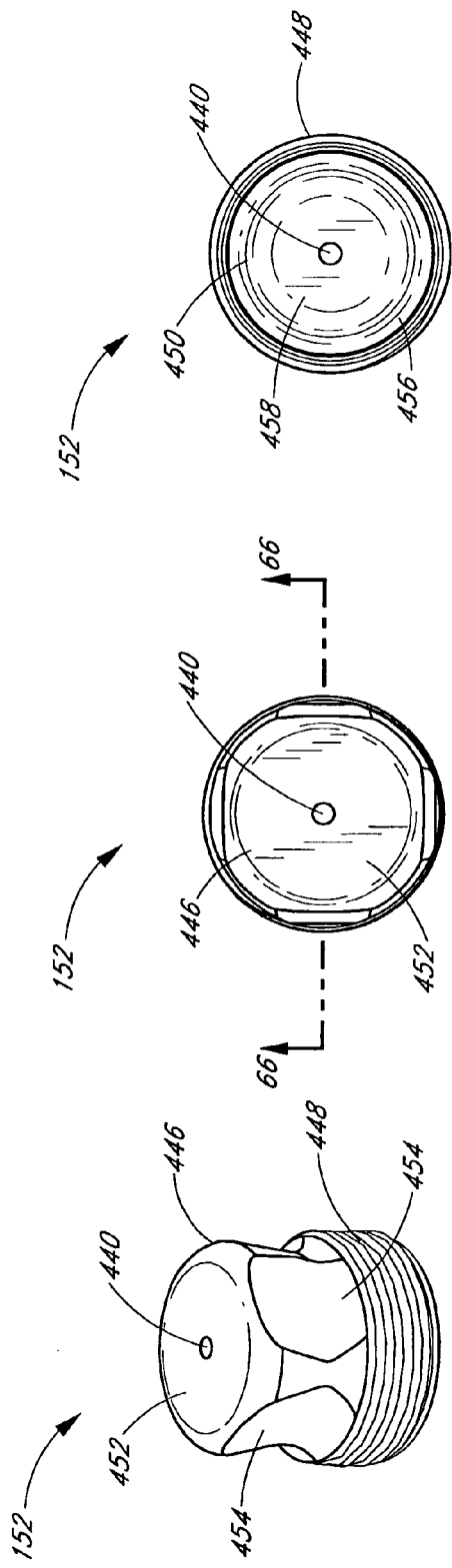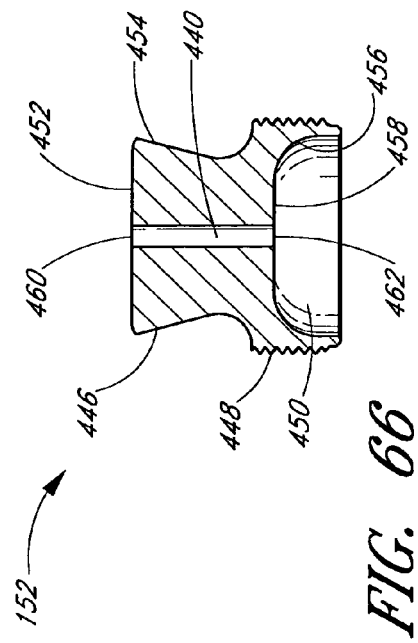

SYSTEMS AND METHODS OF LOADING FLUID IN A PROSTHETIC KNEE

RELATED APPLICATIONS

This application is a continuation-in-part (CIP) of U.S. patent application Ser. No. 10/722,313 now U.S. Pat. No. 7,101,487, filed Nov. 25, 2003, which claims the benefit of U.S. Provisional Patent Application No. 60/467,722, filed May 2, 2003, the entirety of each one of which is hereby incorporated by reference herein.

This application claims the benefit of U.S. Provisional Patent Application No. 60/569,512, filed May 7, 2004, and U.S. Provisional Patent Application No. 60/624,986, filed Nov. 3, 2004, the entirety of each one of which is hereby incorporated by reference herein.

BACKGROUND OF THE INVENTION

1. Field of the Invention

The invention relates in one embodiment to loading fluid in prosthetic devices and, in particular, to a vacuum fill technique for efficiently and substantially uniformly loading a magnetorheological fluid in small gaps within a chamber of a prosthetic knee.

2. Description of the Related Art

Three types of variable-torque brakes have been employed in prosthetic knees in the past: (i) dry friction brakes where one material surface rubs against another surface with variable force; (ii) viscous torque brakes using hydraulic fluid squeezed through a variable sized orifice or flow restriction plate; and (iii) magnetorheological (MR) brakes or dampers where MR fluid (containing small iron particles suspended in the fluid) is squeezed through a fixed orifice or flow restriction plate, with viscosity of the fluid being varied in response to an applied magnetic field. Each of these technologies, as conventionally practiced in the field of prosthetics, can pose certain disadvantages.

Though dry friction brakes can generally provide a substantial torque range for their size, undesirably, they are often difficult to control. After extended use, the frictional pads tend to wear, thereby changing the frictional characteristics of the brake and the torque response for a given commanded torque. Disadvantageously, this can cause unreliable damping performance, and hence adversely affect the gait of the amputee and also cause discomfort to the amputee. Consequently, dry friction brakes may need frequent servicing and/or replacement which undesirably adds to the cost.

Under high loading conditions, viscous torque brakes are susceptible to leakage of hydraulic fluid and possibly other damage due to excessive pressure build-up. Disadvantageously, this can result in an irreversible state, since once the brake unit is overloaded it cannot return to normal. Therefore, such a viscous torque brake for a prosthetic joint is prone to catastrophic failure, and hence can be unreliable and detrimental to the safety of an amputee.

In certain MR brakes and dampers, the interaction of the MR fluid with the device undesirably causes increased pressure, seal deterioration, or a combination of the two. Another possible cause of these adverse effects is decomposition of the MR fluid. Once the seals fail or the MR fluid decomposes, the prosthetic knee is no longer suitable for use.

SUMMARY OF THE INVENTION

The invention in some embodiments relates to systems and methods of loading fluid in a prosthetic knee. A vacuum fill technique is utilized in one embodiment to load magnetorheological fluid within small gaps in a chamber of a prosthetic knee. Advantageously, this allows for an efficient loading scheme thereby desirably allowing for faster manufacturing speed. Another advantage is that the magnetorheological fluid is substantially uniformly distributed within the small gaps thereby desirably providing consistent production.

Some embodiments relate to a method of loading a field responsive fluid in a device to be worn by a wearer at a knee location. The method generally comprises forming an assembly comprising a plurality of first blades and second blades with gaps therebetween in a chamber of an outer housing with at least one of the plurality of first blades and the plurality of second blades being rotatable. A field responsive fluid is provided in a channel that is in fluid communication with the chamber. A vacuum is applied over the assembly and the channel to force the fluid into the chamber.

Some embodiments relate to a method of loading a field responsive fluid in a device to be attached to a limb. The method generally comprises providing an assembly adapted to provide relative movement between two adjacent portions. The assembly comprises a housing that comprises a chamber. A field responsive fluid is provided in a channel that is in fluid communication with the chamber. A vacuum is applied over the assembly and the channel to force the fluid into the chamber.

Some embodiments relate to a method of loading a liquid in miniature gaps of a device to be attached to a limb. The method generally comprises providing an actuator assembly adapted to provide relative movement between two adjacent portions. The assembly comprises a housing that comprises a chamber with gaps therein. A liquid is provided in a channel that is in fluid communication with the chamber. A vacuum is applied over the assembly and the channel to force the liquid into the gaps in the chamber.

Some embodiments relate to a method of loading a field responsive fluid in a chamber. The method generally comprises providing a housing that has a substantially sealed chamber and a port. A channel is connected to the port so that the channel is in fluid communication with the chamber. A predetermined quantity of a field responsive fluid is added to the channel. A vacuum is applied over the housing and the channel to force the fluid into the chamber.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 7 is a simplified perspective view of a core rod of the actuator of FIG. 6 illustrating features and advantages in accordance with an embodiment of the invention.

FIG. 8 is a simplified side view of the core rod of FIG. 7 illustrating features and advantages in accordance with an embodiment of the invention.

FIG. 9 is a simplified right end view of the core rod of FIG. 7 illustrating features and advantages in accordance with an embodiment of the invention.

FIG. 10 is a simplified left end view of the core rod of FIG. 7 illustrating features and advantages in accordance with an embodiment of the invention.

FIG. 11 is a simplified sectional view along line 11—11 of FIG. 8 illustrating features and advantages in accordance with an embodiment of the invention.

FIG. 12 is a simplified perspective view of a right core side of the actuator of FIG. 6 illustrating features and advantages in accordance with an embodiment of the invention.

FIG. 13 is another simplified perspective view of the right core side of FIG. 12 illustrating features and advantages in accordance with an embodiment of the invention.

FIG. 14 is a simplified side view of the right core side of FIG. 12 illustrating features and advantages in accordance with an embodiment of the invention.

FIG. 15 is a simplified front view of the right core side of FIG. 12 illustrating features and advantages in accordance with an embodiment of the invention.

FIG. 16 is a simplified rear view of the right core side of FIG. 12 illustrating features and advantages in accordance with an embodiment of the invention.

FIG. 17 is a simplified perspective view of a left core side of the actuator of FIG. 6 illustrating features and advantages in accordance with an embodiment of the invention.

FIG. 18 is another simplified perspective view of the left core side of FIG. 17 illustrating features and advantages in accordance with an embodiment of the invention.

FIG. 19 is a simplified side view of the left core side of FIG. 17 illustrating features and advantages in accordance with an embodiment of the invention.

FIG. 20 is a simplified front view of the left core side of FIG. 17 illustrating features and advantages in accordance with an embodiment of the invention.

FIG. 21 is a simplified rear view of the left core side of FIG. 17 illustrating features and advantages in accordance with an embodiment of the invention.

FIG. 23 is a simplified perspective view of a magnetic coil of the actuator of FIG. 6 illustrating features and advantages in accordance with an embodiment of the invention.

FIG. 24 is a simplified side view of the magnetic coil of FIG. 23 illustrating features and advantages in accordance with an embodiment of the invention.

FIG. 25 is a simplified sectional view along line 25—25 of FIG. 23 illustrating features and advantages in accordance with an embodiment of the invention.

FIG. 31 is a simplified end view of the inner spline of FIG. 28 illustrating features and advantages in accordance with an embodiment of the invention.

FIG. 32 is a simplified opposite end view of the inner spline of FIG. 28 illustrating features and advantages in accordance with an embodiment of the invention.

FIG. 37 is a simplified perspective view of one of the outer rotors of the actuator of FIG. 6 illustrating features and advantages in accordance with an embodiment of the invention.

FIG. 38 is a simplified front (or rear) view of the outer rotor of FIG. 37 illustrating features and advantages in accordance with an embodiment of the invention.

FIG. 39 is a simplified side view of the outer rotor of FIG. 37 illustrating features and advantages in accordance with an embodiment of the invention.

FIG. 42 is a simplified end view of the outer spline of FIG. 41 illustrating features and advantages in accordance with an embodiment of the invention.

FIG. 43 is a simplified opposite end view of the outer spline of FIG. 41 illustrating features and advantages in accordance with an embodiment of the invention.

FIG. 62 is a simplified graphical representation of desirable pressure variation control provided by embodiments of the pressure control system of FIG. 61 illustrating features and advantages in accordance with an embodiment of the invention.

FIG. 63 is a simplified perspective view of a pyramid stud of the actuator of FIG. 6 illustrating features and advantages in accordance with an embodiment of the invention.

FIG. 64 is a simplified bottom view of the pyramid stud of FIG. 63 illustrating features and advantages in accordance with an embodiment of the invention.

FIG. 65 is a simplified top view of the pyramid stud of FIG. 63 illustrating features and advantages in accordance with an embodiment of the invention.

FIG. 66 is a simplified sectional view along line 66—66 of FIG. 65 illustrating features and advantages in accordance with an embodiment of the invention.

Figure 77:
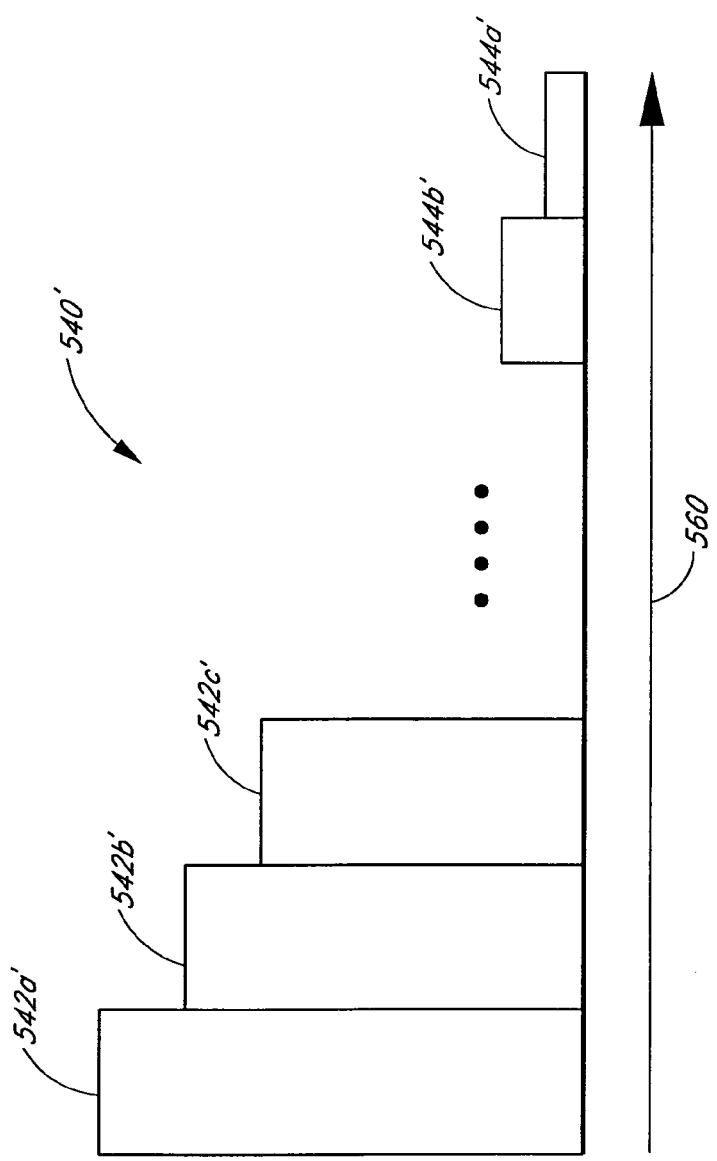

FIG. 77 is a simplified schematic view of another shock absorbing multi-stage bumper system illustrating features and advantages in accordance with an embodiment of the invention.

Figure 78:
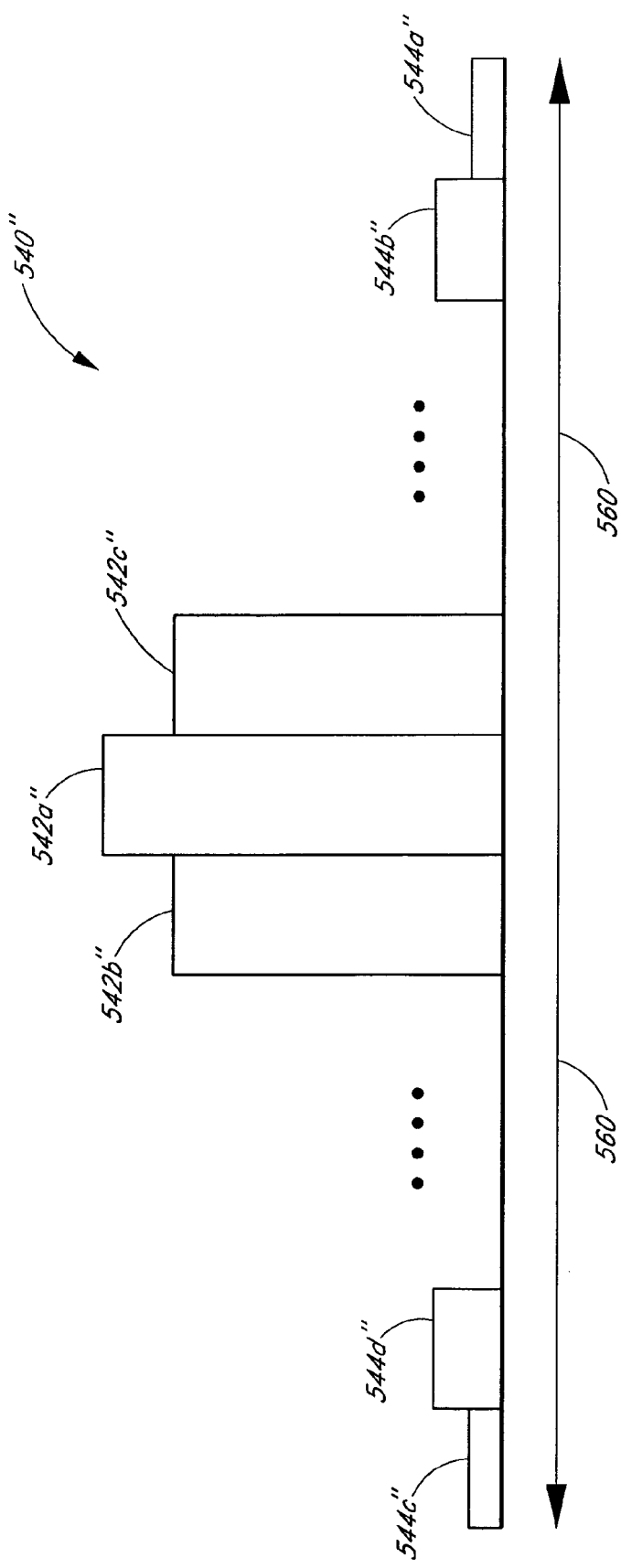

FIG. 78 is a simplified schematic view of yet another shock absorbing multi-stage bumper system illustrating features and advantages in accordance with an embodiment of the invention.

Figure 6:
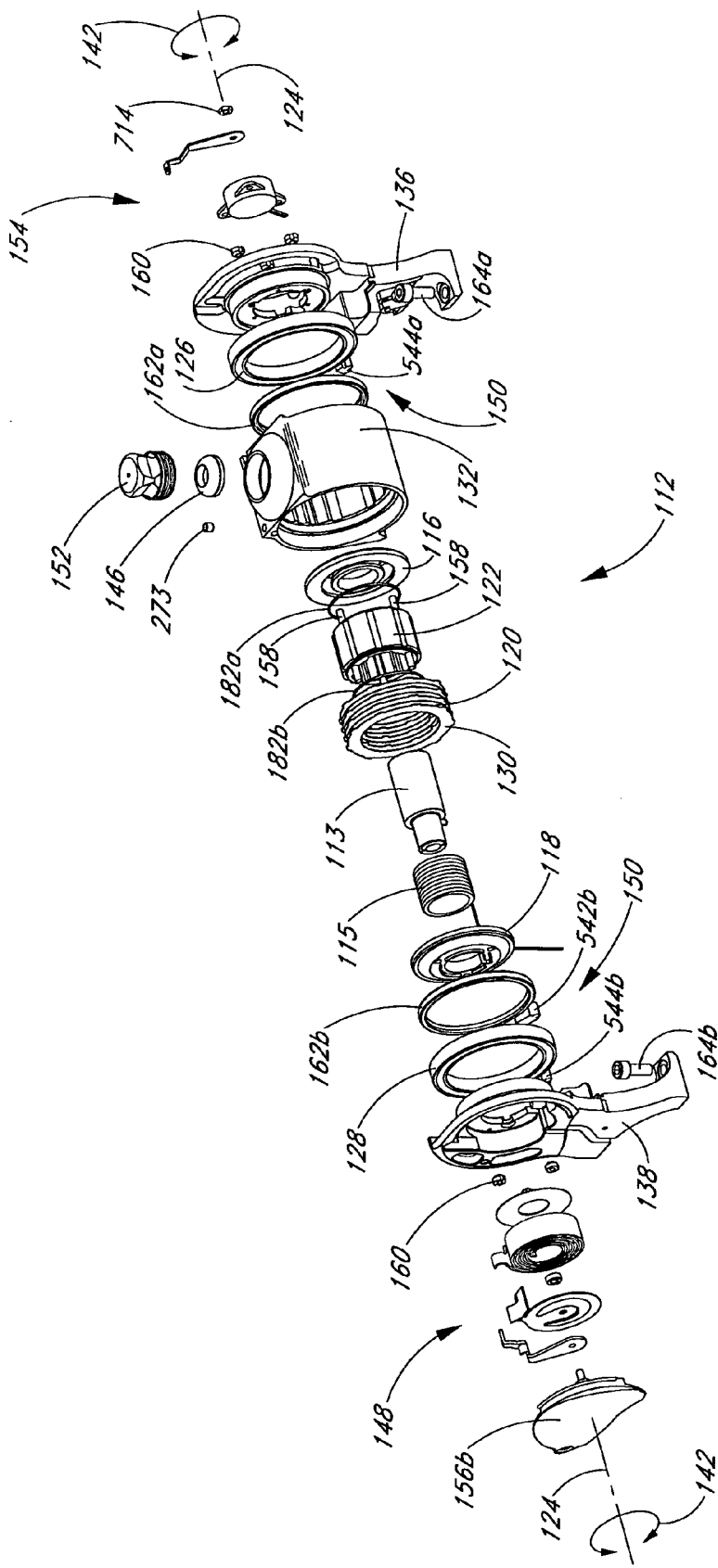
FIG. 6 is a simplified exploded perspective View of the magnetorheological actuator of FIGS. 5A–5E illustrating features and advantages in accordance with an embodiment of the invention.
Figure 79:
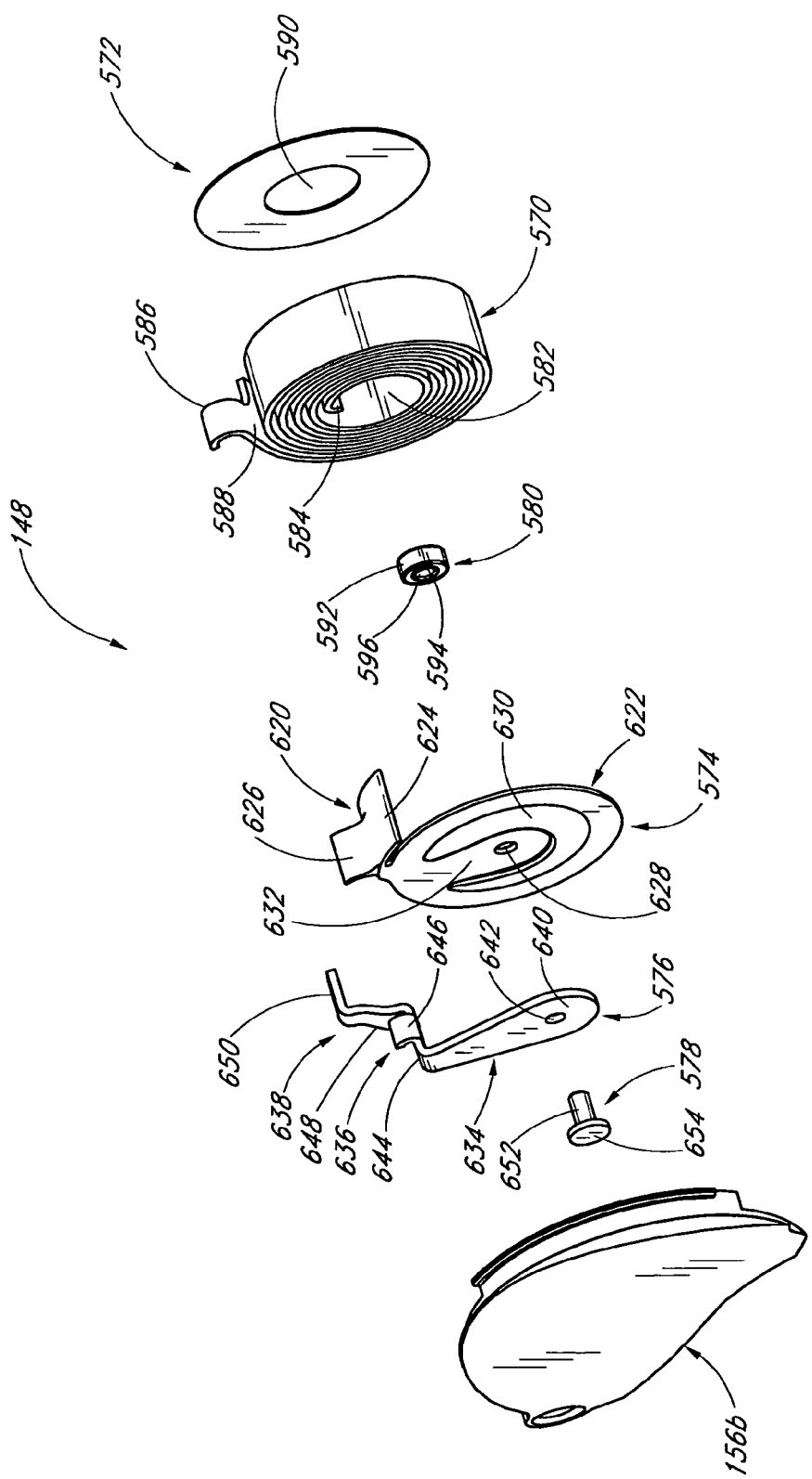

FIG. 79 is a simplified exploded perspective view of an extension assist system of the actuator of FIG. 6 illustrating features and advantages in accordance with an embodiment of the invention.

Figure 80:
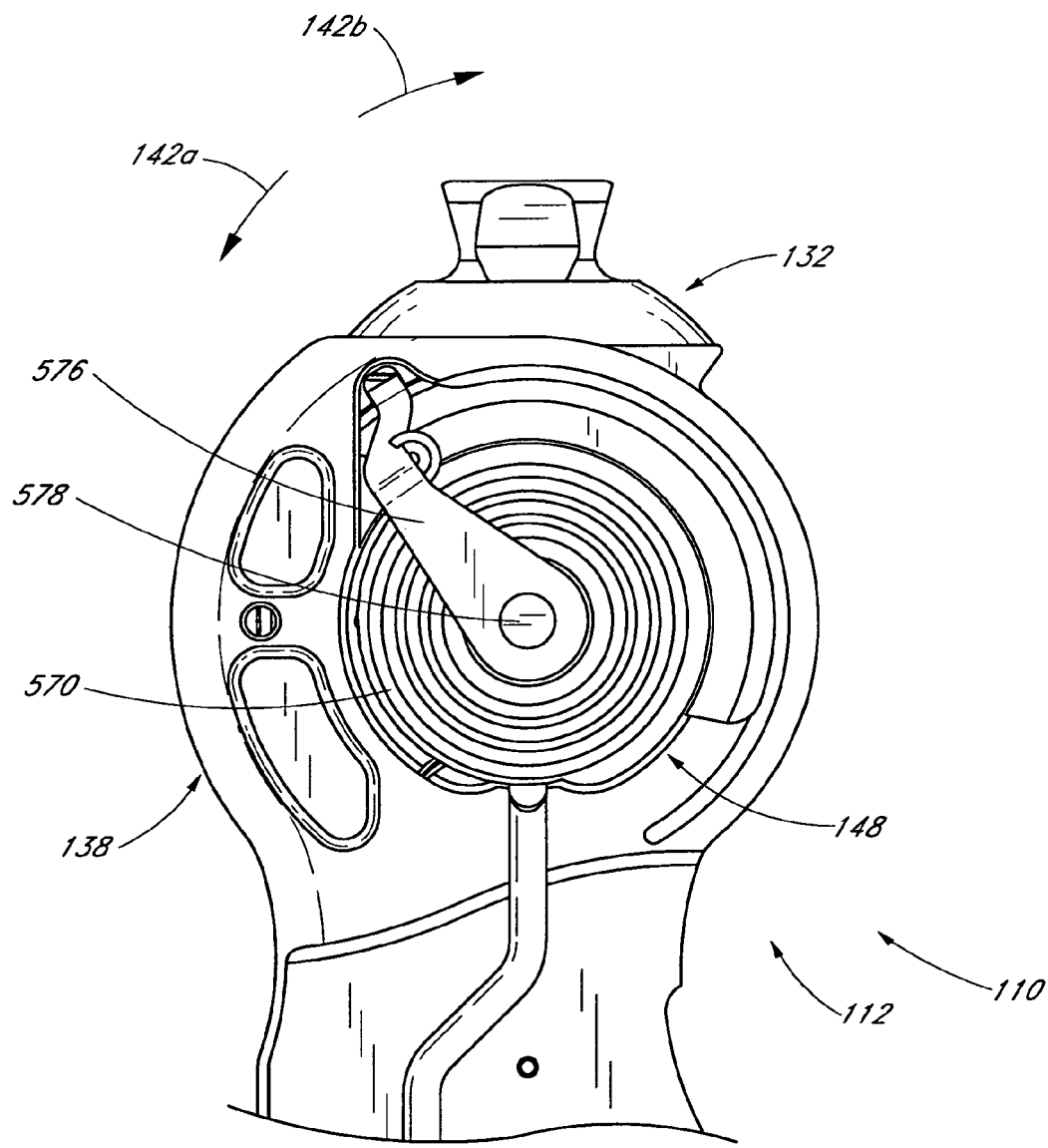

FIG. 80 is a simplified partial side view of the extension assist system of FIG. 79 mounted on the actuator illustrating features and advantages in accordance with an embodiment of the invention.

Figure 81:
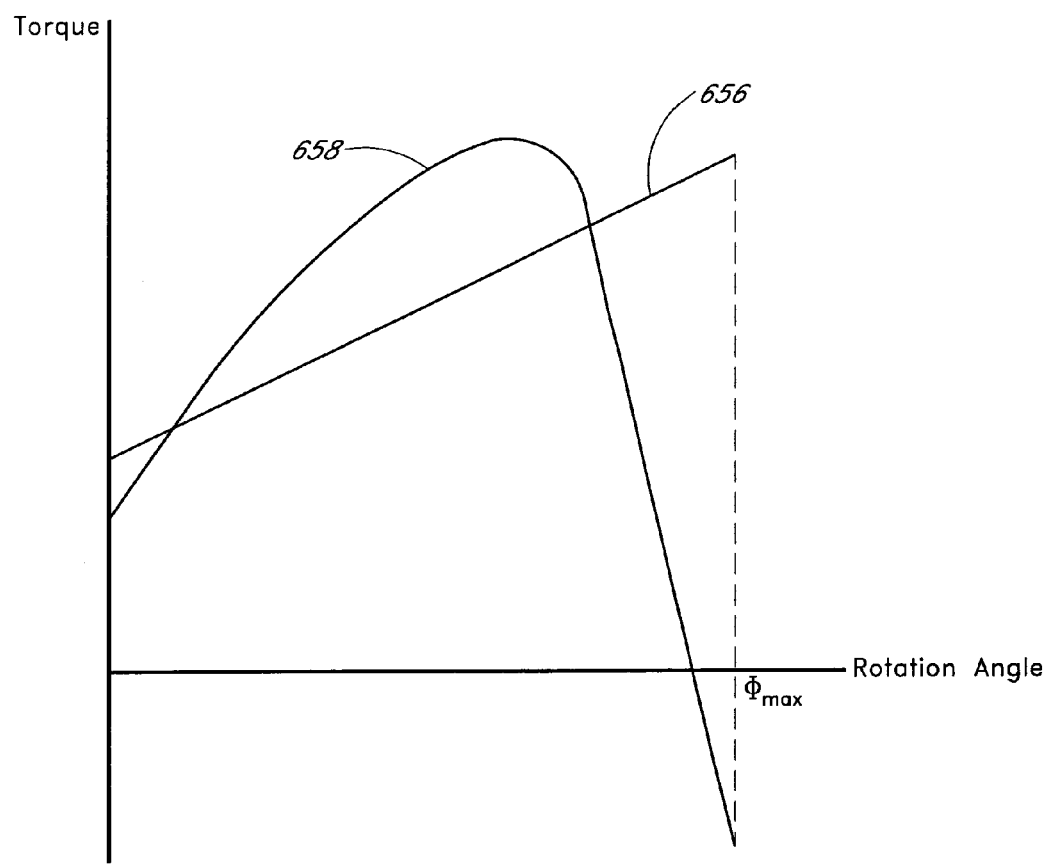

FIG. 81 is a simplified graphical representation of torque versus angle relationships for an extension assist spring of the actuator of FIG. 6 illustrating features and advantages in accordance with some embodiments of the invention.

Figure 82:
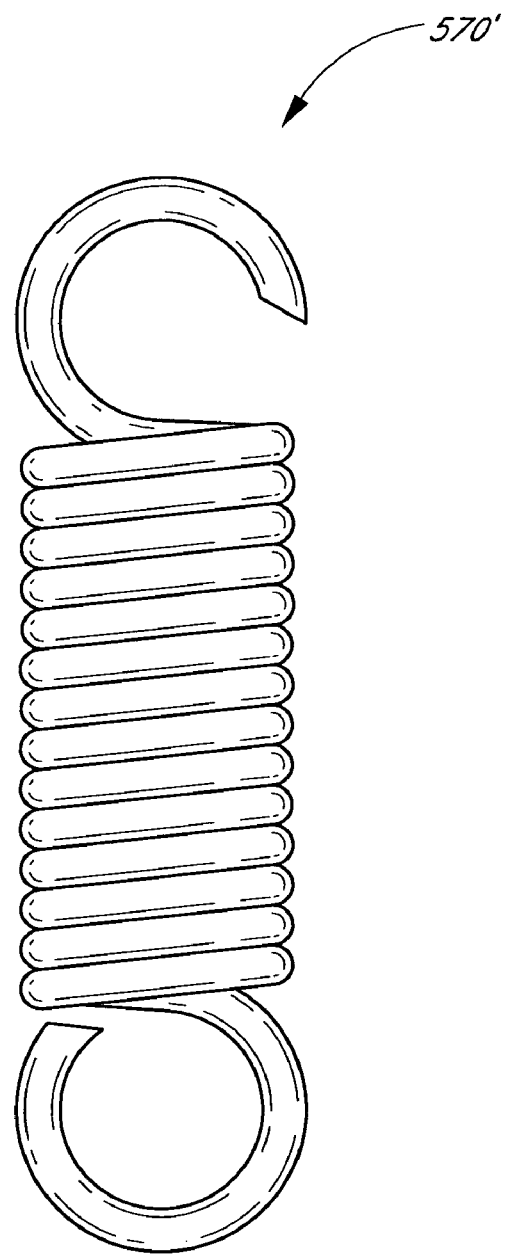

FIG. 82 is a simplified side view of an extension spring for an extension assist system of the actuator of FIG. 6 illustrating features and advantages in accordance with another embodiment of the invention.

Figure 83:
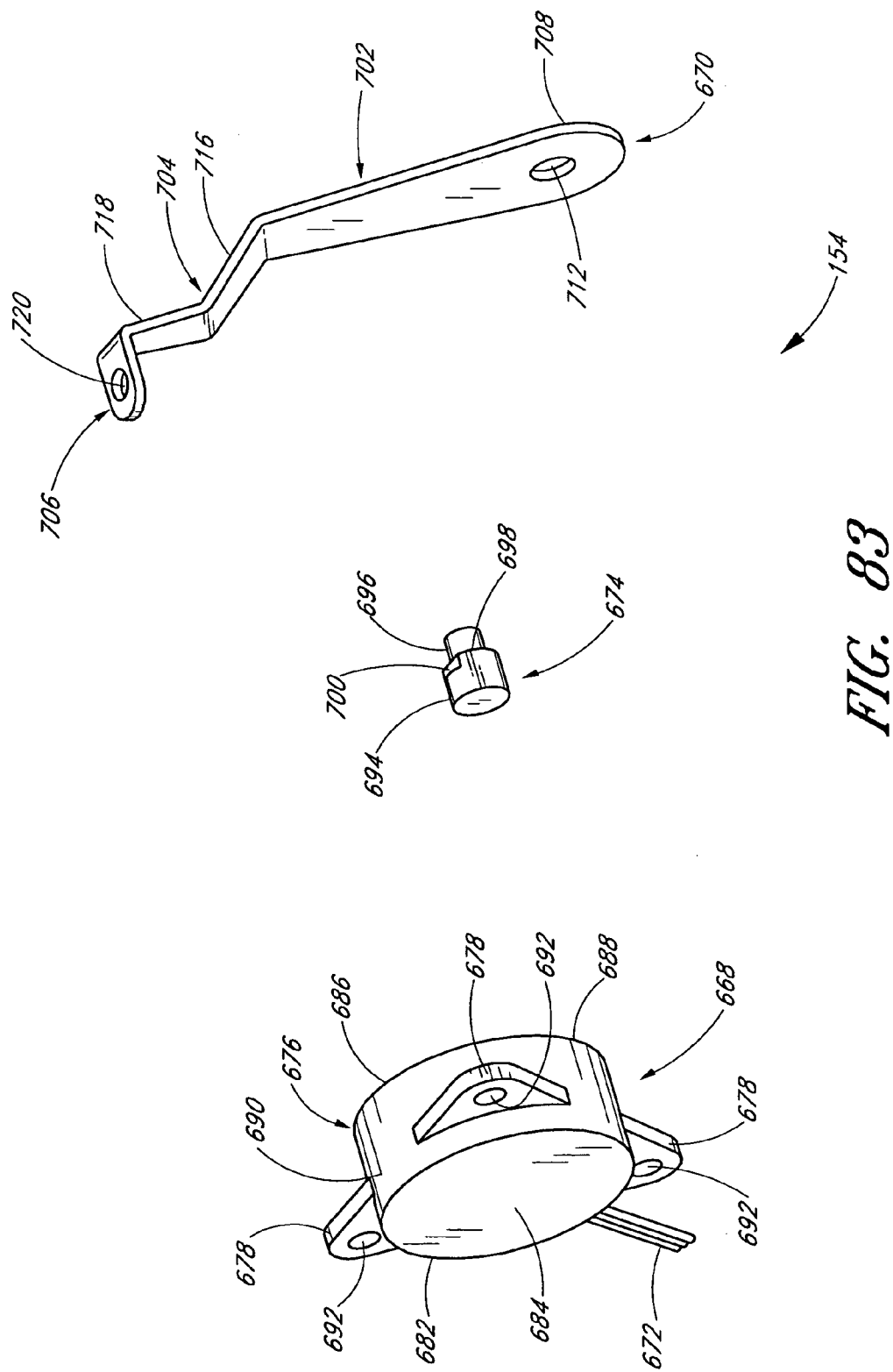

FIG. 83 is a simplified exploded perspective view of an angle sensing system of the actuator of FIG. 6 illustrating features and advantages in accordance with an embodiment of the invention.

Figure 84:
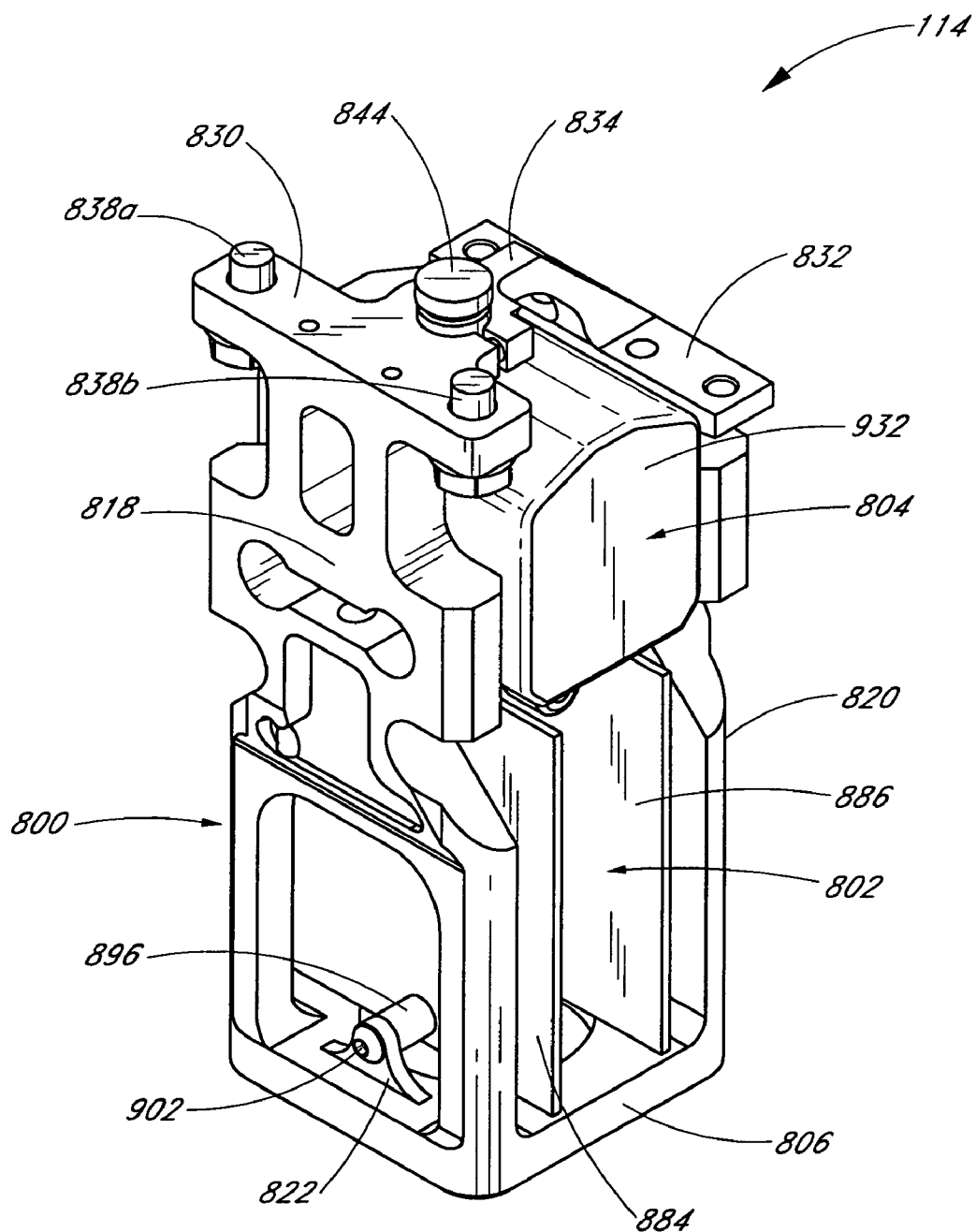

FIG. 84 is a simplified perspective view of a frame and electronics assembly of the prosthetic knee assembly of FIGS. 3A–3D illustrating features and advantages in accordance with an embodiment of the invention.

Figure 85:
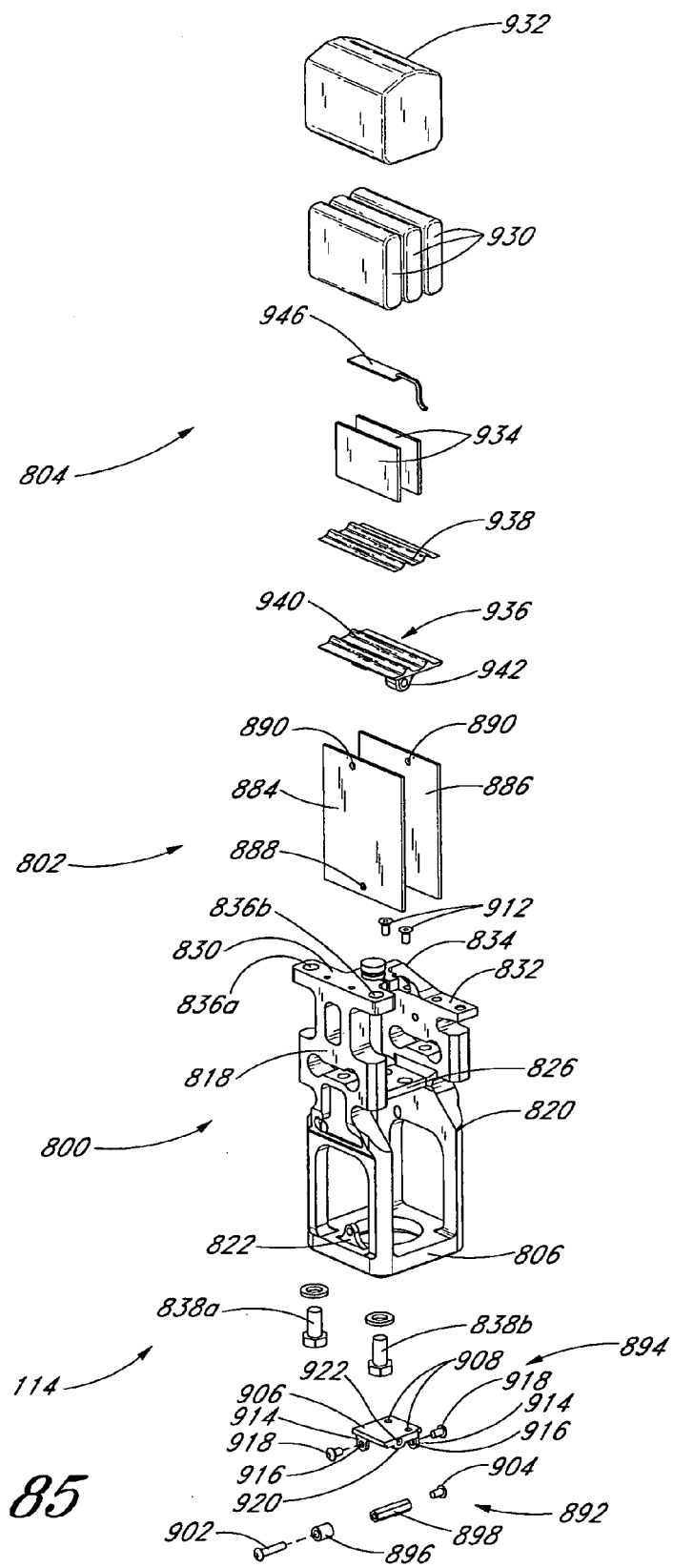

FIG. 85 is a simplified exploded perspective view of the assembly of FIG. 84 illustrating features and advantages in accordance with an embodiment of the invention.

Figure 86:
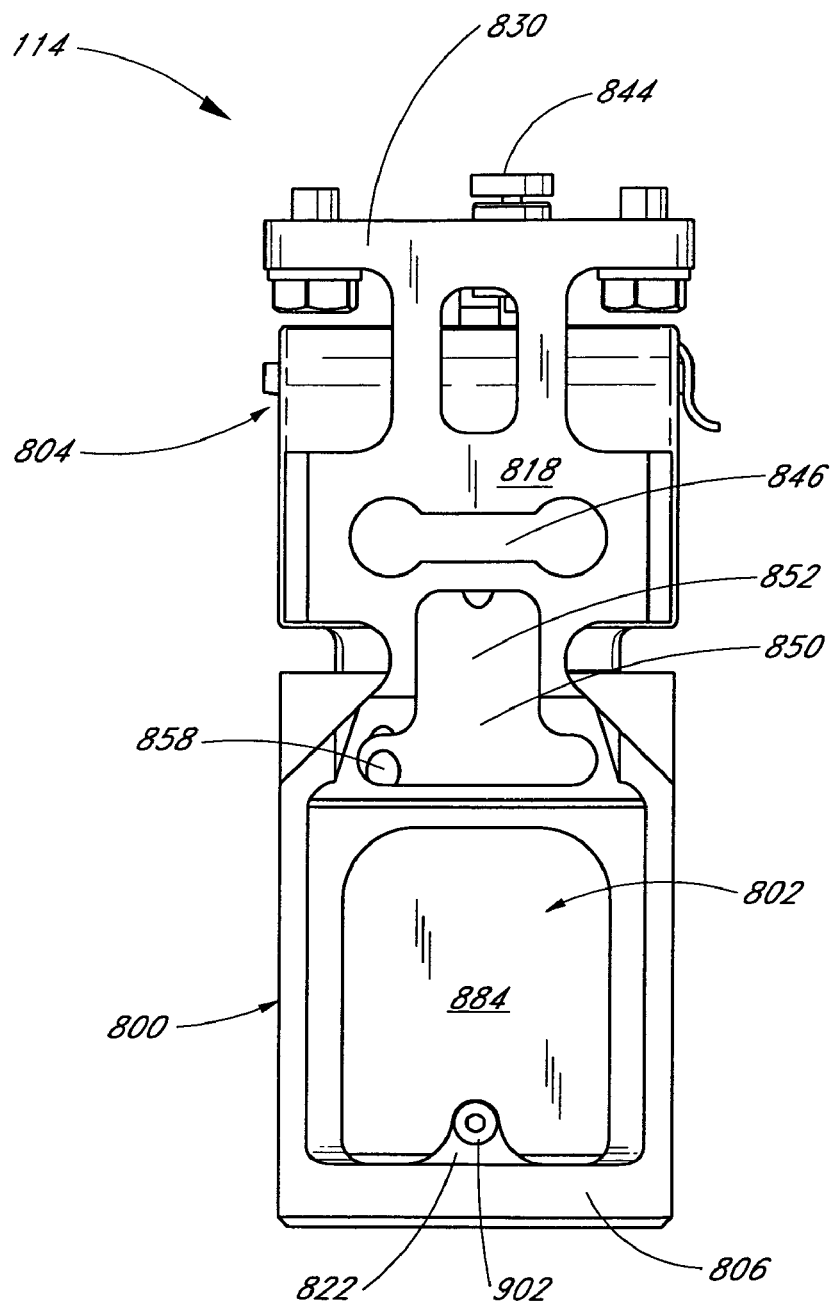

FIG. 86 is a simplified front view of the assembly of FIG. 84 illustrating features and advantages in accordance with an embodiment of the invention.

Figure 87:
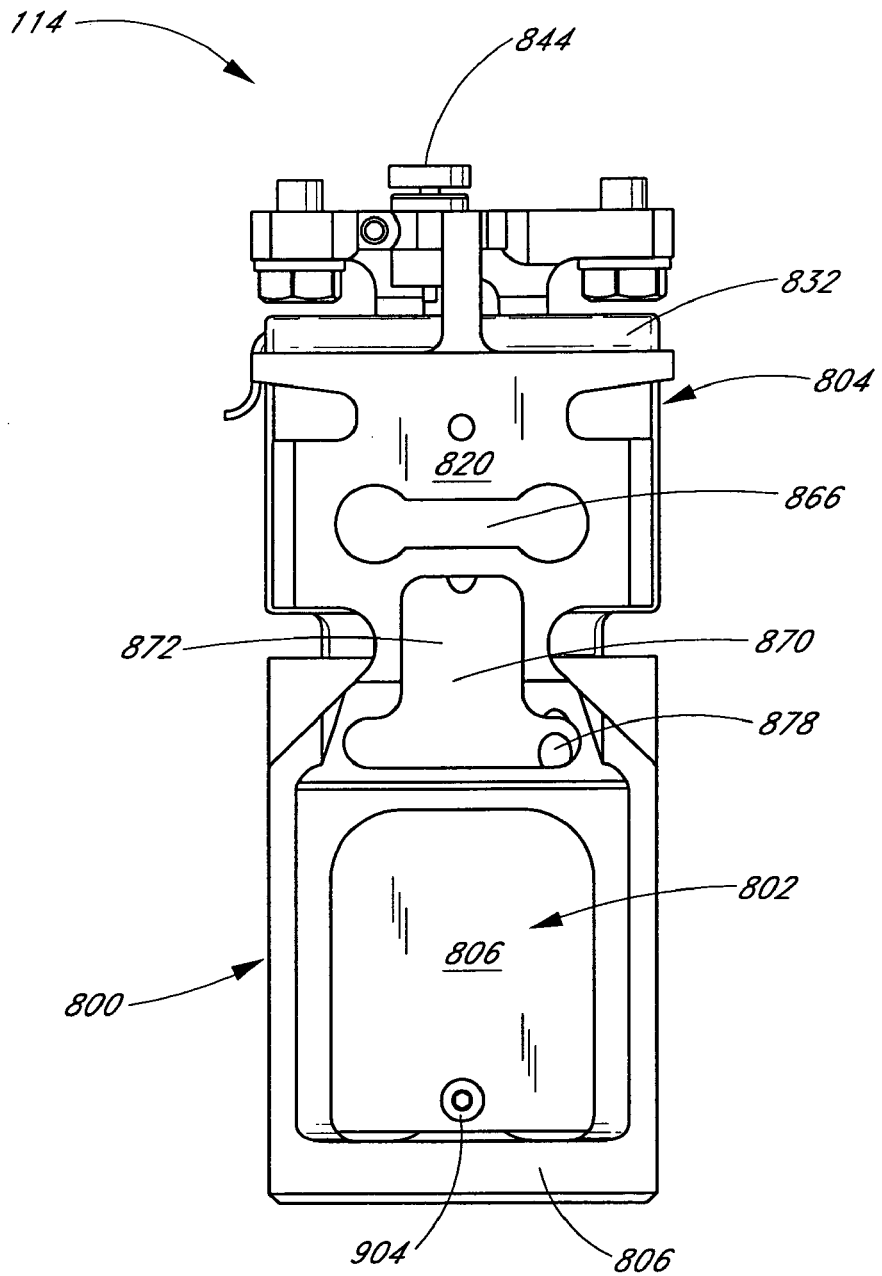

FIG. 87 is a simplified rear view of the assembly of FIG. 84 illustrating features and advantages in accordance with an embodiment of the invention.

Figure 88:
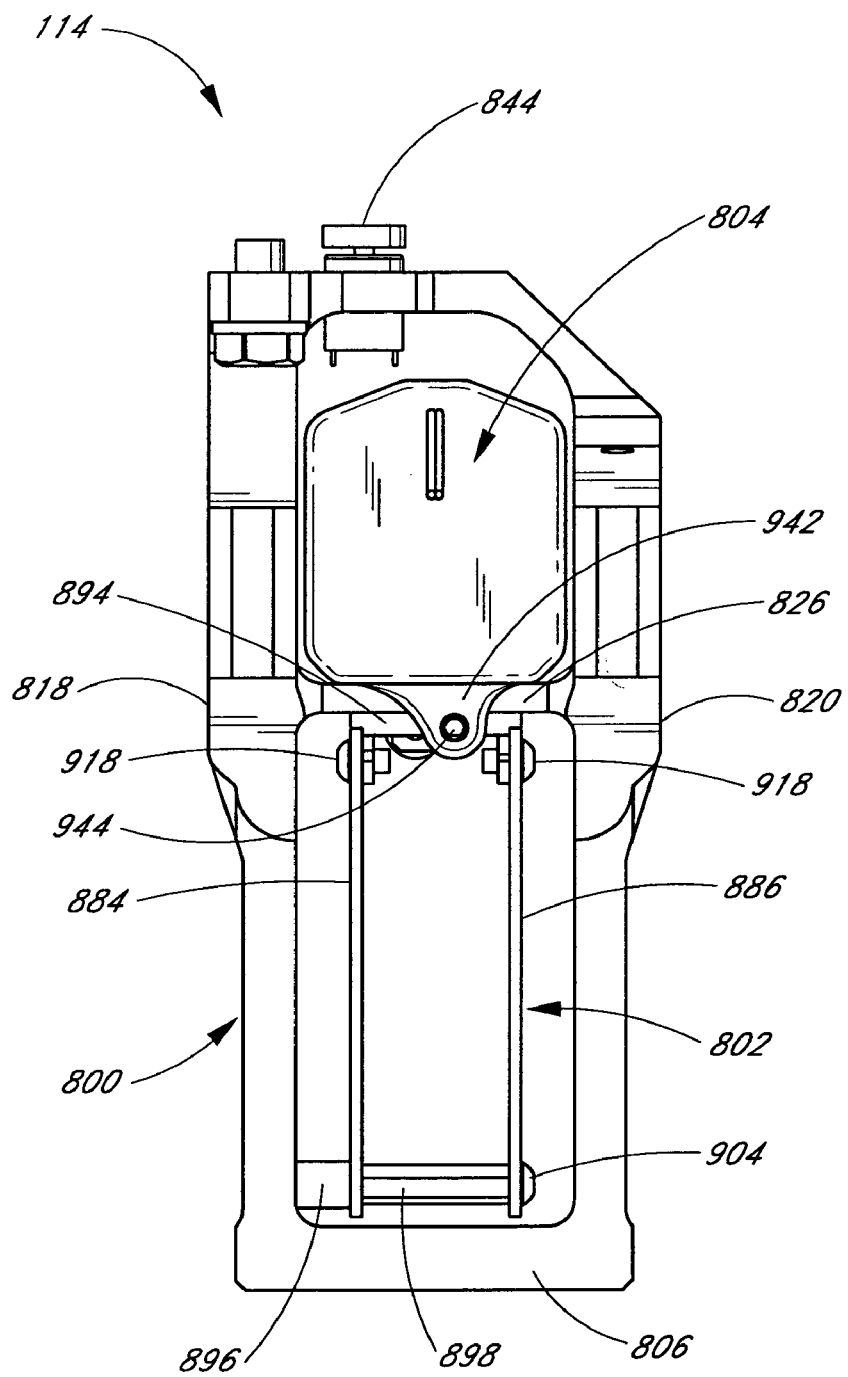

FIG. 88 is a simplified right side view of the assembly of FIG. 84 illustrating features and advantages in accordance with an embodiment of the invention.

Figure 89:
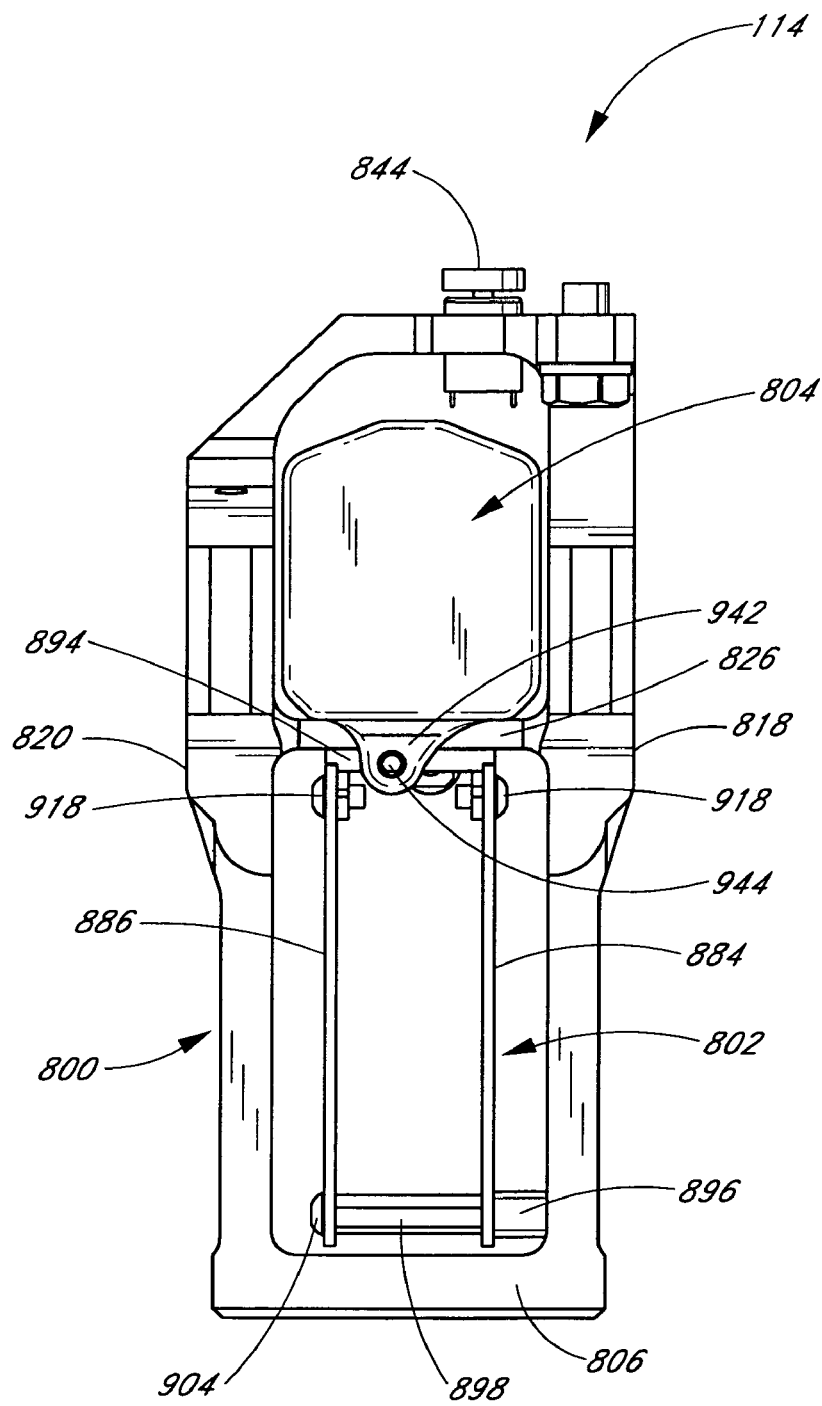

FIG. 89 is a simplified left side view of the assembly of FIG. 84 illustrating features and advantages in accordance with an embodiment of the invention.

Figure 90:
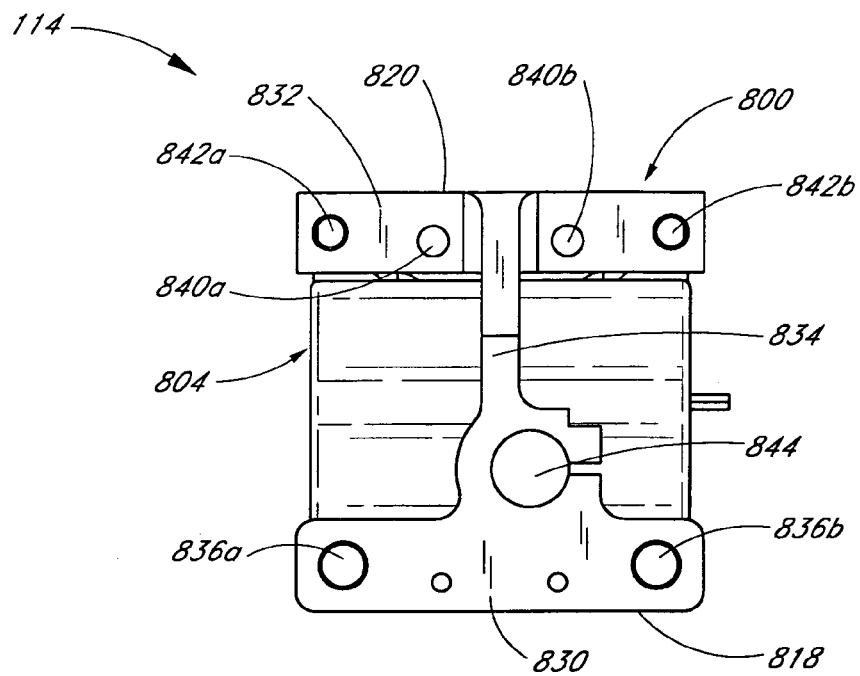

FIG. 90 is a simplified top view of the assembly of FIG. 84 illustrating features and advantages in accordance with an embodiment of the invention.

Figure 91:
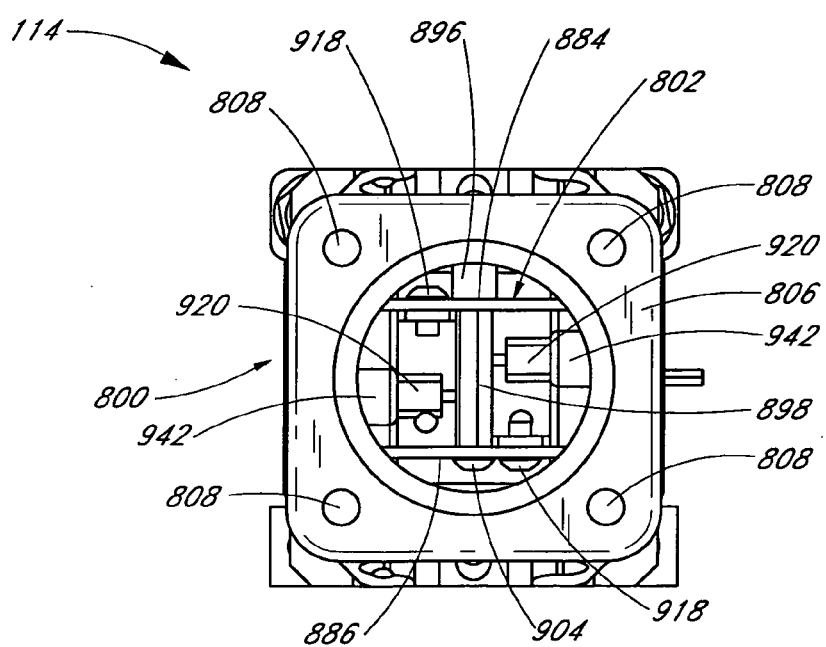

FIG. 91 is a simplified bottom view of the assembly of FIG. 84 illustrating features and advantages in accordance with an embodiment of the invention.

Figure 92:
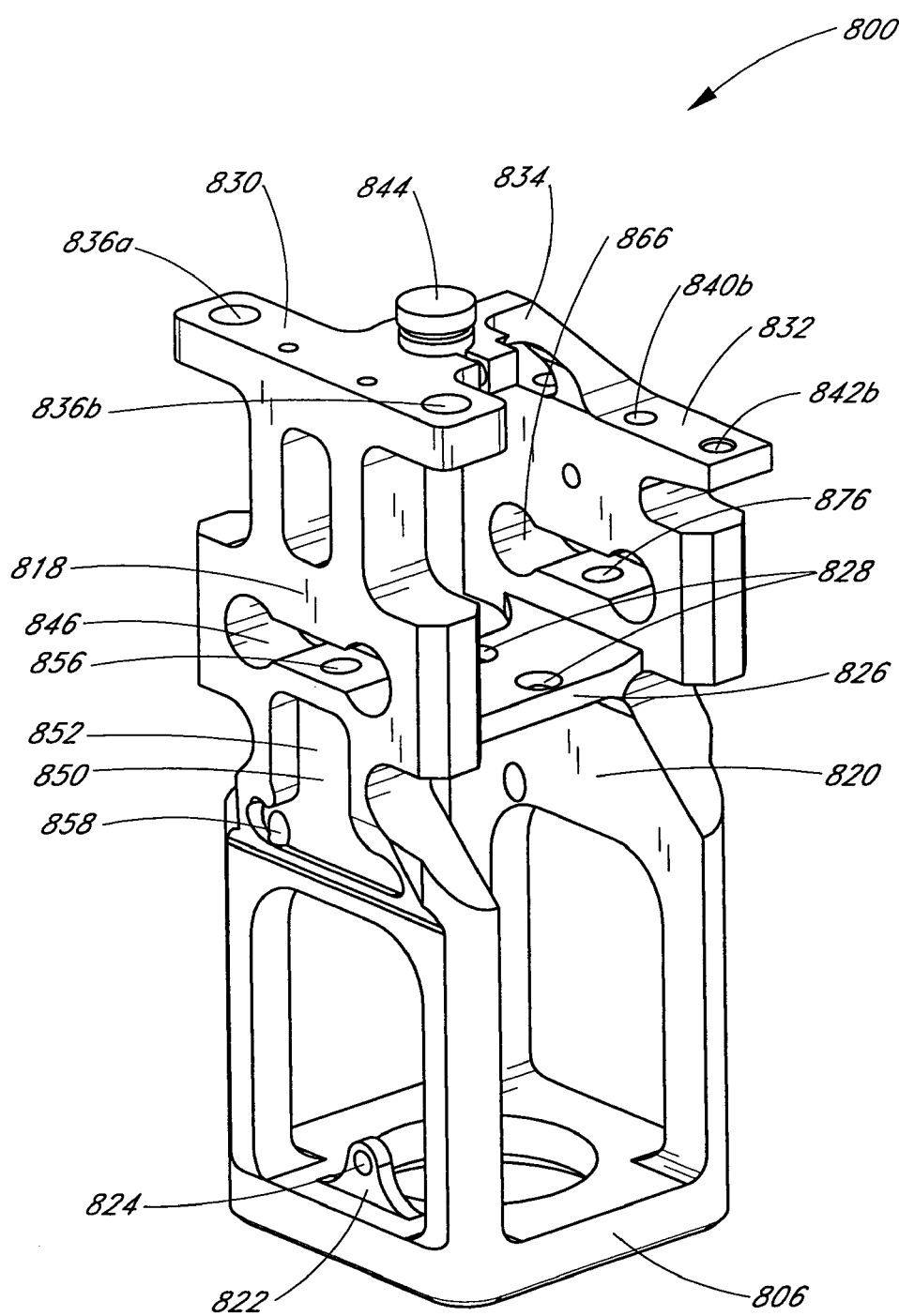

FIG. 92 is a simplified perspective view of a load cell frame of the assembly of FIG. 84 illustrating features and advantages in accordance with an embodiment of the invention.

Figure 93:
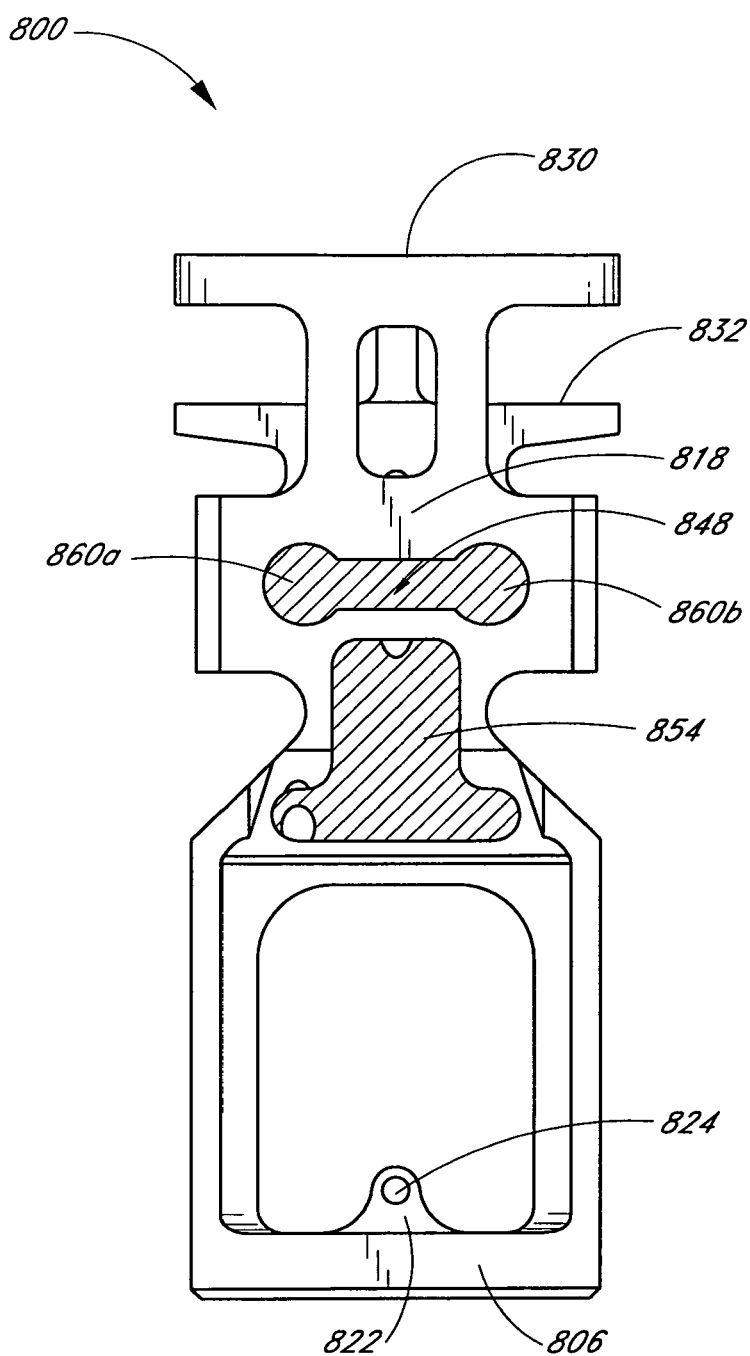

FIG. 93 is a simplified front view of the load cell frame of FIG. 92 illustrating features and advantages in accordance with an embodiment of the invention.

Figure 94:
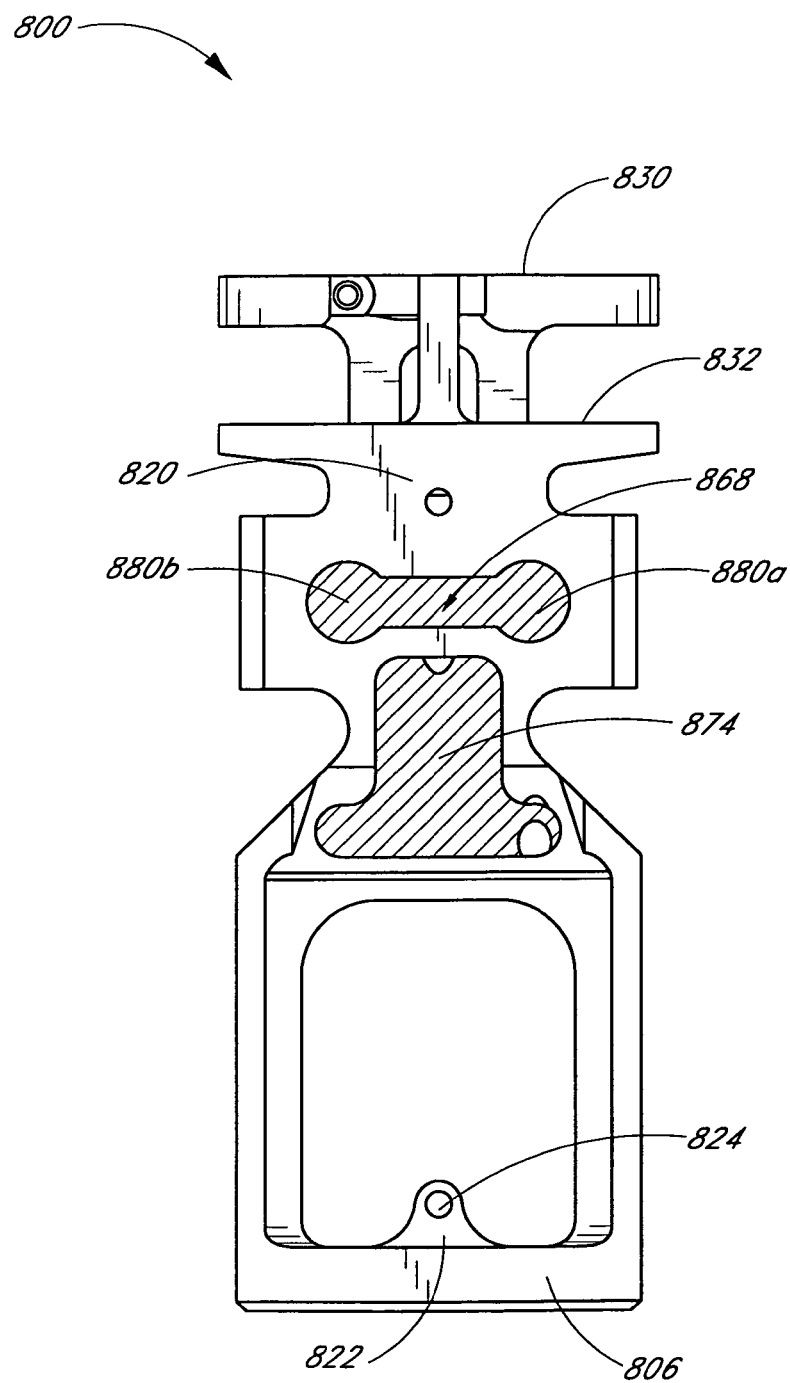

FIG. 94 is a simplified rear view of the load cell frame of FIG. 92 illustrating features and advantages in accordance with an embodiment of the invention.

Figure 95:
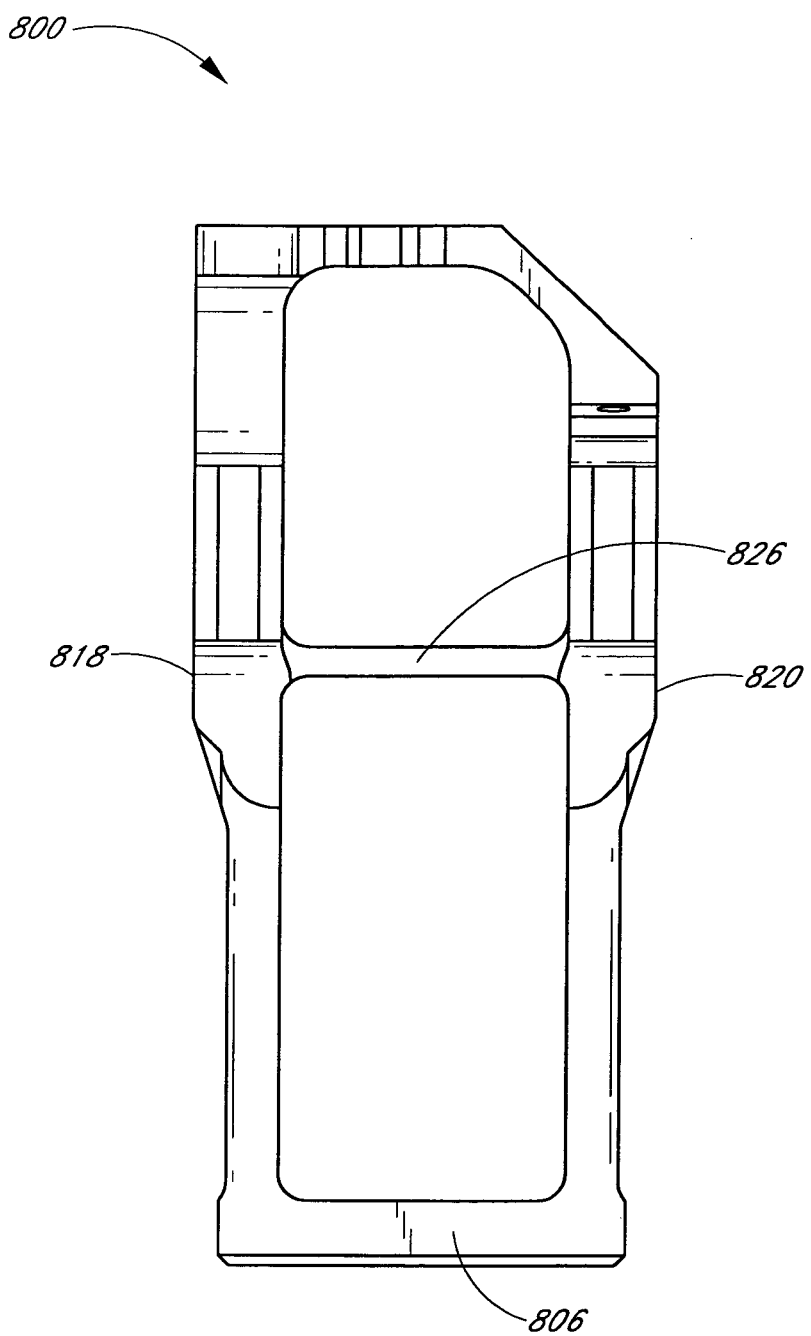

FIG. 95 is a simplified right side view of the load cell frame of FIG. 92 illustrating features and advantages in accordance with an embodiment of the invention.

Figure 96:
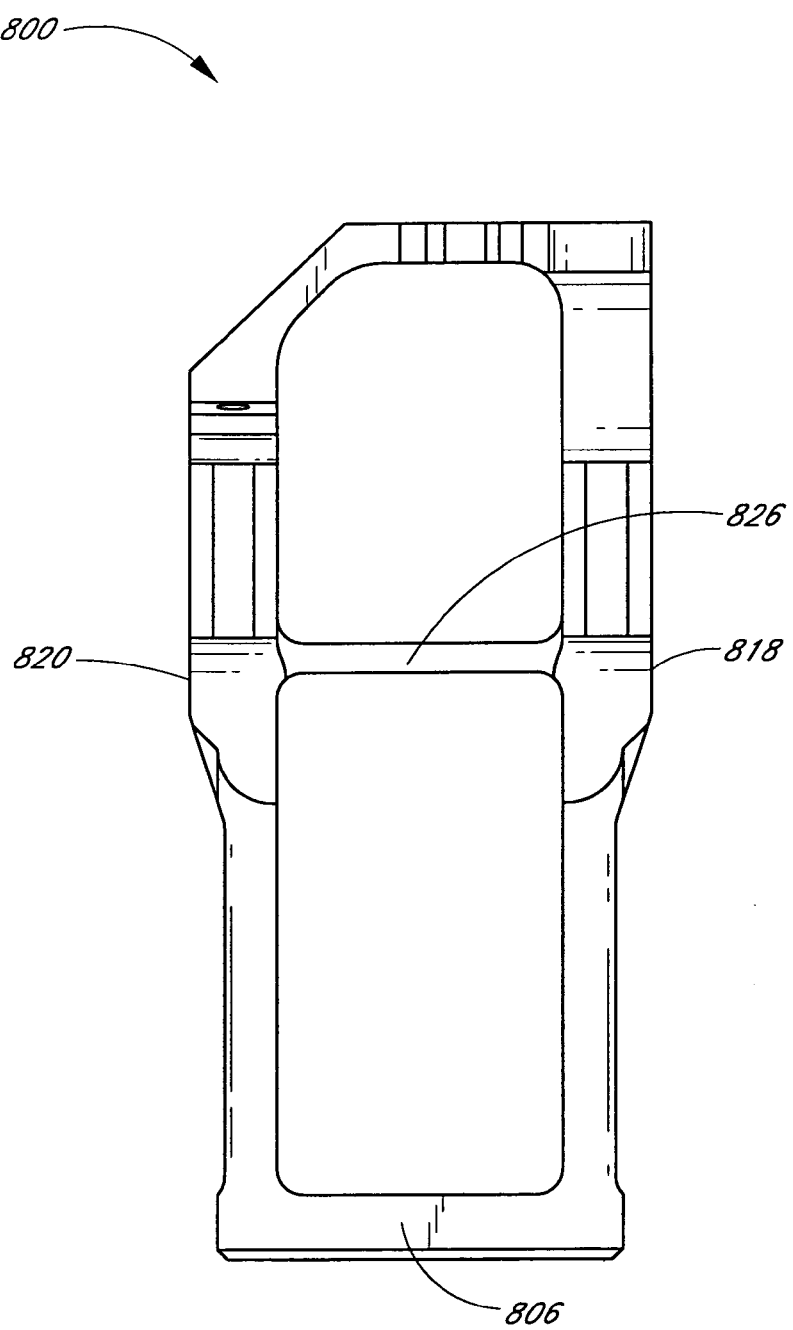

FIG. 96 is a simplified left side view of the load cell frame of FIG. 92 illustrating features and advantages in accordance with an embodiment of the invention.

Figure 97:
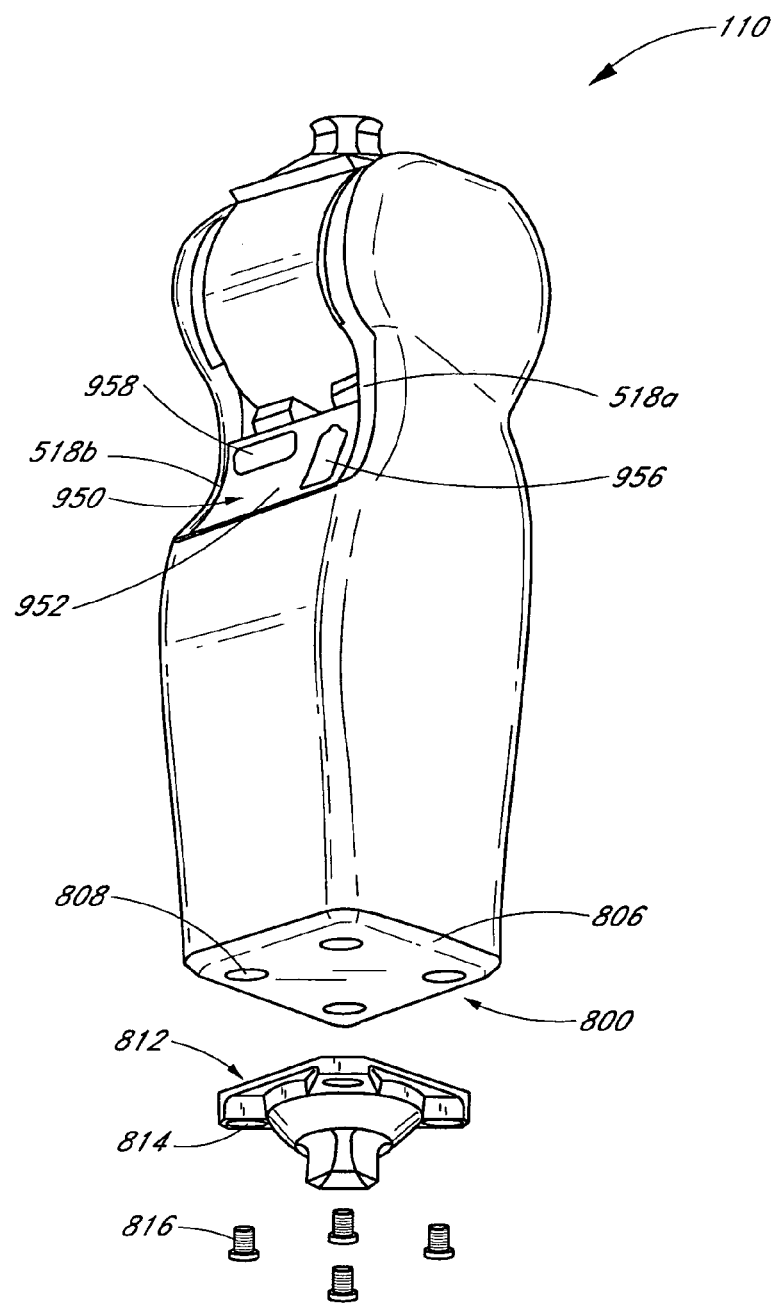

FIG. 97 is a simplified perspective view of a prosthetic knee assembly illustrating features and advantages in accordance with an embodiment of the invention.

Figure 98:
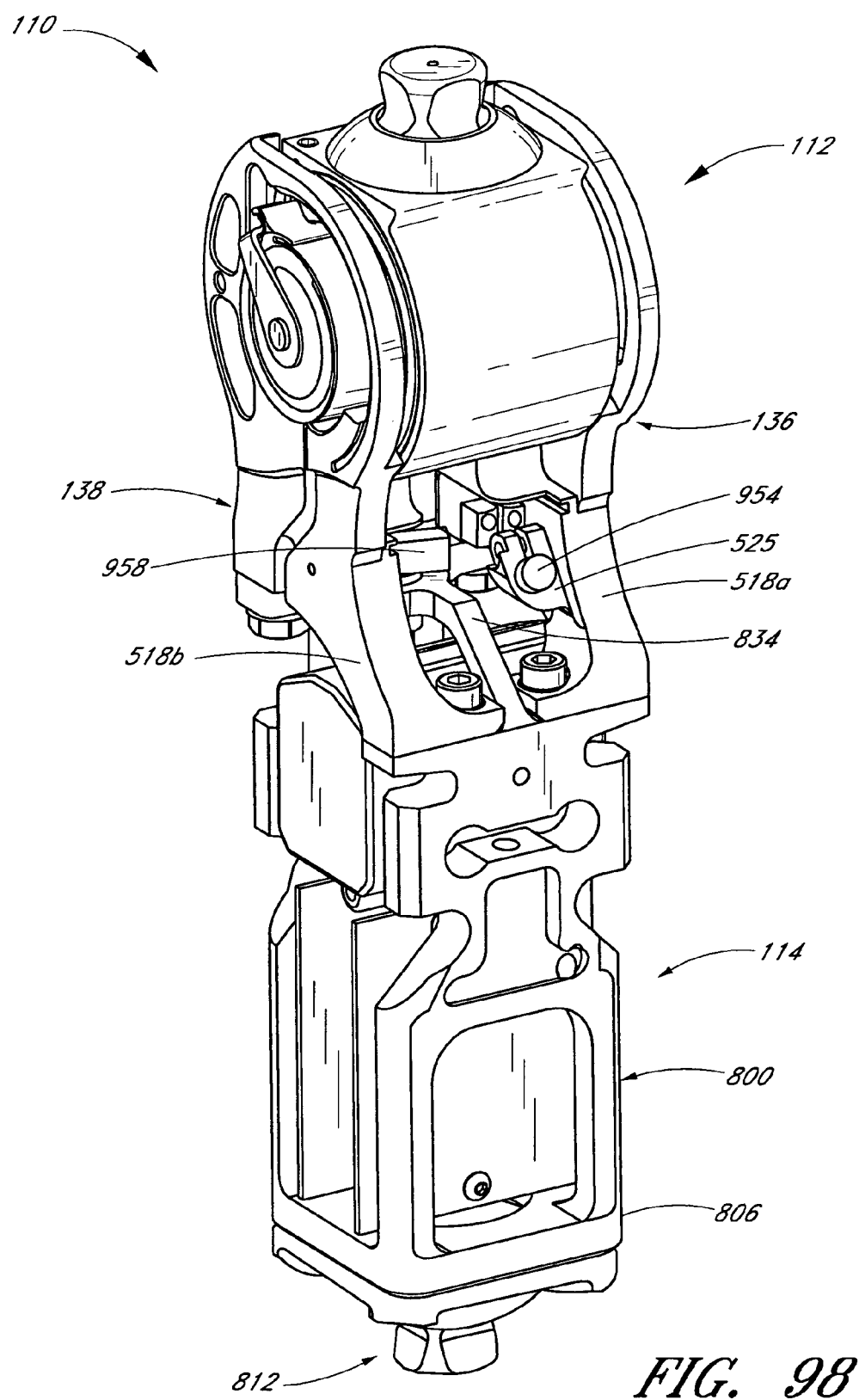

FIG. 98 is another simplified perspective view of a prosthetic knee assembly illustrating features and advantages in accordance with an embodiment of the invention.

Figure 99:
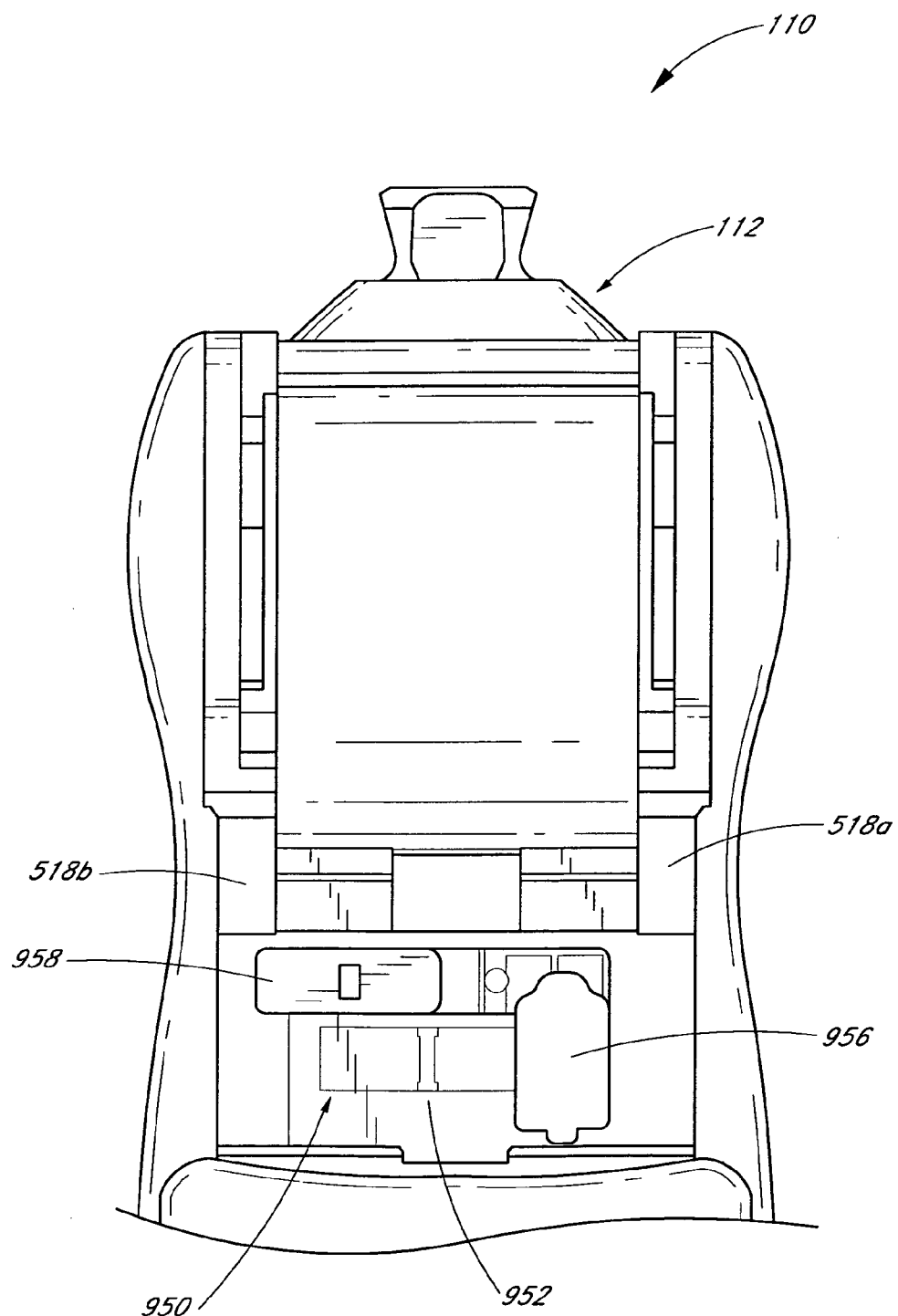

FIG. 99 is a simplified partial rear view of a prosthetic knee assembly illustrating features and advantages in accordance with an embodiment of the invention.

Figure 100:
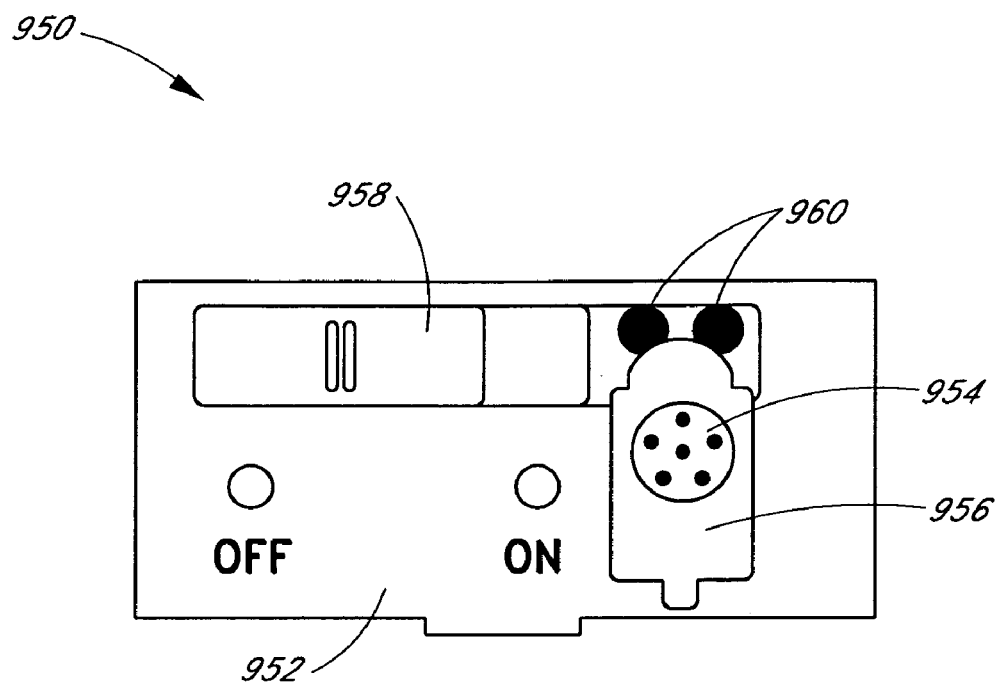

FIG. 100 is a simplified schematic enlarged view of a control panel of the prosthetic knee assembly illustrating features and advantages in accordance with an embodiment of the invention.

Figure 101:
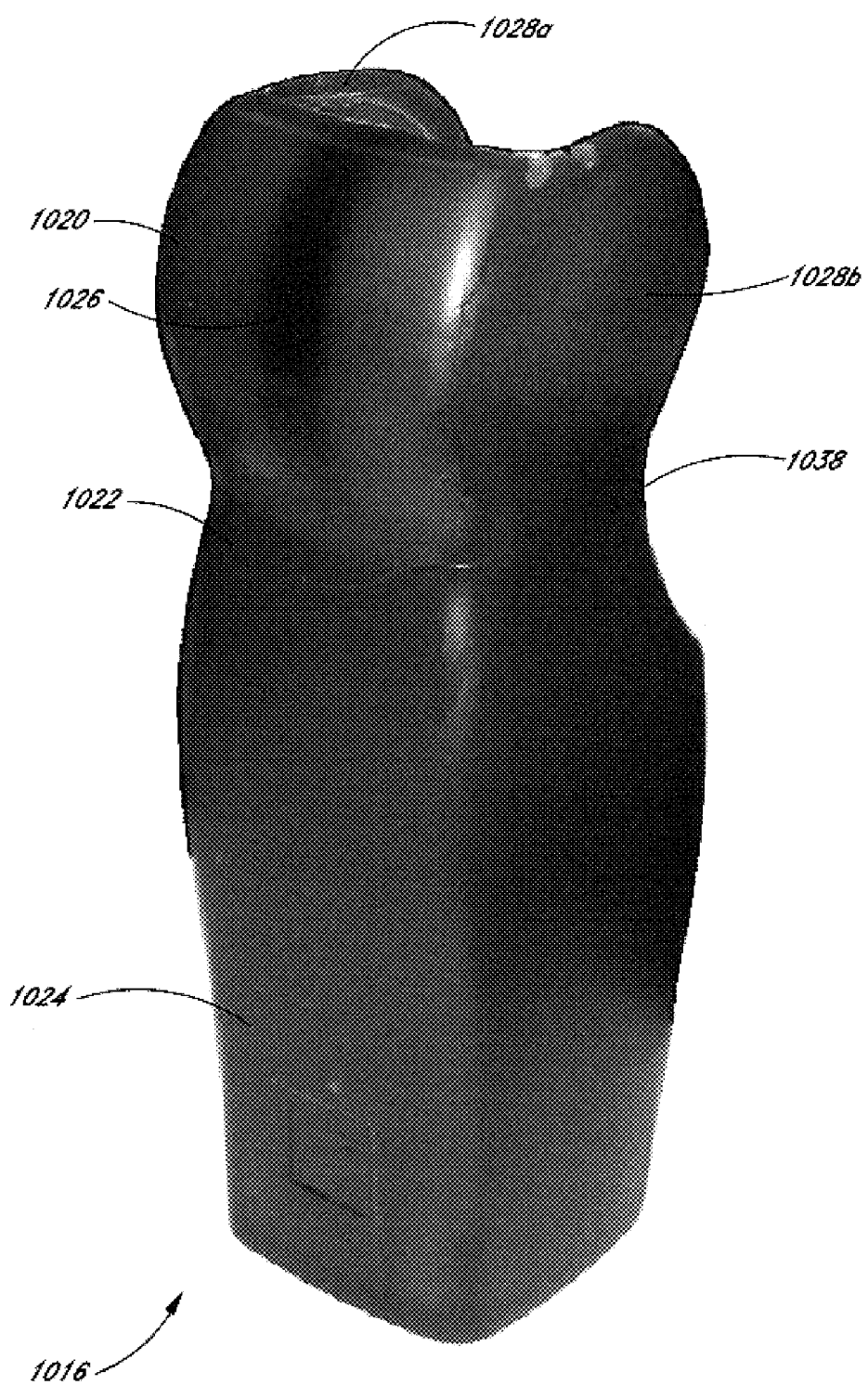

FIG. 101 is a simplified perspective view of a prosthetic knee cover illustrating features and advantages in accordance with an embodiment of the invention.

Figure 102:
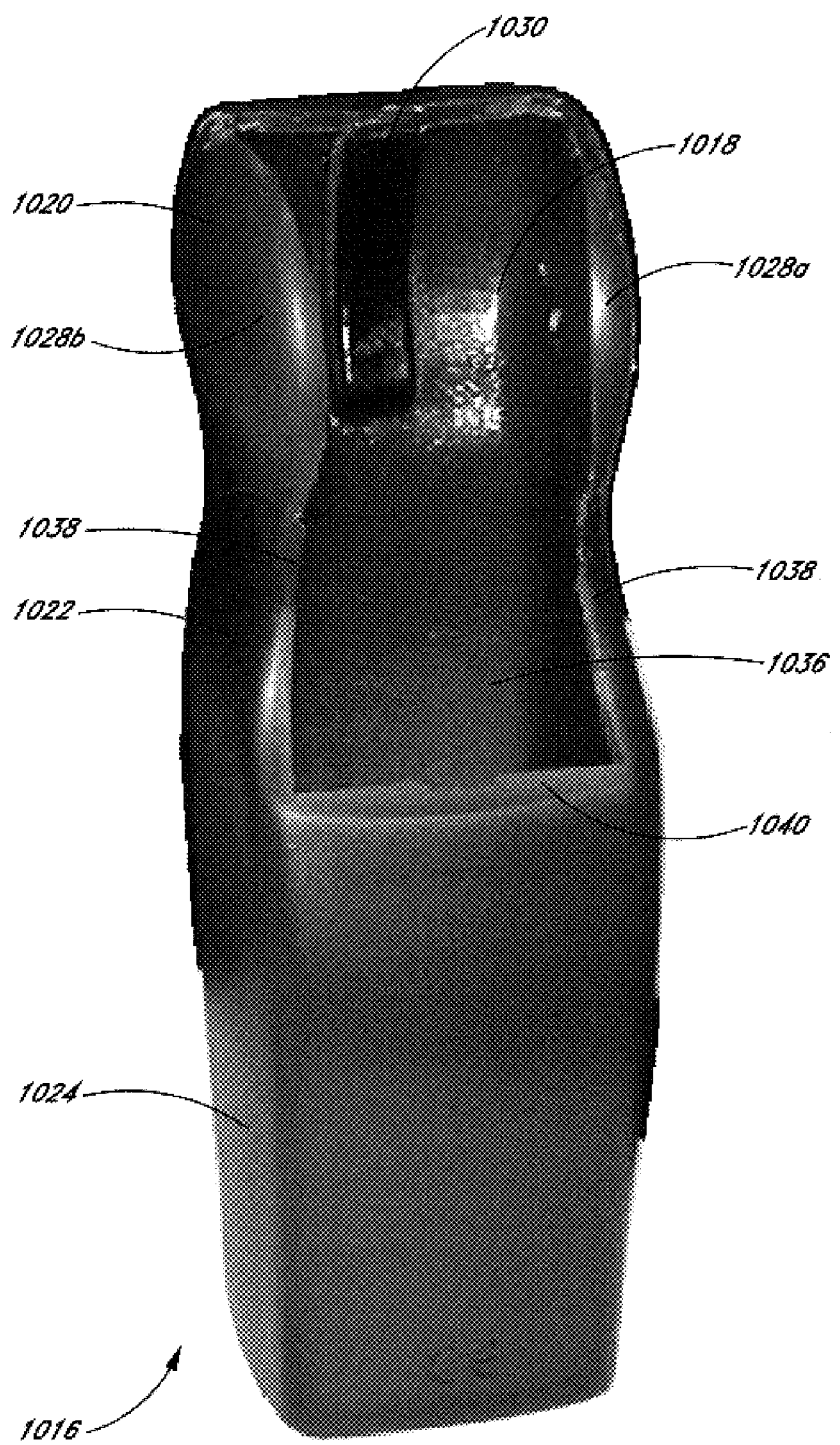

FIG. 102 is another simplified perspective view the knee cover of FIG. 101 illustrating features and advantages in accordance with an embodiment of the invention.

Figure 103:
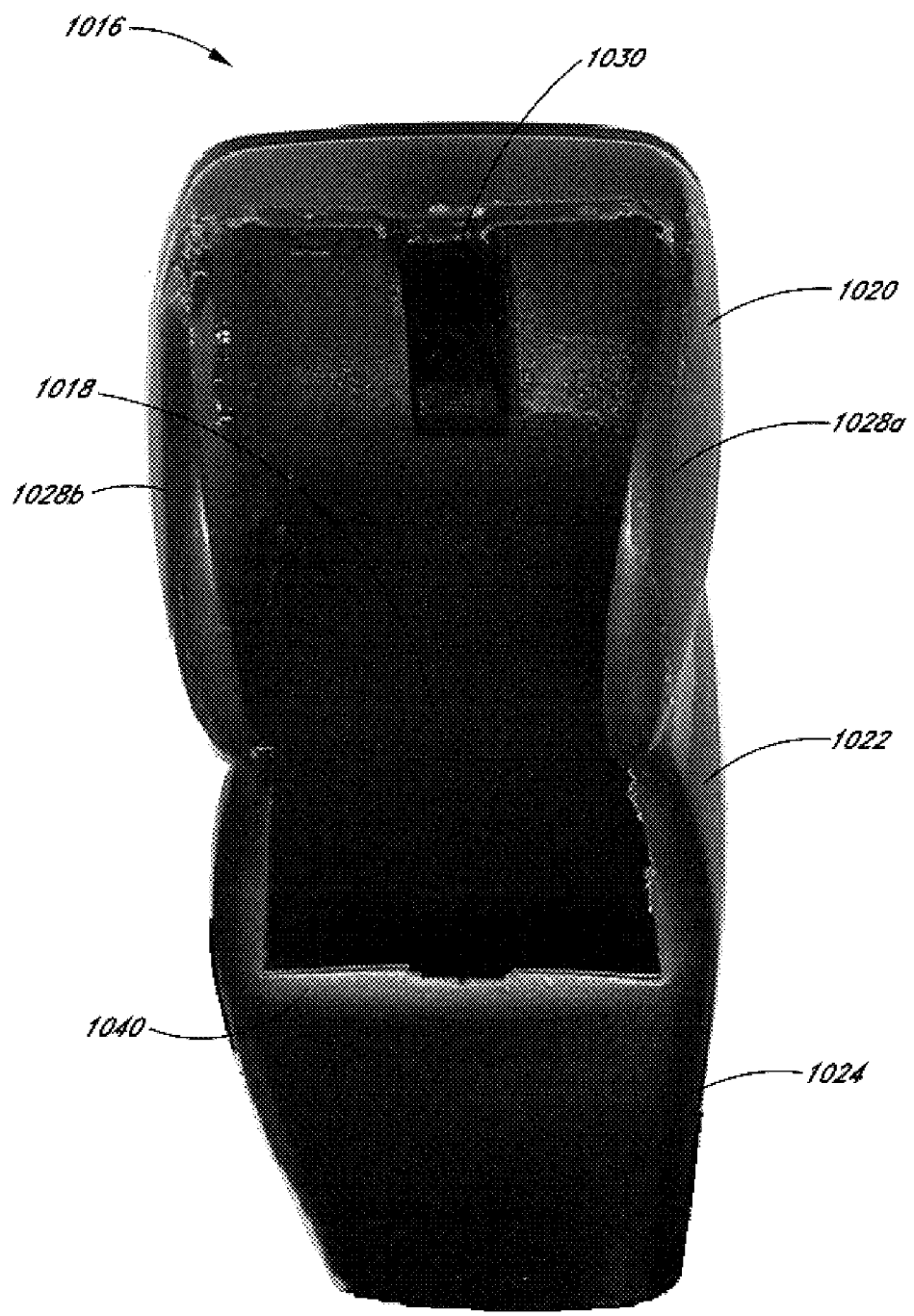

FIG. 103 is yet another simplified perspective view the knee cover of FIG. 101 illustrating features and advantages in accordance with an embodiment of the invention.

Figure 104:
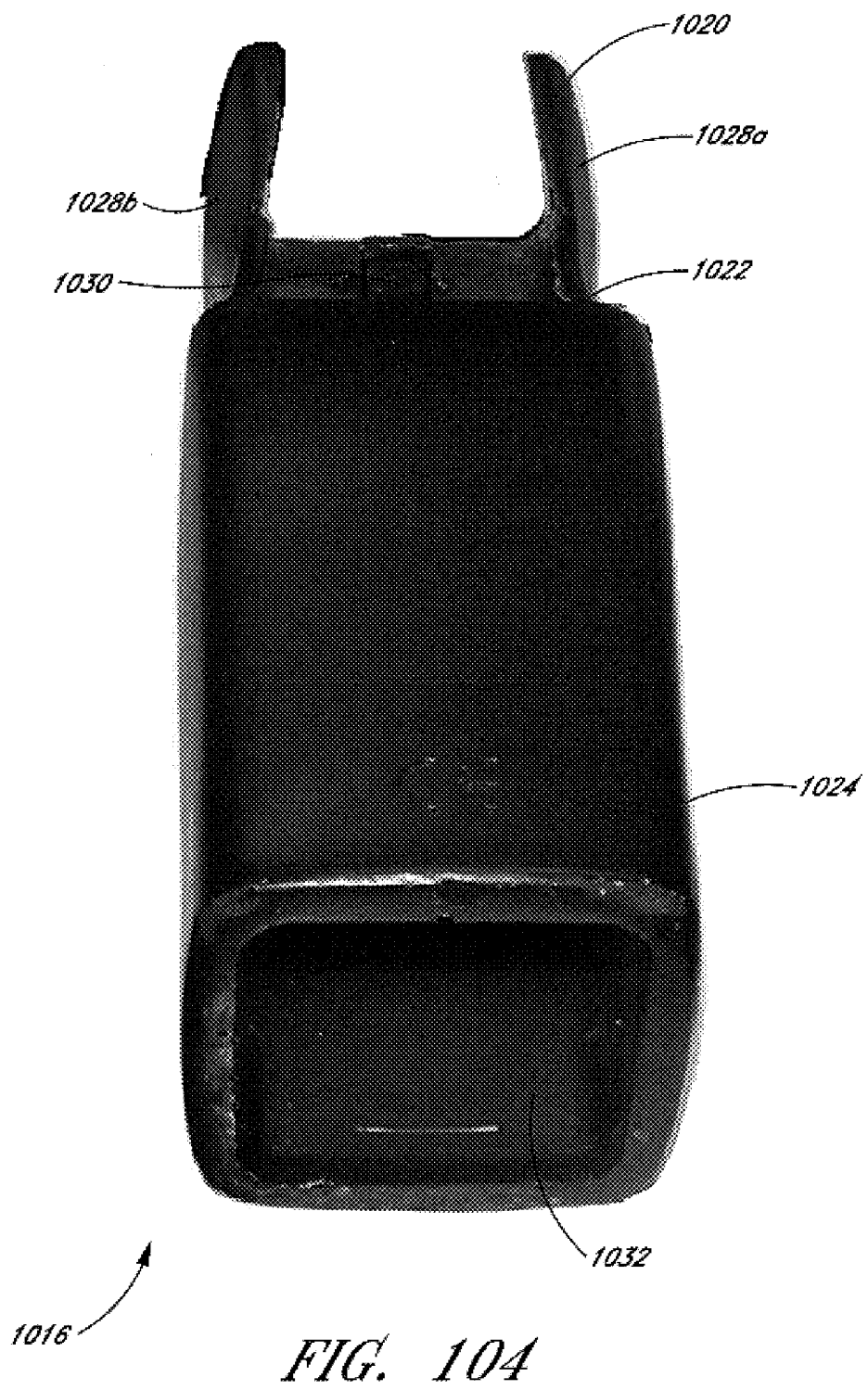

FIG. 104 is still another simplified perspective view the knee cover of FIG. 101 illustrating features and advantages in accordance with an embodiment of the invention.

Figure 105:
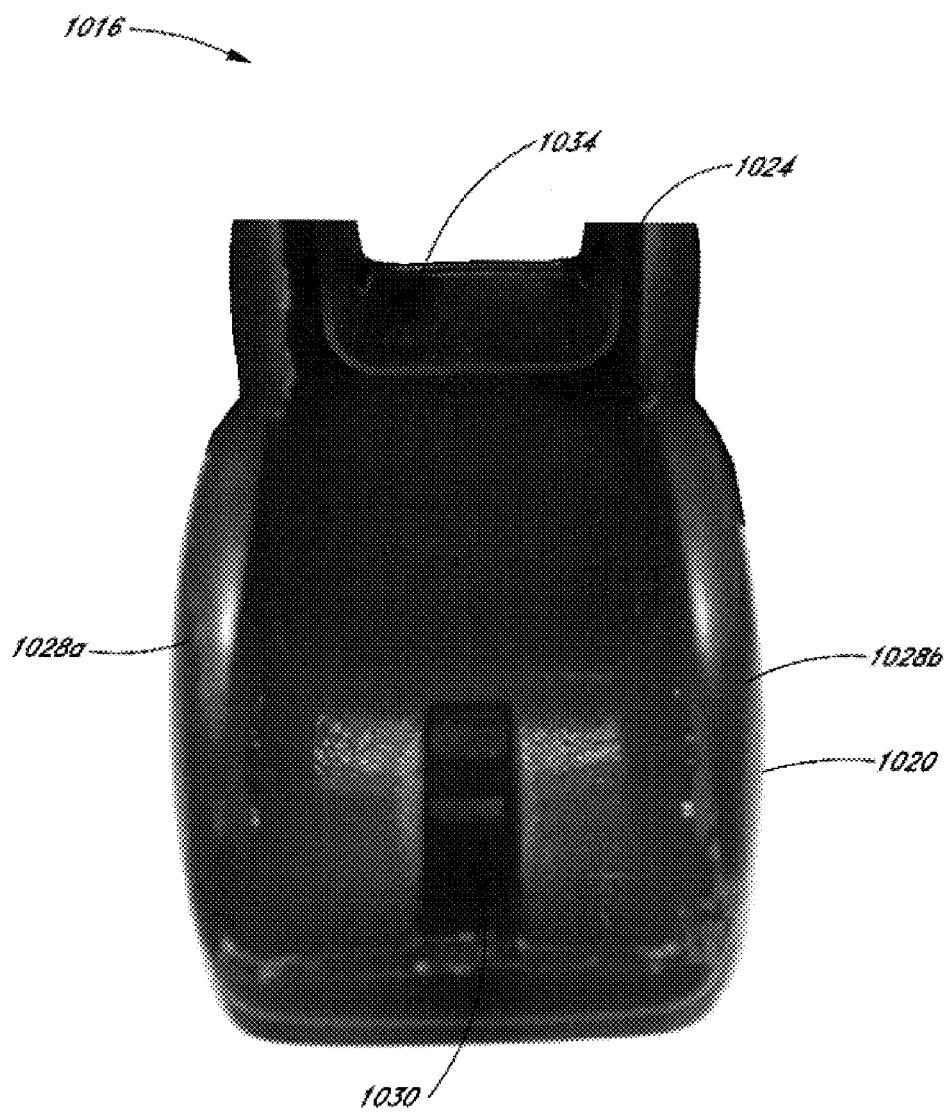

FIG. 105 is a further simplified perspective view the knee cover of FIG. 101 illustrating features and advantages in accordance with an embodiment of the invention.

Figure 106:
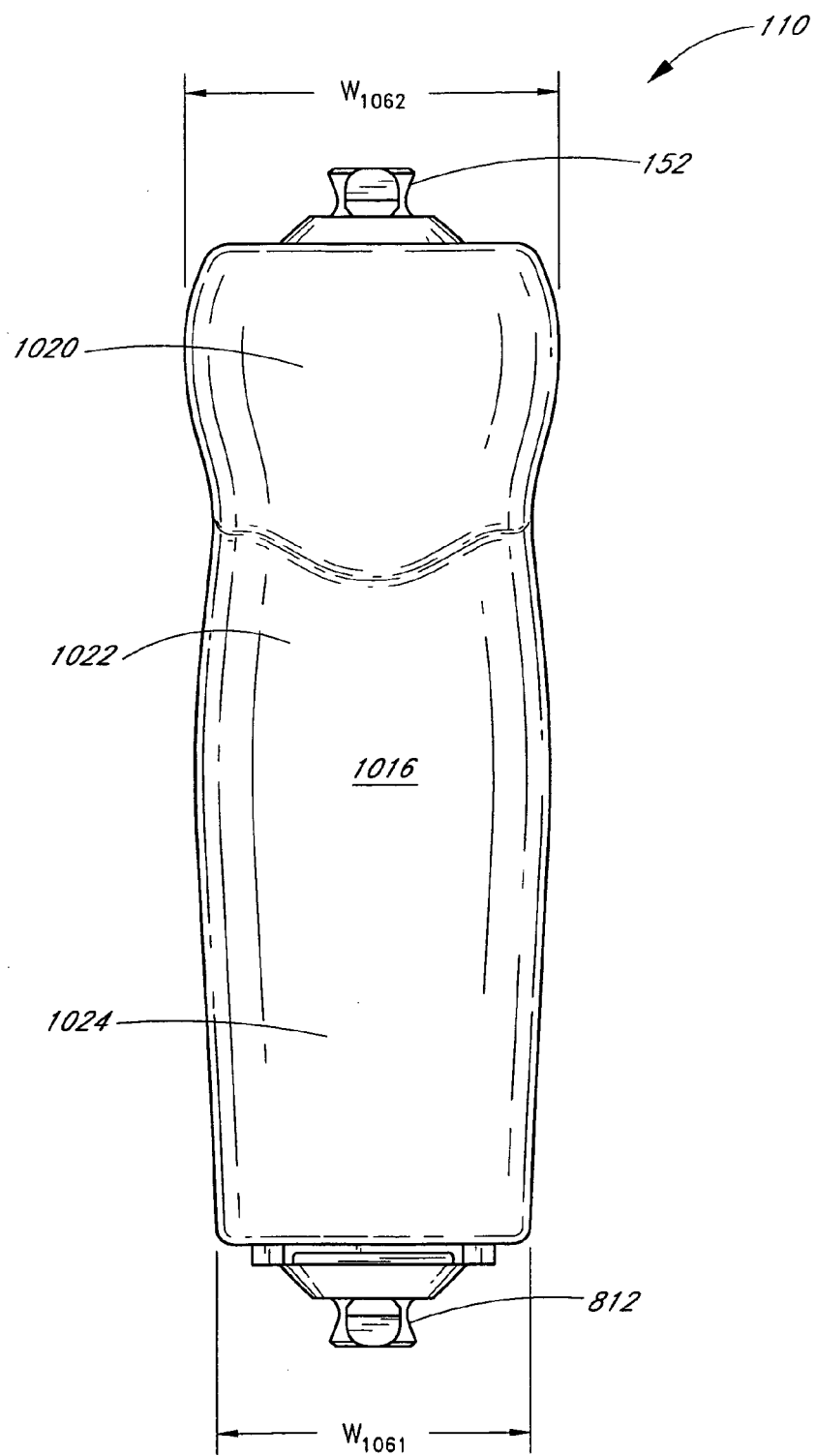

FIG. 106 is a simplified front view of a prosthetic knee assembly including the knee cover of FIG. 101 illustrating features and advantages in accordance with an embodiment of the invention.

Figure 107:
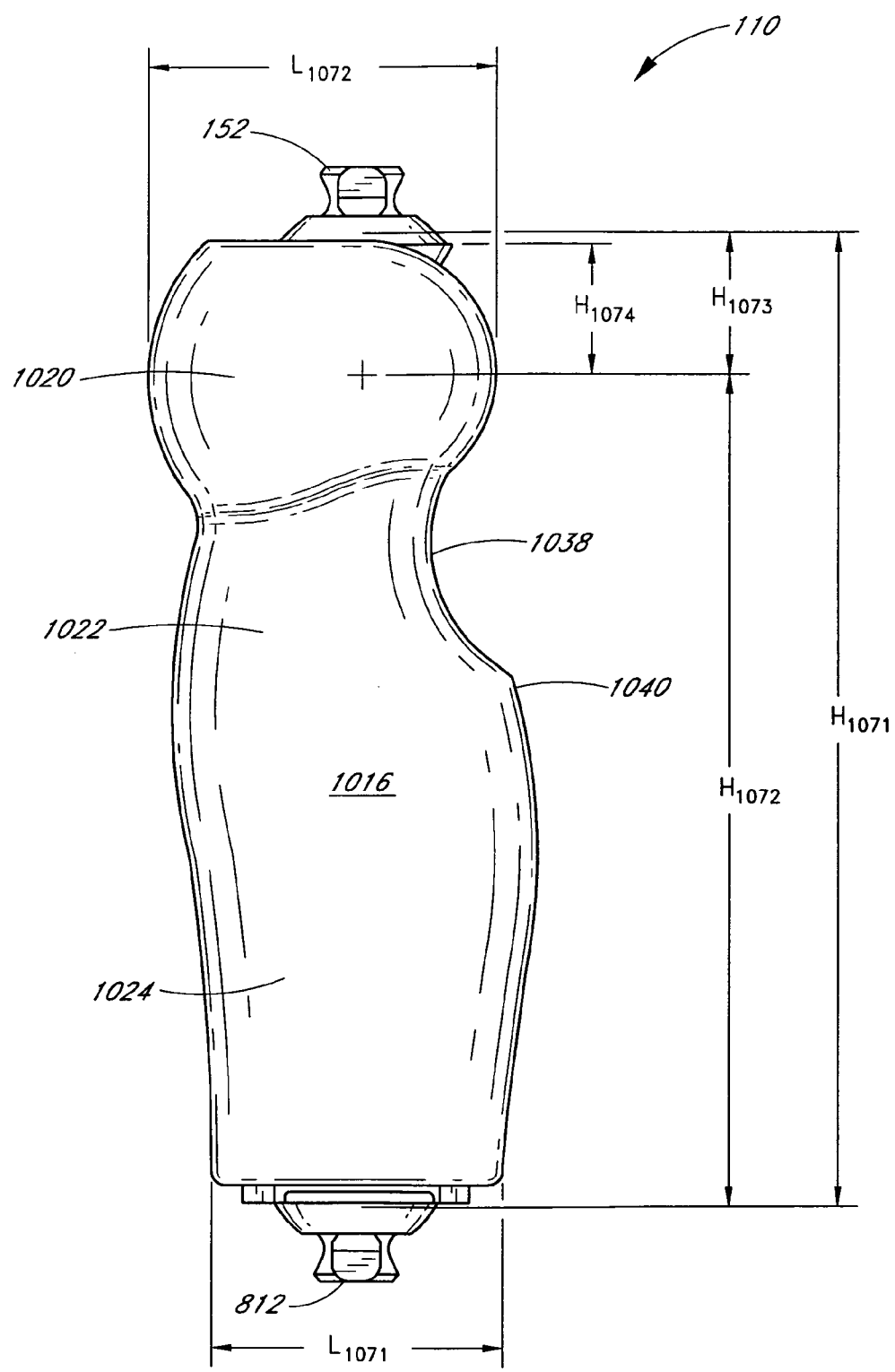

FIG. 107 is a simplified side view of the prosthetic knee assembly of FIG. 106 illustrating features and advantages in accordance with an embodiment of the invention.

Figure 108:
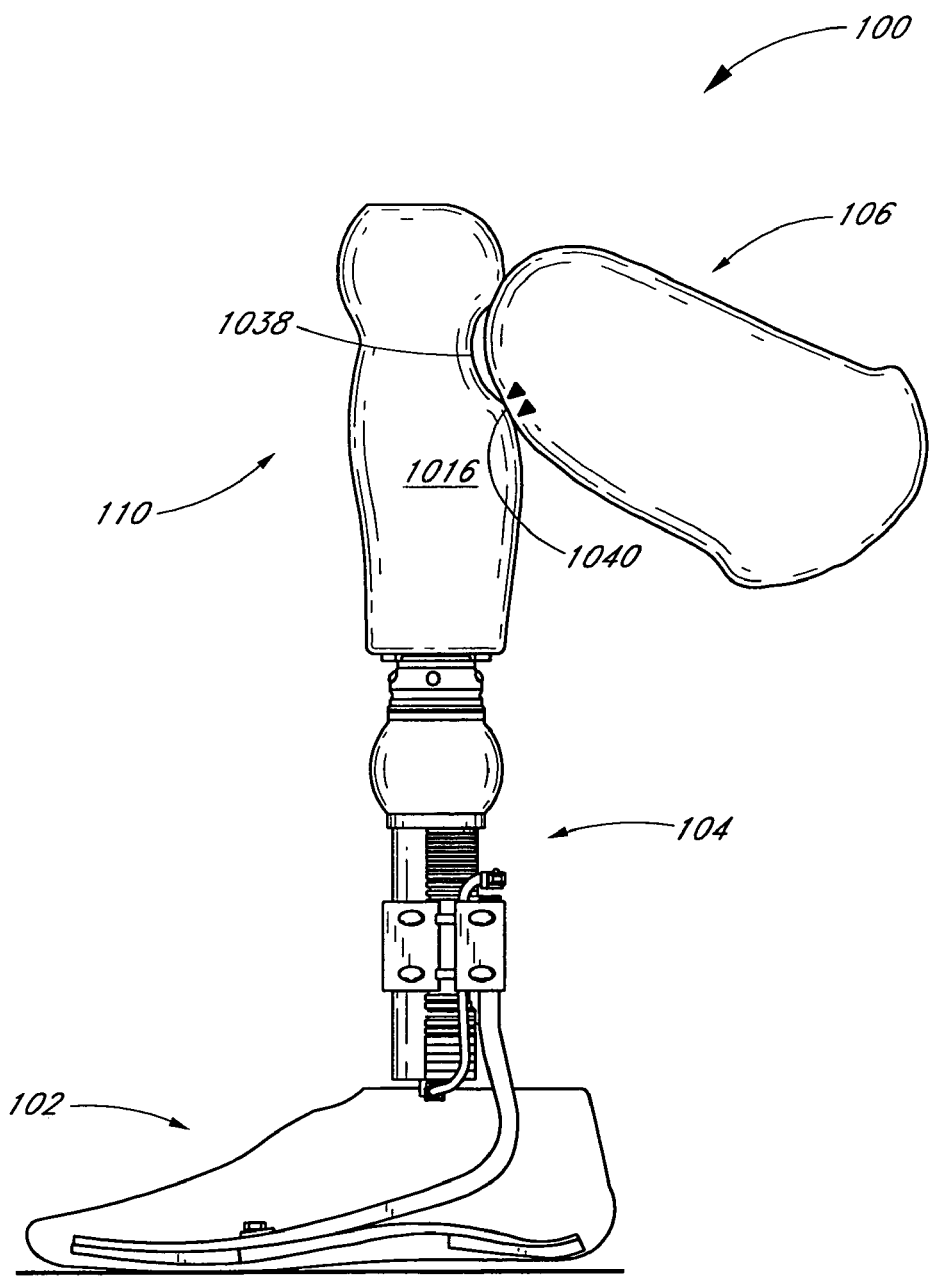

FIG. 108 is a simplified view of a lower limb prosthetic assembly illustrating features and advantages in accordance with an embodiment of the invention.

Figure 109:
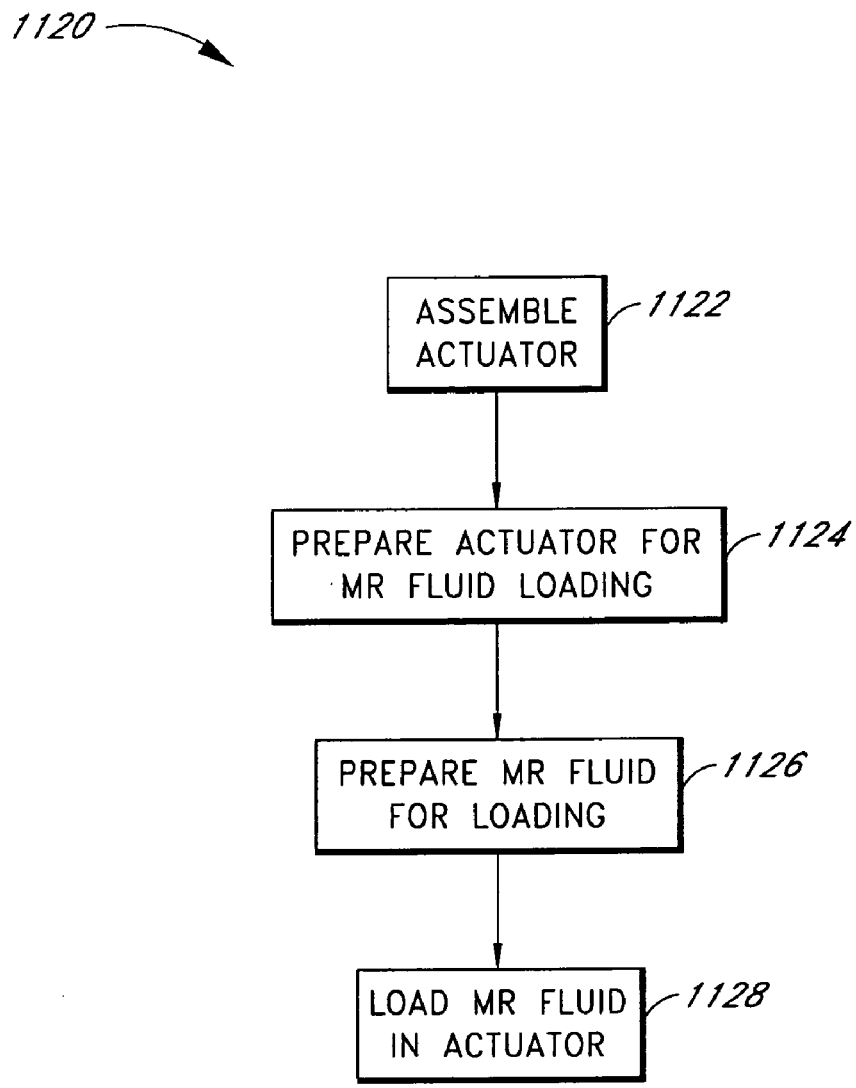

FIG. 109 is a simplified schematic diagram of a method of assembling a prosthetic knee actuator and loading magnetorheological fluid in the actuator illustrating features and advantages in accordance with an embodiment of the invention.

Figure 110:
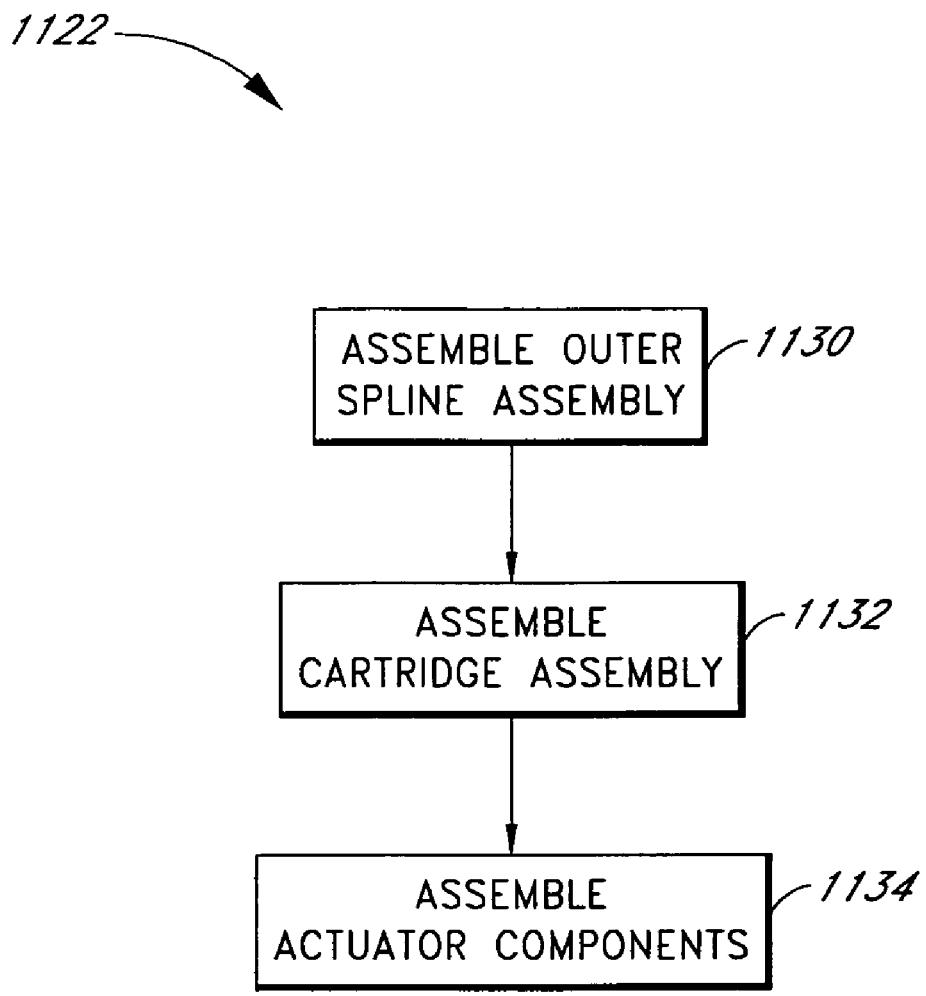

FIG. 110 is a simplified schematic diagram of some acts of assembling the actuator of FIG. 109 illustrating features and advantages in accordance with an embodiment of the invention.

Figure 111:
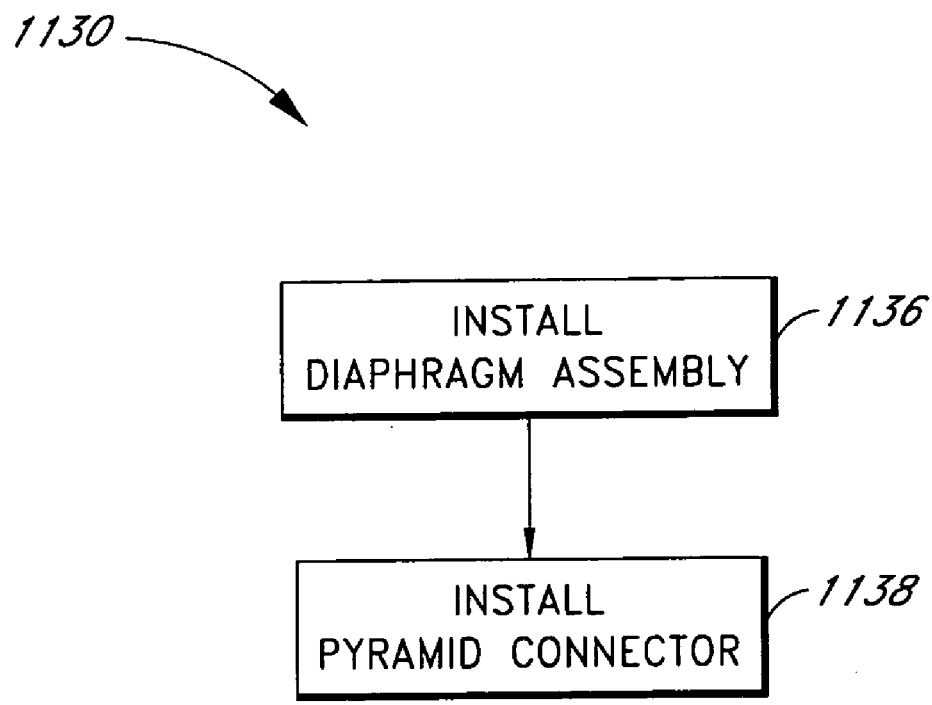

FIG. 111 is a simplified schematic diagram of some acts of assembling an outer spline assembly of the actuator of FIG. 110 illustrating features and advantages in accordance with an embodiment of the invention.

Figure 112:
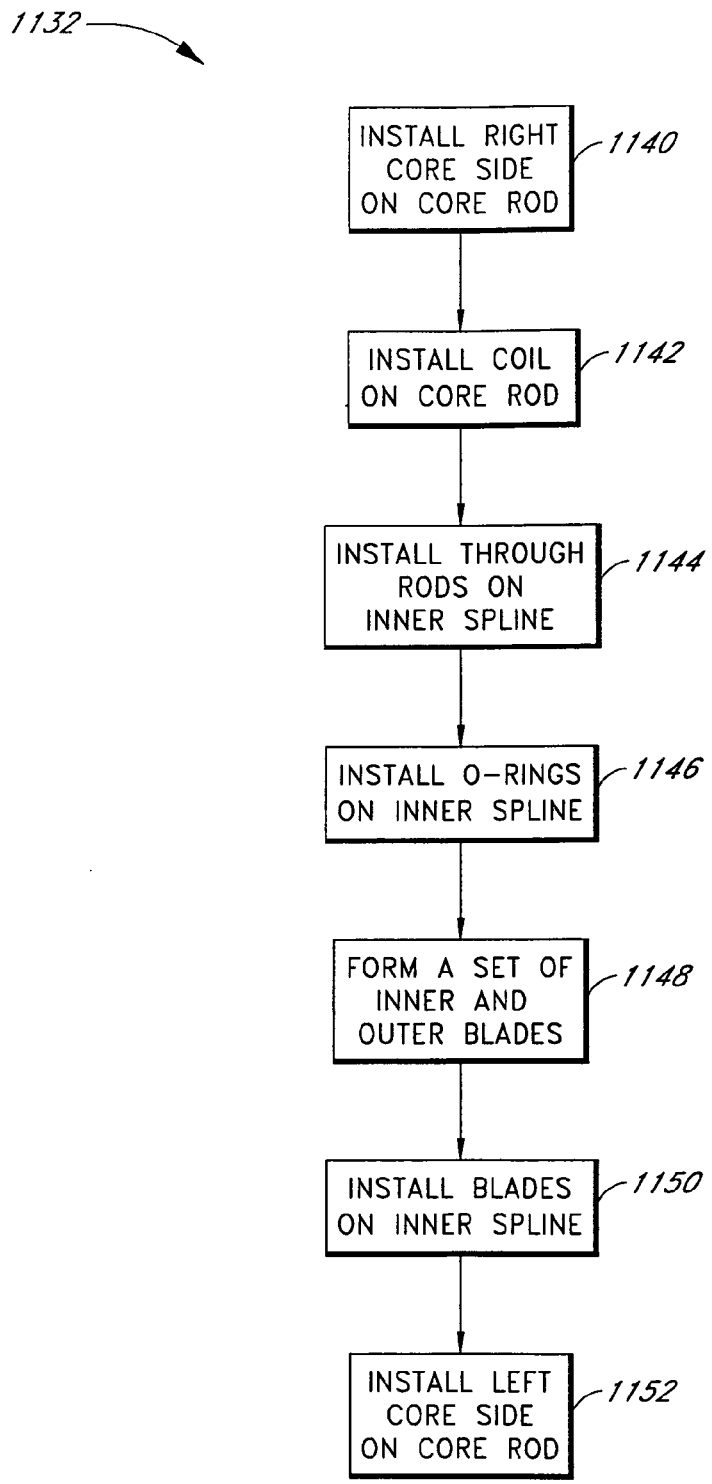

FIG. 112 is a simplified schematic diagram of some acts of assembling a cartridge assembly of the actuator of FIG. 110 illustrating features and advantages in accordance with an embodiment of the invention.

Figure 113:
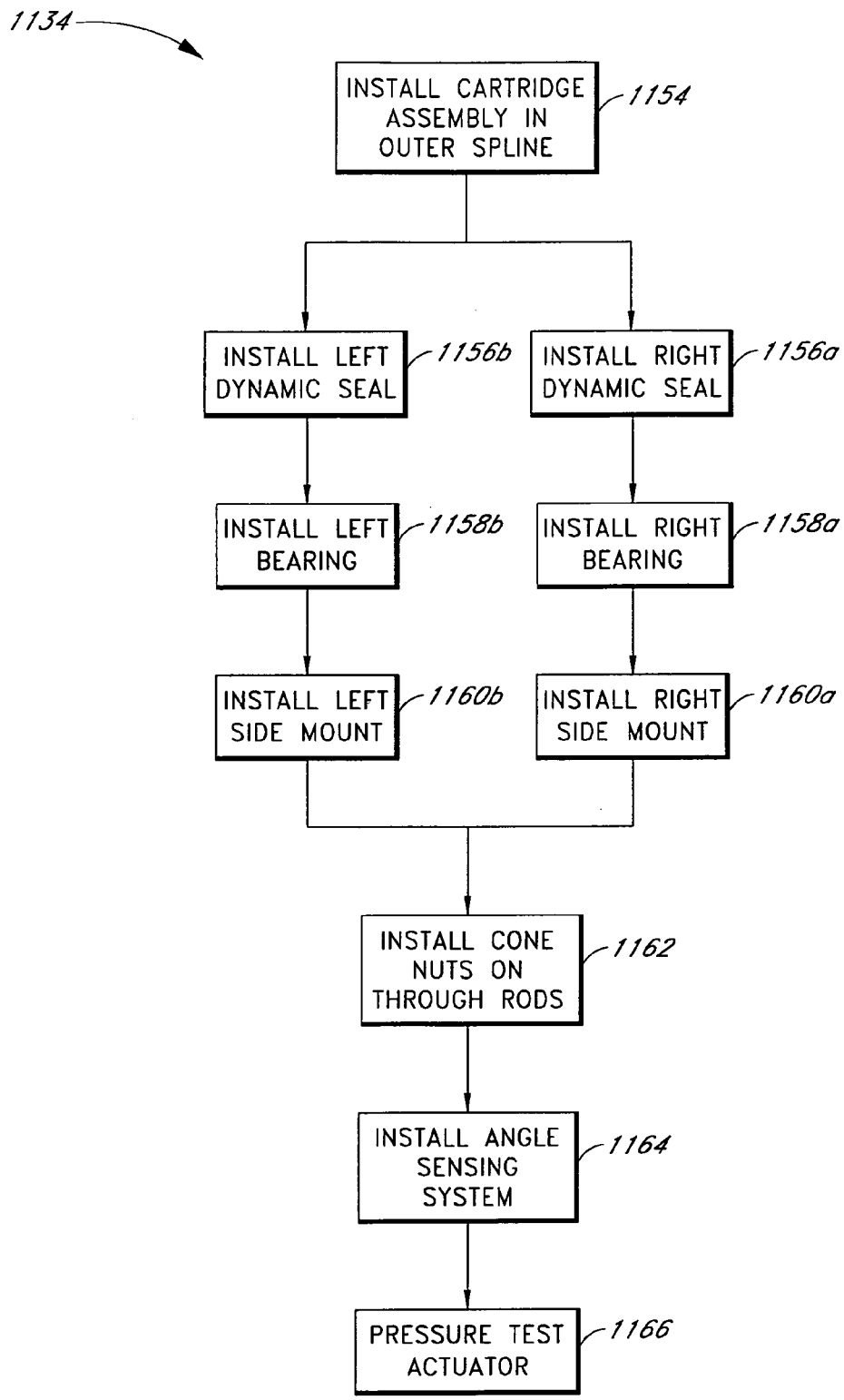

FIG. 113 is a simplified schematic diagram of some acts of assembling components of the actuator of FIG. 110 illustrating features and advantages in accordance with an embodiment of the invention.

Figure 114:
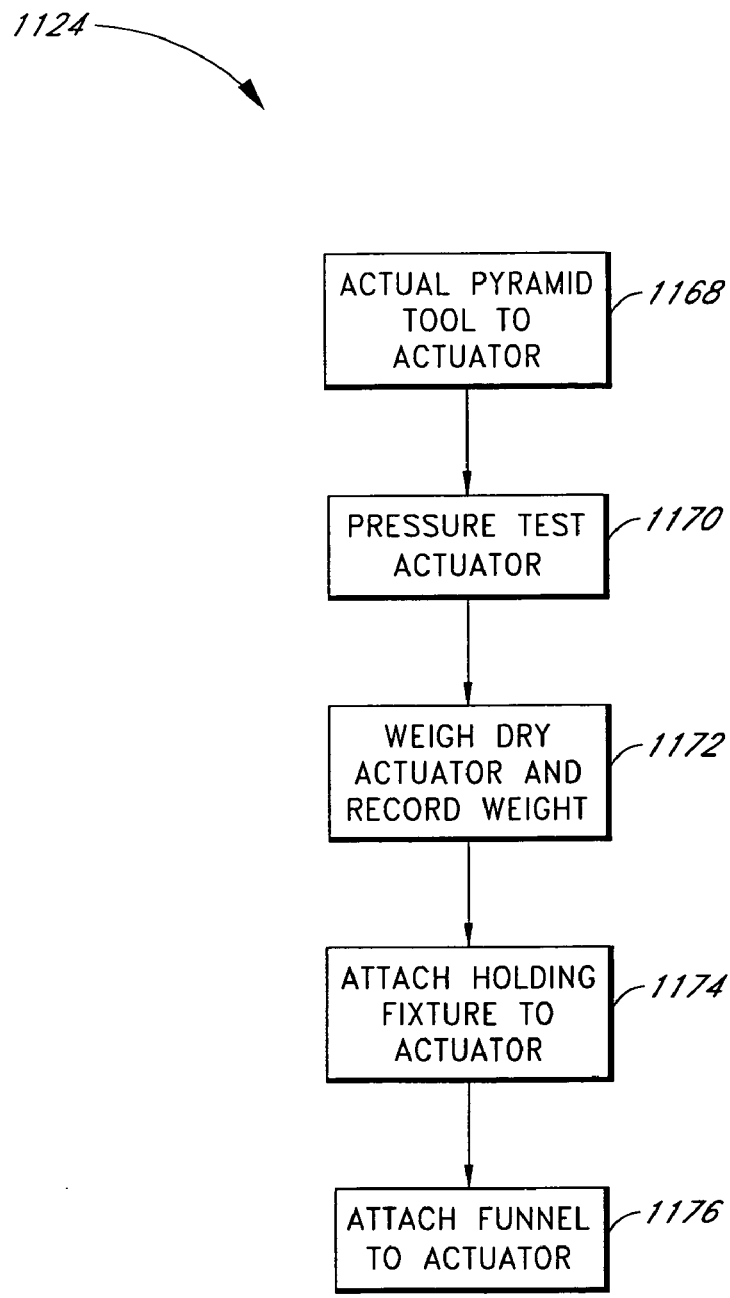

FIG. 114 is a simplified schematic diagram of some acts of preparing the actuator of FIG. 109 for magnetorheological fluid loading illustrating features and advantages in accordance with an embodiment of the invention.

Figure 115:
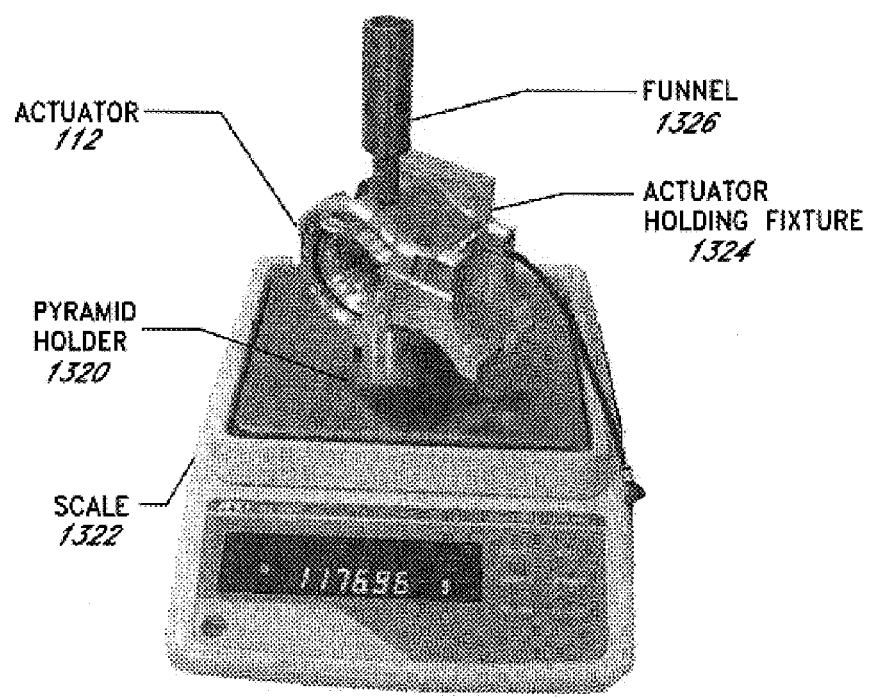

FIG. 115 is a simplified perspective view of the actuator of FIG. 114 on a weighing scale illustrating features and advantages in accordance with an embodiment of the invention.

Figure 116:
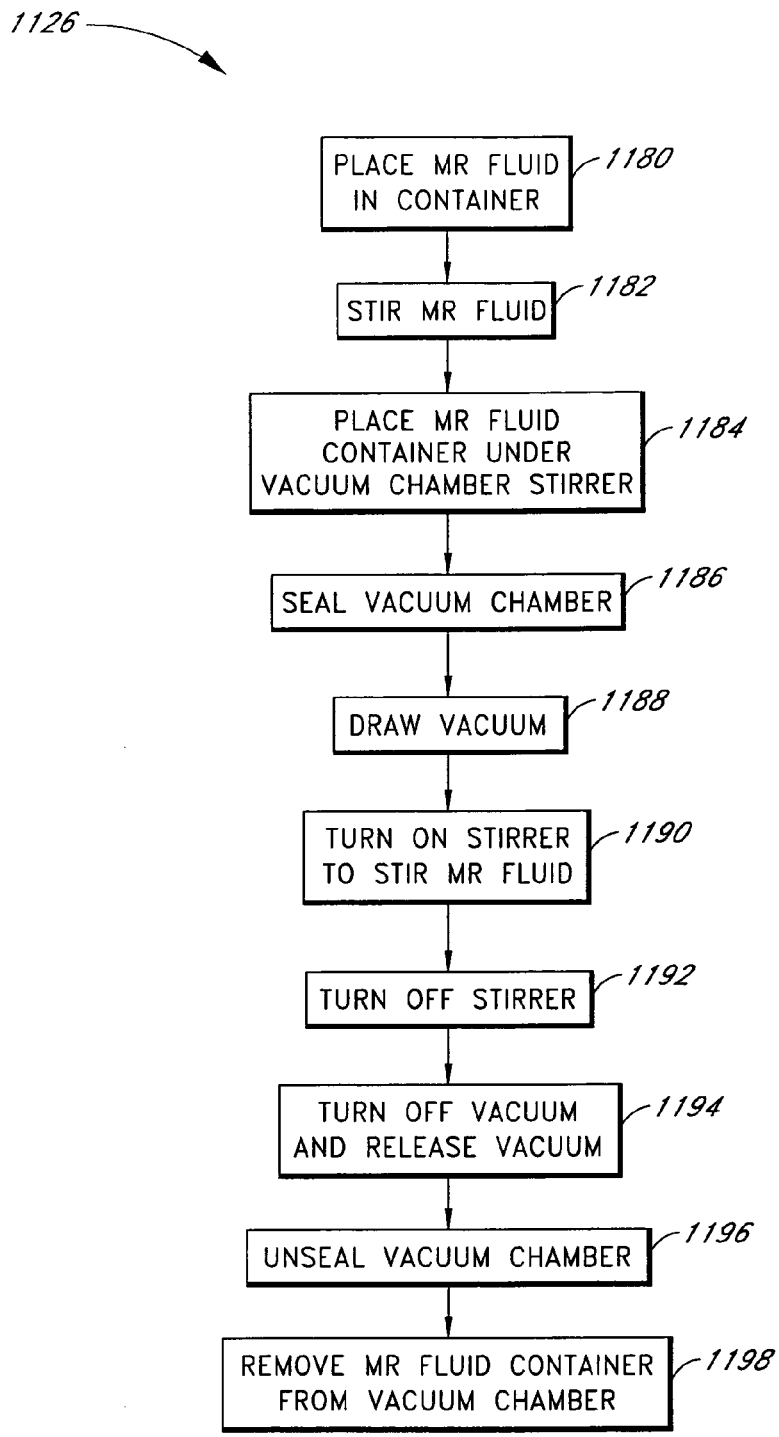

FIG. 116 is a simplified schematic diagram of some acts of preparing the magnetorheological fluid of FIG. 109 for loading illustrating features and advantages in accordance with an embodiment of the invention.

Figure 117:
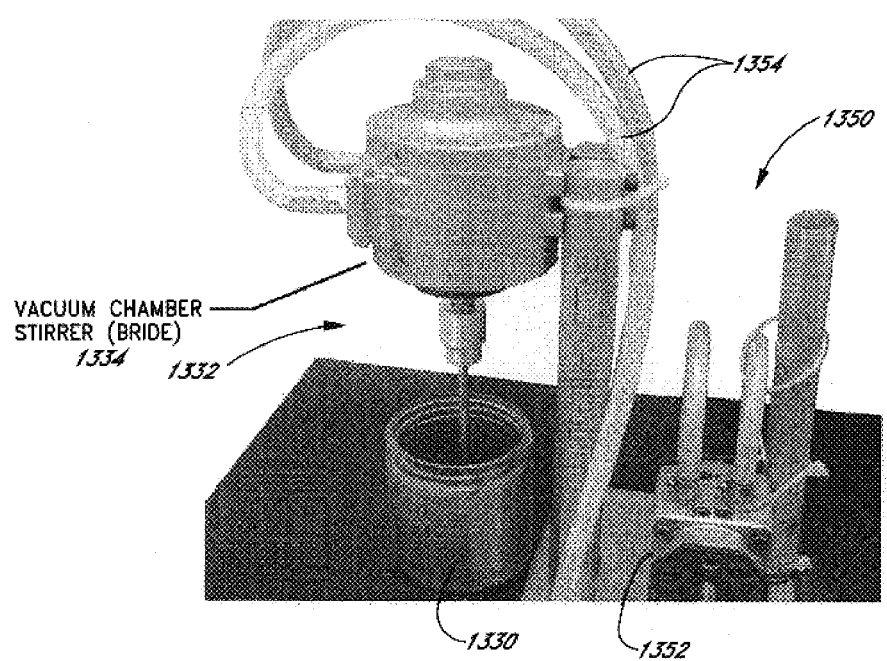

FIG. 117 is a simplified perspective view of a stirrer for the magnetorheological fluid of FIG. 116 illustrating features and advantages in accordance with an embodiment of the invention.

Figure 118:
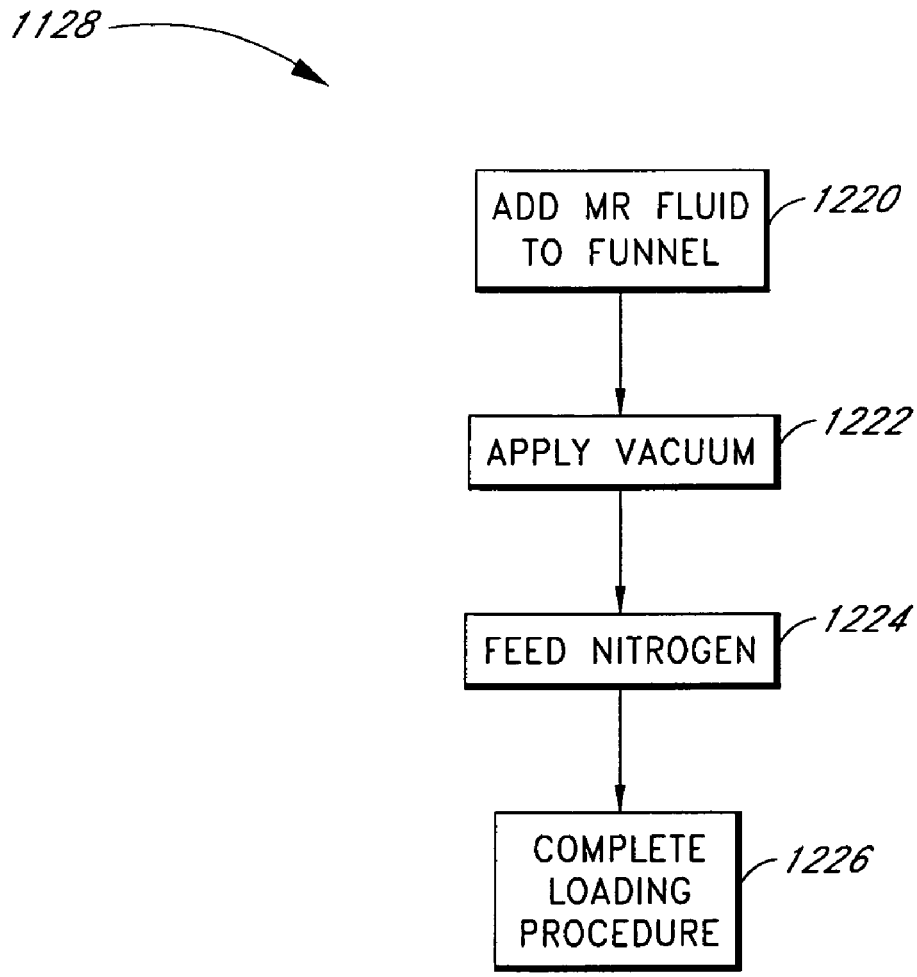

FIG. 118 is a simplified schematic diagram of some acts of loading the magnetorheological fluid in the actuator of FIG. 109 illustrating features and advantages in accordance with an embodiment of the invention.

Figure 119:
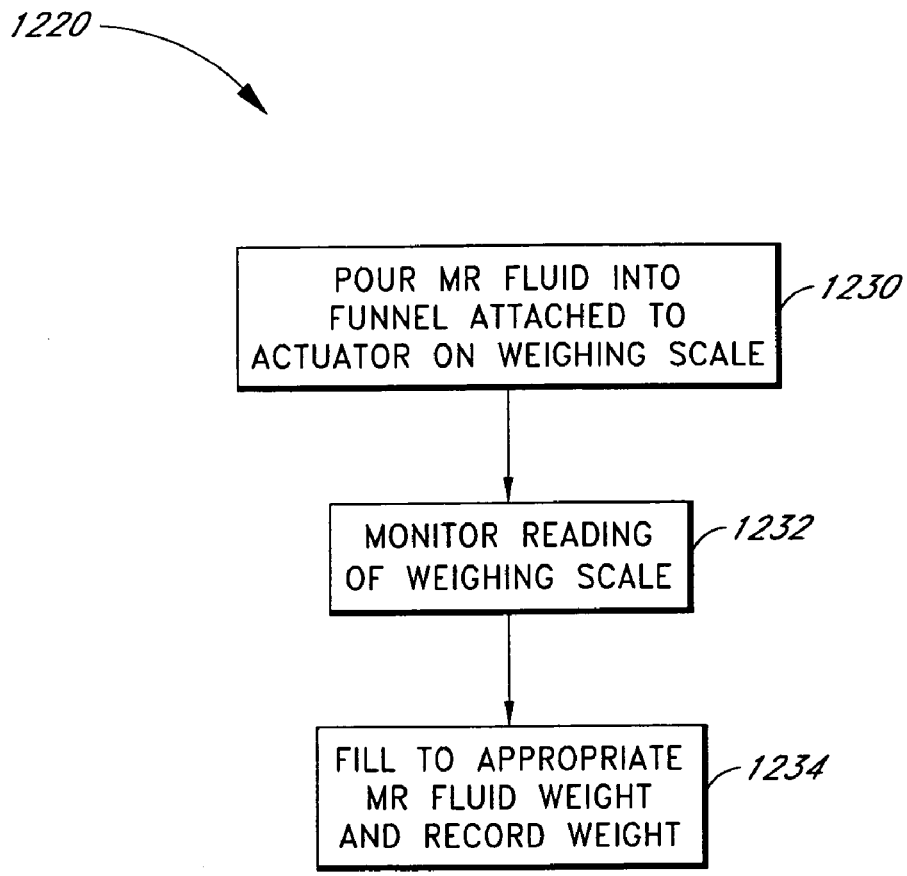

FIG. 119 is a simplified schematic diagram of some acts of adding the magnetorheological fluid to a funnel of FIG. 118 illustrating features and advantages in accordance with an embodiment of the invention.

Figure 120:
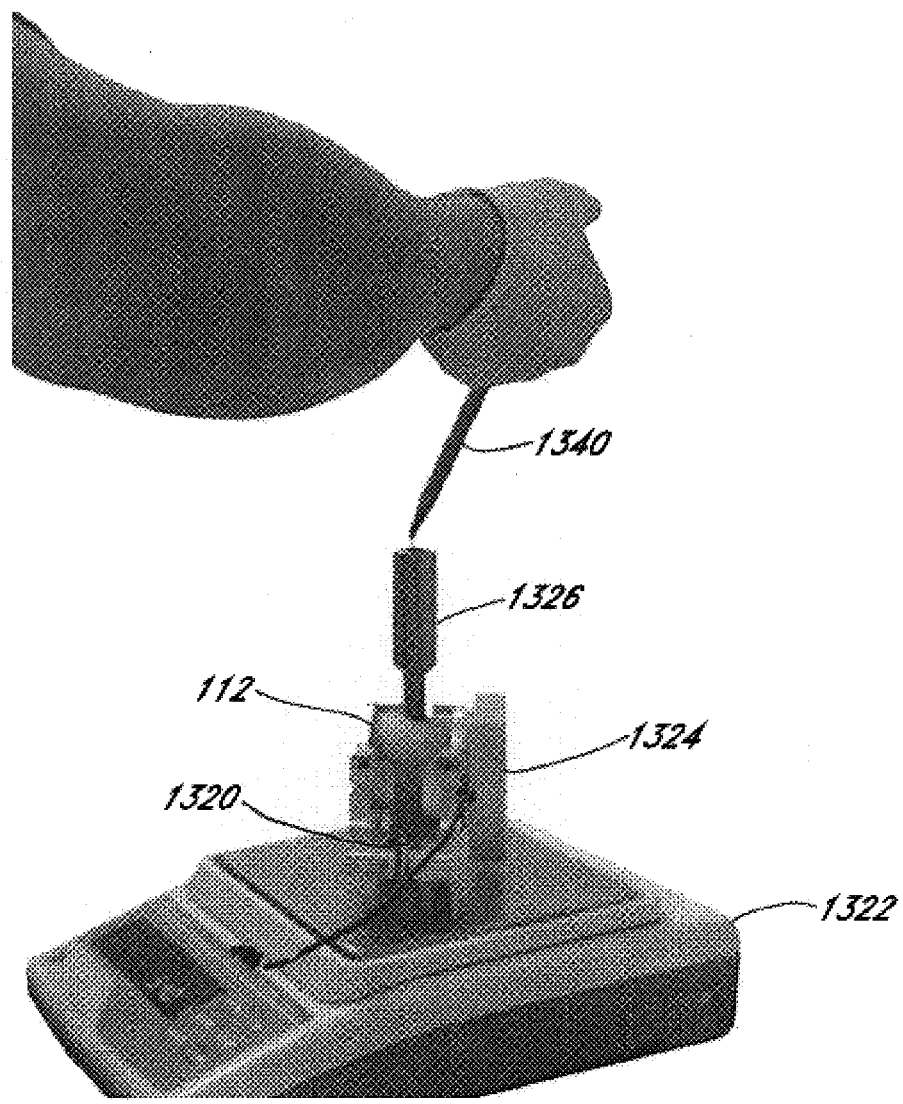

FIG. 120 is a simplified perspective view of pouring the magnetorheological fluid in the funnel of FIG. 119 illustrating features and advantages in accordance with an embodiment of the invention.

Figure 121:
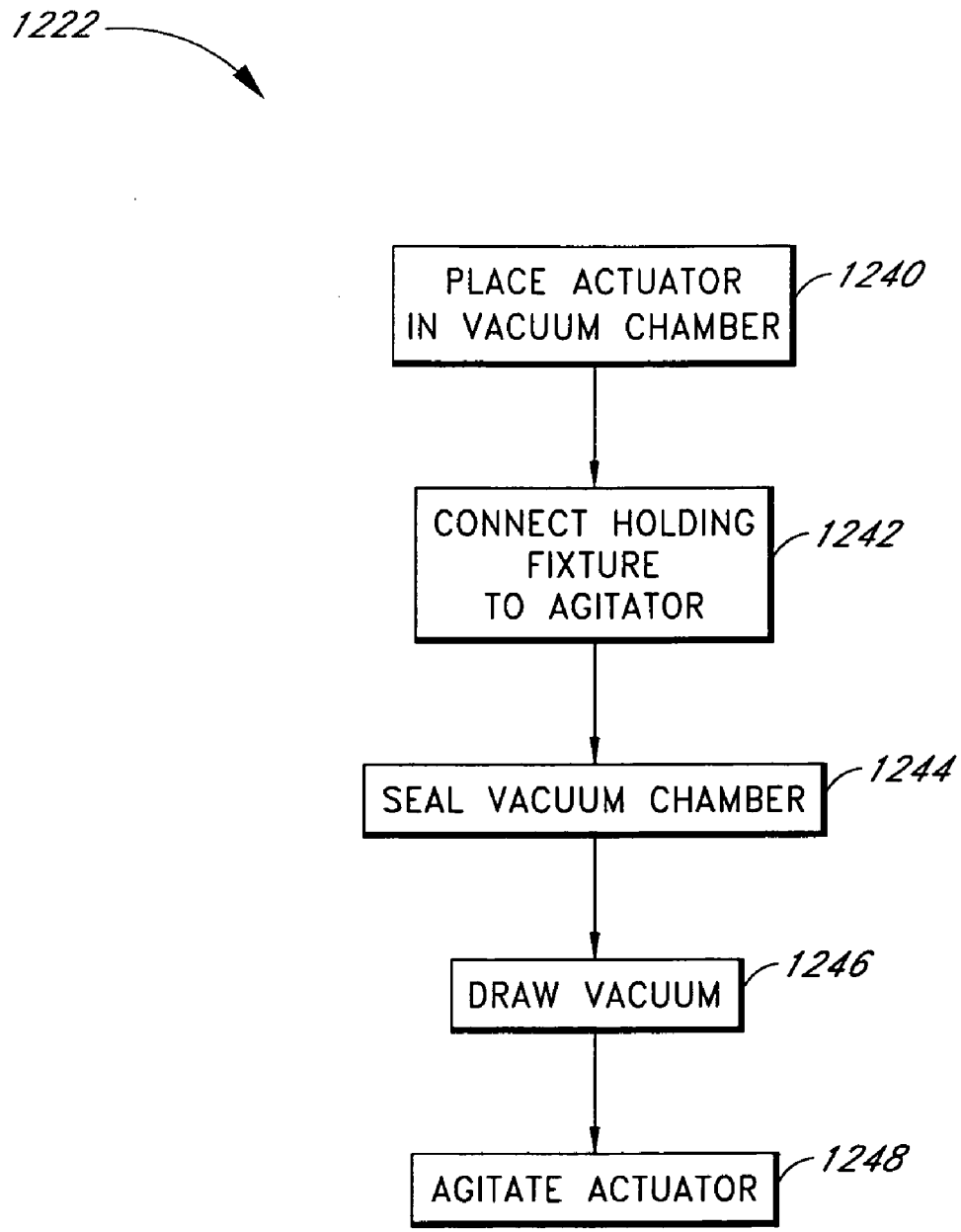

FIG. 121 is a simplified schematic diagram of some acts of applying a vacuum to the magnetorheological fluid and actuator of FIG. 118 illustrating features and advantages in accordance with an embodiment of the invention.

Figure 122:
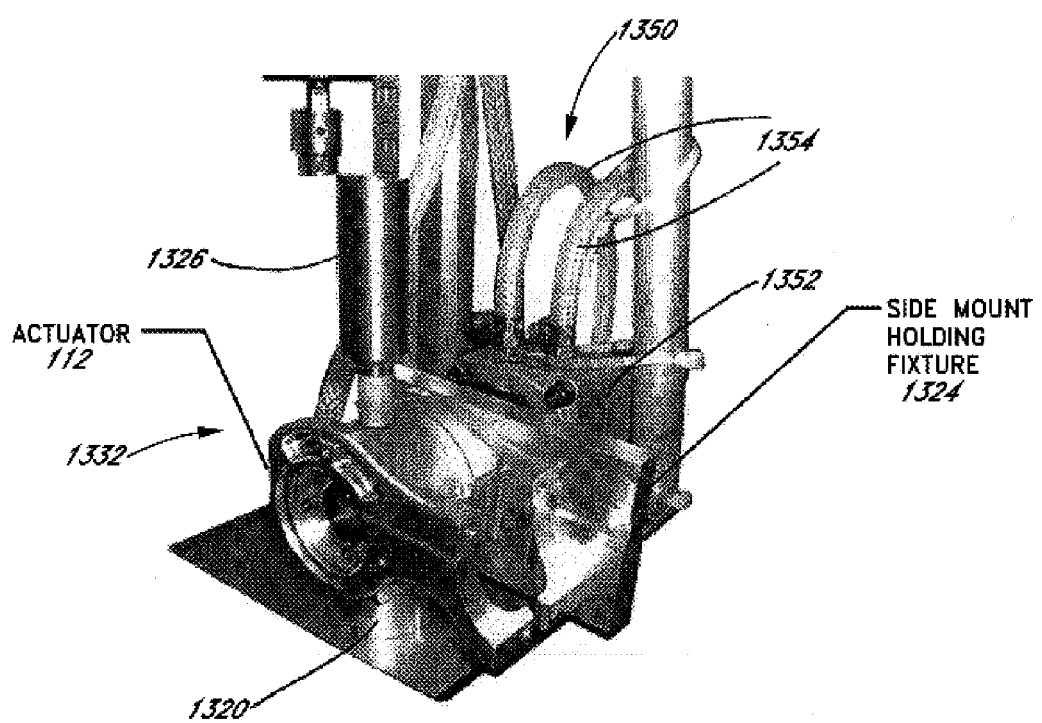

FIG. 122 is a simplified perspective view of the actuator of FIG. 119 in a vacuum chamber illustrating features and advantages in accordance with an embodiment of the invention.

Figure 123:
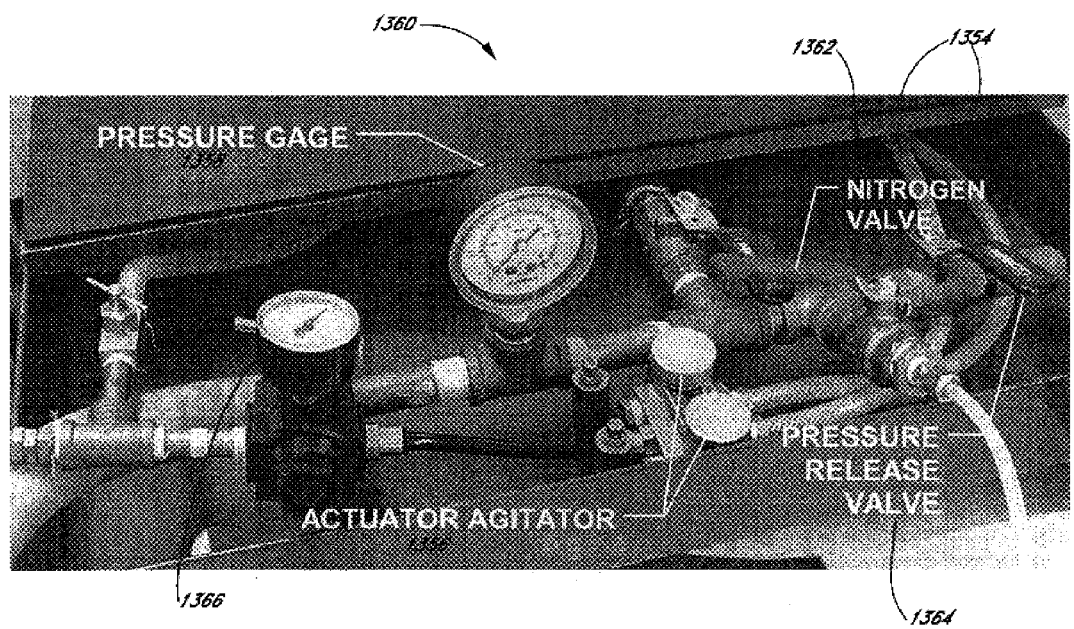

FIG. 123 is a simplified perspective view of a vacuum table and gauges associated with the vacuum chamber of FIG. 122 illustrating features and advantages in accordance with an embodiment of the invention.

Figure 124:
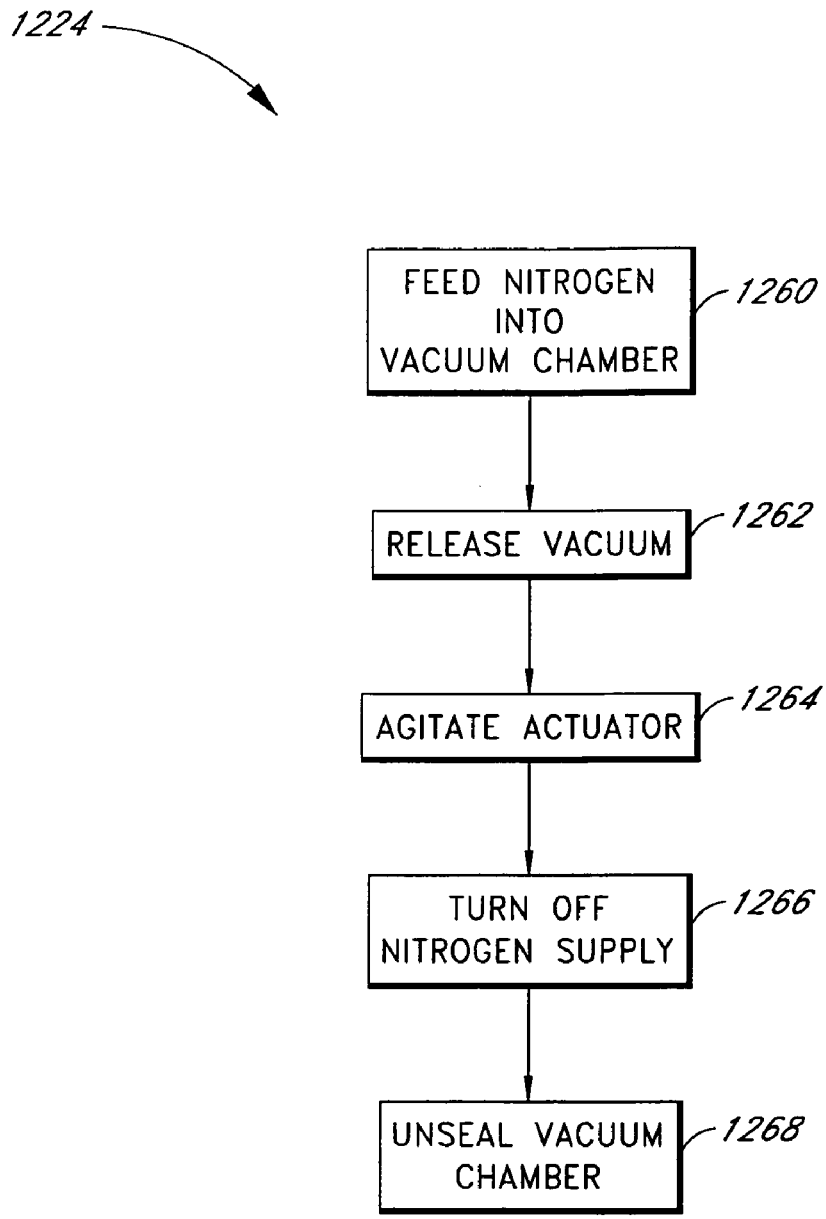

FIG. 124 is a simplified schematic diagram of some acts of feeding nitrogen to the actuator of FIG. 118 illustrating features and advantages in accordance with an embodiment of the invention.

Figure 125:
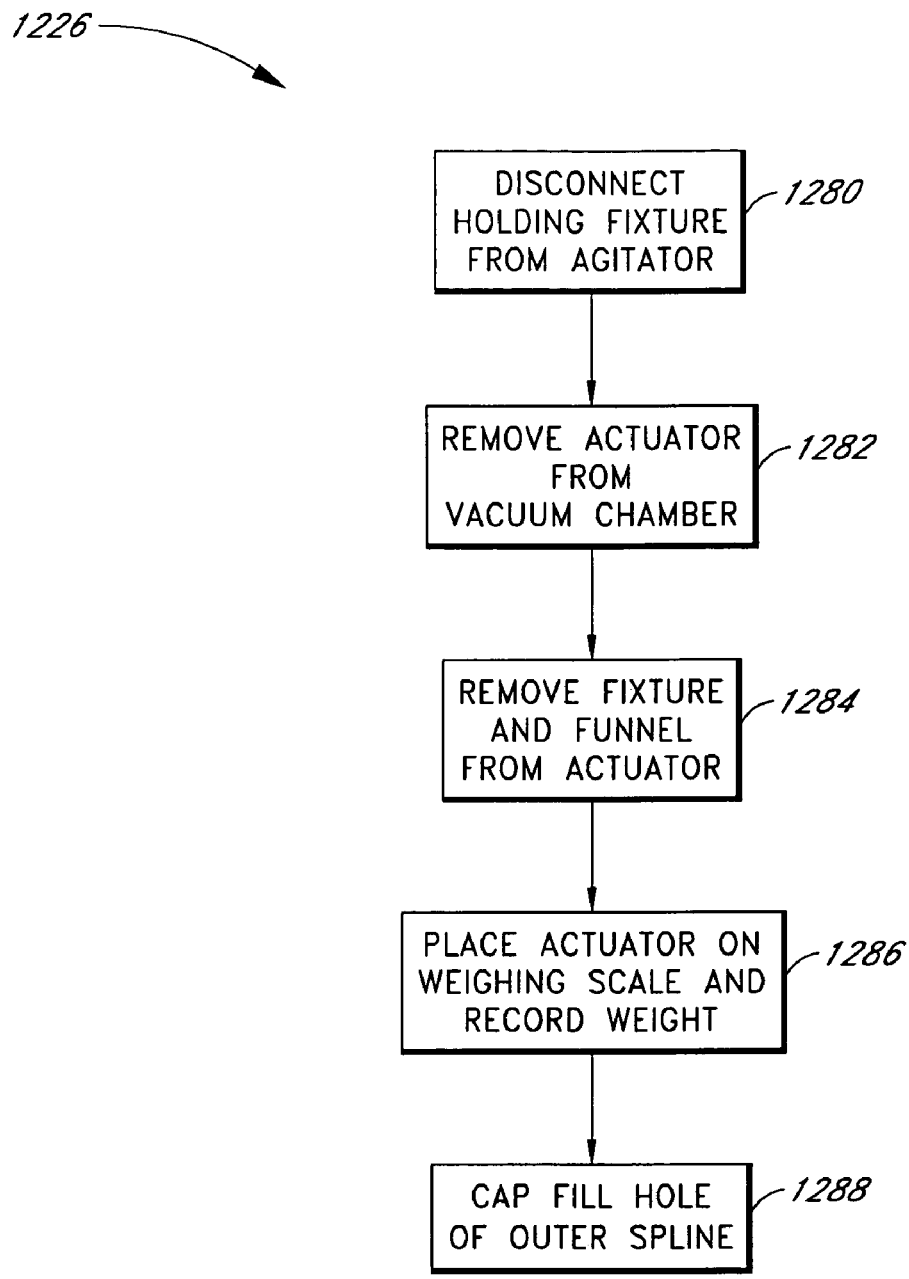

FIG. 125 is a simplified schematic diagram of some acts of completing the loading of the magnetorheological fluid in the actuator of FIG. 118 illustrating features and advantages in accordance with an embodiment of the invention.

DETAILED DESCRIPTION OF THE PREFERRED EMBODIMENTS

Some preferred embodiments of the invention described herein relate generally to prosthetic devices and, in particular, to magnetorheologically actuated controllable braking systems utilized in prosthetic knees for supporting an amputee that allow the amputee to move comfortably, safely and in a substantially natural and life-like manner in various dynamic and static states, terrains and topography.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Understanding normal human walking/running provides the basis for the design and development of effective lower limb prostheses with controlled motion. Normal human locomotion or gait can be described as a series of rhythmical alternating movements of the limbs and trunk which result in the forward progression of the body's center of gravity.

Figure 1:
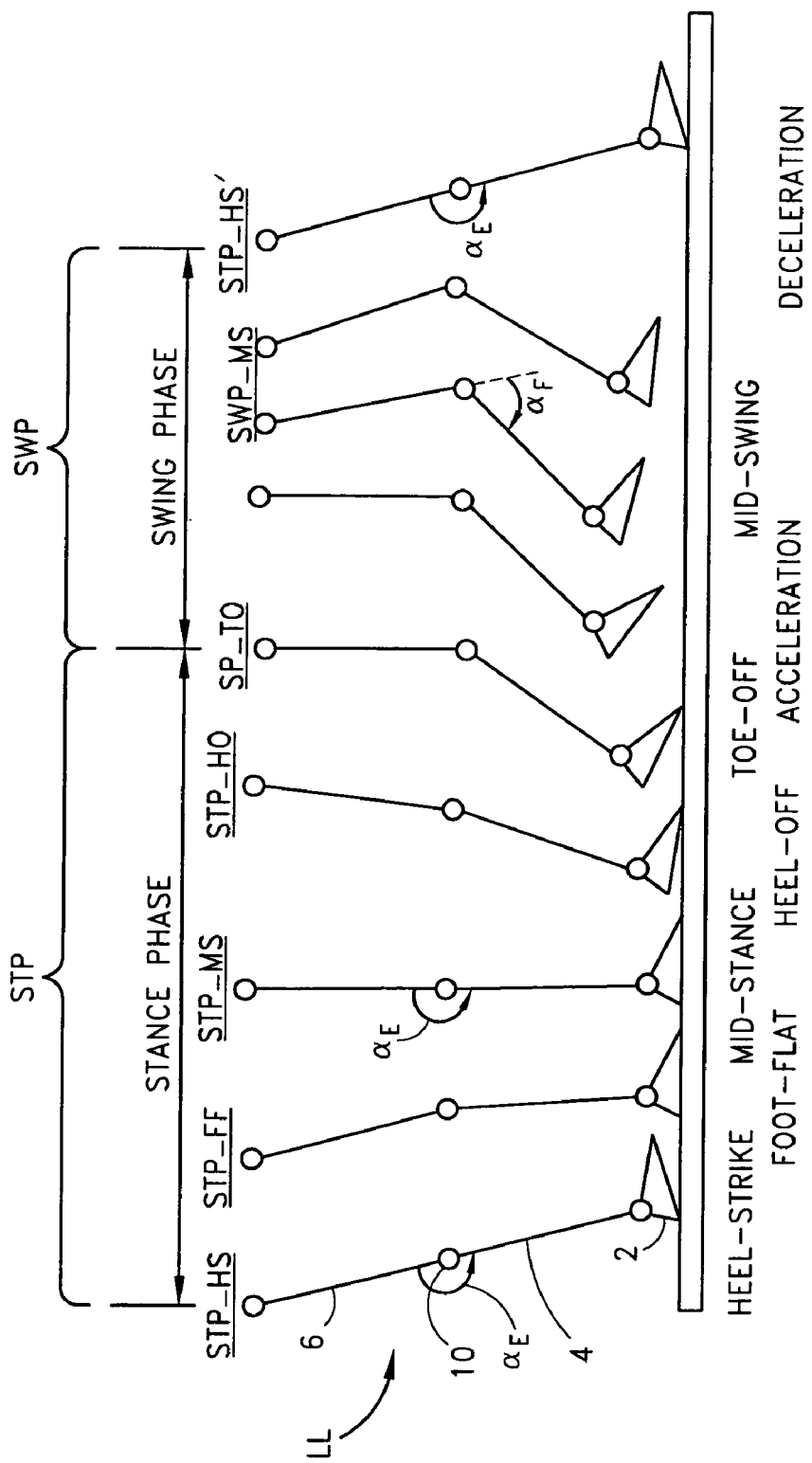
FIG. 1 is a simplified schematic view of one normal human locomotion cycle illustrating the various limb positions during stance and swing phases.

One typical gait cycle, as schematically depicted in FIG. 1, comprises of the activity that occurs between heel strike of one lower limb LL and the subsequent heel strike of the same limb LL. The limb or leg LL generally comprises a foot 2 and a shin portion 4 coupled or articulated to a thigh portion 6 via a knee or knee joint 10. During a single gait cycle each lower limb or extremity passes through one stance or extended phase STP and one swing phase SWP.

The stance phase STP begins at heel-strike STP_HS when the heel touches the floor or supporting ground surface and the stance knee begins to flex slightly. This flexion allows for shock absorption upon impact and also maintains the body's center of gravity at a more constant vertical level during stance.

Shortly after heel-strike STP_HS, the sole makes contact with the ground at the beginning of the foot-flat phase STP_FF. After maximum flexion is reached in the stance knee, the joint begins to extend again, until maximum extension is reached at mid-stance STP_MS as the body weight is swung directly over the supporting extremity and continues to rotate over the foot.

As the body mass above the ankle continues to rotate forward, the heel lifts off the ground at heel-off STP_HO. Shortly after this, the body is propelled forward by the forceful action of the calf-muscles (push-off). The push-off phase terminates when the entire foot rises from the ground at toe-off SP_TO.

During late stance, the knee of the supporting leg flexes in preparation for the foot leaving the ground for swing. This is typically referred to in the literature as "knee break". At this time, the adjacent foot strikes the ground and the body is in "double support mode", that is, both the legs are supporting the body weight.

At toe-off SP_TO, as the hip is flexed and the knee reaches a certain angle at knee break, the foot leaves the ground and the knee continues to flex into the swing phase. During early swing the foot accelerates. After reaching maximum flexion at mid-swing SWP_MS, the knee begins to extend and the foot decelerates. After the knee has reached full extension, the foot once again is placed on the ground at heel-strike STP_HS' and the next walking cycle begins.

Typically, the anatomical position is the upright position, therefore flexion is a movement of a body part away from the extended or stance or anatomical position. Thus, bending of the knee is knee flexion. Extension is a movement of a limb towards the anatomical position, thus knee extension is a movement in the "straightening" direction.

During a typical normal walking progression on a generally level surface, the maximum flexion angle $\alpha_F$ varies between about 70° and 80°. The maximum extension angle $\alpha_E$ is typically about or close to 180°. Thus, in level walking the normal human knee rotates through a range of approximately 70°–80° going from a position of full extension in early and mid stance to 70°–80° of flexion shortly after toe-off. In other situations, such as, in a sitting position, the maximum flexion angle $\alpha_F$ can be greater than about 70°–80° and up to, for example, about 140°–150°.

System Overview

Figure 2:
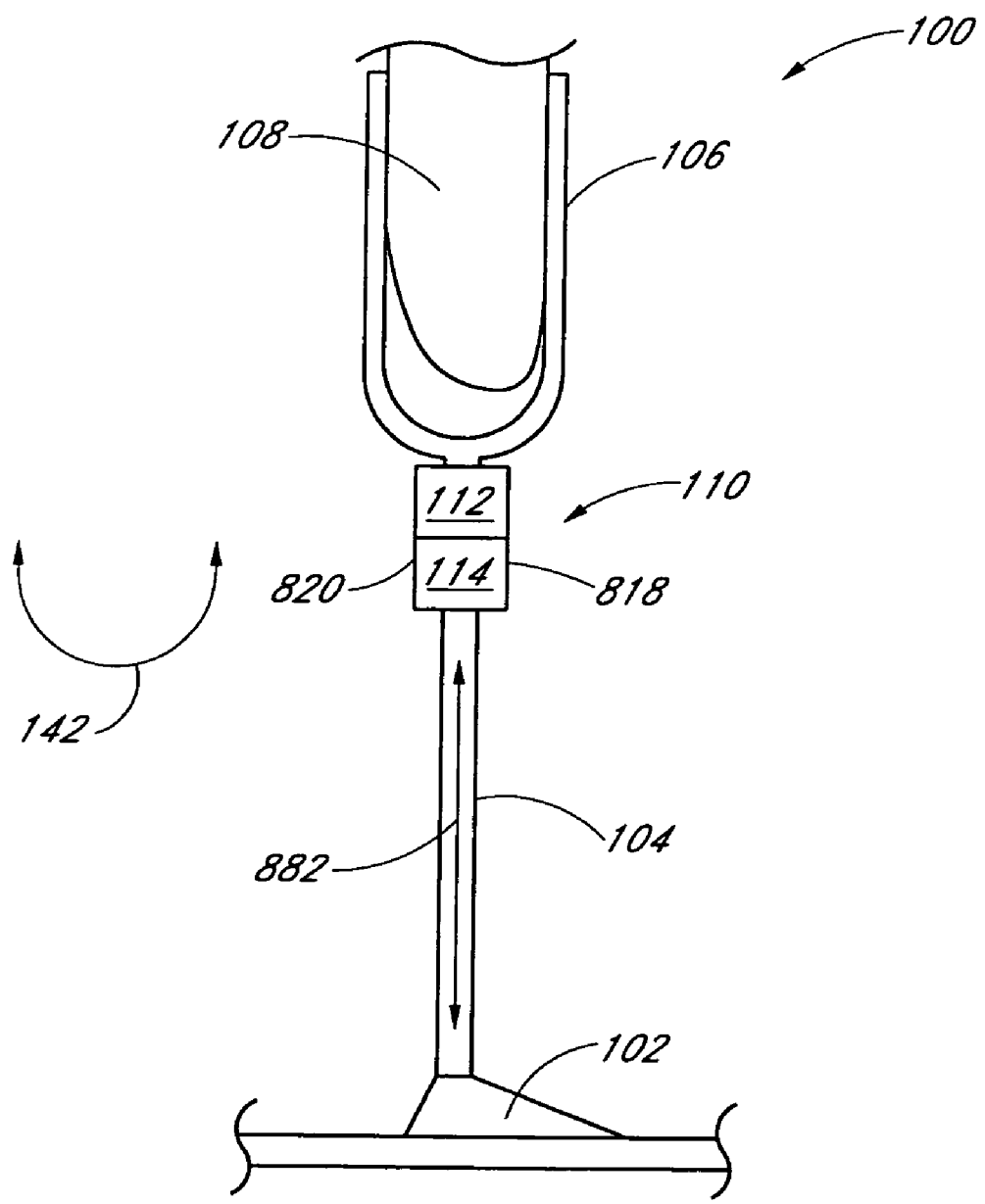
FIG. 2 is a simplified schematic view of a lower limb prosthetic assembly with an electronically controlled prosthetic knee illustrating features and advantages in accordance with an embodiment of the invention.
Figure 3A:
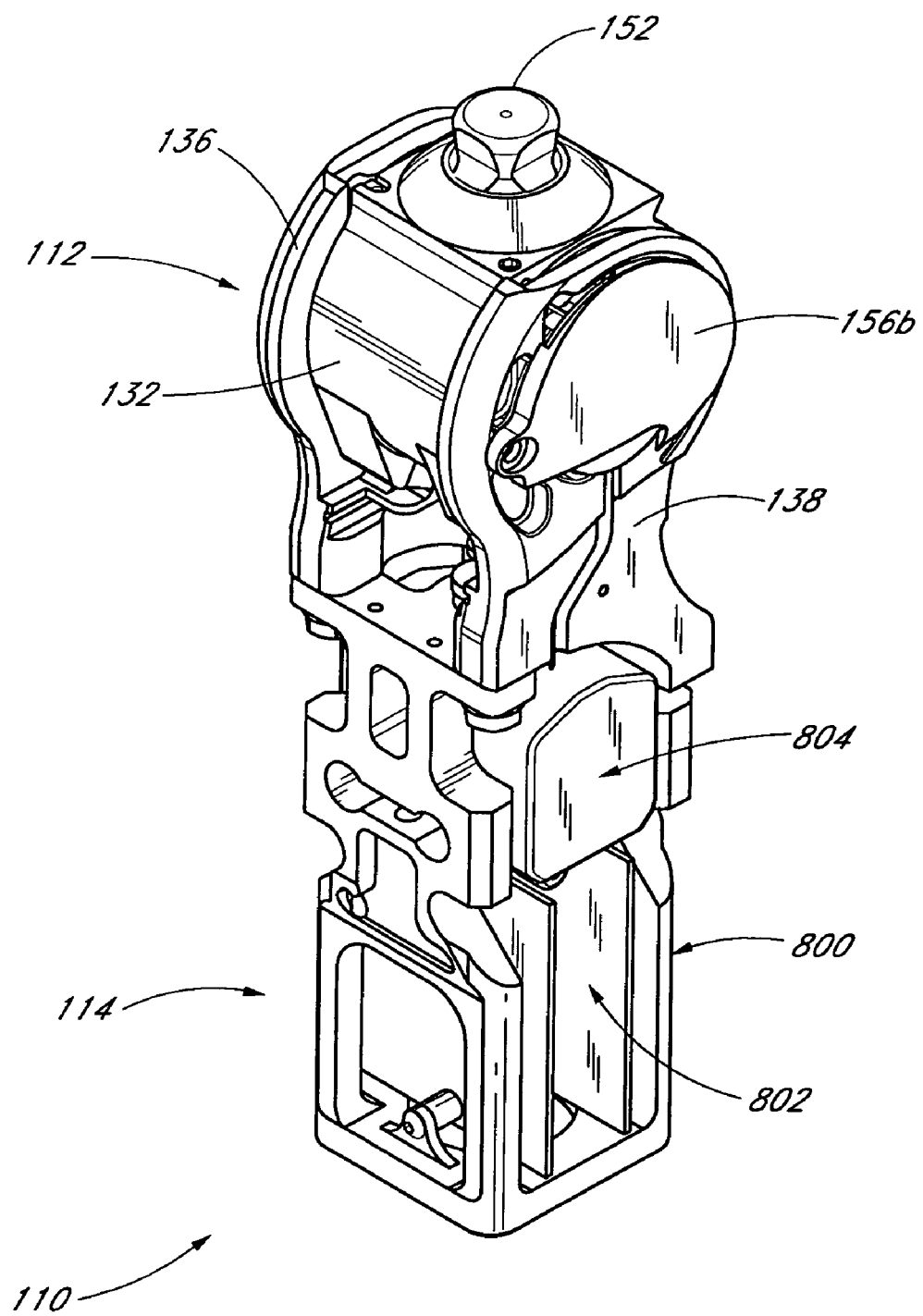
FIGS. 3A–3D are simplified perspective views of a prosthetic knee assembly illustrating features and advantages in accordance with an embodiment of the invention.
Figure 3B:
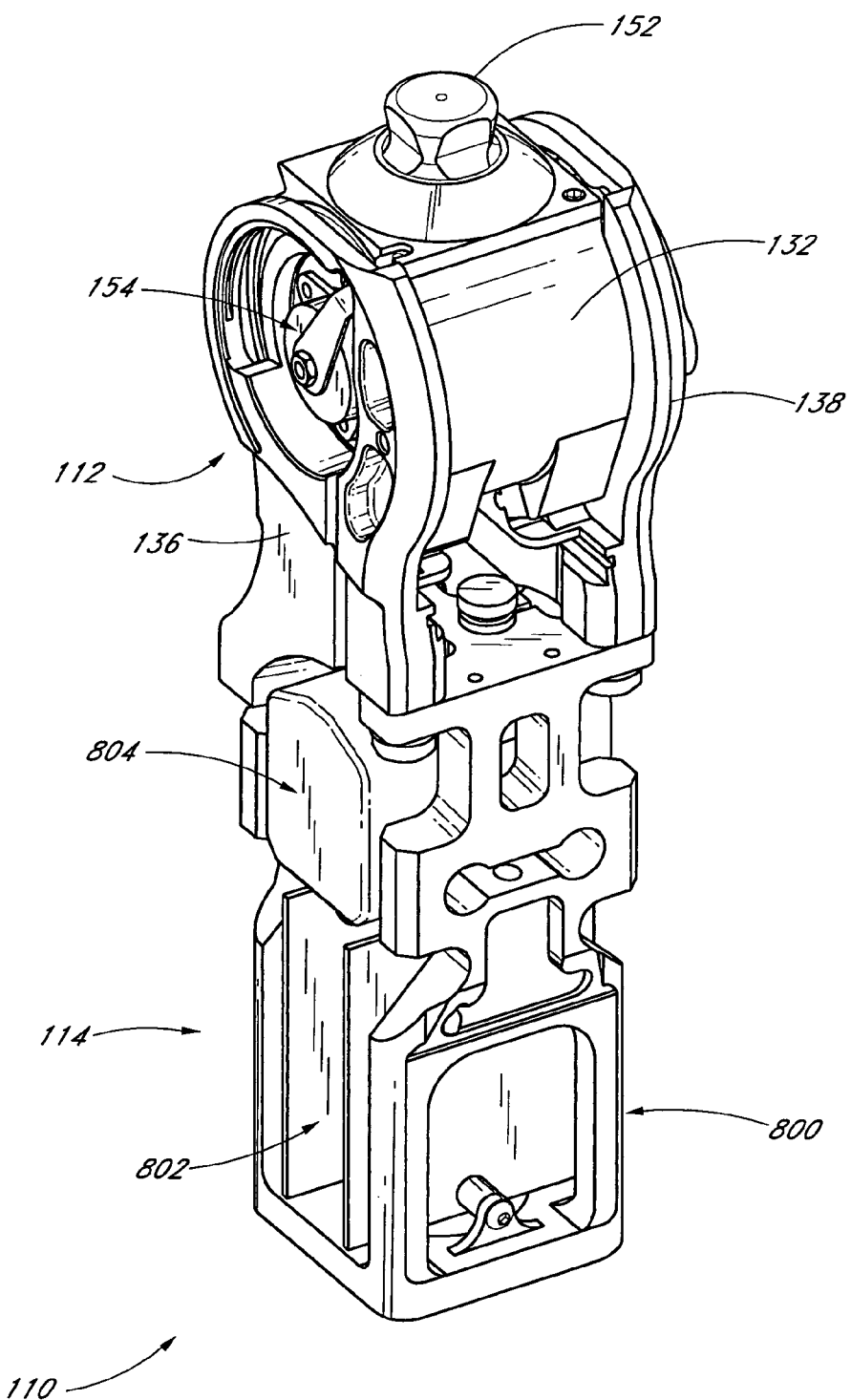
Figure 3C:
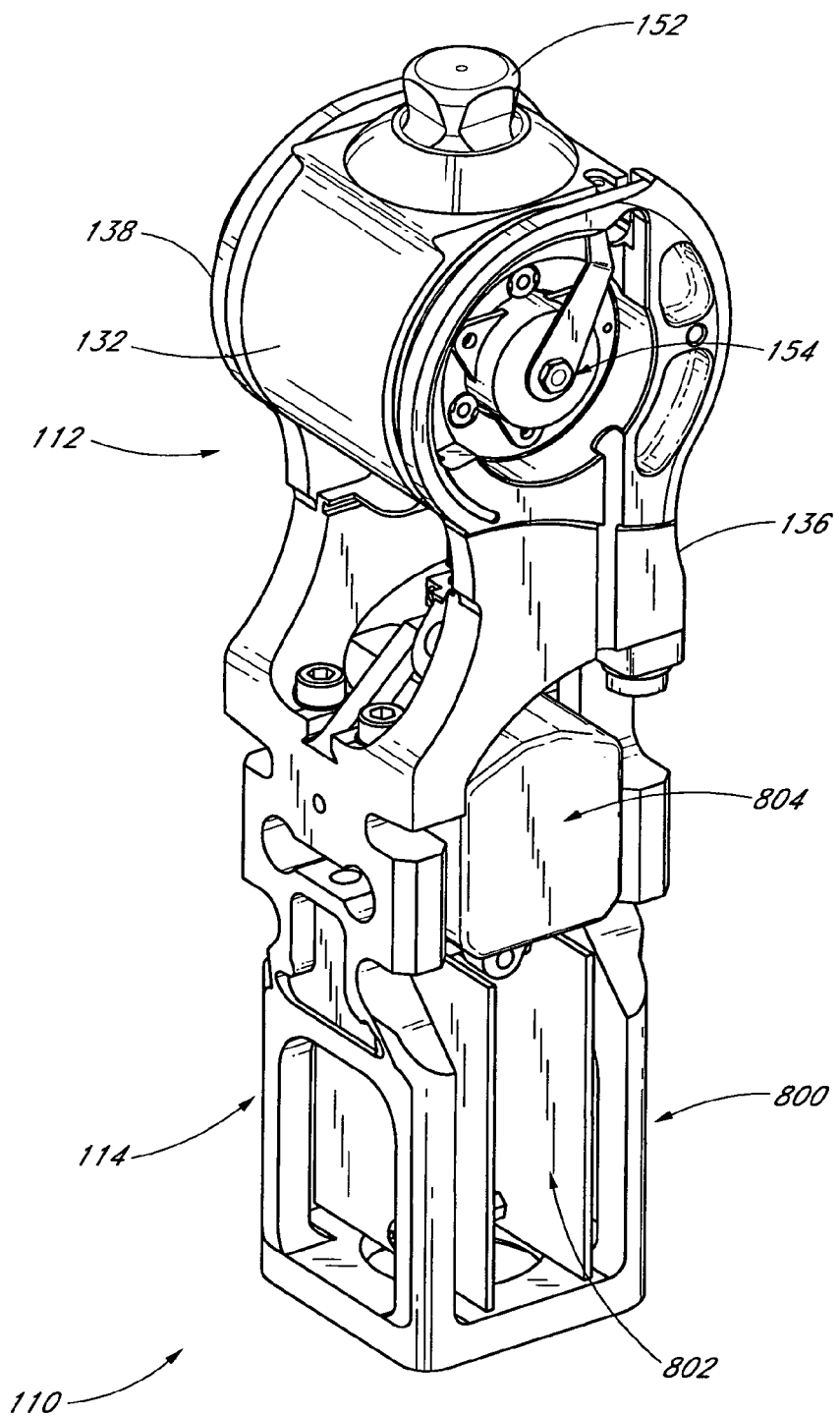
Figure 3D:
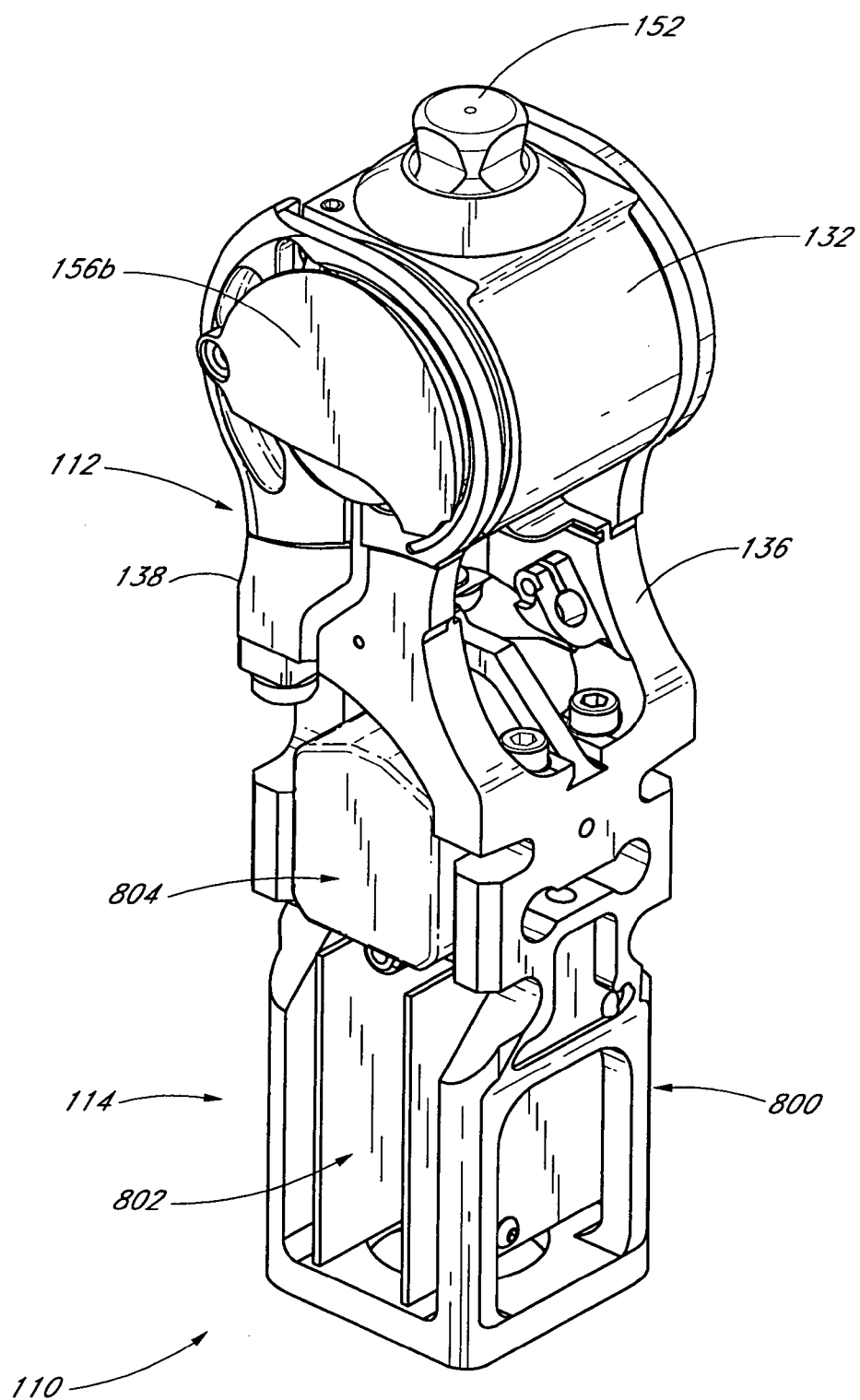

FIG. 2 is a schematic illustration of an embodiment of a lower limb prosthetic assembly, system or prosthesis 100 including an electronically controlled active knee prosthetic assembly, system or prosthesis 110. As described in greater detail later herein, advantageously, the knee prosthesis 110 provides resistive forces to substantially simulate the position and motion of a natural knee joint during ambulation and/or other locomotory or stationary activities performed by an amputee. The prosthetic or artificial knee 110 is desirably safe, reliable and generally comfortable to use by the amputee.

The prosthetic lower limb 100 further includes an artificial or prosthetic foot 102 coupled or mechanically connected to a pylon, tube, shaft or shank portion 104 that connects to a distal or bottom portion of the prosthetic knee 110 and a residual limb or stump socket 106 that connects to a top or proximal end of the prosthetic knee 110. The stump socket 106 receives a residual limb or femur portion 108 of the amputee. A suitable pylon or the like can also be provided between the stump socket 106 and the prosthetic knee 110, as needed or desired.

Embodiments of the invention van be practiced with a wide variety of prosthetic feet. These include Flex-Foot® feet such as Ceterus™, LP Ceterus™, Vari-Flex®, LP Vari-Flex®, Talux® and Elation™. Some embodiments of suitable prosthetic feet and associated devices are disclosed in U.S. Pat. No. 5,181,932, issued Jan. 26, 1993, U.S. Pat. No. 5,181,933, issued Jan. 26, 1993, U.S. Pat. No. 5,728,177, issued Mar. 17, 1998, U.S. Pat. No. 5,766,265, issued Jun. 16, 1998, U.S. Pat. No. 5,800,569, issued Sep. 1, 1998, U.S. Pat. No. 6,511,512, issued Jan. 28, 2003, U.S. Patent Application Publication No. 2003/0093158, published May 15, 2003, U.S. patent application Ser. No. 10/642,125, filed Aug. 15, 2003, U.S. patent application Ser. No. 10/674,736, filed Sep. 30, 2003, and U.S. patent application Ser. No. 10/742,455, filed Dec. 18, 2003, the entirety of each one of which is hereby incorporated by reference herein.

The prosthetic knee 110 generally comprises a variable-torque magnetorheological (MR) actuator assembly or braking system 112 and a frame and electronics assembly or system 114 that also serves as a mount for the knee actuator 112 and facilitates in monitoring and controlling the operation of the knee actuator 112. The prosthetic knee system 110 desirably provides resistive forces to substantially simulate the position and motion of a natural knee joint during ambulation and/or other locomotory activities performed by the amputee.

Advantageously, the prosthetic knee 110 of embodiments of the invention permits the amputee to move and/or adapt comfortably and safely in a wide variety of circumstances. For example, during walking, running, sitting down, or when encountering subtle or drastic changes in the terrain, topography and environment or ambient conditions, such as, when the user lifts a suitcase or walks down a slope or encounters stairs, among others.

The prosthetic knee 110 provides stance control to limit buckling when weight is applied to the limb. In addition, the prosthetic knee 110 provides aerial swing control so that the knee reaches full extension just prior to or at heel-strike in a smooth and natural manner. Moreover, the prosthetic knee 110, by adjusting and/or fine tuning the range and/or magnitudes of the resistive torque level, can be adapted for use with a wide variety of patients having different body weights, heights and activity levels.

The prosthetic knee assembly 110 of embodiments of the invention has particular efficacy when used in conjunction with a trans-femoral (above-knee, A/N) amputee. In modified embodiments, the prosthetic knee joint 110 may be efficaciously adapted for use with a knee-disarticulation (K/D) amputee wherein the amputation is through the knee joint, as needed or desired.

FIGS. 3A–3D show a system overview of the prosthetic knee assembly 110 generally comprising the magnetorheological actuator assembly or system 112 and the frame and electronics assembly or system 114. The frame and electronics assembly 114 also provides power and communicates with the actuator assembly 112 via electrical signals. Each of these systems is described in greater detail below.

Magnetorheological Actuator

Figure 4:
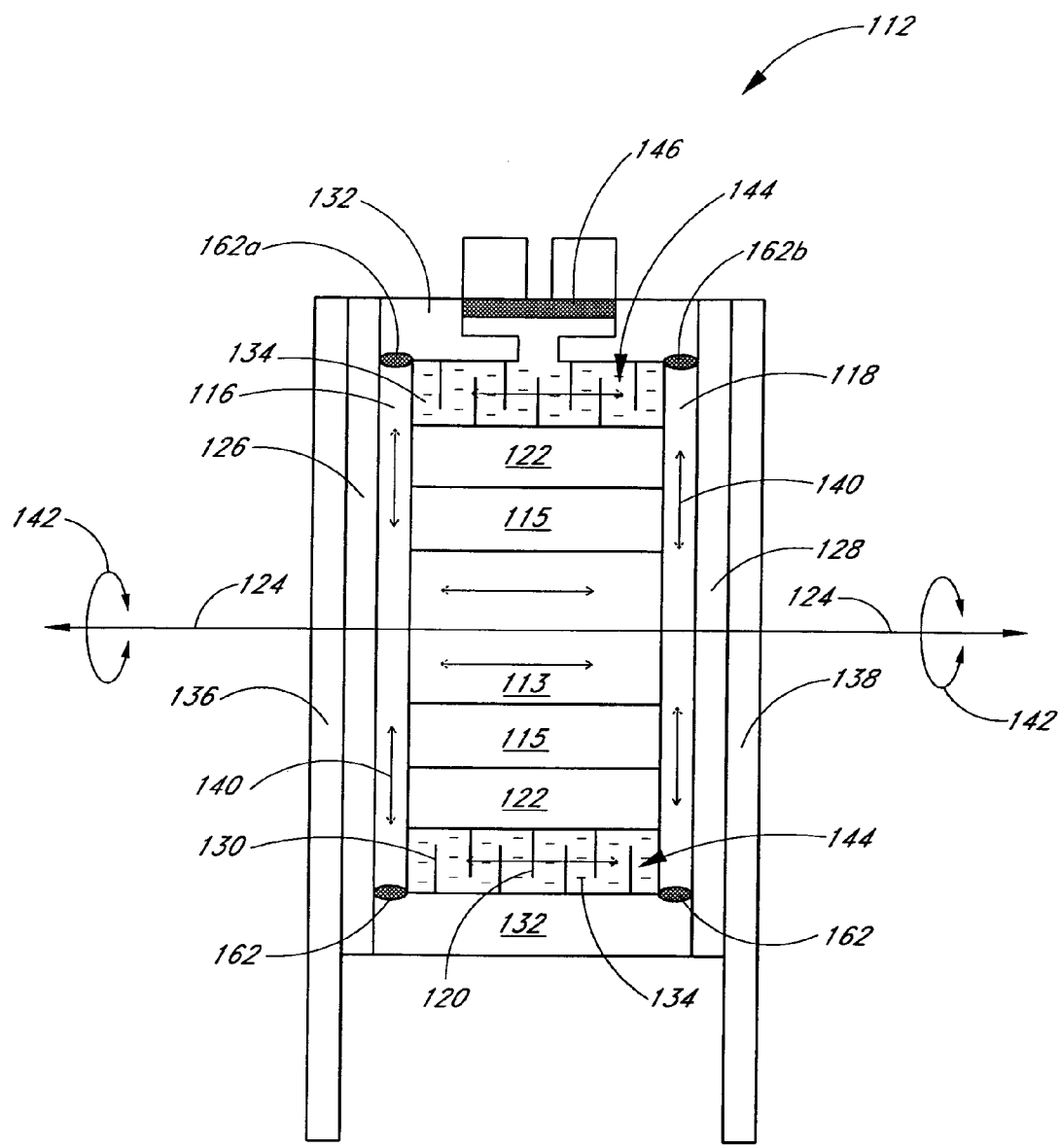
FIG. 4 is a simplified schematic view of a magnetorheological actuator for a prosthetic knee depicting its general configuration and operation and illustrating features and advantages in accordance with an embodiment of the invention.
Figure 5A:
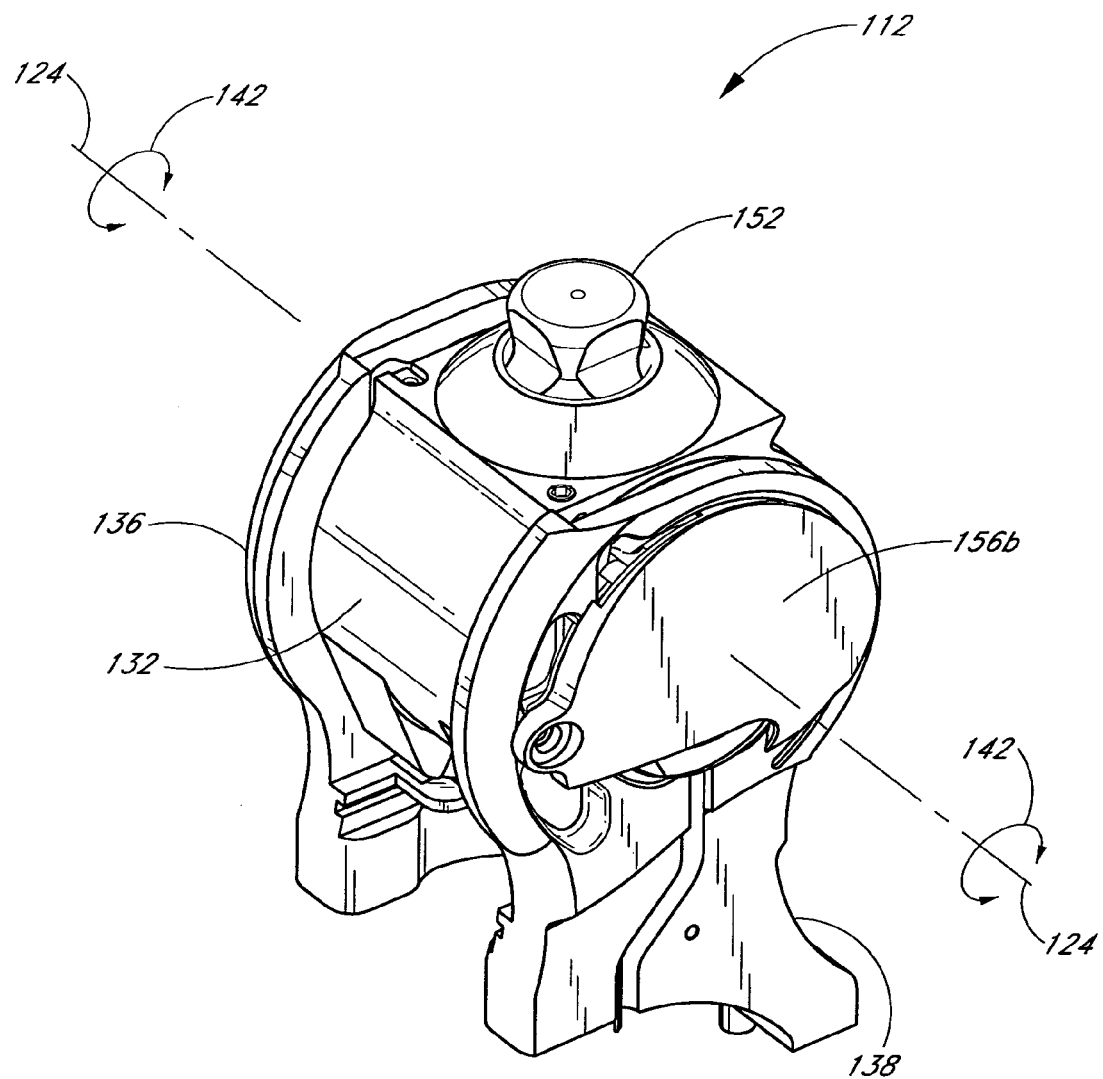
FIGS. 5A–5D are simplified perspective views of a magnetorheological actuator of the prosthetic knee assembly of FIGS. 3A–3D illustrating features and advantages in accordance with an embodiment of the invention.
Figure 5B:
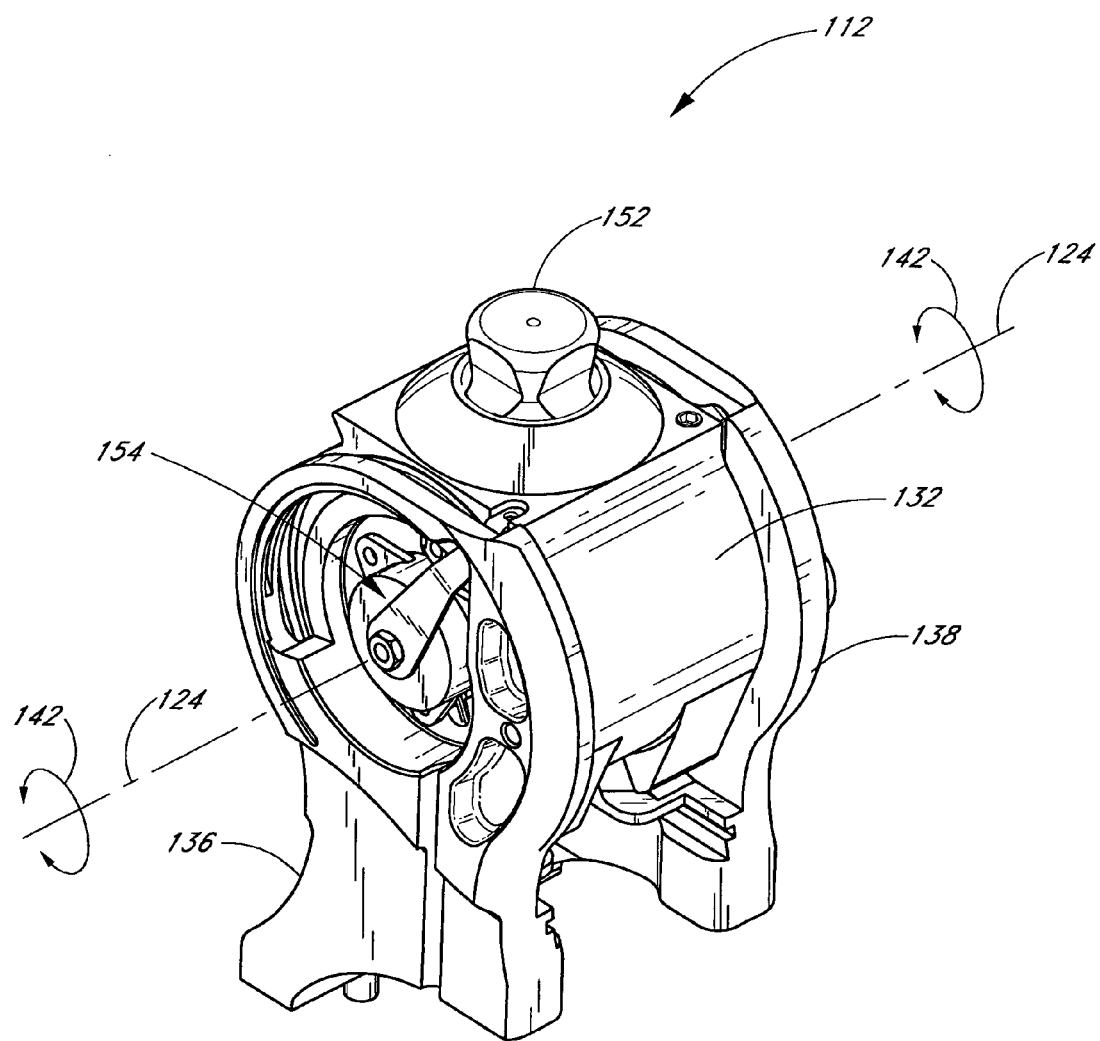
Figure 5C:
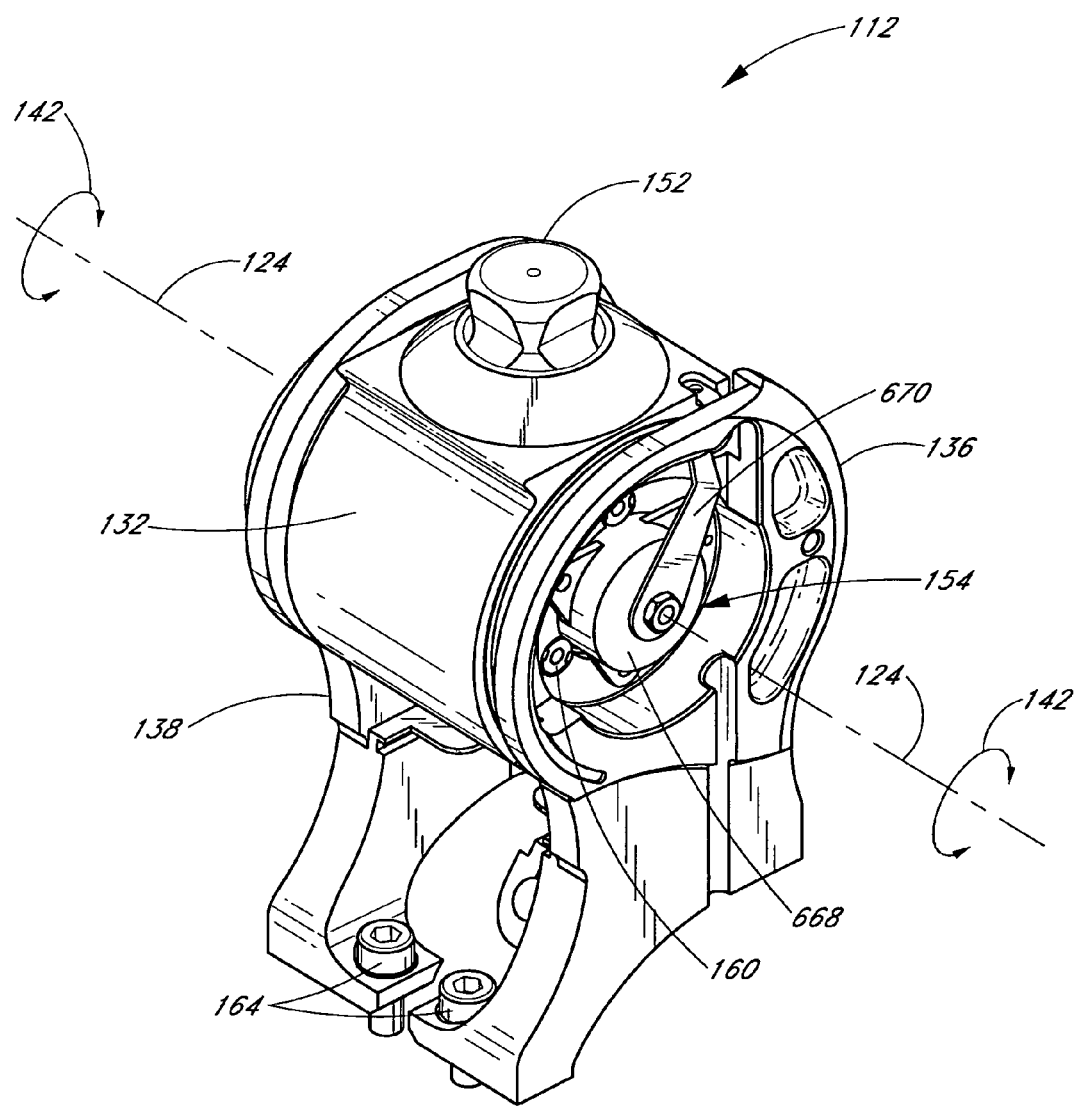
Figure 5D:
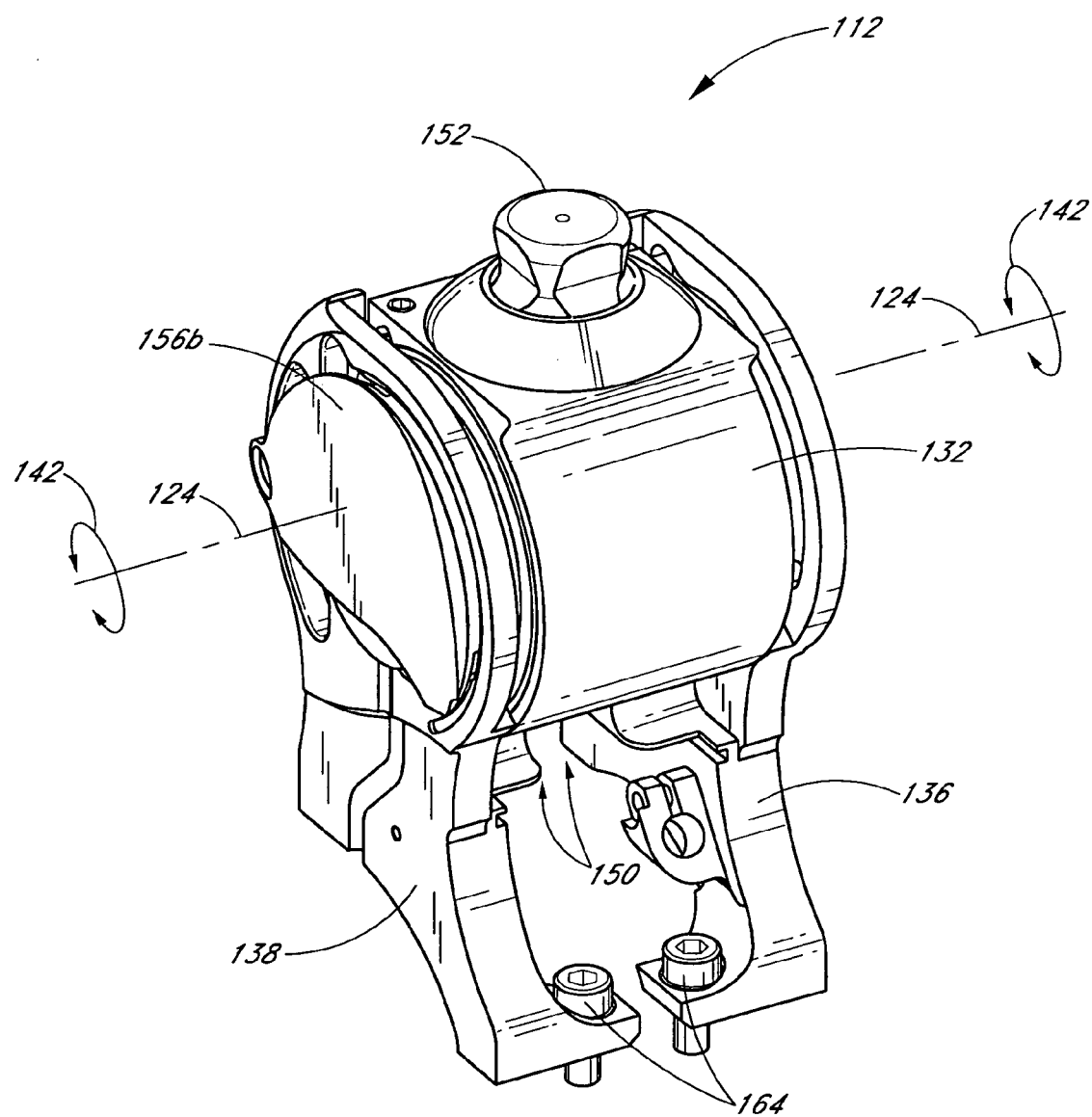
Figure 5E:
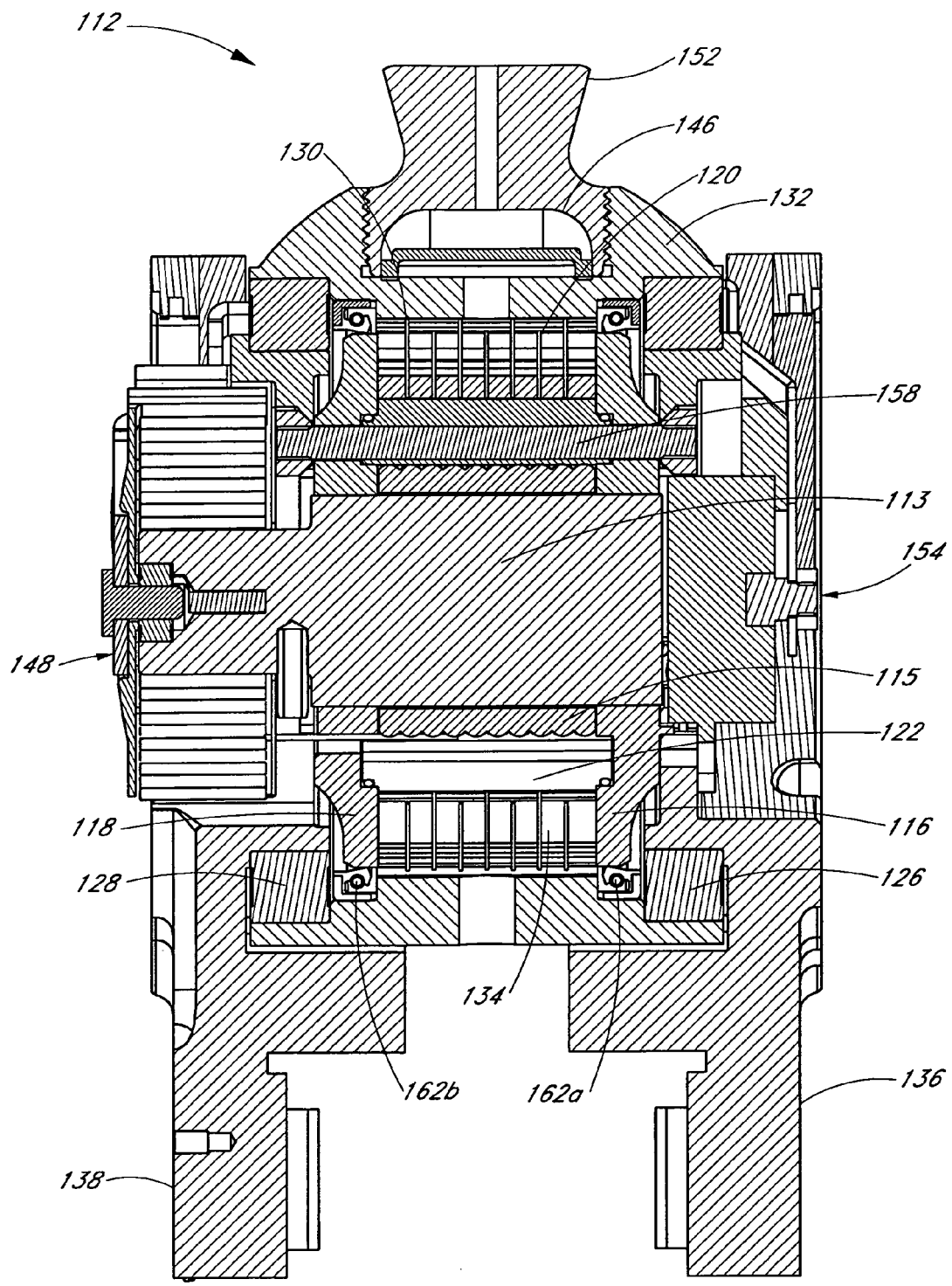
FIG. 5E is a simplified sectional view of a magnetorheological actuator of the prosthetic knee assembly of FIGS. 3A–3D illustrating features and advantages in accordance with an embodiment of the invention.

FIG. 4 shows a conceptual drawing of the rotary magnetorheological (MR) knee actuator or braking system 112 illustrating its general configuration and operation. More detailed drawings and description are provided later below herein. The knee actuator, damper or brake 112 can be considered a device that resists or controls motion or rotation.

The knee actuator 112 includes a substantially central core rod 113 substantially circumscribed or enveloped by an electromagnet or magnetic coil 115 and is mechanically coupled, communicated or connected with a pair of side plates or disks 116, 118. By passing a variable, controlled current through the coil 115, a variable magnetic field is created. As described further below, in some embodiments, the core rod 113 and core sides 116, 118 comprise a ferrous, magnetizable or magnetic material and the like.

The knee actuator 112 further includes a plurality of rotary inner blades, plates or rotors 120 mechanically coupled, communicated or connected with an inner spline 122. The inner spline 122 generally circumscribes or envelops the electromagnetic coil or electromagnet 115 and is mechanically coupled, communicated or connected to the core side plates 116, 118.

In the illustrated embodiment, the inner blades 120 are substantially concentrically arranged about a knee actuator or brake axis of rotation 124. The inner spline 122 is rotatable about the knee joint axis of rotation 124, and hence so are the blades or rotors 120 and the core side plates 116, 118, as generally indicated by arrows 142. Rotation of the inner spline 122 corresponds to rotation or movement of the lower (below the knee) part of the leg. The inner spline 122, and hence the inner blades 120, are substantially irrotationally coupled to or nonrotatable with respect to the pylon 104.

The knee actuator 112 also comprises a plurality of rotary outer blades, plates or rotors 130 mechanically coupled, communicated or connected with an outer spline, housing, shell or rotor head 132. The outer spline 132 generally circumscribes or envelops the inner spline 122 to form a fluid receiving chamber, cavity or passage 144 with the core side plates 116, 118 generally forming at least a portion of the side walls of the chamber 144.

In the illustrated embodiment, the outer blades 130 are substantially concentrically arranged about the axis of rotation 124. The outer spline 132 is rotatable about the knee joint axis of rotation 124, and hence so are the blades or rotors 130, as generally indicated by arrows 142. Rotation of the outer spline 132 corresponds to rotation or movement of the upper (above the knee) part of the leg, for example, the stump socket 106 (see FIG. 2).

As discussed further below, the outer spline 132 is mechanically coupled, communicated or connected to the stump socket 106 using a pyramid adapter or the like, thereby attaching the knee actuator 112 and the prosthetic knee 110 to the stump socket 106. The outer spline 132, and hence the outer blades 130, are substantially irrotationally coupled to or nonrotatable with respect to the stump socket 106 or residual limb 108.

The plurality of inner blades 120 and outer blades 130 are interspersed in an alternating fashion and extend into the chamber 144 that contains magnetorheological (MR) fluid 134. Gaps between adjacent blades 120 and 130 include the magnetorheological (MR) fluid 134. In one embodiment, the MR fluid 134 in the gaps or microgaps between adjacent inner blades 120 and outer blades 130 is in the form of thin lubricating films between adjacent blades 120 and 130.

During knee joint rotation, the MR fluid 134 in the plurality of gaps between the inner blades 120 and outer blades 130 is sheared to generate a damping torque to control the limb rotation. The rotary blades or disks 120 and 130 are preferably formed of a ferrous, magnetizable or magnetic material and the like. Shearing of the MR fluid 134 present between the core side plates 116, 118 and adjacent outer blades 130 can also contribute to the knee damping.

The knee actuator 112 comprises a pair of side mounts, walls or forks 136, 138 that are mechanically coupled, communicated or connected to the inner spline 122 and rotate with it about the knee joint axis of rotation 124, as generally indicated by arrows 142. The side mounts 136, 138 in combination with the outer spline 132 can be considered to form one main outer shell of the knee actuator 112. As discussed further below, the side mounts 136, 138 are connected to the frame and electronics assembly 114 which in turn is connected to a lower (below the knee) part of the leg, for example, the leg pylon 104 (see FIG. 2). Thus, rotation of the side mounts 136, 138 corresponds to rotation of the lower part of the leg.

In a modified embodiment, the connections of the outer spline 132 and side mounts 136, 138 to the upper and lower parts of the legs are reversed. For example, the outer spline 132 may be coupled to the lower leg rotation and the side mounts 136, 138 to the upper leg rotation.

The knee actuator 112 further includes a pair of bearings 126, 128 mechanically coupled, communicated or connected to the outer spline 132 and to respective side mounts, walls or forks 136, 138. The bearings 126, 128 are arranged so that they facilitate rotation of the outer spline 132 substantially independently of the rotation of the side mounts 136, 138.

The central core rod 113 and the electromagnet or coil 115 also rotate along with the rotation of the inner spline 122, the inner blades 120, the core side plates 116, 118 and the side mounts 136, 138. The outer blades 130 rotate together with the rotation of the outer spline 132. This also counter-rotates the inner and outer blades 120 and 130.

The inner blades 120 are substantially rotationally fixed relative to the inner spline 122 and the outer blades 130 are substantially rotationally fixed relative to the outer spline 132. The rotation of the inner blades 120, inner spline 122, outer blades 130 and outer spline 132 is substantially around or about the knee axis of rotation 124 as is the rotation of the core rod 113, core side plates 116, 118 and coil 115.

During various stages of locomotion or knee rotation, the inner blades 120 may rotate while the outer blades 130 are rotationally substantially stationary, or the outer blades 130 may rotate while the inner blades 120 are rotationally substantially stationary, or both the inner blades 120 and the outer blades 130 may rotate or be substantially rotationally stationary. Thus, relative rotational motion is created between the inner blades 120 and the outer blades 130 with the MR fluid 134 being sheared in the gaps between adjacent inner and outer blades 120 and 130. In one embodiment, to establish a frame of reference, it can be assumed that the outer spline 132 is stationary.

Actuation of the magnet or coil 115 causes a magnetic field, circuit or path 140 to be generated or created within the knee actuator 112. In one embodiment, the magnetic field 140 (as indicated by the solid arrowheads) passes laterally (generally parallel to the axis of rotation 124) through the central core rod 113, radially outwards through the core side plate 118, laterally (generally parallel to the axis of rotation 124 in a direction opposite to that through the core rod 113) through the interspersed set of inner blades 120 and outer blades 130 and the magnetorheological fluid 134, and radially inwards through the core side plate 116. As discussed further below, in another embodiment, the polarity of the magnetic field is reversed, and the magnetic field 140 (as indicated by the dashed arrowheads) passes laterally (generally parallel to the axis of rotation 124) through the central core rod 113, radially outwards through the core side plate 116, laterally (generally parallel to the axis of rotation 124 and in a direction opposite to that through the core rod 113) through the interspersed set of inner blades 120 and outer blades 130 and the magnetorheological fluid 134, and radially inwards through the core side plate 118.

The portion of the magnetic field 140 passing through the core rod 113 and side plates 116, 118 generally defines the magnetic return path. The active or functional magnetic field is generally defined by the magnetic path through the inner blades or rotors 120, the outer blades or rotors 130 and the MR fluid 134.

The magnetorheological (MR) fluid 134 is a field responsive (FR) fluid or medium that undergoes a rheology or viscosity change which is dependent on the magnitude of the applied magnetic field. In turn, this variation in fluid viscosity determines the magnitude of the shearing force/stress, torque or torsional resistance generated, and hence the level of damping provided by the knee actuator 112 and/or the prosthetic knee 110. The resistive braking effect is a function of the MR fluid viscosity which in turn is a function of the magnetic field. Thus, by controlling the magnitude of this magnetic field, the rotary motion of the artificial limb is controlled, for example, to control the flexion and extension during swing and stance phases to provide a more natural and safe ambulation for the amputee.

The MR fluid 134 generally comprises polarizable particles, a carrier fluid, and optionally an additive. In some embodiments, as described further below, the MR fluid 134 is specifically designed for use in a shear mode device, such as the prosthetic knee 110. For such a device, mechanically hard particles are desired. The carrier fluid also desirably experiences a less dramatic viscosity change over temperature changes as compared to other fluids.

In some embodiments, the MR fluid 134 has one or more of the following properties: a high magnetic flux capacity and low magnetic remanence and low viscosity while having a large magnetic field induced shearing stress. Advantageously, this allows the prosthetic knee 110 to provide a wide dynamic torque range.

In some embodiments, as described further below, the knee actuator 112 includes a pair of specially designed dynamic seals 162 (162a, 162b). The seals 162 run along rims of the respective side plates 116, 118 and provide a reliable dynamic seal between the side plates 116, 118 and the outer spline 132, thereby desirably allowing rotational motion while preventing leakage of the MR fluid 134 from the chamber 144. The specially designed dynamic seals 162 are configured so that the particles in the MR fluid 134 can flow in and out of the seals 162 (and, in particular, in some embodiments, as described further below, in and out of garter springs of the seals 162) without clogging them and thus advantageously preventing seal failure.

In one embodiment, as discussed further below, the rims of the core side plates 116, 118 are surface hardened to further improve dynamic seal performance. Advantageously, embodiments of the invention can have particular efficacy in providing substantially leak-proof sealing during handling and flow of small particle slurries by utilizing the specially designed dynamic seals 162.

In some embodiments, as described further below, the knee actuator 112 includes a flexible diaphragm assembly or device 146 in fluid communication with the MR fluid 134. The flexible device 146 advantageously prevents or mitigates undesirable pressure build up within the knee actuator 12, for example, due to fluid expansion or outgassing.

In some embodiments, as described further below, the chamber 144 is partially or not fully filled with the MR fluid 134 so that the remaining space contains a compressible gas that allows for fluid expansion and advantageously prevents or mitigates undesirable pressure build up. Also, when the MR fluid out gasses, it out gasses into the gas that is compressible and hence there is low pressure build up.

In some embodiments, as indicated above and also discussed further below, a degaussing technique is used to keep residual magnetism low by changing or reversing the current direction at selected intervals. Thus, the polarity and direction of the magnetic field 140 is reversed as indicated by the solid and dashed arrowheads. Advantageously, this allows the knee to "free-up" and desirably creates a low torque ability and wide dynamic torque range.

Advantageously, there is no or negligible pressure build up within the MR actuated prosthetic knee of embodiments of the invention. This substantially eliminates or reduces the chances of fluid leakage and failure of the knee, and hence desirably adds to the safety of the device.

Also advantageously, the multiple shearing surfaces or flux interfaces, provided by embodiments of the invention, behave like a torque multiplier and allow the viscous torque level to be stepped up to a desired maximum value without the use of an additional transmission or other auxiliary component.

For example, if two flux interfaces can provide a maximum viscous torque of about 1 N/m, then forty flux interfaces will be able to provide a viscous damping torque of about 40 N/m. In contrast, if a 40:1 step-up transmission is used to increase the viscous torque, disadvantageously, not only is the system reflected inertia magnified by a factor of about 1600, but the system weight, size and complexity are undesirably increased.

The multiple shearing surfaces or interfaces of embodiments of the prosthetic knee advantageously allow for a wide dynamic torque range to be achieved which permits safe and/or more natural ambulation for the patient. The low end torque is desirably kept to a minimal, in some embodiments, by a degaussing technique which allows the knee to swing substantially freely, as needed or desired.

Advantageously, the MR actuated prosthetic knee of embodiments of the invention provides a rapid and precise response. Again, this permits the patient to move in a safe and/or more natural manner.

FIGS. 5A–5E and 6 show different views of one embodiment of the prosthetic knee actuator assembly 112. As noted above, the knee actuator 112 generally comprises the core rod 113 and core side plates 116, 118, the coil 115, the inner blades 120 and the inner spline 122, the bearings 126, 128, the outer blades 130 and the outer spline 132, the side mounts 136, 138, the diaphragm assembly 146 and the dynamic seals 162.

As described in greater detail below, the knee actuator 112 further comprises an extension assist assembly or system 148, a shock absorbing or bumper assembly or system 150 on the side mounts 136, 138, a pyramid connector, adapter or stud 152 that facilitates connection to the stump socket 106 or the like, and a knee angle sensing or measuring assembly or system 154. The knee actuator 112 also comprises a plurality of fastening through rods, dowels or studs 158 and associated cone nuts 160, a pair of O-rings, seals or gaskets 182 that provide a seal between the inner spline 122 and associated core side plates 116, 118, and bolts 164 (164a, 164b) that facilitate a rigid connection between the side mounts 136, 138 and the frame and electronics assembly 114.

The knee actuator 112 also comprises a pair of right and left protective side caps 156 (156a, 156b). In the drawings only the left side cap 156b is shown and the right side cap 156a is substantially similar to the left side cap 156b.

Core Rod

FIGS. 7–11 show different views of one embodiment of the core rod 113. The core rod 113 generally includes a core or main body portion or section 166 that engages the core side plates 116, 118 and a mandrel portion or section 168.

The core portion 166 and the mandrel portion 168 are generally cylindrical in shape, though in modified embodiments other suitable shapes may be used with efficacy, as needed or desired. In the illustrated embodiment, the core portion 166 has an outer diameter that is greater than the outer diameter of the mandrel portion 168.

The core or core portion 166 is part of the magnetic return path through the knee actuator 112. The core portion 166 desirably has a substantially constant outer diameter along substantially its entire length. Advantageously, this improves the magnetic properties of the device by reducing or minimizing discontinuities in the magnetic field path.

The outer diameter of the core portion 166 is also dimensioned and configured such that the magnetic coil 115 fits over the core portion 166 with a suitably small tolerance fit. The core portion 166 is desirably compact so as to provide improved and/or suitable power efficiency. Advantageously, this also allows more coil turns in the coil 115 and allows higher and/or improved magnetic flux.

In one embodiment, the outer diameter of the core portion 166 is about 1.9 cm (¾ inch). In another embodiment, the outer diameter of the core portion 166 is in the range from about 1.3 cm (½ inch) to about 2.5 cm (1 inch), including all values and sub-ranges therebetween. In modified embodiments, other suitable dimensions may be efficaciously utilized, as needed or desired.

The core portion 166 has a free end 170 and an opposed end 172 connected to the mandrel portion 168. The free end 168 is dimensioned and configured to matingly engage the right core side 116. The opposite end 172 is dimensioned and configured to matingly engage the left core side 118. The core portion 166, and hence the core rod 113, rotate as the core side plates 116, 118 rotate.

In one embodiment, and as best seen in FIG. 8, the core portion end 170 has a generally circumferential chamfered, beveled or tapered surface 174. Advantageously, this facilitates mating engagement or mechanical connection with the right core side plate 116 utilizing a press fit technique.

The chamfer 174 desirably extends out through and beyond the right core side plate 116. Thus, advantageously, the chamfer 174 does not adversely affect the magnetic field 140 or magnetic properties of the device. This is at least partially because discontinuities in the magnetic field path 140 are substantially prevented, minimized or reduced and the magnetic circuit 140 is not saturated due to the chamfer 174, thereby providing higher flux.

In one embodiment, the core portion end 170 extends beyond the core side plate 116 by about 250 micrometers, microns or μm ($^{10}/_{1000}{}^{th}$ of an inch). In another embodiment, the core portion end 170 extends beyond the core side plate 116 by about 25 micrometers, microns or μm ($^{1}/_{1000}{}^{th}$ of an inch) to about 500 μm ($^{20}/_{1000}{}^{th}$ of an inch), including all values and sub-ranges therebetween. In modified embodiments, the core portion end 170 may extend a greater or lesser distance beyond the core side plate 116 with efficacy, as needed or desired.

In one embodiment, and as best seen in FIG. 8, the core portion end 172 has a generally circumferential chamfered, beveled or tapered surface 176. Advantageously, this facilitates mating engagement or mechanical connection with the left core side plate 116 utilizing a press fit technique.

The chamfer 176 desirably extends out through and beyond the left core side plate 118. Thus, advantageously, the chamfer 176 does not adversely affect the magnetic field 140 or magnetic properties of the device. This is at least partially because discontinuities in the magnetic field path 140 are substantially prevented, minimized or reduced and the magnetic circuit 140 is not saturated due to the chamfer 176, thereby providing higher flux.

In one embodiment, the core portion end 172 extends beyond the core side plate 118 by about 250 micrometers, microns or μm ($^{10}/_{1000}{}^{th}$ of an inch). In another embodiment, the core portion end 172 extends beyond the core side plate 118 by about 25 micrometers, microns or μm ($^{1}/_{1000}{}^{th}$ of an inch) to about 500 μm ($^{20}/_{1000}{}^{th}$ of an inch), including all values and sub-ranges therebetween. In modified embodiments, the core portion end 172 may extend a greater or lesser distance beyond the core side plate 118 with efficacy, as needed or desired.

In one embodiment, the outer diameter of the mandrel portion 168 is dimensioned and configured such that a spring of the extension assist 148 fits over the mandrel portion 168 with a suitably small tolerance fit, as described further below. The mandrel portion 168 has a slot, notch or groove 188 that receives a portion, such as the inner leg, of the spring to desirably provide precision angular location setting between the mating parts. The mandrel portion 168 also comprises a generally circular inner bore 190 that receives a bearing or other rotary transmission device of the extension assist 148.

In the illustrated embodiment, the mandrel portion 168 includes a slot notch or groove 192 through which a cable or wire of the magnetic coil 115 passes through. Advantageously, this provides an exit for the magnetic coil cable and can also facilitate in keeping the magnetic coil cable in place and prevent undesirable motion or movement of the cable.

In one embodiment, the mandrel portion 168 has a pin 194 or the like that is received into a notch of the left core side plate 118 that facilitates in aligning the core rod 113 with one or both of the core side plates 116, 118. The notches 188, 192 may also facilitate in alignment. Other suitable markings, indicia and the like may be efficaciously used to facilitate in alignment and orientation of the various parts of the prosthetic knee device, as needed or desired.

In one embodiment, and as seen for example in FIG. 8, the mandrel portion 168 has at its free end a generally circumferential chamfered, beveled or tapered surface 196. Advantageously, this facilitates mating engagement or mechanical connection with the extension assist spring utilizing a press fit technique or the like.

The core rod 113 desirably comprises a magnetically soft material of high flux saturation density, high magnetic permeability and low coercivity. In one embodiment, the core rod 113 comprises an iron-cobalt (FeCo) alloy with about 17% to about 50% cobalt (Co), including all values and sub-ranges therebetween. Examples of suitable materials include, but are not limited to, VACOFLUX 17 and VACOFLUX 50 as available from Vacuumschmelze of Hanau, Germany.

In one embodiment, the core rod 113 is fabricated by first annealing in air and then machining to the desired dimensions and configuration. Advantageously, the air annealing is economical in cost and results in a suitable hardness (or softness) that is easier to machine. The machining desirably also removes any impurities (e.g., oxidation layer) that may be present or may have been introduced or formed on the surface of the material, since the impurities do not penetrate deeper than a depth of 1–2 mm or less, which is within the depth of machining.

In another embodiment, the core rod 113 is fabricated by annealing in a vacuum or partial vacuum. Optionally, hydrogen annealing, which prevents oxidation, may be used though this tends to be expensive.

In one embodiment, the annealing temperature is about 820° C. In one embodiment, the annealing time is about 4 hours to 10 hours in dry hydrogen. In one embodiment, the rate of cooling is about 100° C./hour until a temperature of about 200° C. is reached and at temperatures lower than that any cooling rate in any atmosphere may be used.

Core Side Plates

The core side plates or disks 116, 118, along with the core portion 166, are part of the magnetic return path through the knee actuator 112. The right core side plate 116 engages the free core end 170 and the left core side plate 118 engages the opposite core end 172. The skilled artisan will appreciate that the right and left side arrangements may be transposed, interchanged or reversed with efficacy, as needed or desired.

FIGS. 12–16 show different views of one embodiment of the right core side plate 116. The right side plate 116 is generally circular in shape and is rotatably fitted within the outer spline 132 such that there can be relative rotational motion between the right side plate 116 and the outer spline 132.

The right side plate 116 includes a substantially central circular cavity, opening or through hole 178a which substantially irrotationally mates with the core end 170. In modified embodiments, other suitable irrotationally interlocking shapes may be efficaciously utilized to provide for mating between the right side plate 116 and the core rod 113.

The mating engagement desirably utilizes an interference or press fit so that the right side plate 116 and the core rod 113 rotate together, in tandem or synchronously. As indicated above, in one embodiment, the chamfer 174 of the core end 170 extends beyond the plate cavity 178a so that it is substantially isolated from the magnetic circuit 140 through the device.

The right side plate 116 includes a plurality of generally equidistantly spaced circularly arranged through holes 180a. Each of the through holes 180a receives a respective one of the through rods 158. The holes 180a are radially outwardly offset relative to the cavity 178a.

The right side plate 116 has an outer peripheral rim or edge 184a which is generally circumferential and on which is rotatably fitted a respective one of the specially designed dynamic seals 162a. As described further below, this provides a dynamic seal between the rotatable right side plate 116 and the inner surface of the outer spline 132 thereby preventing leakage of MR fluid 134. In a modified embodiment, a groove, notch or the like may be provided to receive the dynamic seal 162a or a modified form of it.

In one embodiment, the outer rim 184a is surface hardened to protect the rim or edge 184a from any undesirable scratching or damage during use or, such as, for example, during assembly of the knee actuator 112. Thus, a hardened ring is provided on the seal wear surface that improves the reliability of the dynamic seal.

The surface hardening of the outer rim 184a can be performed by a number of techniques including, but not limited to, plasma coating and the like. In one embodiment, a titanium nitride surface coating or layer provides the desired surface hardening. The titanium nitride coating desirably has a hardness of about 63 HRC though in modified embodiments the hardness can be more or less.

The right side plate 116 has an inwardly facing generally annular recess 186a with an associated edge or chamfered, beveled or tapered surface 198a. As described further below, the recess 186a receives one end of the inner spline 122 to generally align and locate the engaging parts. The inner spline end sealingly contacts the surface 198a via the O-ring 182a at a circular location that is positioned slightly radially outwards from the circle formed by the through holes 180a.

The right side plate 116 has an inwardly facing generally annular shoulder, step or surface 202a that abuts against one end of the magnetic coil 115. A coil protection washer or the like may be provided between the associated coil end and the shoulder 202a, as needed or desired. A tapered surface or portion 206a may be provided on the outer surface of the core plate 116 that advantageously preserves cross sectional path for magnetic flux and facilitates in evening out the magnetic flux as it travels through the side plate 116. The tapered surface or portion 206a can further decrease weight, save material and also provide clearance space to facilitate assembly.

In the illustrated embodiment, the outer surface of the right side plate 116 has one or more shoulders or steps 208a1, 208a2, 208a3 arranged in a generally circular or ring-like fashion for facilitating alignment and coupling with the right side mount 136. Gaps or notches between the shoulders 208a1, 208a2, 208a3 may facilitate alignment during assembly of the knee device and may also provide clearance space, such as, for example, for wires, leads and the like. Other suitable markings or indicia may be efficaciously utilized to facilitate alignment and assembly, as needed or desired.

FIGS. 17–21 show different views of one embodiment of the left core side plate 118. The left side plate 118 is generally circular in shape and is rotatably fitted within the outer spline 132 such that there can be relative rotational motion between the left side plate 118 and the outer spline 132.

The left side plate 118 includes a substantially central circular cavity, opening or through hole 178b which substantially irrotationally mates with the core end 172. In modified embodiments, other suitable irrotationally interlocking shapes may be efficaciously utilized to provide for mating between the left side plate 118 and the core rod 113.

The mating engagement desirably utilizes an interference or press fit so that the left side plate 118 and the core rod 113 rotate together, in tandem or synchronously. As indicated above, in one embodiment, the chamfer 176 of the core end 172 extends beyond the plate cavity 178b so that it is substantially isolated from the magnetic circuit 140 through the device.

The left side plate 118 includes a plurality of generally equidistantly spaced circularly arranged through holes 180b. Each of the through holes 180b receives a respective one of the through rods 158. The holes 180b are radially outwardly offset relative to the cavity 178b.

The left side plate 118 has an outer peripheral rim or edge 184b which is generally circumferential and on which is rotatably fitted a respective one of the specially designed dynamic seals 162b. As described further below, this provides a dynamic seal between the rotatable left side plate 118 and the inner surface of the outer spline 132 thereby preventing leakage of MR fluid 134. In a modified embodiment, a groove, notch or the like may be provided to receive the dynamic seal 162b or a modified form of it.

In one embodiment, the outer rim 184b is surface hardened to protect the rim or edge 184b from any undesirable scratching or damage during use or, such as, for example, during assembly of the knee actuator 112. Thus, a hardened ring is provided on the seal wear surface that improves the reliability of the dynamic seal.

The surface hardening of the outer rim 184b can be performed by a number of techniques including, but not limited to, plasma coating and the like. In one embodiment, a titanium nitride surface coating or layer provides the desired surface hardening. The titanium nitride coating desirably has a hardness of about 63 HRC though in modified embodiments the hardness can be more or less.

The left side plate 118 has an inwardly facing generally annular recess 186b with an associated edge or chamfered, beveled or tapered surface 198b. As described further below, the recess 186b receives one end of the inner spline 122 to generally align and locate the engaging parts. The inner spline end sealingly contacts the surface 198b via the O-ring 182b at a circular location that is positioned slightly radially outwards from the circle formed by the through holes 180b.

The left side plate 118 has an inwardly facing generally annular shoulder, step or surface 202b that abuts against one end of the magnetic coil 115. A coil protection washer or the like may be provided between the associated coil end and the shoulder 202b, as needed or desired. A tapered surface or portion 206b may be provided on the outer surface of the core plate 118 that advantageously preserves cross sectional path for magnetic flux and facilitates in evening out the magnetic flux as it travels through the side plate 118. The tapered surface or portion 206b can further decrease weight, save material and also provide clearance space to facilitate assembly.

In the illustrated embodiment, the outer surface of the left side plate 118 has one or more shoulders or steps 208b1, 208b2, 208b3, 208b4 arranged in a generally circular or ring-like fashion for facilitating alignment and coupling with the left side mount 138. Gaps or notches between the shoulders 208b1, 208b2, 208b3, 208b4 may facilitate alignment during assembly of the knee device and may also provide clearance space, such as, for example, for wires, leads and the like. Other suitable markings or indicia may be efficaciously utilized to facilitate alignment and assembly, as needed or desired.

In the illustrated embodiment, the left side plate 118 includes a notch, groove or recess 212 generally between the shoulders 208b3, 208b4. Advantageously, the notch 212 and the gap between the 208b3, 208b4 provides clearance space for passage of a cable, lead or wire of the magnetic coil 115. Alternatively, or in addition, a similar cable-receiving notch may be provided on the right side plate 118, as needed or desired.

The core side plates 116, 118 desirably comprise a magnetically soft material of high flux saturation density, high magnetic permeability and low coercivity while maintaining suitable mechanical properties such as hardness, strength and ductility. In one embodiment, the core side plates 116, 118 comprise an iron-cobalt (FeCo) alloy with about 50% iron (Fe) and about 50% cobalt (Co) such as VACODUR 50 as available from Vacuumschmelze of Hanau, Germany. VACODUR 50 has the desired magnetic properties and optimum mechanical properties including improved strength and ductility.

In modified embodiments, the core side plates 116, 118 can comprise an iron-cobalt (FeCo) alloy with about 17% to about 50% cobalt (Co), including all values and sub-ranges therebetween. Examples of suitable materials include, but are not limited to, VACOFLUX 17 and VACOFLUX 50 as available from Vacuumschmelze of Hanau, Germany.

In one embodiment, the core side plates 116, 118 are fabricated by first annealing in air and then machining to the desired dimensions and configuration. Advantageously, the air annealing is economical in cost and results in a suitable hardness (or softness) that is easier to machine. The machining desirably also removes any impurities (e.g., oxidation layer) that may be present or may have been introduced or formed on the surface of the material, since the impurities do not penetrate deeper than a depth of 1–2 mm or less, which is within the depth of machining.

In another embodiment, the core side plates 116, 118 are fabricated by annealing in a vacuum or partial vacuum. Optionally, hydrogen annealing, which prevents oxidation, may be used though this tends to be expensive.

In one embodiment, the annealing temperature is about 820° C. In one embodiment, the annealing time is about 4 hours to 10 hours in dry hydrogen. In one embodiment, the rate of cooling is about 100° C./hour until a temperature of about 200° C. is reached and at temperatures lower than that any cooling rate in any atmosphere may be used.

Bearings

Figure 22:
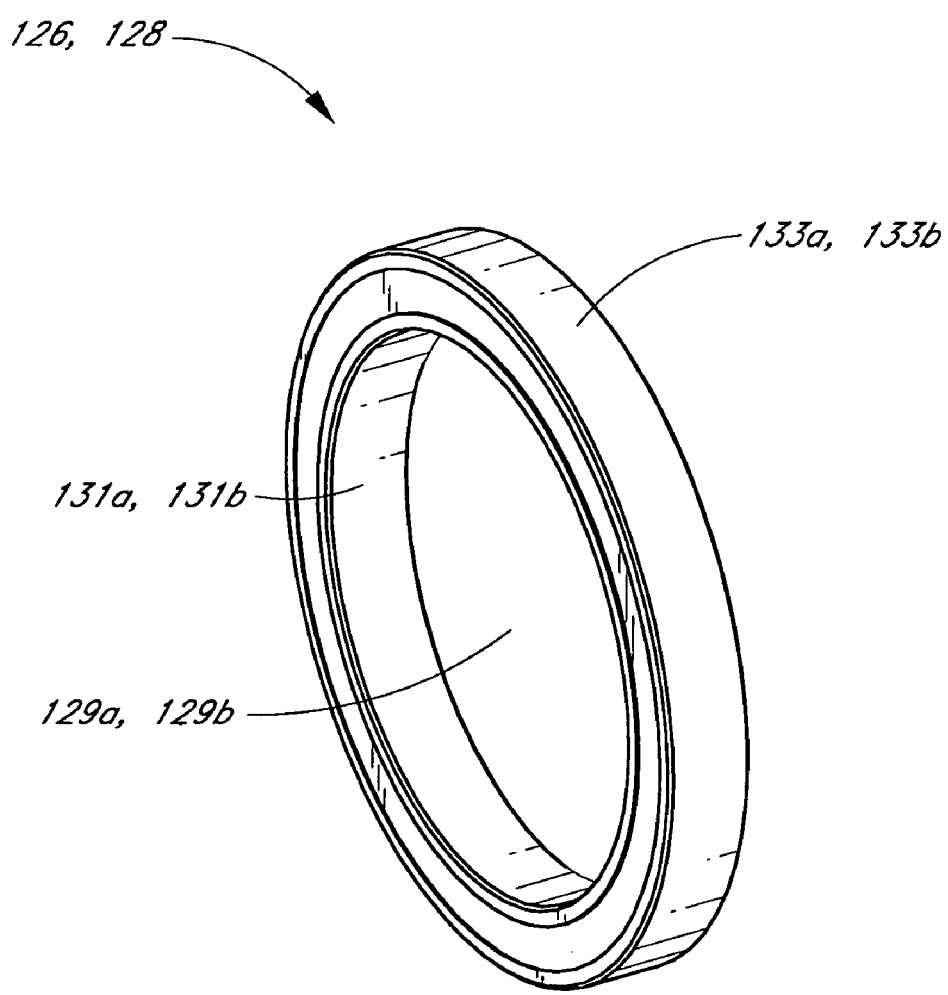
FIG. 22 is a simplified perspective view of a bearing of the actuator of FIG. 6 illustrating features and advantages in accordance with an embodiment of the invention.
Figure 27:
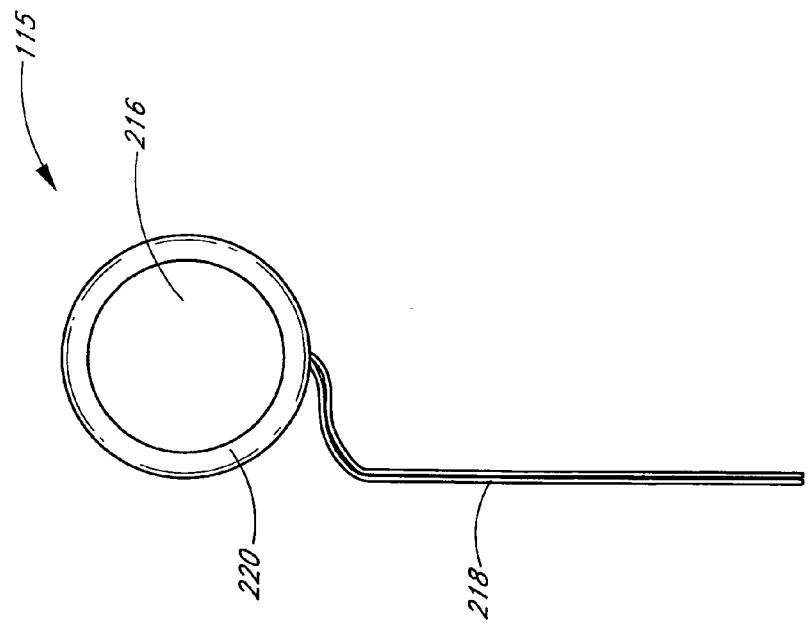
FIG. 27 is a simplified rear end view of the magnetic coil of FIG. 23 illustrating features and advantages in accordance with an embodiment of the invention.
Figure 26:
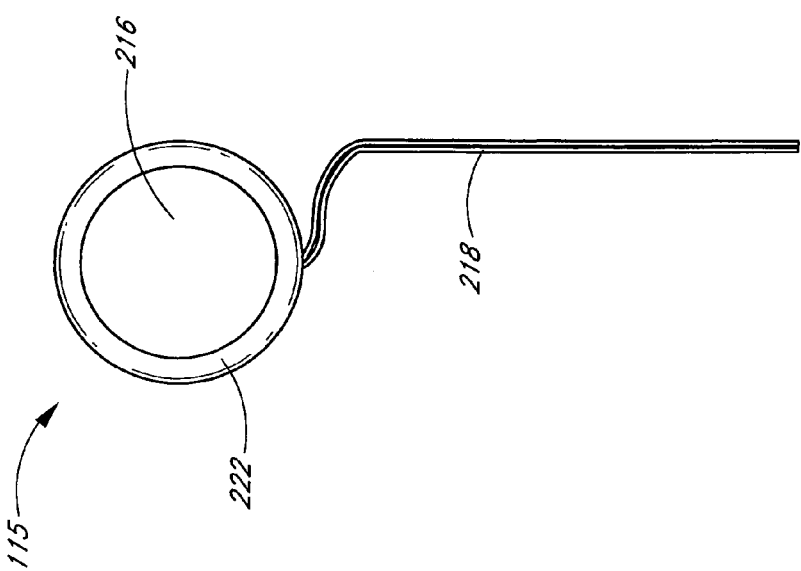
FIG. 26 is a simplified front end view of the magnetic coil of FIG. 23 illustrating features and advantages in accordance with an embodiment of the invention.

FIG. 22 shows the bearings 126, 128 in accordance with one embodiment. The bearings 126, 128, in one embodiment, form a press fit with the outer spline 132 and the respective side mounts 136, 138. The bearings 126, 128 are arranged so that they facilitate rotation of the outer spline 132 substantially independently of the rotation of the side mounts 136, 138.

Each of the bearings 126, 128 generally comprises a respective central cavity 129a, 129b, a respective inner bearing surface 131a, 131b and an outer bearing surface. The inner bearing surfaces 131a, 131b are engaged with respective side mounts 136, 138 to facilitate rotation and the outer bearing surfaces 133a, 133b are engaged with the outer spline 132 to facilitate rotation.

The bearings 126, 128 can comprise any one of a number of suitable devices that transmit rotary motion and/or load while reducing frictional wear between the coupled components. In one embodiment, the bearings 126, 128 comprise ball bearings. In modified embodiments, the bearings 126, 128 can comprise any suitable combination of ball bearings, roller bearings, ball thrust bearings, roller thrust bearings, tapered roller bearings and the like, as needed or desired.

Magnetic Coil

FIGS. 23–27 show different views of one embodiment of the magnetic coil, electromagnetic or wire spool 115. In the illustrated embodiment, the magnetic coil 115 is without a bobbin or is bobbin-less and comprises copper wire or winding 214. Advantageously, the bobbin-less coil 115 has an increased relative proportion of copper which desirably results in improved performance efficiency and/or reduced electrical resistance.

The coil wire 214 is arranged in a generally circular arrangement and has a generally cylindrical cavity or through passage 216 which fits over the core portion 166 of the core rod 113 to mechanically connect the magnetic coil 115 and the core rod 113. Thus, as the core rod 113 (and core side plates 116, 118) rotate so does the magnetic coil 115. In one embodiment, the coil 115 forms a close slip fit with the core rod 113, for example, with a clearance of about $5/1000^{th}$ of an inch or less.

The coil wire 214 terminates in a power input or connection cable or lead wires 218 that is connected to a battery, power source or the like. The cable 218 is desirably shielded. The cable 218 passes through the mandrel portion slot 192 and the left side plate notch 212, along the left side mount 138 and finally connects to the frame and electronics assembly 114. A suitable connector or the like is provided at the free end of the cable 218 to facilitate connection to the frame and electronics assembly 114.

The coil wire 214 has a pair of generally annular spaced opposed ends 220, 222 which are in mechanical communication with a respective one of the core side plate annular shoulders 202a, 202b. The coil ends 220, 222 may directly abut against respective shoulders 202a, 202b or coil protection washers (e.g. foam washers) may be placed between the coil ends 220, 222 and respective shoulders 202a, 202b, as needed or desired.

The coil wire 214 cross-section is generally circular or ellipsoidal. In a modified embodiment, the coil wire 214 cross-section is generally square or rectangular. The square or rectangular cross-section desirably provides for a higher packing efficiency though the cost can also be higher.

In another embodiment, a plurality of magnetic coils arranged in parallel are utilized to generate the magnetic field within the knee actuator 112. The multiple coil arrangement has an increased relative proportion of copper which desirably results in improved performance efficiency and/or reduced electrical resistance. The multiple coil arrangement can also provide enhanced frequency response characteristics.

Inner Spline

FIGS. 28–32 show different views of one embodiment of the rotary inner spline 122. The inner spline 122 generally circumscribes or envelops the magnetic coil or electromagnet 115 and is coupled or mechanically connected to the side plates 116, 118. The inner blades or rotors 120 are fitted over the inner spline 122 and are generally concentrically arranged about the brake axis of rotation 124. The inner spline 122 is rotatable about the knee joint axis of rotation 124, and hence so are the blades or rotors 120 and the core side plates 116, 118. Rotation of the inner spline 122 corresponds to rotation or movement of the lower (below the knee) part of the leg.

In the illustrated embodiment, the inner spline 122 is generally cylindrical in shape and comprises a substantially central cylindrical cavity or through hole 224. The inner spline cavity 224 receives the electromagnet or magnetic coil 115 which is rotatable along with the inner spline 122.

The exterior surface of the inner spline 122 comprises a plurality of longitudinal grooves, notches, splines or keyways 226 that extend generally parallel to the axis of rotation 124 and securely engage or mate with corresponding teeth or keys of the inner blades 120. In the illustrated embodiment, the inner spline 122 comprises nine substantially equally spaced grooves 226. In modified embodiments, fewer or more teeth-engaging grooves arranged in other suitable manners may be efficaciously utilized, as needed or desired.

The grooves 226 are desirably generally rectangular or square shaped to facilitate reliable load or torque transmission between the inner spline 122 and the inner rotors 120. In modified embodiments, the grooves 226 may have other suitable shapes such as round, semi-circular, curved, polygonal, and combinations thereof among others, with efficacy, as needed or desired.

In the illustrated embodiment, the inner spline 122 includes three longitudinal dowel-receiving holes, cavities or passages 228 that are arranged substantially equidistantly and in a generally circular fashion. In modified embodiments, fewer or more dowel-receiving passages arranged in other suitable manners may be efficaciously utilized, as needed or desired.

The passages 228 are substantially aligned with the holes 180a, 180b of respective core side plates 116, 118. The passages 228 (and holes 180a, 180b) receive a respective one of the studs or rods 158 to secure selected components of the knee actuator 112, such as the core side plates 116, 118 and the inner spline 122.

In the illustrated embodiment, the inner spline cavity 224 further includes a plurality of longitudinal recesses 230. The recesses 230 desirably serve to reduce the weight of the inner spline 122, and hence that of the knee actuator 112 and prosthetic knee 110.

Figure 29:
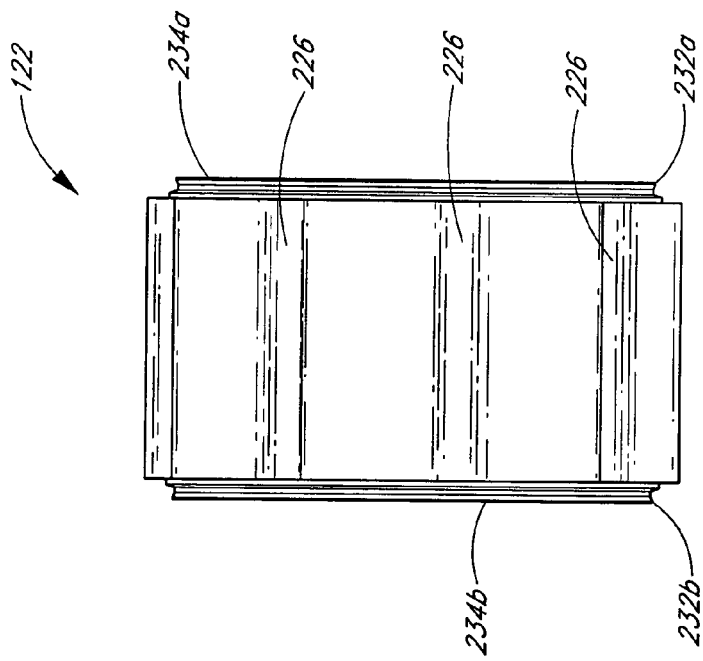
FIG. 29 is a simplified side view of the inner spline of FIG. 28 illustrating features and advantages in accordance with an embodiment of the invention.
Figure 28:
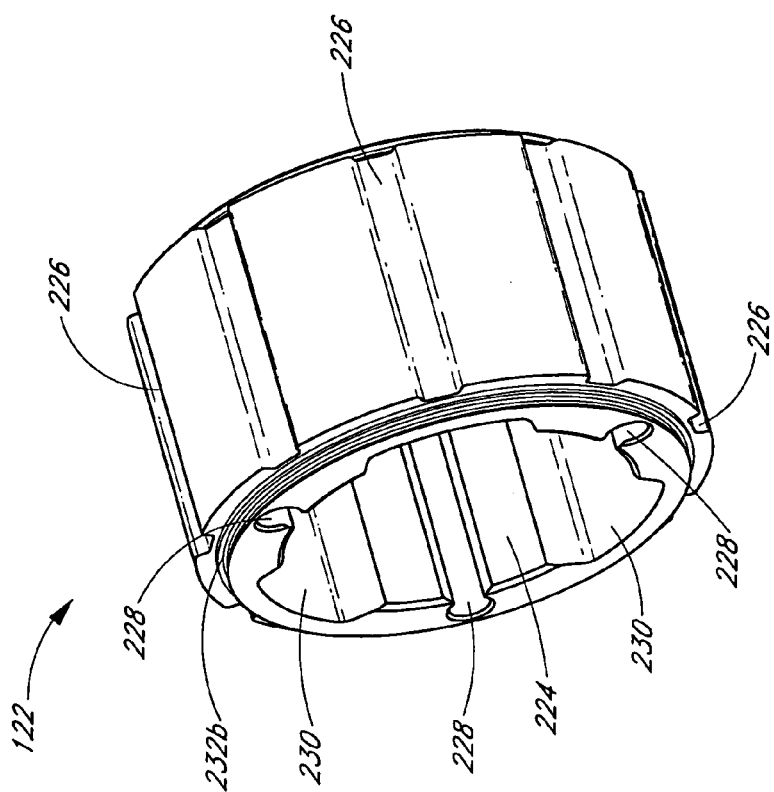
FIG. 28 is a simplified perspective view of an inner spline of the actuator of FIG. 6 illustrating features and advantages in accordance with an embodiment of the invention.
Figure 30:
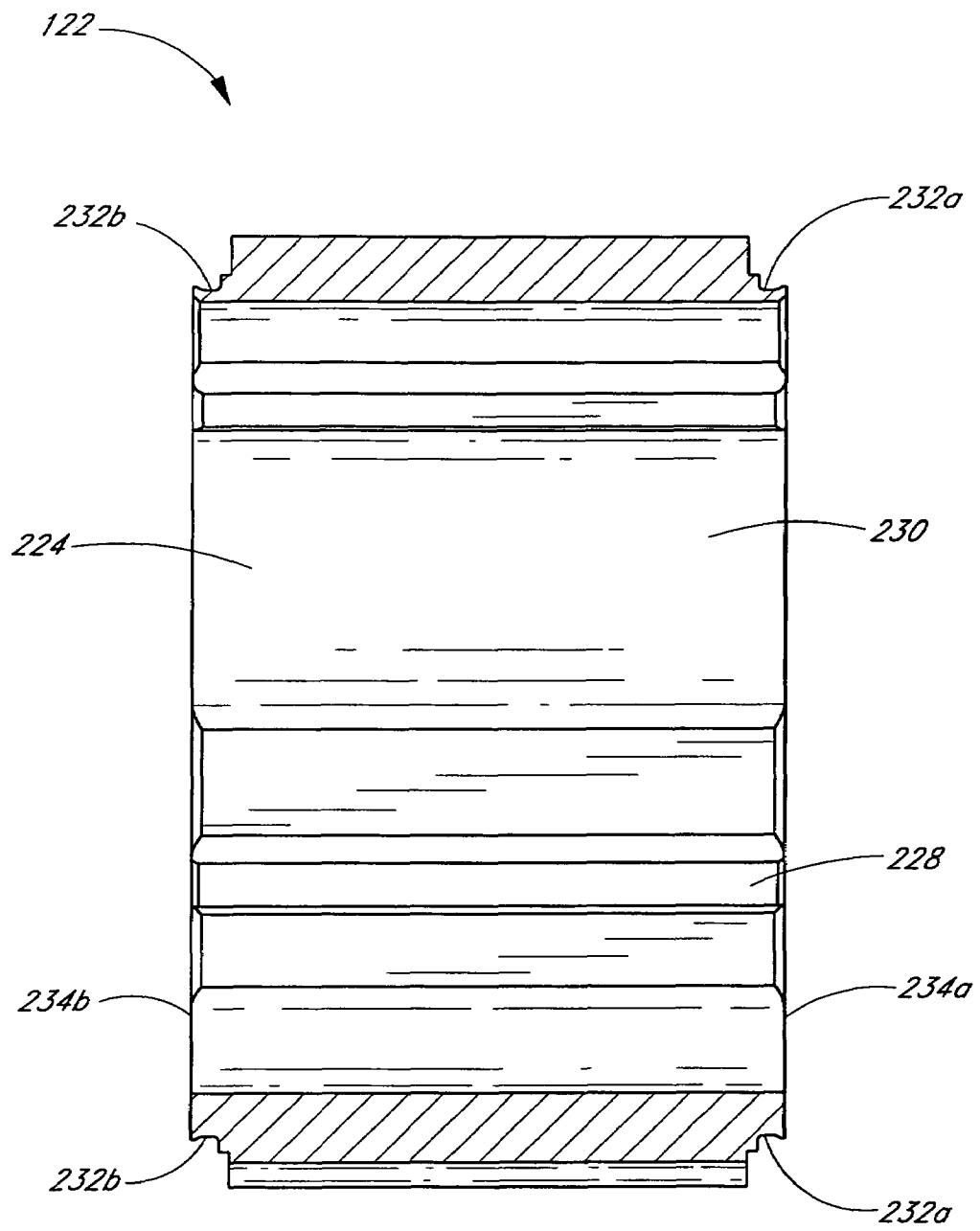
FIG. 30 is a simplified sectional view along line 30—30 of FIG. 31 illustrating features and advantages in accordance with an embodiment of the invention.

In the illustrated embodiment, and as best seen in FIGS. 29 and 30, inner spline ends 234a, 234b each have a respective generally circular groove or flange 232a, 232b that receives a respective one of the O-rings or gaskets 182a, 182b. The inner spline ends 234a, 234b extend at least partially into the respective core side plate recesses 186a, 186b.

The O-rings 182a, 182b seal against respective side plate edges or surfaces 198a, 198b to form a static seal between the rotatable inner spline 122 and the rotatable core side plates 116, 118 since these components rotate together during knee rotation. The static seal desirably prevents leakage of MR fluid 134 from the knee actuator chamber 144 (see, for example, FIG. 4). In one embodiment, the O-rings 182 comprise Viton® which has desirable properties to operate with oils and the like. In modified embodiments, the O-rings 182 can comprise any one of a number of suitable seal-providing materials such as rubber, Teflon® and Neoprene among others, as needed or desired.

The inner spline 122 is desirably fabricated from titanium or a titanium alloy, such as 6Al-4V titanium alloy, to provide a non-ferrous yet strong, hard surface with low weight to engage the rotors 120 and transmit torque from them. Advantageously, the use of titanium or titanium alloys provides a near zero magnetic permeability and a yet strong, hard surface. An additional benefit is that the high resistivity of the material (titanium or titanium alloy) reduces energy losses due to induced eddy currents. In modified embodiments, the inner spline 122 can be efficaciously fabricated from other suitable metals, alloys, plastics, ceramics, among others, as required or desired.

The inner spline 122 is desirably formed by machining, such as wire electro-discharge machining (EDM). In another embodiment, the inner spline 122 is formed by broaching. In modified embodiments, the inner spline 122 can be efficaciously fabricated from other suitable techniques, for example, casting, forging, molding, laser processing, among others, as required or desired.

Inner Rotors

Figures 34, 35:
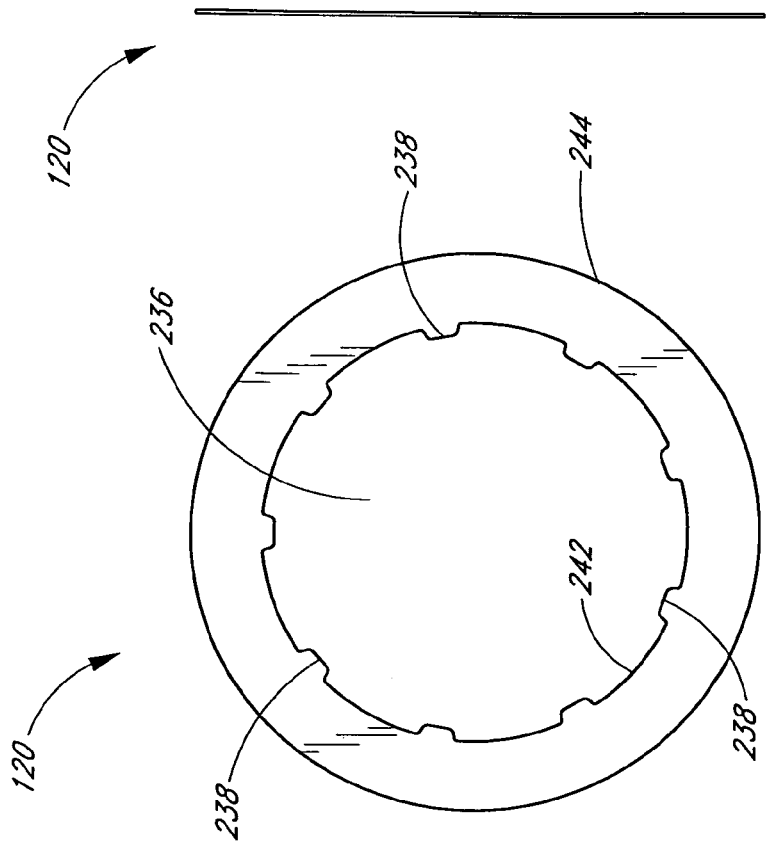
FIG. 34 is a simplified front (or rear) view of the inner rotor of FIG. 33 illustrating features and advantages in accordance with an embodiment of the invention.
FIG. 35 is a simplified side view of the inner rotor of FIG. 33 illustrating features and advantages in accordance with an embodiment of the invention.
Figure 33:
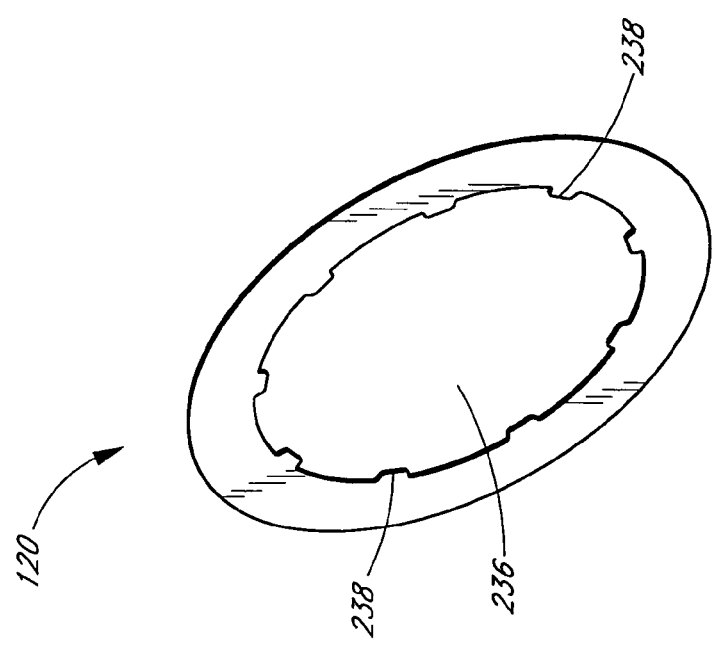
FIG. 33 is a simplified perspective view of one of the inner rotors of the actuator of FIG. 6 illustrating features and advantages in accordance with an embodiment of the invention.

FIGS. 33–35 show different views of one embodiment of the rotary inner blades, plates or rotors 120. The inner blades 120 are mechanically coupled, communicated or connected with the inner spline 122 and are substantially concentrically arranged about the knee actuator or brake axis of rotation 124. The inner blades 120 rotate with the inner spline 122 about the axis of rotation 124.

In the illustrated embodiment, the inner blades 120 are generally circular in shape with an annular or ring shaped profile and a generally uniform and thin thickness. The blades 120 comprise a substantially central cavity or through hole 236 that receive the inner spline 122. The blades 120 have a plurality of inwardly extending teeth, splines or keys 238 on their inner edges or peripheries 242 that engage or mate with the inner spline grooves or key-ways 226 to secure the blades 120 to the inner spline 122.

In the illustrated embodiment, the inner blades 120 each comprise nine approximately equally spaced teeth 238 which are generally rectangular or square shaped to facilitate torque or load transmission between the blades 120 and the inner spline 122. In modified embodiments, the blades 120 may efficaciously comprise fewer or more teeth 238 arranged in other suitable manners and having modified shapes, such as other polygonal, semi-circular or curved configurations, as needed or desired.

The inner blades 120 desirably comprise a magnetically soft material of high flux saturation density, high magnetic permeability and low coercivity while maintaining suitable mechanical properties such as hardness, strength and ductility. The low coercivity advantageously results in minimal or low build-up of residual magnetism within the device. In one embodiment, the inner blades 120 comprise an iron-cobalt (FeCo) alloy with about 50% iron (Fe) and about 50% cobalt (Co) such as VACODUR 50 as available from Vacuumschmelze of Hanau, Germany. VACODUR 50 has the desired magnetic properties and optimum mechanical properties including improved strength and ductility. In another embodiment, the inner blades 120 comprise spring steel which is desirably magnetically soft and mechanically hard to enhance durability and minimize wear.

In modified embodiments, the inner blades 120 may comprise other suitable materials that are magnetically soft and mechanically hard to enhance durability and minimize wear. These include blue temper steel and silicon steel.

The inner blades 120 are desirably formed by machining, such as wire electro-discharge machining (EDM). Advantageously, this permits a high degree of manufacturing precision and avoids or mitigates any undesirable backlash, jarring or play between the rotors 120 and inner spline 122 which may otherwise cause discomfort to the patient. In another embodiment, the inner blades 120 are formed by stamping. In yet another embodiment, the inner blades 120 are formed by laser processing. In modified embodiments, the inner blades 120 can be efficaciously fabricated from other suitable techniques, for example, casting, forging, molding, among others, as required or desired.

Figure 36:
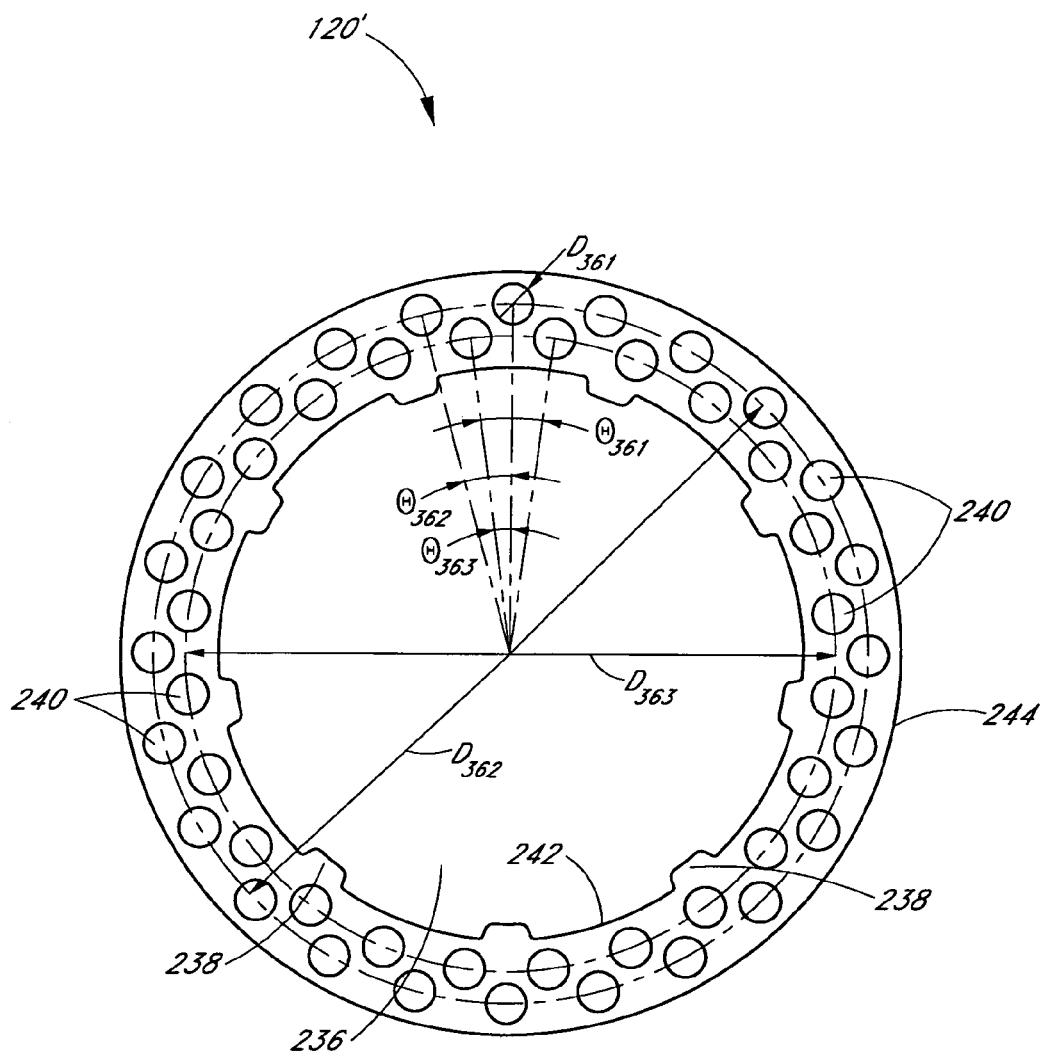
FIG. 36 is a simplified front (or rear view) of an inner rotor illustrating features and advantages in accordance with another embodiment of the invention.

FIG. 36 shows an inner blade 120' in accordance with a modified embodiment. The inner blade 120' has a plurality of through holes 240. Alternatively, or in addition, cross channels may be provided at inner and/or outer edges 242, 244 of the blade 120'.

The holes 240 (and/or cross channels) impose a discontinuous path that can, in some embodiments, desirably improve magnetic properties of the knee device. In some embodiments, advantageously, the holes 240 (and/or cross channels) can improve the high-end torque, add to device life by increasing the MR fluid volume and improve power efficiency.

In the illustrated embodiment, the holes 240 are arranged in generally circular rows with a staggered configuration, though in modified embodiments other suitable hole arrangements may be efficaciously used, as needed or desired. In one embodiment, the hole diameter $D_{361}$ is about 2.71 mm (0.1065 inches), the outer row diameter $D_{362}$ is about 44.58 mm (1.755 inches), the inner row diameter $D_{363}$ is about 40.51 mm (1.595 inches), the angles $\theta_{361}$ and $\theta_{362}$ are about 15° and the angle $\theta_{363}$ is about 7.5°. In modified embodiments, other suitable dimensions may be used with efficacy, as needed or desired.

In a modified embodiment, the rotors 120 have a generally polygonal inner periphery with multiple sides, for example, six, eight, twelve, etc., for interlocking with a mating configuration of the inner spline 122. This embodiment may or may not include the inner blade teeth 238.

Outer Rotors

FIGS. 37–39 show different views of one embodiment of the rotary outer blades, plates or rotors 130. The outer blades 130 are mechanically coupled, communicated or connected with an outer spline, housing, shell or rotor head 132 and are substantially concentrically arranged about the axis of rotation 124. The outer blades 130 rotate with the outer spline 132 about the axis of rotation 124.

In the illustrated embodiment, the outer blades 130 are generally circular in shape with an annular or ring shaped profile and a generally uniform and thin thickness. The blades 130 comprise a substantially central cavity or through hole 246 that non-contactingly receives the inner spline 122. The blades 130 have a plurality of outwardly extending teeth, splines or keys 248 on their outer edges or peripheries 254 that engage or mate with grooves or key-ways on the interior of the rotatable outer spline 132 to secure the blades 130 to the outer spline 132.

In the illustrated embodiment, the outer blades 130 each comprise nine approximately equally spaced teeth 248 which are generally rectangular or square shaped to facilitate engagement and torque or load transmission between the blades 130 and the outer spline 132. In modified embodiments, the blades 130 may efficaciously comprise fewer or more teeth 248 arranged in other suitable manners and having modified shapes, such as other polygonal, semi-circular or curved configurations, as needed or desired.

The outer blades 130 desirably comprise a magnetically soft material of high flux saturation density, high magnetic permeability and low coercivity while maintaining suitable mechanical properties such as hardness, strength and ductility. The low coercivity advantageously results in minimal or low build-up of residual magnetism within the device. In one embodiment, the outer blades 130 comprise an iron-cobalt (FeCo) alloy with about 50% iron (Fe) and about 50% cobalt (Co) such as VACODUR 50 as available from Vacuumschmelze of Hanau, Germany. VACODUR 50 has the desired magnetic properties and optimum mechanical properties including improved strength and ductility. In another embodiment, the outer blades 130 comprise spring steel which is desirably magnetically soft and mechanically hard to enhance durability and minimize wear.

In modified embodiments, the outer blades 130 may comprise other suitable materials that are magnetically soft and mechanically hard to enhance durability and minimize wear. These include blue temper steel and silicon steel.

The outer blades 130 are desirably formed by machining, such as wire electro-discharge machining (EDM). Advantageously, this permits a high degree of manufacturing precision and avoids or mitigates any undesirable backlash, jarring or play between the rotors 130 and outer spline 132 which may otherwise cause discomfort to the patient. In another embodiment, the outer blades 130 are formed by stamping. In yet another embodiment, the outer blades 130 are formed by laser processing. In modified embodiments, the outer blades 130 can be efficaciously fabricated from other suitable techniques, for example, casting, forging, molding, among others, as required or desired.

Figure 40:
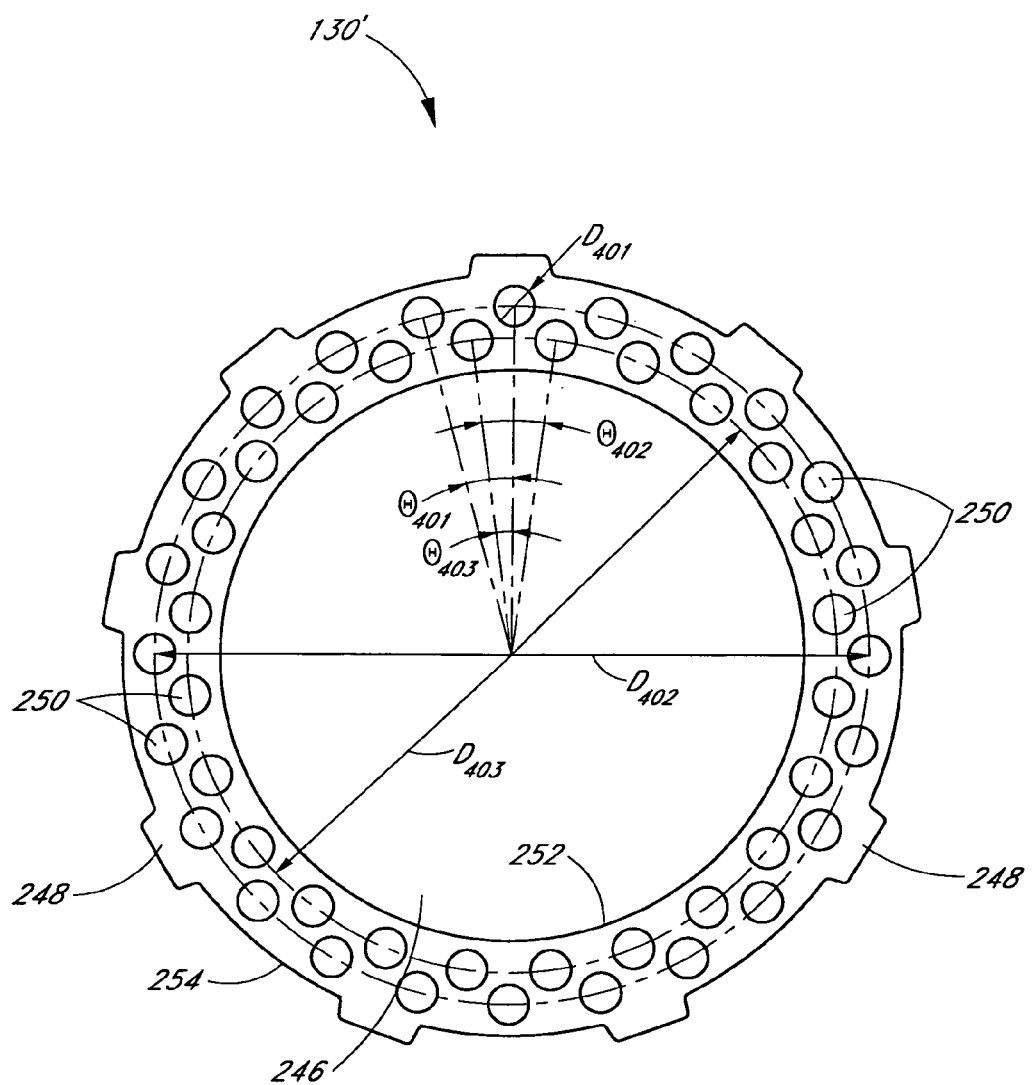
FIG. 40 is a simplified front (or rear view) of an outer rotor illustrating features and advantages in accordance with another embodiment of the invention.
Figure 41:
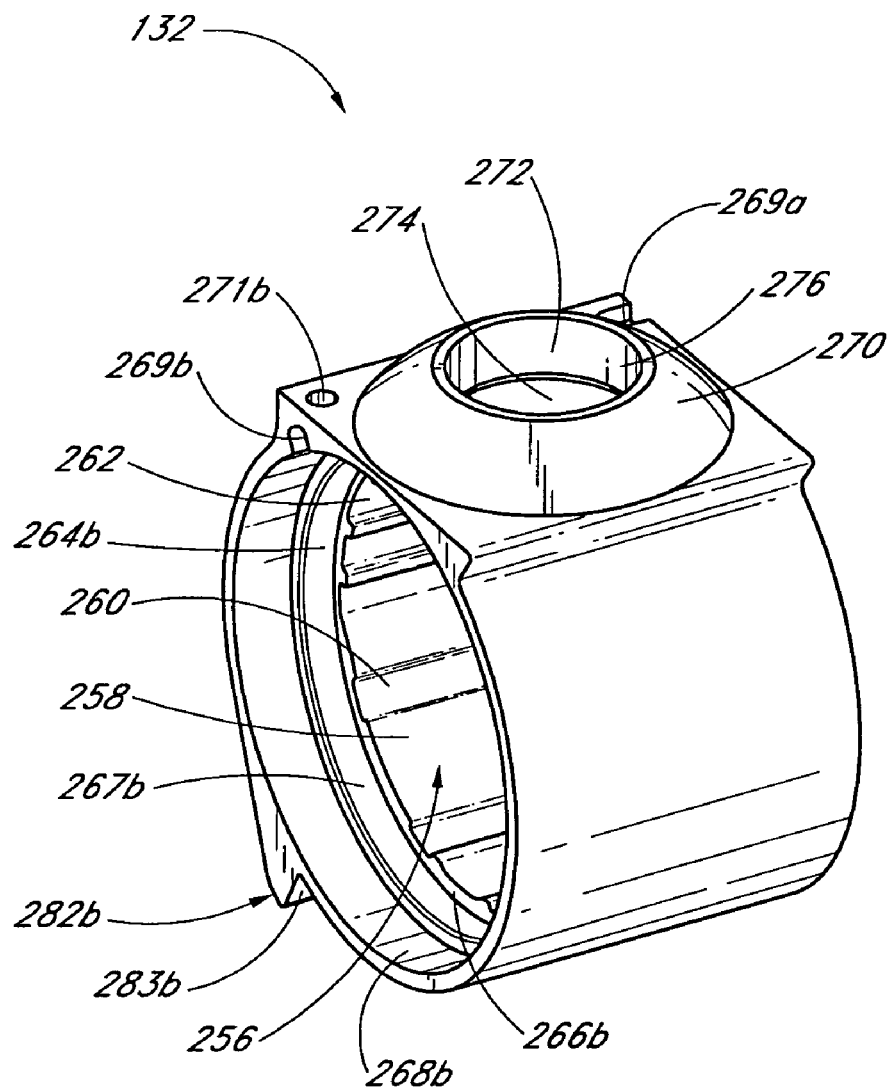
FIG. 41 is a simplified perspective view of an outer spline of the actuator of FIG. 6 illustrating features and advantages in accordance with an embodiment of the invention.
Figure 44:
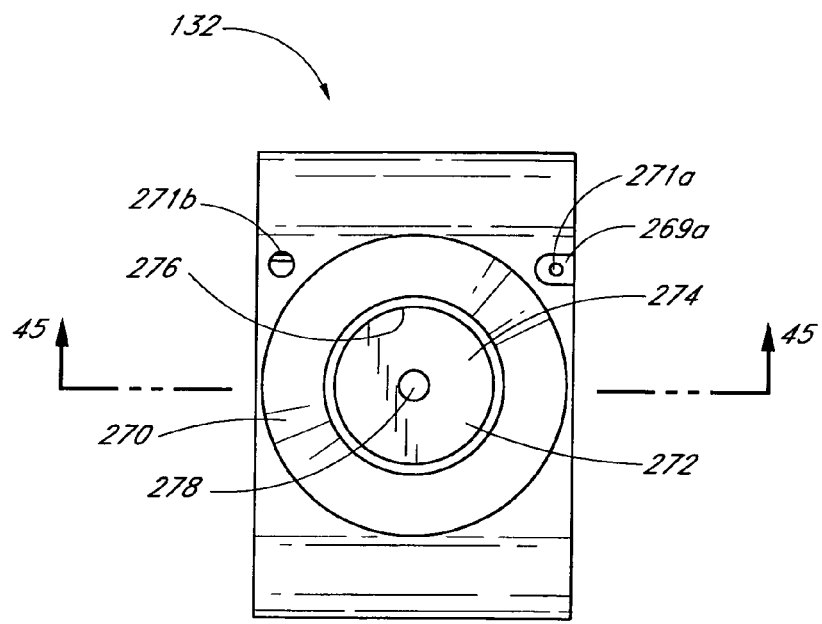
FIG. 44 is a simplified top view of the outer spline of FIG. 41 illustrating features and advantages in accordance with an embodiment of the invention.
Figure 45:
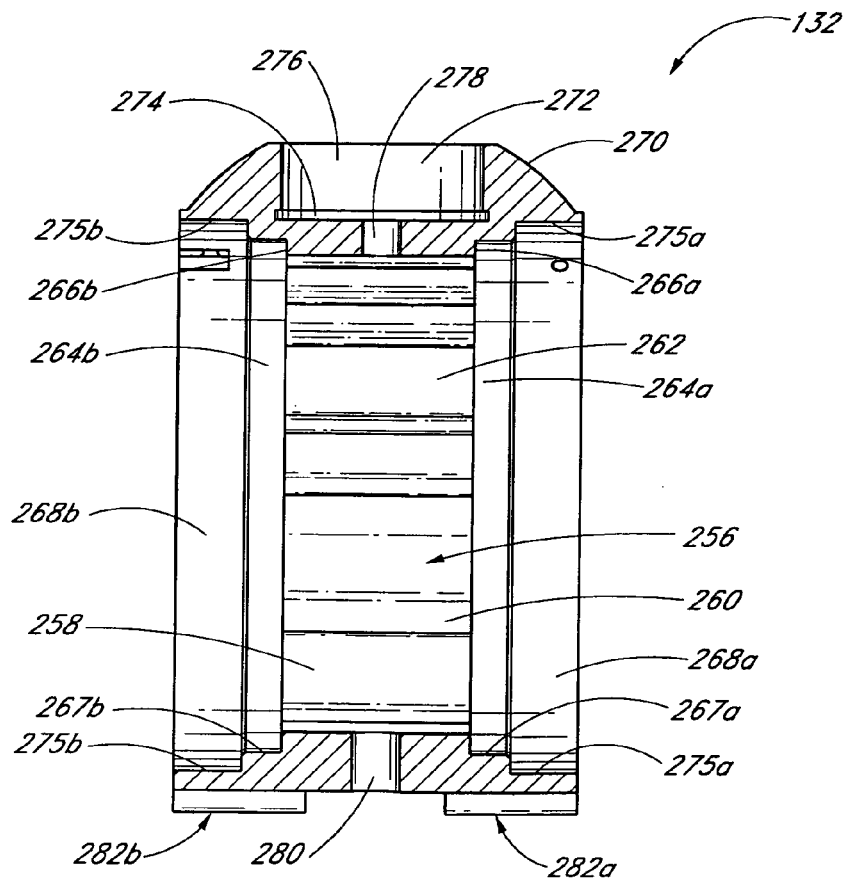
FIG. 45 is a simplified sectional view along line 45—45 of FIG. 44 illustrating features and advantages in accordance with an embodiment of the invention.

FIG. 40 shows an outer blade 130' in accordance with a modified embodiment. The outer blade 130' has a plurality of through holes 250. Alternatively, or in addition, cross channels may be provided at inner and/or outer edges 252, 254 of the blade 130'.

The holes 250 (and/or cross channels) impose a discontinuous path that can, in some embodiments, desirably improve magnetic properties of the knee device. In some embodiments, advantageously, the holes 250 (and/or cross channels) can improve the high-end torque, add to device life by increasing the MR fluid volume and improve power efficiency.

In the illustrated embodiment, the holes 250 are arranged in generally circular rows with a staggered configuration, though in modified embodiments other suitable hole arrangements may be efficaciously used, as needed or desired. In one embodiment, the hole diameter $D_{401}$ is about 2.71 mm (0.1065 inches), the outer row diameter $D_{402}$ is about 44.58 mm (1.755 inches), the inner row diameter $D_{403}$ is about 40.51 mm (1.595 inches), the angles $\theta_{401}$ and $\theta_{402}$ are about 15° and the angle $\theta_{403}$ is about 7.5°. In modified embodiments, other suitable dimensions may be used with efficacy, as needed or desired.

In a modified embodiment, the rotors 130 have a generally polygonal outer periphery with multiple sides, for example, six, eight, twelve, etc., for interlocking with a mating configuration of the outer spline 132. This embodiment may or may not include the outer blade teeth 248.

Rotor Arrangement and Spacing

The inner blades 120 and outer blades 130 are interspersed in an alternating fashion about the axis of rotation 124. The blades 120, 130 extend into the chamber 144 (see, for example, FIG. 4) that contains magnetorheological (MR) fluid 134. Gaps between adjacent blades 120 and 130 include the magnetorheological (MR) fluid 134. During knee joint rotation, the MR fluid 134 in the gaps between the inner blades 120 and outer blades 130 is sheared to generate a damping torque to control the limb rotation.

The inner blades 120 are substantially rotationally fixed relative to the inner spline 122 and the outer blades 130 are substantially rotationally fixed relative to the outer spline 132. The rotation of the inner blades 120, inner spline 122, outer blades 130 and outer spline 132 is substantially around or about the knee axis of rotation 124.

During various stages of locomotion or knee rotation, the inner blades 120 may rotate while the outer blades 130 are rotationally substantially stationary, or the outer blades 130 may rotate while the inner blades 120 are rotationally substantially stationary, or both the inner blades 120 and the outer blades 130 may rotate or be substantially rotationally stationary. Thus, relative rotational motion is created between the inner blades 120 and the outer blades 130 with the MR fluid 134 being sheared in the gaps between adjacent inner and outer blades 120 and 130.

The optimal blade gap size or spacing ($G_b$) depends on several factors. One factor is the size or diameter ($D_p$) of the particles of the MR fluid 134. The gap size ($G_b$) can be selected to optimize fluid longevity by being at least about the order of the particle size ($D_p$). Other factors include the thickness of the blades 120, 130 and the number of blades 120, 130.

It is also desirable to minimize the MR fluid gap between adjacent rotors 220 and stators 230 since the power needed to saturate the total MR fluid gap is a strong function of the gap size ($G_b$). Thus, advantageously, a smaller gap size renders the knee device more efficient and reduces power consumption.

In one embodiment, the gap size or blade spacing ($G_b$) is about 18 microns or µm (0.0007 inches). In another embodiment, gap size or blade spacing ($G_b$) is in the range from about 13 µm (0.0005 inches) to about 130 µm (0.005 inches), including all values and sub-ranges therebetween. In yet another embodiment, gap size or blade spacing ($G_b$) is in the range from about 5 µm (0.0002 inches) to about 250 µm (0.01 inches), including all values and sub-ranges therebetween. A more durable MR fluid, some embodiments of which are described in further detail below, desirably allows for a smaller gap size ($G_b$).

In one embodiment, the ratio of the gap size ($G_b$) and the particle size ($D_p$) is generally given by the following relationship, including all values and sub-ranges therebetween, with the upper limit of the range generally corresponding to the largest gap size and the smallest particle size:

$$1 \le \frac{G_b}{D_p} \le 650$$

In one embodiment, the knee actuator 112 comprises $N_{outer}$ outer blades 130 and $N_{inner}$ inner blades 120 where $N_{inner}=(N_{outer}-1)$ and $N_{outer}$ and $N_{inner}$ are positive integers. The outer blades 130 and the inner blades 120 alternate to form a blade stack or set with an outer blade 130 at the beginning and end of the blade stack. This results in $N_{inner}$ number of flux interfaces and ($2 \times N_{inner}$) or ($N_{inner}+N_{outer}-1$) fluid gaps between the blades 120 and 130 in which the magnetorheological (MR) fluid 134 resides. When the side plates 116, 118 are included in the configuration, this results in $N_{outer}$ number of flux interfaces and ($2 \times N_{outer}$) or ($N_{inner}+N_{outer}+1$) fluid gaps in which the magnetorheological (MR) fluid 134 resides.

In one embodiment, the knee actuator 112 comprises about 59 blades with 29 inner blades 120 and 30 outer blades 130. In another embodiment, the knee actuator 112 comprises about 61 blades with 30 inner blades 120 and 31 outer blades 130. In yet another embodiment, the knee actuator 112 comprises about 83 blades with 41 inner blades 120 and 42 outer blades 130. In still another embodiment, the knee actuator 112 comprises about 81 blades with 40 inner blades 120 and 41 outer blades 130. In a further embodiment, the knee actuator 112 comprises about 85 blades with 42 inner blades 120 and 43 outer blades 130. In modified embodiments, fewer or more blades 120, 130 may be efficaciously utilized, as needed or desired.

In one embodiment, the inner blades 120 have a thickness of about 0.2 mm (0.008 inches). In another embodiment, the inner blades 120 have a thickness of about 0.25 mm (0.010 inches). In yet another embodiment, the inner blades 120 have a thickness of about 0.3 mm (0.012 inches). In modified embodiments, other suitable dimensions and thickness may be efficaciously utilized, as needed or desired.

In one embodiment, the outer blades 130 have a thickness of about 0.2 mm (0.008 inches). In another embodiment, the outer blades 130 have a thickness of about 0.25 mm (0.010 inches). In yet another embodiment, the outer blades 130 have a thickness of about 0.3 mm (0.012 inches). In modified embodiments, other suitable dimensions and thickness may be efficaciously utilized, as needed or desired.

In some embodiments, the thickness of the inner blades 120 is greater than the thickness of the outer blades 130. In one embodiment, the inner blades 120 have a thickness of about 0.3 mm (0.012 inches) and the outer blades 130 have a thickness of about 0.25 mm (0.010 inches). In another embodiment, the inner blades 120 have a thickness of about 0.3 mm (0.012 inches) and the outer blades 130 have a thickness of about 0.2 mm (0.008 inches). In modified embodiments, other suitable dimensions and thickness may be efficaciously utilized, as needed or desired.

In one embodiment, the inner blades 120 have a thickness about 25% greater than the thickness of the outer blades 130. In another embodiment, the inner blades 120 have a thickness about 50% greater than the thickness of the outer blades 130. In yet another embodiment, the inner blades 120 have a thickness about 20% to about 60%, including all values and sub-ranges therebetween, greater than the thickness of the outer blades 130. In modified embodiments, other suitable dimensions and thickness may be efficaciously utilized, as needed or desired.

The induced yield stress or viscous torque is proportional to the overlap area between an inner-outer blade pair multiplied by twice the number of inner blades. This desirably allows the viscous torque or yield stress to be increased or decreased by selecting or predetermining the number of blades 120, 130 and/or the overlap or mating surface area between adjacent blades 120, 130 and/or the gap size therebetween.

Outer Spline

FIGS. 41–45 show different views of one embodiment of the rotary outer spline, housing, shell or rotor head 132. The outer spline 132 generally circumscribes and houses the inner blades 120 and the inner spline 122 to form the fluid receiving chamber, cavity or passage 144. The inner spline 122 in turn generally circumscribes the magnetic coil 115 and the core portion 166.

The outer blades or rotors 130 are fitted within the outer spline 132 and rotate with the outer spline 132 about the axis of rotation 124. Rotation of the outer spline 132 corresponds to rotation or movement of the upper (above the knee) part of the leg, for example, the stump socket 106 (see FIG. 2).

In the illustrated embodiment, the outer spline 132 is generally cylindrical in shape and comprises a substantially central cylindrical cavity or through hole 256. The cavity 256 has a sealed interior chamber 258 that receives the inner spline 122 and forms the sealed outer annular MR fluid chamber 144 (see, for example, FIG. 4) in which the blades 120, 130 extend and rotate. The core side plates 116, 118 are positioned in the cavity 256 to generally form at least a portion of the side walls of the chamber 144 and the specially configured dynamic seals 162 reliably seal the device against undesirable leakage.

The surface of the interior chamber 256 (and/or fluid chamber 144) comprises a plurality of longitudinal grooves, notches, splines or key-ways 260 that extend generally parallel to the axis of rotation 124 and securely engage or mate with corresponding teeth or keys 248 of the outer blades 130. In the illustrated embodiment, the outer spline 132 comprises nine substantially equally spaced grooves 260. In modified embodiments, fewer or more teeth-engaging grooves arranged in other suitable manners may be efficaciously utilized, as needed or desired.

The grooves 260 are desirably generally rectangular or square shaped to facilitate reliable load or torque transmission between the outer spline 132 and the outer rotors 130. In modified embodiments, the grooves 260 may have other suitable shapes such as round, semi-circular, curved, polygonal, and combinations thereof among others, with efficacy, as needed or desired.

In the illustrated embodiment, the surface of the interior chamber 256 (and/or fluid chamber 144) comprises a plurality of cross channels 262 that extend generally parallel to the grooves 260. The channels 262 advantageously provide for increased volume of the interior chamber 256 (and/or fluid chamber 144), thereby permitting greater capacity to hold the MR fluid 134. The channels 262 are desirably positioned on the upper or top portion of the interior chamber 256 (and/or fluid chamber 144), thus substantially preventing any undesirable accumulation of particles of the MR fluid 134 therein.

The outer spline cavity 256 further includes a pair of generally circular recesses 264 (264a, 264b) on either side of the interior chamber interior chamber 256 (and/or fluid chamber 144) that receive a respective one of the core side plates 116, 118 and dynamic seals 162a, 162b. The recesses 264a, 264b have respective seal engaging surfaces, flanges or shoulders 266a, 266b and 267a, 267b that abut against a respective one of the dynamic seals 162a, 162b, thereby preventing undesirable fluid leakage from the chamber 256. As discussed further below, the dynamic seals 162 rotate with the outer spline 132.

The outer spline cavity 256 further includes a pair of generally circular recesses 268 (268a, 268b) on either side of respective recesses 264a, 264b. The recesses 268a, 268b receive a respective one of the bearings 126, 128. The recesses 268a, 268b have respective bearing surfaces, flanges or shoulders 275a, 275b that engage respective outer bearing surfaces 133a, 133b of respective bearings 126, 128. In one embodiment, the bearings 126, 128 form a press fit within respective outer spline recesses 268a, 268b.

In one embodiment, the outer spline 132 includes, near its top end and proximate the right recess 268a, a slot, cavity or opening 269a that receives an arm portion of the angle sensor assembly 154, as described further below. In the illustrated embodiment, the slot 269a is generally rectangular or U-shaped though in modified other suitable shapes may be used, as needed or desired. A threaded hole 271a is in communication with the slot 269a and extends downwardly from the slot 269a for attaching the angle sensor arm portion therein.

In one embodiment, the outer spline 132 includes, near its top end and proximate the left recess 268b, a slot, cavity or opening 269b that receives an arm portion of the extension assist assembly 148, as described further below. In the illustrated embodiment, the slot 269b is generally rectangular or U-shaped though in modified embodiments other suitable shapes may be used, as needed or desired.

A threaded hole 271b is in communication with the slot 269b and extends downwardly towards the slot 269b. The threaded hole 271b engages a set screw 273 (see, for example, FIG. 6) or the like for securing the extension assist arm portion within the slot 269b.

The outer spline 132 has a generally frusto-conical or domed top end or portion 270 with a generally cylindrical central cavity or cup 272 with a base surface 274. The cavity 272 has a threaded side wall 276 with female threads or counter bores that engage corresponding male threads of the pyramid adapter 152 to connect the outer spline 132 and adapter 152.

The convex dome shape of the outer spline top end 270 desirably facilitates connection between the pyramid adapter 152 and the stump socket 106. The distal end of the stump socket 106 (or an annular connection member there at) can have a spherically concave distal edge with substantially the same radius of curvature as the convex dome of the outer spline top end 270. Thus, when the distal end of the stump socket 106 (or an annular connection member there at) is seated on the domed top end 270, it allows relative pivoting and rotation therebetween to provide proper orientation between the stump socket 106 and the outer spline 132 (and/or prosthetic knee 110).

The cavity 272, in some embodiments, houses the diaphragm assembly 146 which is in fluid communication with the chamber 144 (and/or chamber 258) via a port 278, described with respect FIGS. 55–62 below. The diaphragm assembly 146 is generally below the pyramid connector 152. As discussed further below, advantageously, the diaphragm assembly 146 prevents or mitigates undesirable pressure build up within chamber 144 (and/or chamber 258) and prevents undesirable fluid leakage.

In the illustrated embodiment, the outer spline 132 includes a bottom or lower threaded port or hole 280 in fluid communication with the chamber 144 (and/or chamber 258). As discussed further below, in some embodiments, the port 280 is used to fill MR fluid 134 in to the chamber 144 (and/or chamber 258) utilizing an efficient and specially configured fill scheme. After the MR fluid 134 has been loaded into the actuator 112, the hole 280 is closed with a set screw or the like.

In the illustrated embodiment, the outer surface of the outer spline 132 comprises a pair of spaced stops or fangs 282 (282a, 282b) with respective engaging or contacting surfaces 283 (283a, 283b). At full knee extension, the stops 282a, 282b engage or contact the specially designed shock absorbing bumper assembly 150 to prevent further knee rotation. Similarly, one or more stops may be provided on the outer spline 132, for example, at 284, in conjunction with associated hard stops or bumper or bumper assemblies on the side mounts 136, 138 to control the maximum knee flexion to a predetermined flexion angle, as needed or desired.

In one embodiment, the outer spline 132 is fabricated from titanium or a titanium alloy, such as 6Al -4V titanium alloy, to provide a non-ferrous yet strong, hard surface with low weight to engage the rotors 130 and transmit torque from them. Advantageously, the use of titanium or titanium alloys provides a near zero magnetic permeability and a yet strong, hard surface. An additional benefit is that the high resistivity of the material (titanium or titanium alloy) reduces energy losses due to induced eddy currents.

In another embodiment, the outer spline 132 comprises anodized 7075-T6 aluminum alloy. Advantageously, the hard anodized aluminum alloy surface protects the surfaces of the outer spline grooves 260 against surface damage and hence eliminates or mitigates any backlash, jarring or play. In modified embodiments, the outer spline 132 can be efficaciously fabricated from other suitable metals, alloys, plastics, ceramics, among others, as required or desired. In one embodiment, the outer spline 132 is nickel plated.

The outer spline 132 is desirably formed by machining, such as wire electro-discharge machining (EDM). In another embodiment, the outer spline 132 is formed by broaching. In modified embodiments, the outer spline 132 can be efficaciously fabricated from other suitable techniques, for example, casting, forging, molding, laser processing, among others, as required or desired.

Dynamic Seals

Figure 46:
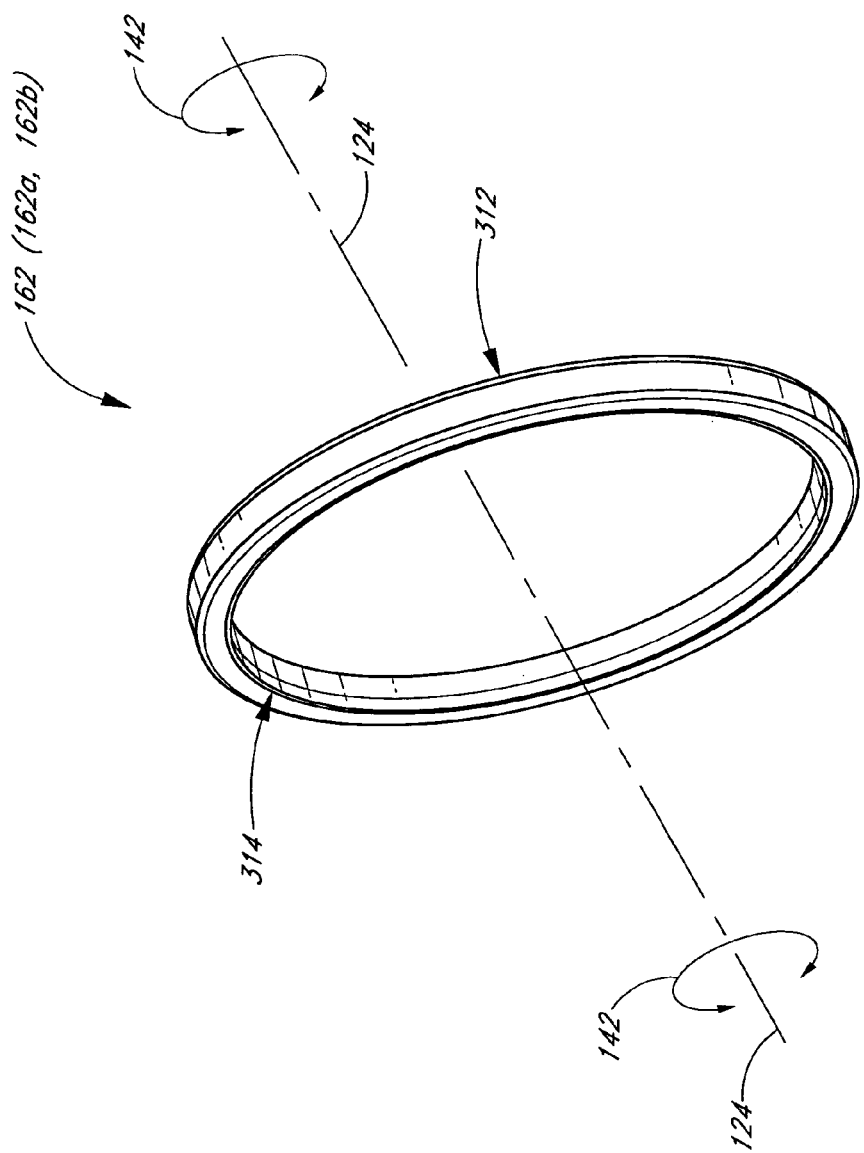
FIG. 46 is a simplified perspective view of a dynamic seal of the actuator of FIG. 6 illustrating features and advantages in accordance with an embodiment of the invention.
Figure 47:
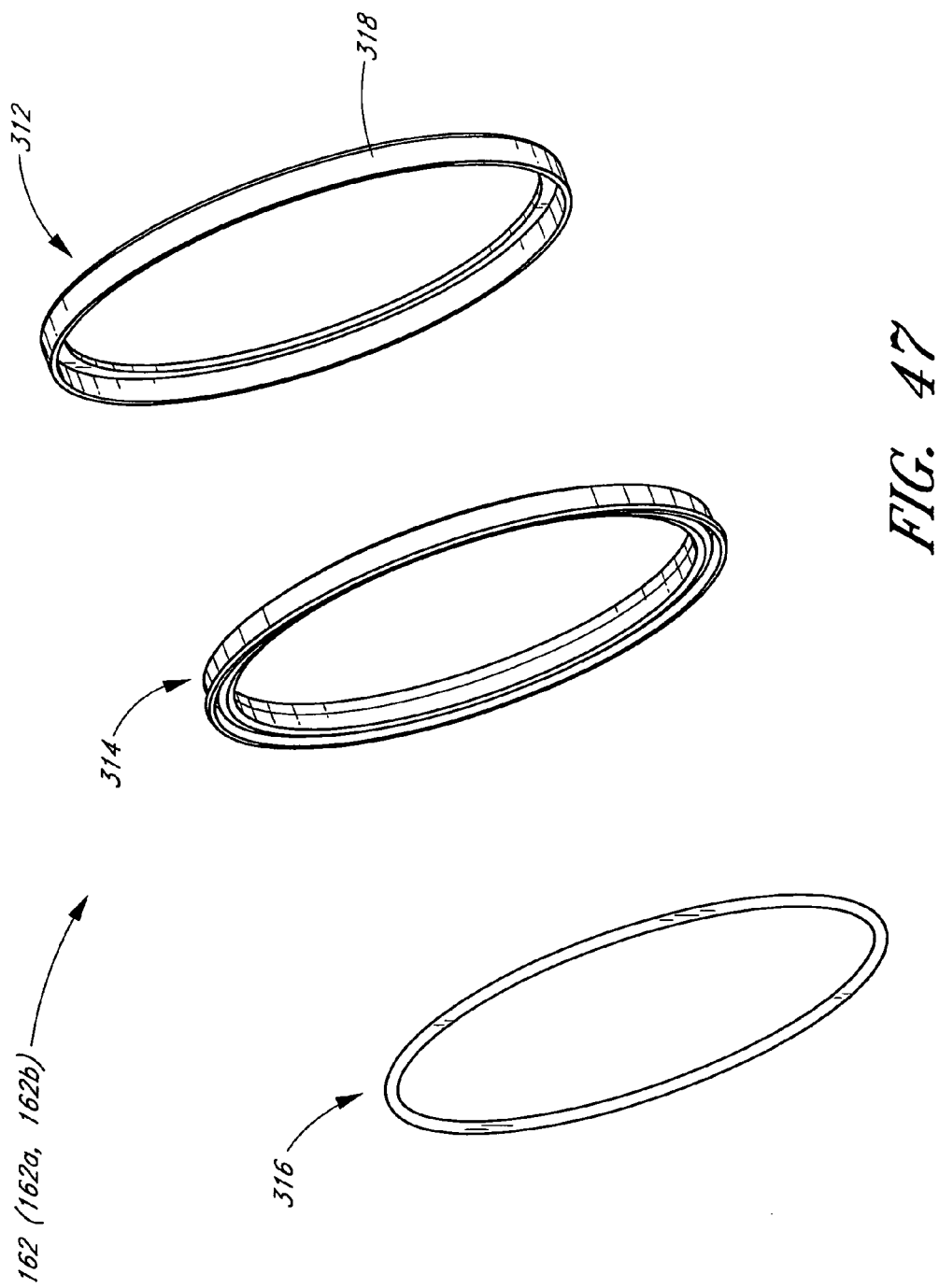
FIG. 47 is a simplified exploded perspective view of the dynamic seal of FIG. 46 illustrating features and advantages in accordance with an embodiment of the invention.
Figure 48:
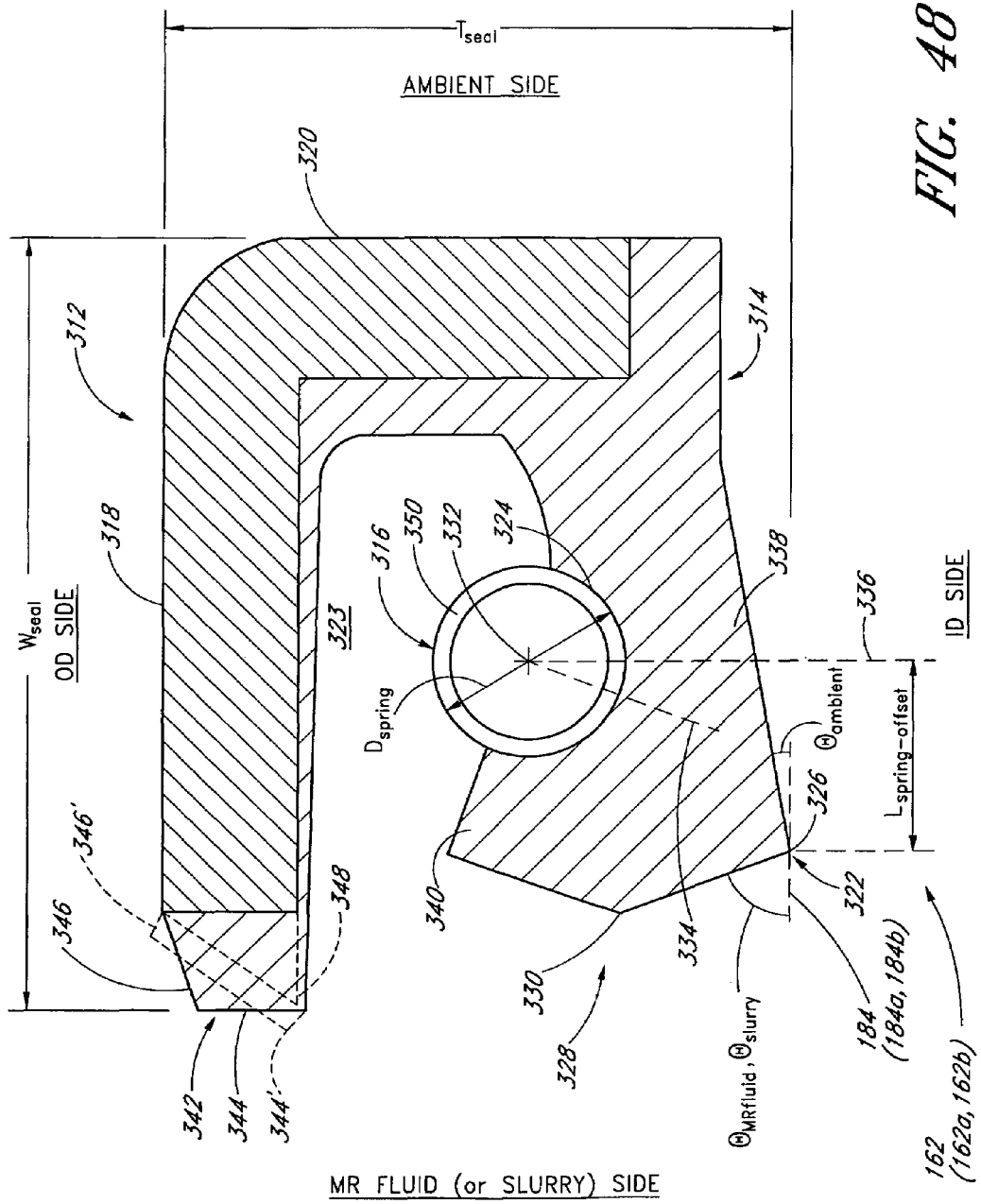
FIG. 48 is a simplified cross-section view of the dynamic seal of FIG. 46 illustrating features and advantages in accordance with an embodiment of the invention.
Figure 49:
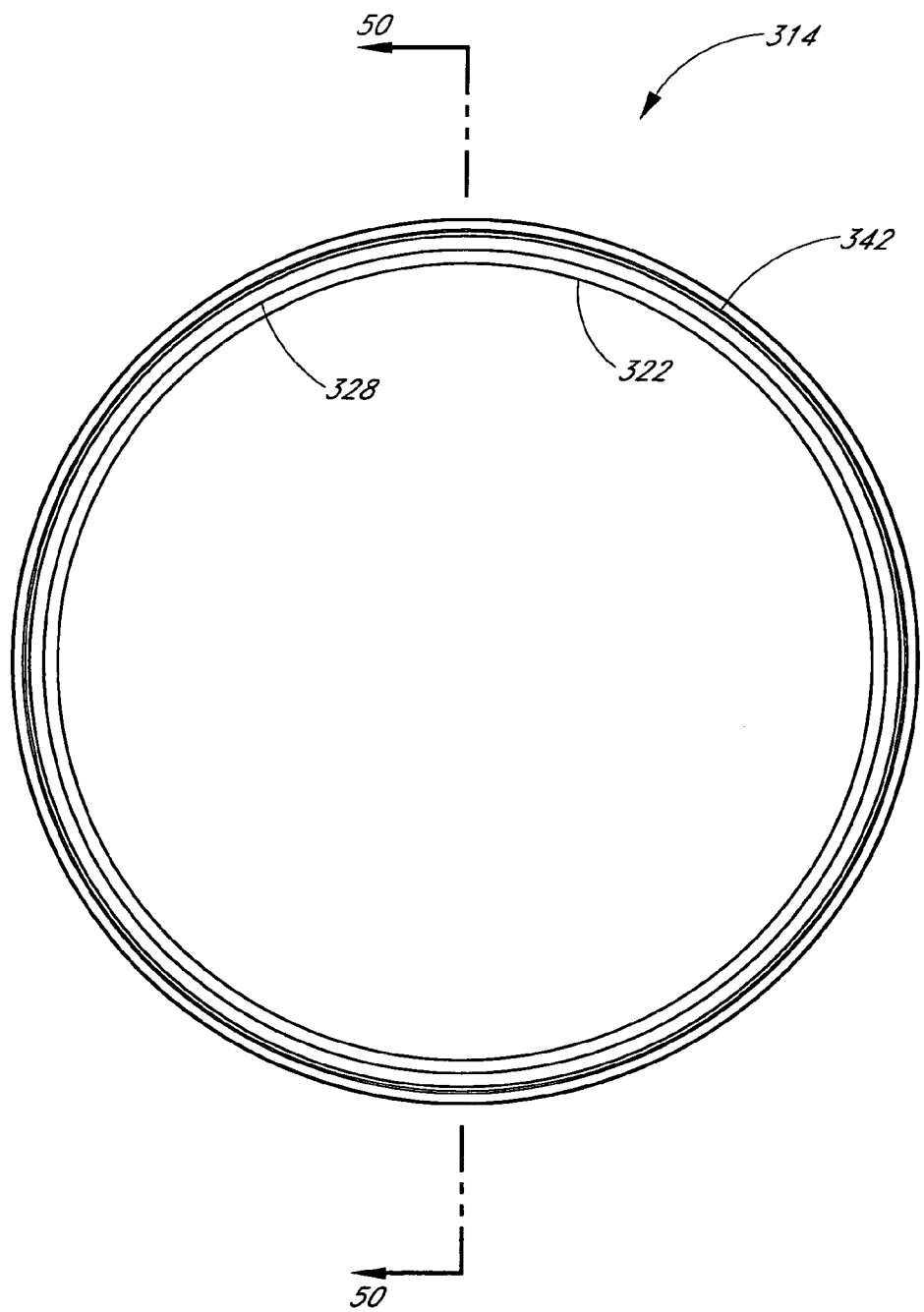
FIG. 49 is a simplified front view of a lip seal element of the dynamic seal of FIG. 46 illustrating features and advantages in accordance with an embodiment of the invention.
Figure 50:
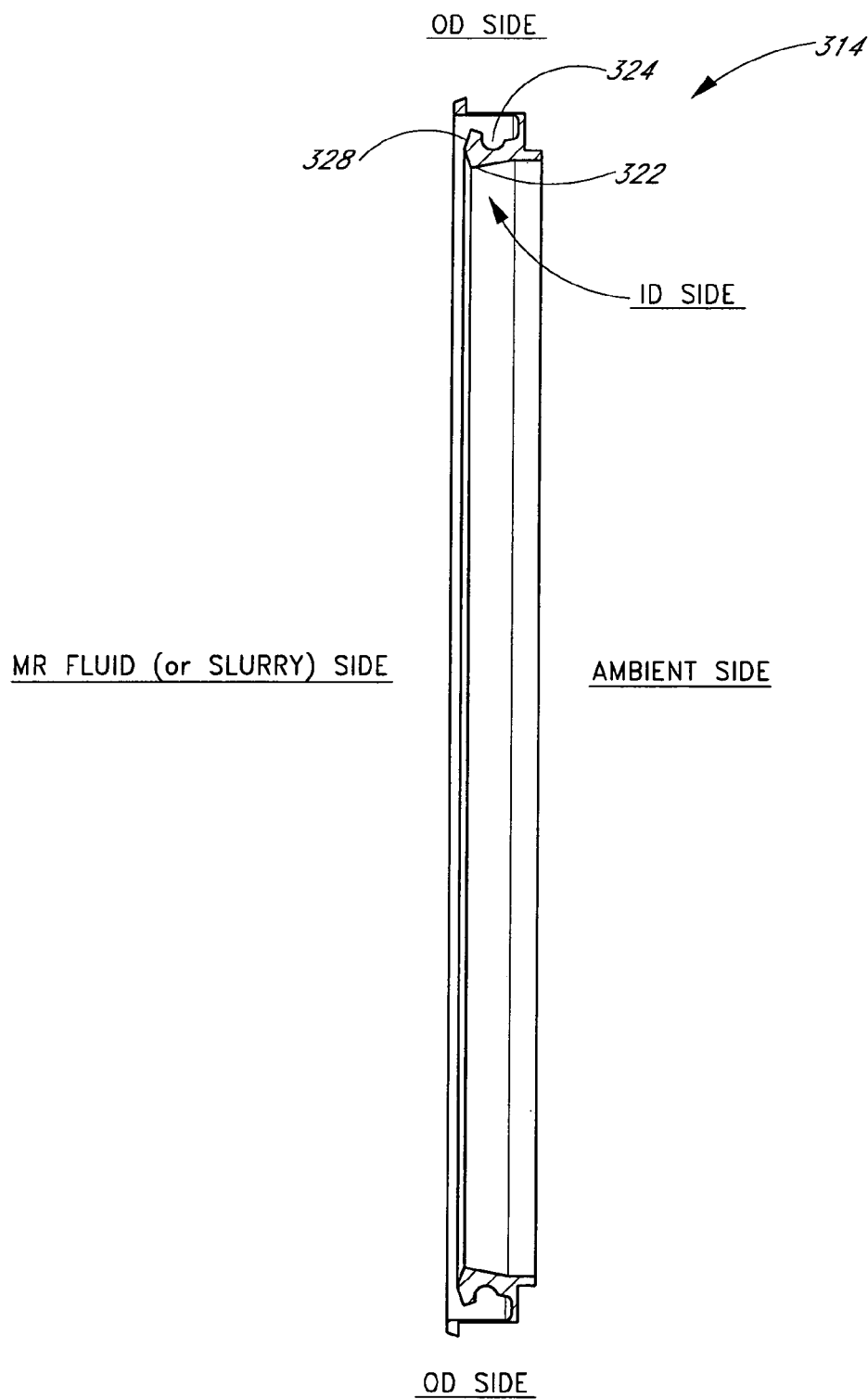
FIG. 50 is a simplified sectional view along line 50—50 of FIG. 49 illustrating features and advantages in accordance with an embodiment of the invention.

FIGS. 46–48 show different views of one embodiment of the rotary dynamic "radial" seals 162 (162*a*, 162*b*). The dynamic seal 162 generally comprises a protective seal can, case, shell or housing 312, a seal element or lip seal 314 and an internal garter spring 316. FIGS. 49 and 50 show different views of one embodiment of the lip seal element 314.

As described further below, the dynamic seal 162 of embodiments of the invention is specially configured and designed with a pre-loaded tensioned garter spring 316 with predetermined coil spacing that is at least as large as the size of particles or maximum size of particles in the MR fluid 134. Desirably, this allows MR fluid particles to flow in and out of the dynamic seal 162 without clogging the seal and advantageously provides for a reliable dynamic seal.

The dynamic seals 162 of embodiments of the invention create a barrier between surfaces in relative motion which, in the prosthetic knee embodiments, are rotatable surfaces of the core side plates 116, 118 and the outer spline 132 to prevent leakage of MR fluid from the chamber 144 therebetween. At any given knee rotation, the core side plates 116, 118 may rotate while the outer spline 132 is rotationally fixed, or the outer spline 132 may rotate while the core side plates 116, 118 are rotationally fixed, or the core side plates 116, 118 and the outer spline 132 may all rotate.

The dynamic seals 162*a*, 162*b* fit over a respective of the outer rims 184*a*, 184*b* (see, for example, FIGS. 14 and 19) of respective core side plates 116, 118 and rotate with the outer spline 132. The dynamic seals 162*a*, 162*b* are positioned in a respective one of the recesses or cavities 264*a*, 264*b* (see, for example, FIG. 45) of the rotatable outer spline 132.

In the illustrated embodiment, the seal case 312 is generally circular in shape and has a generally L-shaped cross section. The seal case 312 desirably provides rigidity to the dynamic seal 162.

As best seen in FIG. 48, the seal case 312 generally fits over the seal element 314 and is attached to it, for example, by bonding. The seal case 312 has an upper outer or OD surface 318 that generally defines the dynamic seal outer diameter (OD) and a rear outer surface 320 that faces away from the MR fluid side and towards the air, atmosphere or ambient side. In one embodiment, the seal case surfaces 318 of respective dynamic seals 162*a*, 162*b* form a press fit within a respective one of the outer spline surfaces 267*a*, 267*b*.

In one embodiment, the seal case 312 comprises stainless steel to provide the desired strength characteristics. In modified embodiments, the seal case 312 can be efficaciously fabricated from other suitable metals, alloys, plastics, ceramics, among others, as required or desired. In one embodiment, the seal case 312 is coated with a corrosion inhibitor to provide enhanced durability.

In one embodiment, the seal case 312 is fabricated by laser cutting a generally circular ring from a metal or alloy such as sheet steel. The rings are desirably roll-formed to prevent the finished seals from distorting when fabricating stresses are relieved by installation, age and temperature forces. The formed ring may be grit blasted to provide a suitable finish, as needed or desired, and coated with a bonding agent that provides suitable adhesion to the seal element material. In modified embodiments, the seal case 312 can be efficaciously fabricated from other suitable techniques, for example, machining, casting, forging, molding, laser processing, among others, as required or desired.

The seal element 314 is generally circular and has one or more sealing lips which provide for dynamic sealing. The seal element 314 has a generally circular spring-loaded seal lip 322 at the dynamic seal inner diameter (ID) and a garter spring cavity 323. The seal lip 322 is kept in position by the garter spring 316 which is housed in a generally circular internal groove or notch 324 generally above the seal lip 322. The groove 324 has a semi-circular cross section.

The seal lip 322 has a tip 326 at generally its inner-most diameter location. The seal lips 322 and their tips 326 of respective dynamic seals 162*a*, 162*b* dynamically engage or seal against a respective one of the generally circular outer rims 184*a*, 184*b* (see, for example, FIGS. 14 and 19) of respective core side plates 116, 118. The seal lips 322 are rotatable with the outer spline 132 and dynamically sealingly rotate over the core plate rims 184*a*, 184*b*.

In the illustrated embodiment of FIG. 48, the seal element 314 can include another generally circular seal lip 328 with a tip 330 facing the inner or MR fluid side. The core side plate rims 184*a*, 184*b* and the outer spline surfaces 266*a*, 266*b* are generally perpendicular to one another.

Referring in particular to the embodiment of FIG. 48, the configuration and arrangement of the seal lips 322, 328 and/or the groove 324 and/or the garter spring 316 can provide several advantages. One advantage is that the spring 316 provides optimized loading of the seal lip 322 and its tip 326 and enhanced seal performance.

In the illustrated embodiment of FIG. 48, the spring centerline 332 is offset relative to the tip 326 as generally denoted by $L_{spring\text{-}offset}$ and the centerline plane 334 of the spring groove 324 is skewed or not coincident with the plane 336 through the circumference of the spring 316. In some embodiments, the former may also be stated as the tip 322 not being directly below the spring 316 or its centerline 332 while the latter may also be stated as the plane 334 being skewed or not perpendicular to the core plate rim surface 184 (184*a*, 184*b*).

One important advantage of providing the offset, generally denoted by length $L_{spring\text{-}offset}$, is that it allows for the use of a sharper, steeper or larger MR fluid side angle $\theta_{MRfluid}$ (or slurry side angle $\theta_{slurry}$). The sharper angle $\theta_{MRfluid}$ (or $\theta_{slurry}$) desirably creates a higher pressure or load point/area contact between the resilient tip 326 and the associated rim surface 184 during their relative motion, thereby desirably allowing for reliable and secure sealing.

In one embodiment, the angle $\theta_{MRfluid}$ (or $\theta_{slurry}$) is about 70°. In another embodiment, the angle $\theta_{MRfluid}$ (or $\theta_{slurry}$) is in the range from about 60° to about 75°, including all values and sub-ranges therebetween. In yet another embodiment, the angle $\theta_{MRfluid}$ (or $\theta_{slurry}$) is in the range from about 45° to about 80°, including all values and sub-ranges therebetween. In modified embodiments, the angle $\theta_{MRfluid}$ (or $\theta_{slurry}$) may efficaciously be lower or higher, as needed or desired.

In one embodiment, the spring offset length $L_{spring\text{-}offset}$ is about the same as the garter spring cross-sectional diameter $D_{spring}$. In one embodiment, the offset length $L_{spring\text{-}offset}$ is about 1 mm (0.04 inches). In another embodiment, the offset length $L_{spring\text{-}offset}$ is in the range from about 0.5 mm to about 1.5 mm, including all values and sub-ranges therebetween. In yet another embodiment, the offset length $L_{spring\text{-}offset}$ is in the range from about 0–0.1 mm to about 2 mm, including all values and sub-ranges therebetween. In modified embodiments, the offset length $L_{spring-offset}$ may efficaciously be lower or higher, as needed or desired.

In the illustrated embodiment of FIG. 48, the seal lip 322 includes or is associated with support material 338 generally below, or closer to the dynamic seal inner diameter, than the spring 316 and/or the spring groove 324. The support material 338 desirably provides enhanced strength and/or improves the dynamic seal quality between the lip 322 and the associated core side plate rim 184.

In the illustrated embodiment of FIG. 48, a shallow or small air, atmosphere or ambient side angle $\theta_{ambient}$ is provided. Desirably, this improves the seal quality between the lip 322 and the associated core side plate rim 184 and/or may provide enhanced strength.

In one embodiment, the angle $\theta_{ambient}$ is about 10°. In another embodiment, the angle $\theta_{ambient}$ is in the range from about 7.5° to about 30°, including all values and sub-ranges therebetween. In yet another embodiment, the angle $\theta_{ambient}$ is in the range from about 5° to about 40°, including all values and sub-ranges therebetween. In modified embodiments, the angle $\theta_{ambient}$ may efficaciously be lower or higher, as needed or desired.

In the illustrated embodiment of FIG. 48, the seal lip 328 includes or is associated with support material 340 adjacent to the spring 316. The support material 340 is on the MR fluid side (or slurry side) and at least a portion of it is above, or closer to the dynamic seal outer diameter, than the spring centerline 332. Advantageously, the support 340 facilitates in keeping the tensioned, loaded or extended spring 316 in its place in the track or groove 324.

The seal element 314 further includes a support portion or structure 342 at generally the dynamic seal outer diameter (OD). The support structure has MR fluid (or slurry) facing surface 344 and a outer diameter side facing surface 346 that may be tapered.

The seal surfaces 344 of respective dynamic seals 162a, 162b engage or seal against a respective one of the generally circular surfaces 266a, 266b (see, for example, FIG. 45) of the outer spline 132. This engagement is substantially irrotational since the dynamic seals 162 rotate with the outer spline 132.

The seal surfaces 346 of respective dynamic seals 182a, 182b may engage or seal against a respective one of the generally circular surfaces 267a, 267b (see, for example, FIG. 45) of the outer spline 132. This engagement is substantially irrotational since the dynamic seals 162 rotate with the outer spline 132.

As shown in phantom in FIG. 48, the seal portion 342 may include one or more generally circular sealing lips such as the seal lip 344' and the seal lip 346', as needed or desired. The seal case 312 may have a tip 348 associated with the seal portion 342 to provide enhanced rigidity, as needed or desired.

The seal lips 344' of respective dynamic seals 182a, 182b engage or seal against a respective one of the generally circular surfaces 266a, 266b of the outer spline 132. The seal lips 346' of respective dynamic seals 182a, 182b may engage or seal against a respective one of the generally circular surfaces 267a, 267b of the outer spline 132.

The seal element 314 desirably comprises a flexible material such as a rubber, an elastomer, an elastomeric compound or the like that provides suitable sealing characteristics. In one embodiment, the seal element 314 comprises Viton®. In another embodiment, the seal element 314 comprises Nitrile, sometimes referred to as NBR or BUNA-N. In modified embodiments, the seal element 314 can be efficaciously fabricated from other suitable materials such as Teflon®, Neoprene and the like, as required or desired.

In one embodiment, the seal element 314 comprises a material having a durometer (shore D) hardness of about 70. In another embodiment, the seal element 314 comprises a material having a durometer hardness in the range from about 65 to about 75, including all values and sub-ranges therebetween. In modified embodiments, other suitable hardnesses may efficaciously be used, as needed or desired.

In one embodiment, the seal element 314 is fabricated by molding. The seal element 314 is bonded to the steel case 312. In modified embodiments, the seal element 314 can be efficaciously fabricated utilizing other suitable techniques, as needed or desired.

The garter spring 316 is generally circular in overall shape and is fitted within the seal element groove 324. The garter spring 316 has a generally circular cross section with the spring centerline 332 and comprises a plurality of coils 350.

The garter spring 316 is tensioned and applies a pressure or load on the seal lip 322 and its tip 326 to provide a strong and reliable seal. In one embodiment, the garter spring 316 also applies pressure or load on the seal lip 328.

Figure 51:
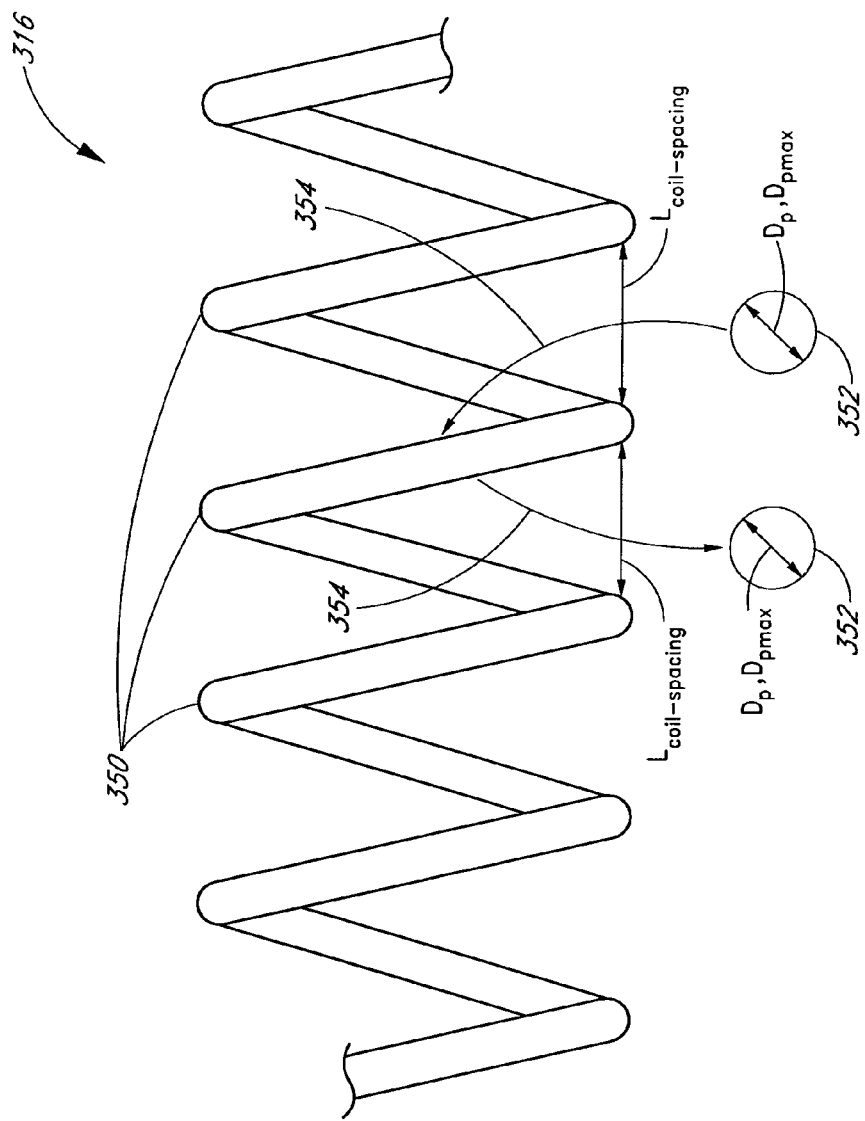
FIG. 51 is a simplified schematic enlarged partial view of a garter spring of the dynamic seal of FIG. 46 showing the spacing between spring coils and illustrating features and advantages in accordance with an embodiment of the invention.

FIG. 51 schematically shows the coils 350 of the garter spring 316. The spring coils 350 are advantageously spaced by an optimal and/or predetermined spacing or gap ($L_{coil-spacing}$) so that they allow MR fluid (or slurry) particles 352 to flow or swim in and out (as generally denoted by arrows 354) of the coils 350 while maintaining a load that keeps the garter spring 316 mounted within the groove 324 and prevents undesirable displacement of the spring 316.

The pre-loaded or "stretched out" garter spring 316 has a coil gap $L_{coil-spacing}$ that is at least as large as the MR fluid (or slurry) particle size or diameter ($D_p$) or at least as large as the largest MR fluid (or slurry) particle size or diameter ($D_{pmax}$). The small particles 352 can gain access to the spring(s) 316 due to the small particle sizes involved, the dynamics of the rotational motion and the MR fluid vacuum fill techniques of embodiments of the invention (as described further below and used to fill the MR fluid in the knee actuator). The rotational engagement, as opposed to a static one, can allow the MR fluid 134 and its small particles 352 to contact the spring coils 350.

Advantageously, embodiments of the invention provide a dynamic seal 162 having the specially configured garter spring 316 with coil spacing $L_{coil-spacing}$ that desirably prevents the small particles 352 to get "stuck" within the spring coils 350, thereby desirably preventing seal deterioration or failure. This may be accomplished, for example, by shortening or adjusting the spring length or circumference and/or by increasing or adjusting the tensioning of the spring 316.

Fully covering the dynamic seal garter spring is not a feasible or practical way to protect it from clogging. One major disadvantage is that it is difficult and unfeasible to fabricate such a dynamic seal. Another major disadvantage is that during MR fluid loading procedures, such as the MR fluid vacuum loading conditions of embodiments of the invention (as described further below and used to fill the MR fluid in the knee actuator), the cover can undesirably expand, rupture and/or become dislodged which will render the seal inoperable. Embodiments of the invention provide a simple and elegant solution to overcome these advantages by optimizing the coil gap size $L_{coil-spacing}$, as described further below.

In some embodiments, the relationship between the coil gap or spacing size $L_{coil-spacing}$ and the MR fluid particle size or diameter $D_p$ or the MR fluid maximum particle size or diameter $D_{pmax}$ can generally be given by the following, where $k \geq 1$:

$$L_{coil\text{-}spacing} = kD_p$$

or $$L_{coil\text{-}spacing} = kD_{pmax}$$

In one embodiment, k is about 1.25. In another embodiment, k is about 1.5. In yet another embodiment, k is about 2. In still another embodiment, k is in the range from about 1.2 to about 5, including all values and ranges therebetween. In a further embodiment, k is in the range from about 1.1 to about 10, including all values and ranges therebetween. In modified embodiments, other suitable values for k may be efficaciously used, as needed or desired.

The particle size and the particle size distribution may have a wide range of values, for example, from about 0.2 microns (μm) to about 50 μm. TABLE 1 below illustrates some exemplifying values and ranges for the gap size $L_{coil\text{-}spacing}$ for various values and ranges of k and the particle size $D_p$ or the maximum particle size $D_{pmax}$ within the MR fluid 134 or other slurry or multi-phase mixture.

(1.96 inches) and the spring centerline circumference is about 15.7 cm (6.17 inches). In one embodiment, the spring cross section diameter $D_{spring}$ is about 1.02 mm (0.04 inches). In modified embodiments, other suitable spring dimensions may be efficaciously utilized, as needed or desired.

In one embodiment, the garter spring 316 comprises stainless steel such as SAE 30302/30304 stainless steel. In modified embodiments, the garter spring 316 can be efficaciously fabricated from other suitable metals, alloys, plastics, ceramics, among others, as required or desired.

The inner diameter (ID) of the dynamic seals 162a, 162b is dimensioned so that they fit over respective outer diameters (or rims 184a, 184b) of respective core side plates 116, 118 and apply a radially inwards pressure or load to dynamically seal the MR fluid 134 (or slurry) within the knee device 112. The inner diameters of the dynamic seals 162a, 162b are slightly smaller than the respective outer diameters of the core side plates 116, 118 so that the seal garter springs 316 are tensioned (or their tension increases) when mounted on respective rims 162a, 162b.

In one embodiment, the inner diameter (ID) of the dynamic seals 162a, 162b is about 4.69 cm (1.846 inches)

TABLE 1

Some Embodiments of Values and Ranges of $L_{coil\text{-}spacing}$, $D_p$ or $D_{pmax}$ in microns (μm)

| k | 0.2 | 0.5 | 1 | 2 | 3 | 4 | 5 | 10 | 25 | 50 |
|---|---|---|---|---|---|---|---|---|---|---|
| 1.25 | 0.25 | 0.625 | 1.25 | 2.5 | 3.75 | 5 | 6.25 | 12.5 | 31.25 | 62.5 |
| 1.5 | 0.3 | 0.75 | 1.5 | 3 | 4.5 | 6 | 7.5 | 15 | 22.5 | 75 |
| 2 | 0.4 | 1 | 2 | 4 | 6 | 8 | 10 | 20 | 50 | 100 |
| 1.2–5 | 0.24–1 | 0.6–2.5 | 1.2–5 | 2.4–10 | 3.6–15 | 4.8–20 | 6–25 | 12–50 | 30–125 | 60–250 |
| 1.1–10 | 0.22–2 | 0.55–5 | 1.1–10 | 2.2–20 | 3.3–30 | 4.4–40 | 5.5–50 | 11–100 | 27–250 | 55–500 |

Figure 52:
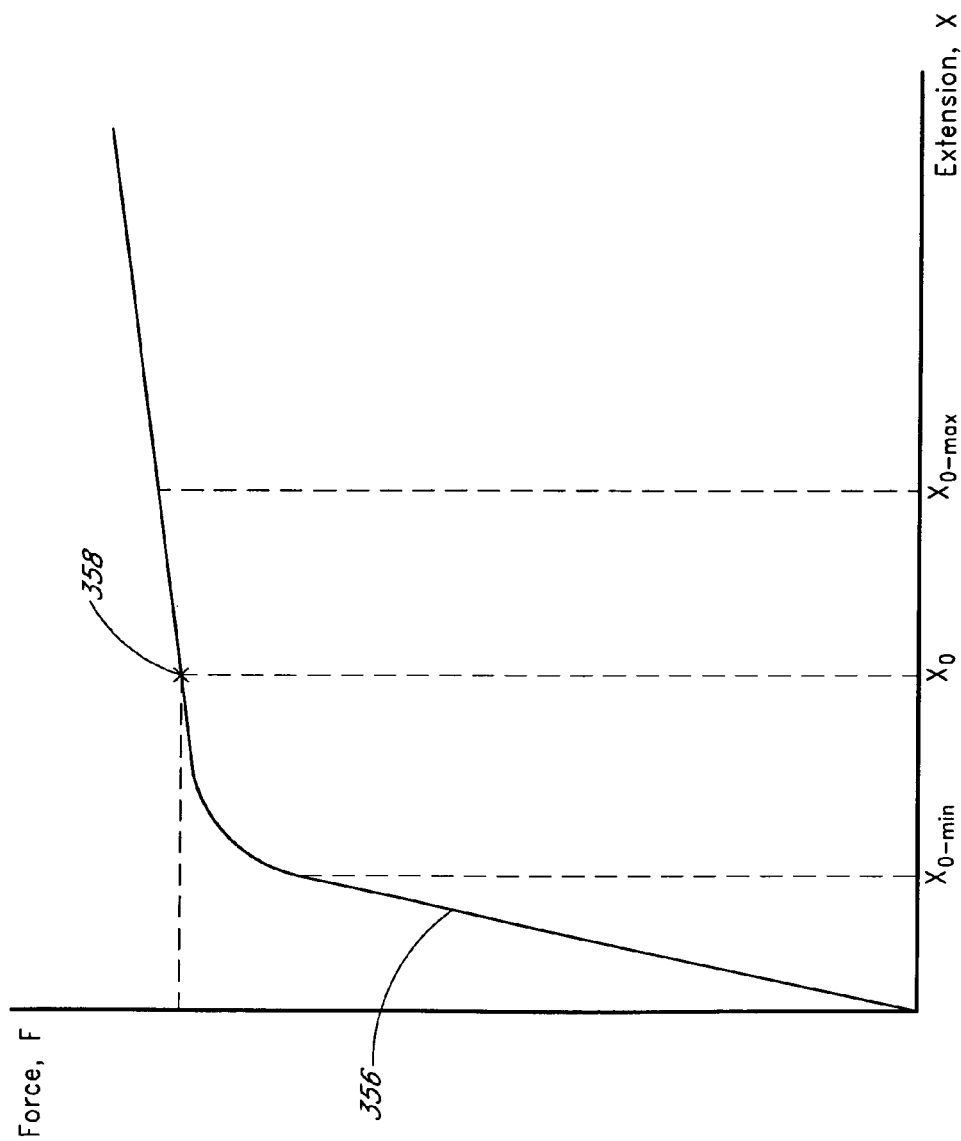
FIG. 52 is simplified schematic deflection curve of a garter spring of the dynamic seal of FIG. 46 showing operational points and ranges and illustrating features and advantages in accordance with embodiments of the invention.

FIG. 52 shows one graphical example of a deflection curve 356 of the garter spring 316. The deflection curve 356 schematically illustrates the relationship between the force or loading of the spring 316 and its extension or deflection distance. The garter spring 316 is tensioned to an optimum force value or range so that it provides the desired coil gap $L_{coil\text{-}spacing}$ that prevents the MR fluid (or slurry) particles 352 from clogging the spring 316 and while preventing excessive spring loading that may cause spring failure or cause the spring 316 from jumping out of its track or groove 324.

FIG. 52 schematically illustrates some suitable force-extension operational points and ranges for the spring 316. In one embodiment, the spring 316 is tensioned to operate at point 358 on the deflection curve 356 so that its extension is generally at point $x_o$. In another embodiment, the spring 316 may be tensioned over a range of points on the deflection curve 356 such that its extension is generally between the range $x_{o\text{-}min}$ and $x_{o\text{-}max}$. In modified embodiments, other suitable spring loading operational points and ranges may be efficaciously used, giving due consideration to the goals of providing reliable dynamic seals, maintaining suitable coil spacing $L_{coil\text{-}spacing}$ and generally avoiding excessive loading, as needed or desired.

In one embodiment, the garter spring 316 is fabricated from an extension spring portion having a length of about 14.6 cm (5.75 inches). The spring portion is formed into the generally circular garter spring 316 and fitted with the seal element groove 324 to spring-load the seal element 314. In one embodiment, the spring centerline diameter is about cm and the outer or rim diameter of the core side plates 116, 118 (or shafts) is about 4.80 cm (1.89 inches). In modified embodiments, other suitable dimensions may be efficaciously used, as needed or desired.

In one embodiment, the inner diameters of the dynamic seals 162a, 162b are about 2.5% smaller than the respective outer or rim diameters of the core side plates 116, 118. In another embodiment, the inner diameters of the dynamic seals 162a, 162b are about 2% to about 3%, including all values and sub-ranges therebetween, smaller than the respective outer or rim diameters of the core side plates 116, 118. In yet another embodiment, the inner diameters of the dynamic seals 162a, 162b are about 1% to about 5%, including all values and sub-ranges therebetween, smaller than the respective outer or rim diameters of the core side plates 116, 118. In still another embodiment, the inner diameters of the dynamic seals 162a, 162b are about 0.5% to about 10%, including all values and sub-ranges therebetween, smaller than the respective outer or rim diameters of the core side plates 116, 118. In modified embodiments, other suitable diameter and/or size variations may be efficaciously utilized, as needed or desired.

The outer diameter (OD) of the dynamic seals 162, 162b is dimensioned so that when the seals 162a, 162b are mounted on respective core side rims 184a, 184b the seals 162a, 162b form a press fit within respective recesses or housing bores 264a, 264b of the outer spline 132. More specifically, the outer surfaces 318 of the seal cases 312 form a press or interference fit with respective surfaces 267a, 267b of respective outer spline recesses or housing bores 264a, 264b.

In one embodiment, the outer diameter (ID) of the dynamic seals 162a, 162b is about 5.410 cm (2.130 inches) and the diameter of the housing bore surfaces 267a, 267b is about 5.398 cm (2.125 inches). In modified embodiments, other suitable dimensions may be efficaciously used, as needed or desired.

Referring in particular to FIG. 48, in one embodiment, the dynamic seal width $W_{seal}$ is about 3.81 mm (0.15 inches). In one embodiment, the dynamic seal thickness $T_{seal}$ is about 6.96 mm (0.274 inches). In modified embodiments, other suitable dimensions may be efficaciously used, as needed or desired.

In one embodiment, the contact path width between the seal lips 322 and respective core side plate rims 184a, 184b is in the range from about 102 microns or μm (0.004 inches) to about 152 μm (0.006 inches), including all values and sub-ranges therebetween. In another embodiment, the contact path width between the seal lips 322 and respective core side plate rims 184a, 184b is in the range from about 51 μm (0.002 inches) to about 254 μm (0.01 inches), including all values and sub-ranges therebetween. In yet another embodiment, the contact path width between the seal lips 322 and respective core side plate rims 184a, 184b is in the range from about 25 μm (0.001 inches) to about 508 μm (0.02 inches), including all values and sub-ranges therebetween. In modified embodiments, other suitable contact path widths may be efficaciously utilized, as needed or desired.

The "lip force" is generally defined as the force per unit length applied by the spring-loaded primary seal lips 322 on respective core side plate rims 184a, 184b. In one embodiment, the lip force is in the range from about 0.5 Newtons/cm or N/cm (0.3 lbs/inch) to about 0.7 N/cm (0.4 lbs/inch), including all values and sub-ranges therebetween. In another embodiment, the lip force is in the range from about 0.44 Newtons/cm or N/cm (0.25 lbs/inch) to about 1.75 N/cm (1 lbs/inch), including all values and sub-ranges therebetween. In yet another embodiment, the lip force is in the range from about 0.35 Newtons/cm or N/cm (0.2 lbs/inch) to about 3.5 N/cm (2 lbs/inch), including all values and sub-ranges therebetween. In modified embodiments, other suitable lip forces may be efficaciously utilized, as needed or desired.

During assembly, the dynamic seals 162a, 162b are mounted on respective rims 184a, 184b of respective core side plates 116, 118. The seals 162a, 162b are generally perpendicular to the outer diameter sealing surface of respective rims 184a, 184b.

In one embodiment, the inner diameters or sealing lips 322 of respective dynamic seals 162a, 162b are coated with grease such as silicone grease and the like prior to installation. Desirably, this facilitates the sealing lips 322 in sliding into place over respective rims 162a, 162b and protects the lips 322 during the initial run-in phase. If desired, other portions of the seal elements 314 may be coated with grease, as suitable.

As also discussed above, in one embodiment, the core plate outer rims 184a, 184b are surface hardened to protect the rims or edges 184a from any undesirable scratching or damage during use or assembly, such as during installation of the seals 162a, 162b. This rim hardening also advantageously improves the dynamic sealing between the seal lips 322 and respective rims 184a, 184b.

The dynamic seals 162a, 162b while mounted on respective core side plates 116, 118 are press fitted within respective outer spline recesses or housing bores 264a, 264b. The outer diameter surfaces of the dynamic seals 162a, 162b engage respective surfaces 267a, 267b of respective outer spline recesses 264a, 264b. More specifically, the outer surfaces 318 of the seal cases 312 form a press or interference fit with respective housing bore surfaces 267a, 267b.

In one embodiment, an impregnation sealant is applied to the joints or cracks between the outer diameter surfaces of the dynamic seals 162a, 162b and the respective engaging surfaces 267a, 267b of respective outer spline recesses 264a, 264b. Desirably, the impregnation sealant seals the small or microscopic voids at the interface between outer diameter surfaces of the dynamic seals 162a, 162b and the respective outer spline surfaces 267a, 267b.

In one embodiment, the impregnation sealant comprises Loctite® 990 impregnation sealant. The impregnation sealant flows into the small or microscopic voids, pores or openings at the interface between the outer diameter surfaces of the dynamic seals 162a, 162b and the respective outer spline surfaces 267a, 267b and cures to form a tough thermoset polymer that provides a reliable seal.

The impregnation sealant can be cured in an oven or at room temperature. In one embodiment, the sealant is cured in an oven for about 30 minutes at about 150° Fahrenheit (F). In another embodiment, the sealant is cured for about 3 hours under ambient conditions. In modified embodiments, other suitable curing times and temperatures may be efficaciously utilized, as needed or desired.

The dynamic seals 162a, 162b rotate with the rotation of the outer spline 132 and hence independently of the rotation of the core side plates 116, 118. The seal elements 314, and more particularly the primary seal lips 322, rotatingly interact with and dynamically seal against the outer diameter surfaces of respective core side plate rims 184a, 184b as the knee joint rotates.

In embodiments of the prosthetic knee, the dynamic seals 162 contain the MR fluid 134, that is sheared during knee joint rotation, within the fluid chamber 144. The specially designed dynamic seals 162, including the specially configured garter springs 316, can also have application and use in other rotary configurations with slurry flows, solid particle and liquid flows, solid liquid two-phase flows or solid and liquid multi-phase flows.

Embodiments of the invention encompass providing dynamic seals and methods of handling small particle slurries and the like. For example, the dynamic seal(s) 162 can be used on a rotating shaft with a bearing and other rotary flow situations involving small particle slurries and the like. The small particles can range in size or diameter from about $\frac{1}{10}^{th}$ of a micron to about a thousand microns, including all values and sub-ranges therebetween.

Modified embodiments of the dynamic seals may be used in linear, Cartesian, axial and reciprocating flows involving small particle slurries and the like. These can include a piston-cylinder arrangement. The small particles can range in size or diameter from about $\frac{1}{10}^{th}$ of a micron to about a thousand microns, including all values and sub-ranges therebetween.

Figure 53:
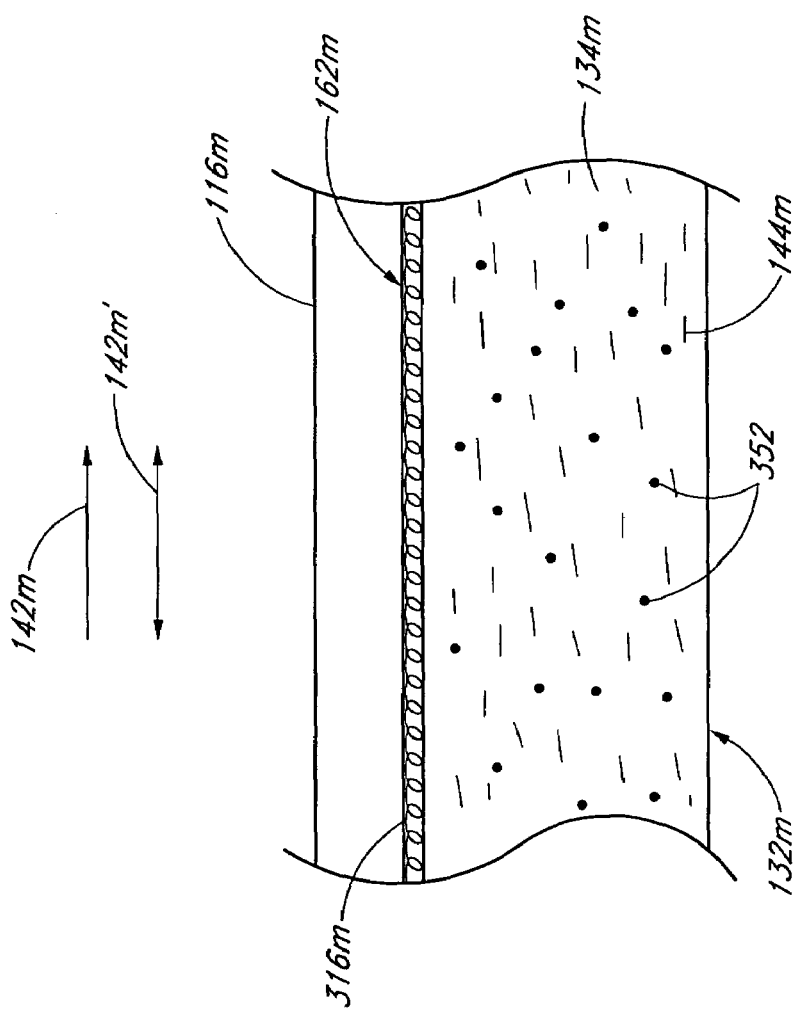
FIG. 53 is a simplified schematic view of a slurry flow arrangement with a dynamic seal illustrating features and advantages in accordance with a modified embodiment of the invention.

FIG. 53 shows the use of a modified dynamic seal 162m in a linear or Cartesian geometry that may have a one- two- or three-dimensional flow. A slurry 134m, including small particles 352m, flows within a chamber 144m of a housing 132m and there is relative motion between a plate 116m and the housing 132m generally denoted by arrows 142m or 142m' (reciprocating motion).

The dynamic seal 162m is provided at the interface between the plate 116m and the housing 132m. As discussed above and herein, the specially designed dynamic seal 162m has a pre-loaded or "stretched out" garter spring 316m that has a coil gap $L_{coil-spacing}$ that is large enough for the slurry particles 352m to flow or swim in and out of the spring coils. The garter spring 316m may be kept tensioned by providing hooks or the like at its ends.

Figure 54:
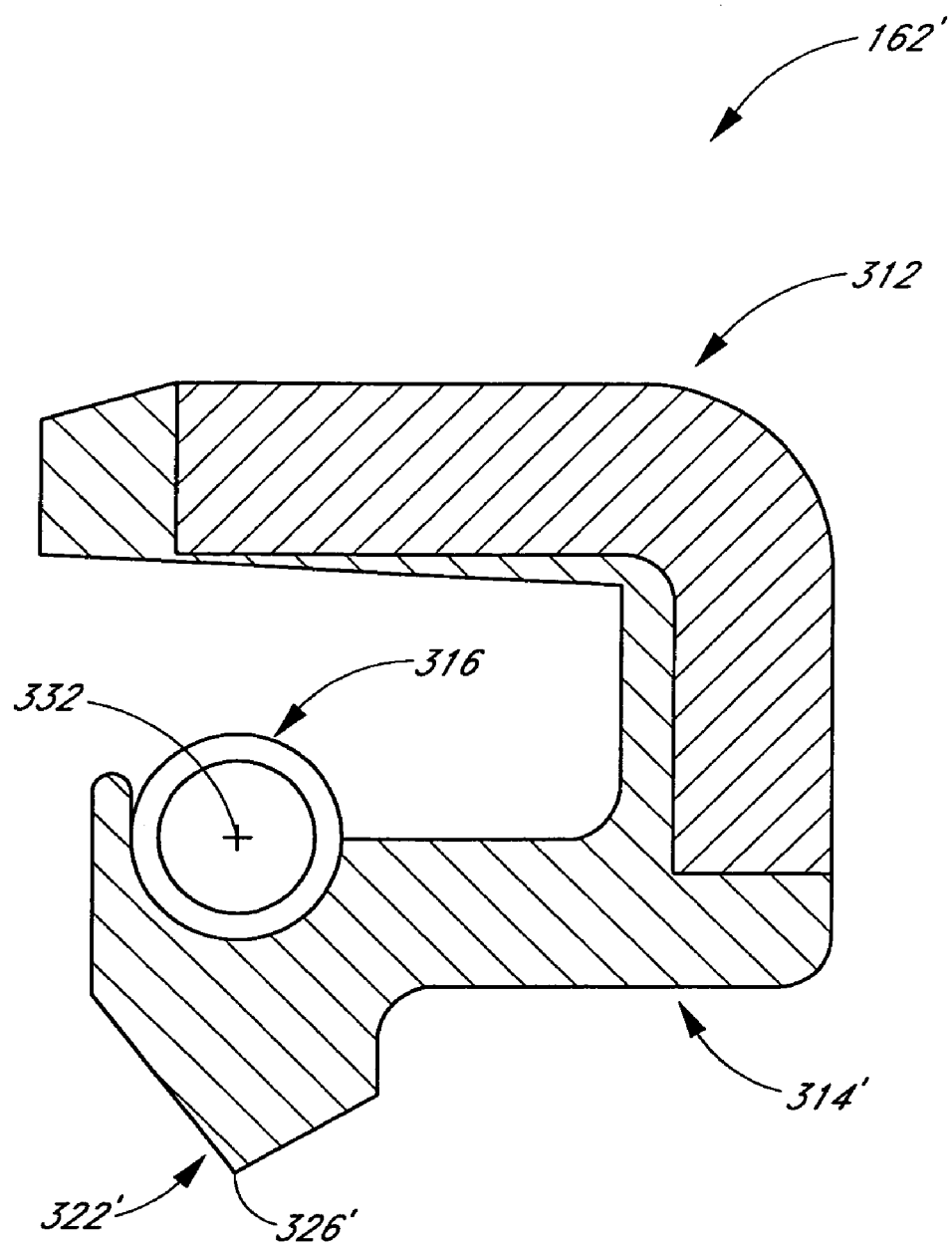
FIG. 54 is a simplified cross-section view of a dynamic seal of the actuator of FIG. 6 illustrating features and advantages in accordance with another embodiment of the invention.
Figure 56:
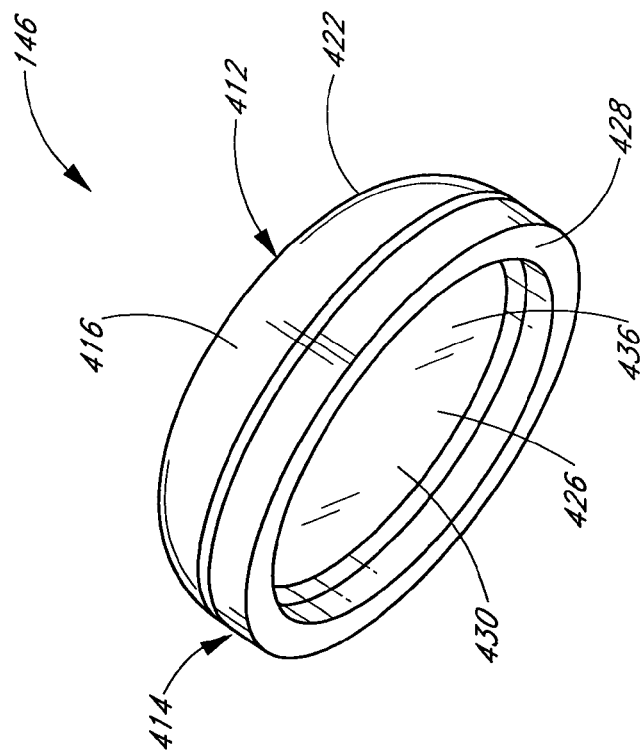
FIG. 56 is another simplified perspective view of the diaphragm assembly of FIG. 55 illustrating features and advantages in accordance with an embodiment of the invention.
Figure 55:
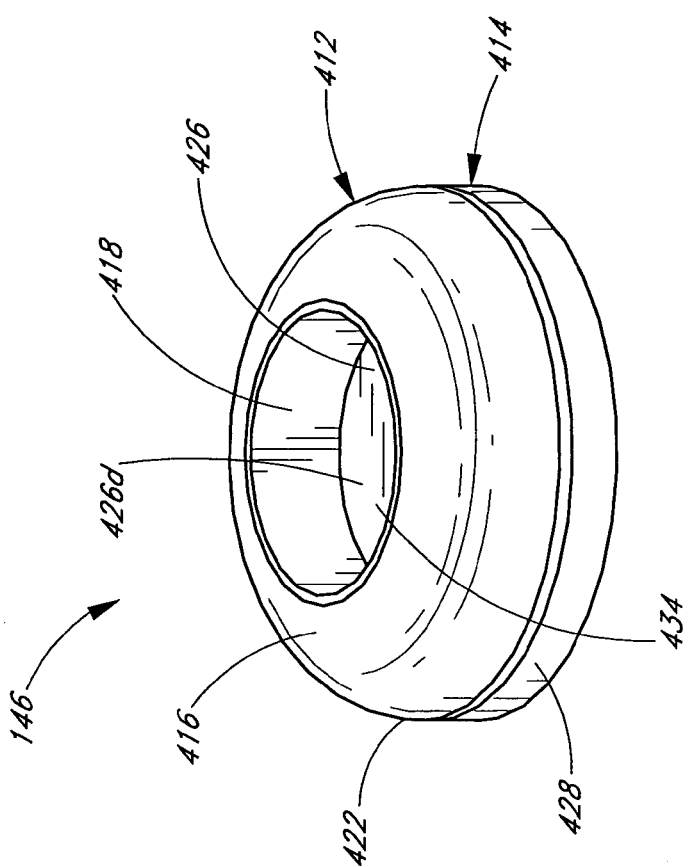
FIG. 55 is a simplified perspective view of a diaphragm assembly of the actuator of FIG. 6 illustrating features and advantages in accordance with an embodiment of the invention.
Figure 58:
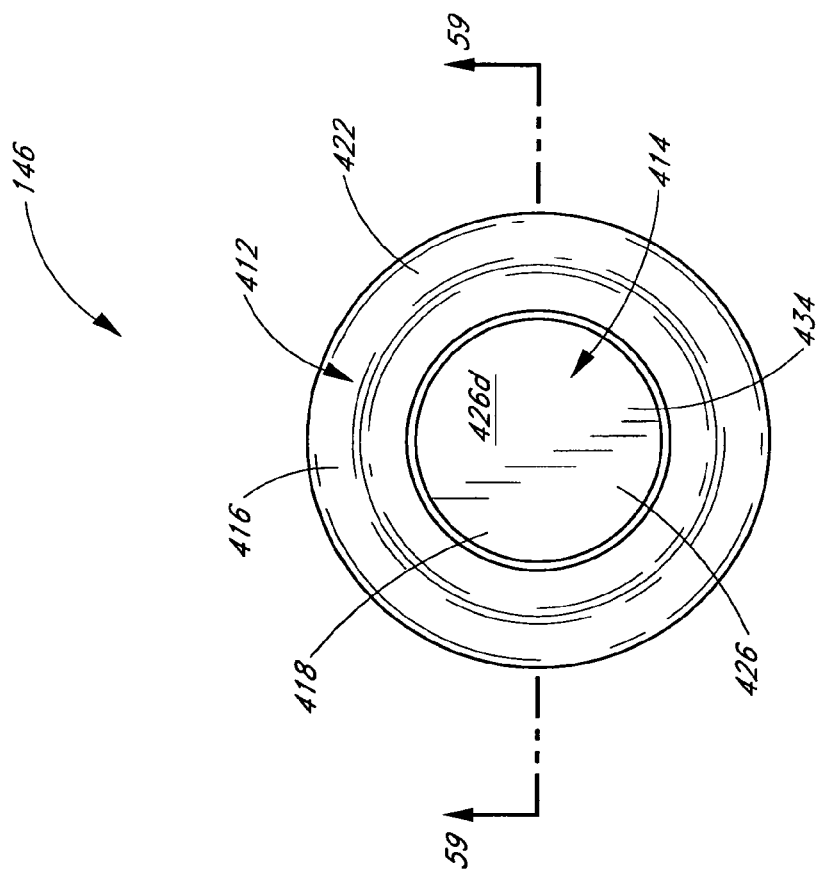
FIG. 58 is a simplified top view of the diaphragm assembly of FIG. 55 illustrating features and advantages in accordance with an embodiment of the invention.
Figure 57:
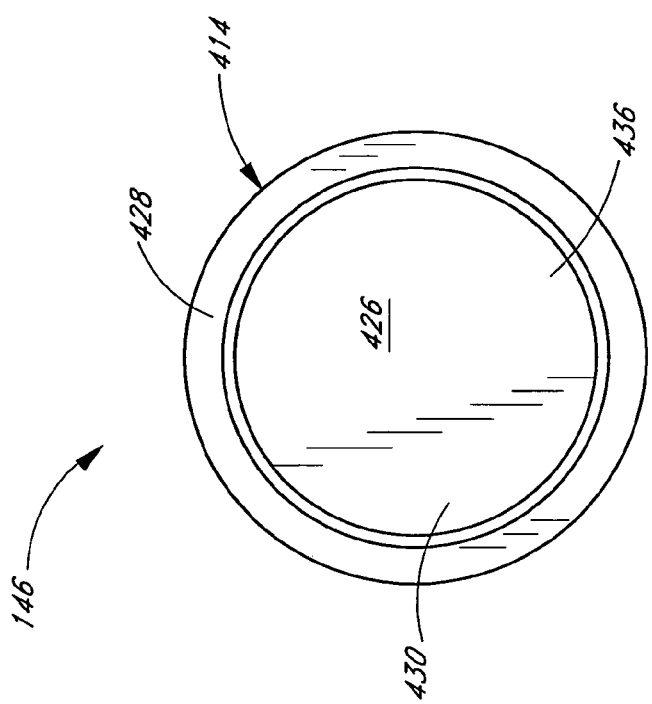
FIG. 57 is a simplified bottom view of the diaphragm assembly of FIG. 55 illustrating features and advantages in accordance with an embodiment of the invention.
Figure 59:
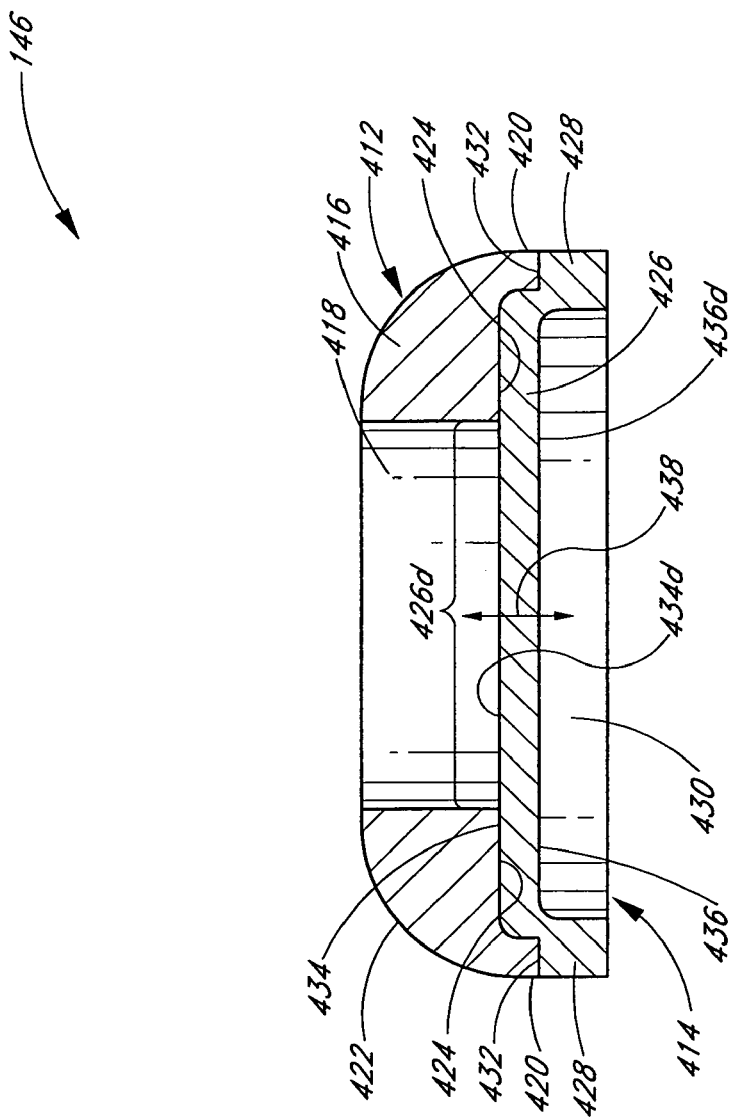
FIG. 59 is a simplified sectional view along line 59—59 of FIG. 58 illustrating features and advantages in accordance with an embodiment of the invention.

FIG. 54 shows a dynamic seal 162' in accordance with a modified embodiment. As shown in the figure, in this embodiment, the seal element 314' has modified features and includes a seal lip 322' with a tip 326' that is substantially directly below the garter spring 316 or the spring centerline 332.

Diaphragm Assembly

FIGS. 55–60 show different views of one embodiment of the diaphragm assembly or device 146. The diaphragm assembly 146 generally comprises a cap or dome portion 412 connected to a diaphragm or membrane portion 414.

The diaphragm assembly 146 of embodiments of the invention advantageously prevents or mitigates undesirable pressure build-up within the knee actuator 112 and more particularly in the sealed MR fluid chamber 144, thereby desirably providing a pressure control mechanism. The pressure build-up that the diaphragm assembly 146 facilitates in preventing or mitigating may occur, for example, due to MR fluid outgassing or expansion due to heat within the chamber 144.

The diaphragm assembly 146 is seated on the base surface 274 of the outer spline cavity 272 (see, for example, FIG. 45) and is generally above the MR fluid chamber 144. The diaphragm assembly 146 is sized and configured to generally fit within a cavity or recess of the pyramid connector 152, as discussed further below.

In the illustrated embodiment, the diaphragm assembly 146 and its features have generally circular, cylindrical, annular or frusto-conical configurations. In modified embodiments other suitable shapes may be efficaciously utilized, as needed or desired.

The cap portion 412 supports the diaphragm portion 414 and, in one embodiment, comprises a substantially rigid material. The cap portion 412 generally comprises a convex dome 416, a generally central cavity or opening 418 and a lip 420.

The dome 416 is generally circular or annular and has a convex outer surface 422 sized and configured to engage or abut against a corresponding concave dome surface of the pyramid adapter 152, as also discussed further below. In one embodiment, grease, such as silicone grease or the like, is applied to one or both of the convex outer surface 422 and the concave dome surface of the pyramid adapter 152 to provide a reliable seal.

The opening 418 is generally circular or cylindrical. The opening or passage 418 has an open end that communicates with a through passage of the pyramid connector 152 (as discussed further below) exposed to ambient or atmospheric pressure and an opposite end that is closed by the diaphragm portion 414.

The lip 420 and a lower interior surface 424 (see FIG. 59) of the cap portion 412 engage or abut against the diaphragm portion 414. The lip 420 is generally circular or annular and is received in a generally circumferential recess of the diaphragm portion 414.

The flexible diaphragm portion 414 desirably prevents or mitigates undesirable pressure build-up in the sealed MR fluid chamber 144 and is in fluid communication with the MR fluid 134 and the chamber 144. The diaphragm portion 414 generally comprises a diaphragm or membrane 426, a lip 428, a generally central cavity 430 and a groove or recess 432.

The flexible diaphragm 426 is generally circular and is in the form of a membrane having a predetermined thickness. The diaphragm 426 has an upper or outer surface 434 and a generally opposed lower or inner surface 436 in communication with the diaphragm cavity 430.

The diaphragm 426 has a generally central diaphragm element section 426d (see, for example, FIGS. 55 and 58–60) that is deflectable to relieve pressure-build-up. The diaphragm element 426d is generally circular and, in one embodiment, has a generally uniform thickness. The thickness of the diaphragm element 426d is desirably such that it provides suitable flexibility (or resiliency) while maintaining sufficient structural strength.

The diaphragm element 426d has a corresponding upper or outer surface 434d and a lower or inner surface 436d. The generally annular portion of the diaphragm upper surface 434 that surrounds the deflectable upper surface 434d engages or is in contact with the cap lower surface 424.

The diaphragm lip 428 generally defines the circumference or periphery of the diaphragm cavity 430. The lip 428 is generally circular or annular and is seated on or engages base surface 274 of the outer spline cavity 272 (see, for example, FIG. 45). In one embodiment, grease, such as silicone grease or the like, is applied to the lip 428 to provide a reliable seal with the outer spline base surface 274 and/or the pyramid connector 152.

The groove 432 is generally circular or annular and runs around the diaphragm 426. The groove 432 receives the lip 420 of the cap portion 412 to facilitate alignment and connection between the cap portion 412 and diaphragm portion 414 of the diaphragm assembly.

The diaphragm cavity 430 is generally circular and has a closed end generally defined by the lower surface 436 and an opposed open end at the base surface 274 of the outer spline cavity 272. The diaphragm cavity 430 spaces the diaphragm lower surface 436 and the outer spline base surface 274. The diaphragm cavity 430 is in fluid communication with the outer spline port 278 and hence with the MR fluid chamber 144.

The opposed cavities 418 and 430 are on opposite sides of the deflectable diaphragm element 426d and are sealingly substantially isolated from one another. The cavity 418 is on the side of the diaphragm upper surface 434d and is exposed to ambient or atmospheric pressure $P_{ambient}$. The cavity 430 is on the side of the diaphragm lower surface 434d (or 434) and is exposed to the pressure $P_{chamber}$ in the MR fluid chamber 144.

Advantageously, the flexible diaphragm element 426d can deflect due to any undesirable pressure build-up within the chamber 144 and relieve and control the pressure therein to a suitable or predetermined value. This deflection is generally denoted by arrows 438 wherein an outward deflection is caused by a pressure increase and an inward deflection depicts a pressure decrease such as after a temporary pressure rise, for example, due to the cooling of the MR fluid and its contraction.

Desirably, the solid diaphragm element 426d provides a flexible medium that controls and limits undesirable pressure build-up in the knee actuator 112 and more particularly in the fluid chamber 144. This substantially prevents any adverse effect on the knee performance, for example, because of seal failure and fluid leakage.

Figure 60:
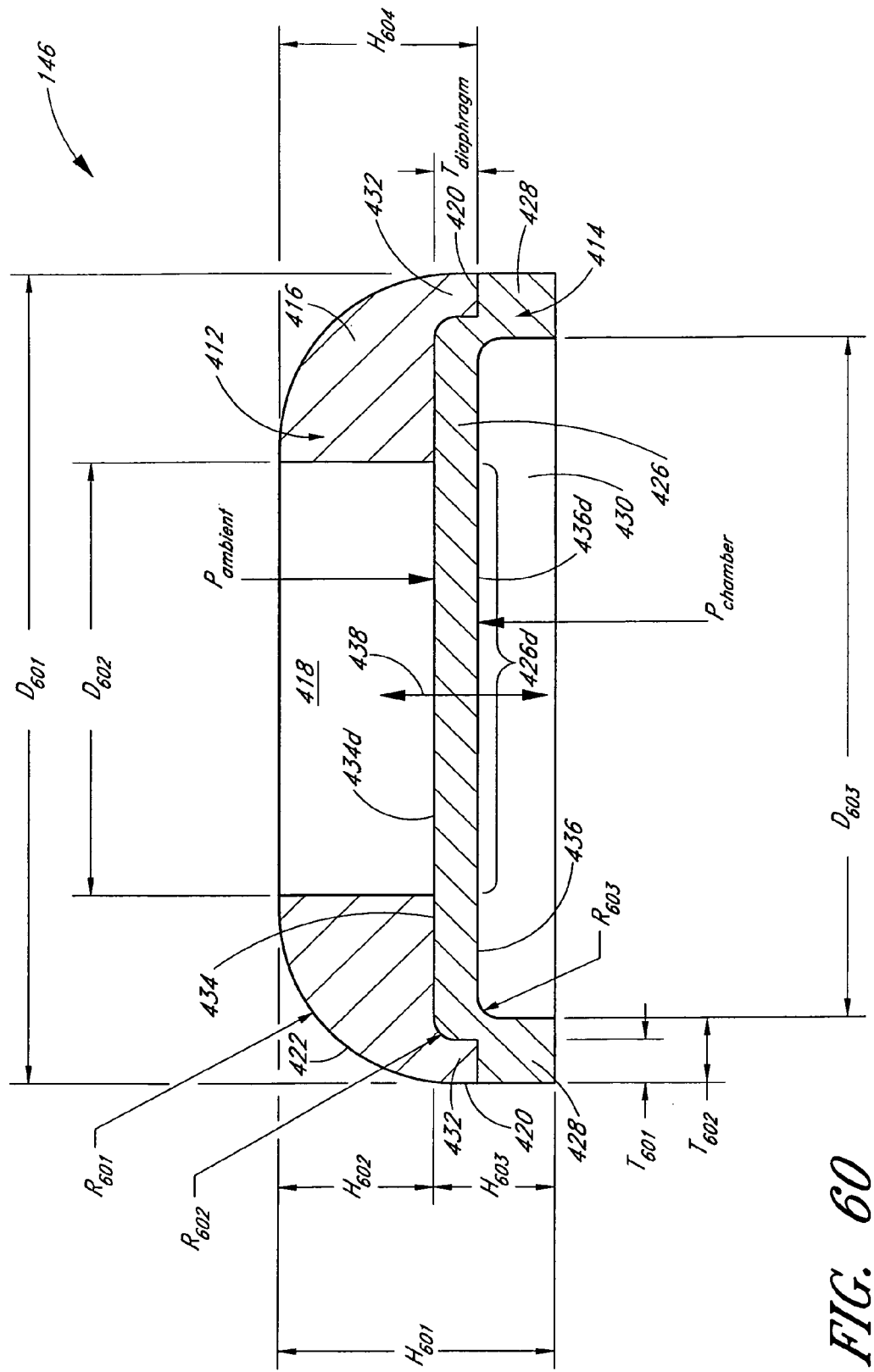
FIG. 60 is another simplified sectional view of the diaphragm assembly of FIG. 55 illustrating features and advantages in accordance with an embodiment of the invention.

Referring in particular to FIG. 60, in one embodiment, the diaphragm assembly diameter $D_{601}$ is about 18.7 mm, the cap cavity diameter $D_{602}$ is about 10 mm and the diaphragm cavity diameter $D_{603}$ is about 15.7 mm. In modified embodiments, other suitable dimensions may be efficaciously used, as needed or desired.

In one embodiment, the diaphragm thickness $T_{diaphragm}$ is about 1 mm. In another embodiment, the diaphragm thickness $T_{diaphragm}$ is in the range from about 0.75 mm to about 1.5 mm, including all values and sub-ranges therebetween. In yet another embodiment, the diaphragm thickness $T_{diaphragm}$ is in the range from about 0.5 mm to about 3 mm, including all values and sub-ranges therebetween. In modified embodiments, other suitable dimensions may be efficaciously used, as needed or desired.

In one embodiment, the diaphragm assembly height $H_{601}$ is about 6.25 mm to about 6.4 mm, the cap portion height $H_{602}$ is about 3.5 mm, the diaphragm portion height $H_{603}$ is about 2.75 mm to about 2.9 mm and the height $H_{604}$ is about 4.5 mm. In modified embodiments, other suitable dimensions may be efficaciously used, as needed or desired.

In one embodiment, the cap portion lip thickness $T_{601}$ is about 1 mm and the diaphragm portion lip thickness $T_{602}$ is about 1.5 mm. In modified embodiments, other suitable dimensions may be efficaciously used, as needed or desired.

In one embodiment, the radius of curvature $R_{601}$ is about 4 mm, the radius of curvature $R_{602}$ is about 0.5 mm and the radius of curvature $R_{603}$ is about 0.5 mm. In modified embodiments, other suitable dimensions may be efficaciously used, as needed or desired.

The cap portion 412 is desirably fabricated from a suitably strong material that can support the diaphragm portion 414. In one embodiment, the cap portion 412 comprises a strong, durable and tough polymer such as nylon, for example, nylon 66 having a Rockwell hardness of about 100. The nylon may be reinforced for enhanced performance, as needed or desired. In modified embodiments, other suitable materials may be efficaciously used, as needed or desired.

The diaphragm portion 414 is desirably fabricated from a flexible and/or resilient material. In one embodiment, the diaphragm portion 414 comprises silicone (CF-13 or CF-15). In another embodiment, the diaphragm portion 414 comprises Vulkollan® polyurethane which desirably has a high tensile strength, high abrasion resistance and a Shore A hardness of about 70. In modified embodiments, other suitable materials may be efficaciously used, as needed or desired.

In one embodiment, the cap portion 412 is formed by machining and the diaphragm portion 414 is molded to the cap portion 412. In another embodiment, the cap portion 412 is formed by machining, the diaphragm portion 414 is formed by molding and the two are attached to one another, for example, adhesively or by using glue or the like.

In one embodiment, the diaphragm assembly 146 including the cap portion 412 and the diaphragm portion 414 are formed as an integral unit, for example, by molding. The diaphragm assembly 146 can comprise, for example, silicone. The diaphragm assembly 146 could be constructed so that the deflectable diaphragm element 426d is thin enough to be flexible yet strong and the other elements of the diaphragm assembly 146 are configured to comprise sufficient material to provide suitable rigidity, strength and/or durability, as needed or desired.

Figure 61:
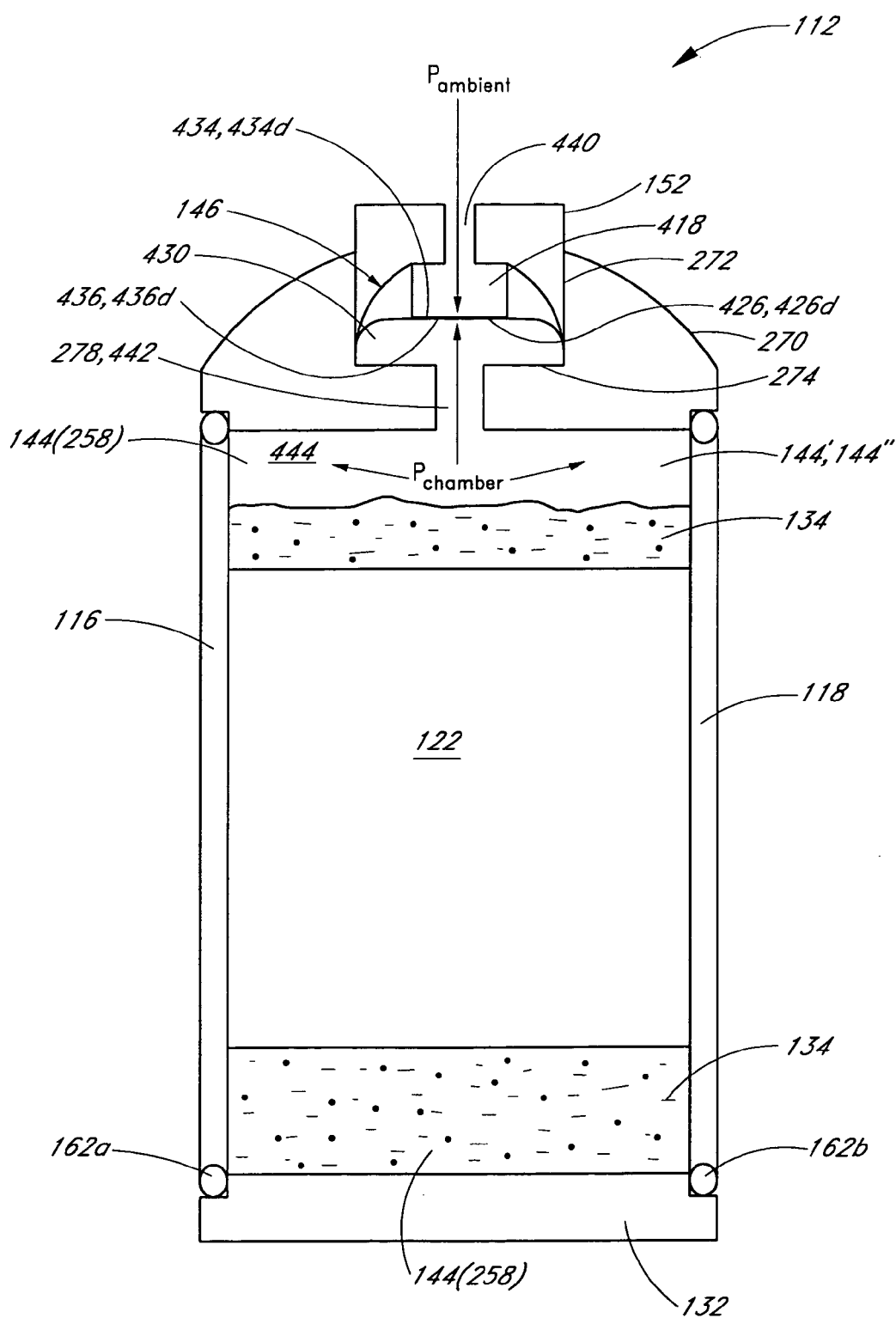
FIG. 61 is a simplified schematic view of a prosthetic knee actuator pressure control system illustrating features and advantages in accordance with embodiments of the invention.

FIG. 61 schematically illustrates pressure control mechanisms of the knee actuator 112 in accordance with embodiments of the invention. The upper surface 434d of the deflectable diaphragm element 426d is exposed to ambient or atmospheric pressure $P_{ambient}$ through a pyramid passage 440 while the lower surface 436d is exposed to the pressure $P_{chamber}$ within the chamber 144. As discussed above and herein, the flexible diaphragm assembly 146 provides a pressure control mechanism in accordance with some embodiments.

The outer spline 132 generally circumscribes or envelops the inner spline 122 to form the generally annular chamber 144 with the core side plates 116, 118 generally forming at least a portion of the side walls of the chamber 144. The sealed chamber 144 is a portion of the chamber 258 of the outer spline 132. The rotors 120, 130 (not shown in FIG. 61) extend into the chamber 144. The chamber 144 contains the MR fluid 134.

A sealed chamber 144' can also be defined as including the chamber 144 and the outer spline port 278. Another sealed chamber 144" may be defined as including the chamber 144, the port 278 and the diaphragm cavity 430 or portion 442 of the outer spline cavity 272 generally enclosed by the diaphragm portion 412 or diaphragm 426.

In some embodiments, the free space of the chamber 144 (or 144' or 144") is only partially filled with the MR fluid 134 (in one embodiment, about 1 milliliter) while the remaining space of the chamber 144, the outer spline port 278 and the outer spline cavity portion 442 is filled with a compressible gas 444 such as nitrogen, air and the like to provide a pressure control mechanism. Advantageously, the gas 444 provides a compressible medium that controls and limits undesirable pressure build-up in the knee actuator 112 and more particularly in the fluid chamber 144. This substantially prevents any adverse affect on the knee performance, for example, because of seal failure and fluid leakage.

As also indicated above, the pressure build-up that the compressible gas 444 facilitates in preventing or mitigating may occur, for example, due to MR fluid outgassing or expansion due to heat within the chamber 144. The gas 444 desirably compresses to maintain the desired pressure level.

In one embodiment, about 70% of the free space volume of the chamber 144 (or 144' or 144") is filled with MR fluid 134 and the remaining volume is filled with the compressible gas 444. In another embodiment, about 65% to about 75%, including all values and sub-ranges therebetween, of the free space volume of the chamber 144 (or 144' or 144") is filled with MR fluid 134 and the remaining volume is filled with the compressible gas 444. In yet another embodiment, about 60% to about 80%, including all values and sub-ranges therebetween, of the free space volume of the chamber 144 (or 144' or 144") is filled with MR fluid 134 and the remaining volume is filled with the compressible gas 444. In still another embodiment, about 50% to about 90%, including all values and sub-ranges therebetween, of the free space volume of the chamber 144 (or 144' or 144") is filled with MR fluid 134 and the remaining volume is filled with the compressible gas 444. In modified embodiments, more or less of the chamber 144 (or 144' or 144") may be filled with MR fluid, as needed or desired.

In one embodiment, substantially all of the free space volume of the chamber 144 is filled with MR fluid 134 and the outer spline port 278 and the outer spline cavity portion 442 contain the compressible gas 444. In another embodiment, substantially all of the free space volume of the chamber 144 and the outer spline port 278 are filled with MR fluid 134 and the outer spline cavity portion 442 contains the compressible gas 444. Other suitable combinations of MR fluid volume and compressible gas volume may be efficaciously used, as needed or desired.

In one embodiment, the free space volume of the chamber 144 (or 144' or 144") is about 10 milliliters (mL). In another embodiment, the free space volume of the chamber 144 (or 144' or 144") is in the range from about 5 mL to about 15 mL, including all values and sub-ranges therebetween. In yet another embodiment, the free space volume of the chamber 144 (or 144' or 144") is in the range from about 1 mL to about 20 mL, including all values and sub-ranges therebetween. In modified embodiments, other suitable chamber volumes may be efficaciously utilized, as needed or desired.

Embodiments of the invention provide systems and methods of controlling or relieving pressure within a magnetorheologically actuated prosthetic knee 110. As schematically illustrated in FIG. 62, these embodiments control the pressure so that it does not generally exceed an upper limit or predetermined pressure $P_{chamber-max}$. Stated differently, these embodiments control the pressure variation to within generally a maximum or predetermined pressure differential $\Delta P$ from the ambient or atmospheric pressure $P_{ambient}$. Without any pressure control mechanisms, the chamber pressure can reach undesirably high values, $P_{chamber-high}$, which can adversely affect device performance, for example, by causing seal malfunction or failure.

Some embodiments control the sealed chamber pressure $P_{chamber}$ by utilizing the flexible diaphragm assembly 146 that includes a flexible solid medium such as the deflectable diaphragm element 426d to advantageously relieve undesirable pressure build-up. Some embodiments control the sealed chamber pressure $P_{chamber}$ by utilizing a compressible gaseous medium such as the compressible gas 444 (e.g., nitrogen, air or the like) to advantageously relieve undesirable pressure build-up. Some embodiments control the sealed chamber pressure $P_{chamber}$ by utilizing the flexible diaphragm assembly 146 in combination with the compressible gaseous medium so that the deflectable diaphragm element 426d and the compressible gas 444 both facilitate pressure control to advantageously relieve undesirable pressure build-up and, in some embodiment, are in fluid communication with one another and the MR fluid 134.

Pyramid Adapter

FIGS. 63–66 show different views of one embodiment of the pyramid connector, stud or adapter 152. The pyramid connector 152 generally comprises a proximal boss portion 446, a distal threaded portion 448 and a cavity, cup or recess 450 in fluid communication with the pyramid passage 440.

The pyramid connector 152 mechanically connects the outer spline 132 and the stump socket 106, thereby attaching the knee actuator 112 and the prosthetic knee 110 to the stump socket 106. The outer spline 132, and hence the outer blades 130, are substantially irrotationally coupled to or nonrotatable with respect to the stump socket 106 or residual limb 108. Stated differently, rotation of the outer spline 132 and the outer blades 130 generally corresponds to rotation of the stump socket 106 or residual limb 108.

The pyramid connector 152 is generally positioned over the diaphragm assembly 146 which is seated on the base surface 274 of the outer spline cavity 272 and generally within the cavity 272. The pyramid passage 440 exposes the upper surface 434d of the deflectable diaphragm element 426d to ambient or atmospheric pressure conditions and the pyramid cavity 450 sealingly fits over the convex dome surface 422 to advantageously facilitate the pressure control mechanism in accordance with some embodiments.

The boss portion 446 is generally frusto-pyramidal in shape and has a generally flat top surface 452. The frusto-pyramidal boss portion 446 has a plurality of angled faces 454 for receiving angled set screws or the like associated with the distal end of the stump socket 106 (or a suitable connection member there at). Once the set screws are tightened against respective angled faces 454 of the boss portion 446, the stump socket 106 will be locked in the desired orientation with respect to the outer spline 132.

The combination of the domed top portion 270 of the outer spline 132 and the frusto-pyramidal boss portion 446 distal end of the stump socket 106 (or a suitable connection member there at) advantageously provides for angular adjustments of the stump socket 106 (or a pylon assembly) with respect to the outer spline 132, and hence the knee actuator 112 and prosthetic knee 110.

The pyramid threaded portion 448 has male threads that engage female threads or counter bores of the threaded side wall 276 of the outer spline cavity or cup 272 to connect the outer spline 132 and adapter 152. The pyramid connector 152 is desirably bonded to the outer spline 132 to secure it in place, for example, by utilizing epoxy or the like on the respective mating male and/or female threads. During assembly, notches, markings, indicia and/or reference surfaces may be used for proper alignment and connection of the pyramid connector 152 to the domed top portion 270 of the outer spline 132.

The pyramid cavity 450 has a generally circular or annular concave domed surface 456 and a generally flat circular central surface 458. The cavity 450 is desirably sized and configured such that the diaphragm assembly 146 sealingly fits within it.

The concave inner domed surface 456 engages or abuts against the convex outer surface 422 of the diaphragm assembly cap portion 412 and, in some embodiments, also the diaphragm portion lip 428. In one embodiment, grease, such as silicone grease or the like, is applied to one or both of the convex outer surface 422 of the cap portion 412 and the concave dome surface 456 of the pyramid adapter 152 to provide a reliable seal. Grease, such as silicone grease or the like, may also be applied to any engaging surface of the diaphragm portion lip 428 and the concave dome surface 456 to provide a reliable seal. Advantageously, this facilitates in sealing the MR fluid chamber 144 and isolate it from undesirable ambient or atmospheric exposure.

The flat surface 458 of the pyramid recess 450 is generally aligned with the open end of the passage 418 of the diaphragm assembly cap portion 412. The passage 418 communicates with the pyramid tube 440 that is exposed to ambient or atmospheric pressure The pyramid tubular passage 440 has one end 460 that opens at the boss portion surface 452 and a second opposed end 462 that opens at the cavity flat surface 458 such that the tubular passage 440 is in fluid communication with the upper surface 434d of the deflectable diaphragm element 426d. This exposes the upper surface 434d ambient or atmospheric pressure $P_{ambient}$. In modified embodiments, other tubular arrangements associated with the diaphragm assembly 146 and/or the pyramid connector 152 may be utilized to provide the desired pressure exposure, as needed or desired.

In one embodiment, the pyramid connector 152 comprises titanium or a titanium alloy. In another embodiment, the pyramid connector 152 comprises aluminum or a aluminum alloy. In modified embodiments, the pyramid connector 152 can be efficaciously fabricated from other suitable metals, alloys, plastics, ceramics, among others, as required or desired.

The pyramid connector 152 desirably allows for proper coupling and alignment between the outer spline 132 and the stump socket 106. The pyramid connector 152 also, in some embodiments, advantageously facilitates the pressure control mechanism embodiments of the diaphragm assembly 146 by providing housing space and selective exposure to ambient or atmospheric conditions while maintaining the seal integrity of the MR fluid chamber 144.

Side Mounts

The side mounts, walls or forks 136, 138 are mechanically coupled, communicated or connected to respective core side plates 116, 118 and the inner spline 122. The side mounts 136, 138 are further connected to the frame and electronics assembly 114 which in turn is connected to a lower (below the knee) part of the leg, for example, the leg pylon 104 (see FIG. 2). Thus, rotation of the side mounts 136, 138 corresponds to rotation or motion of the leg pylon 104.

Figure 67:
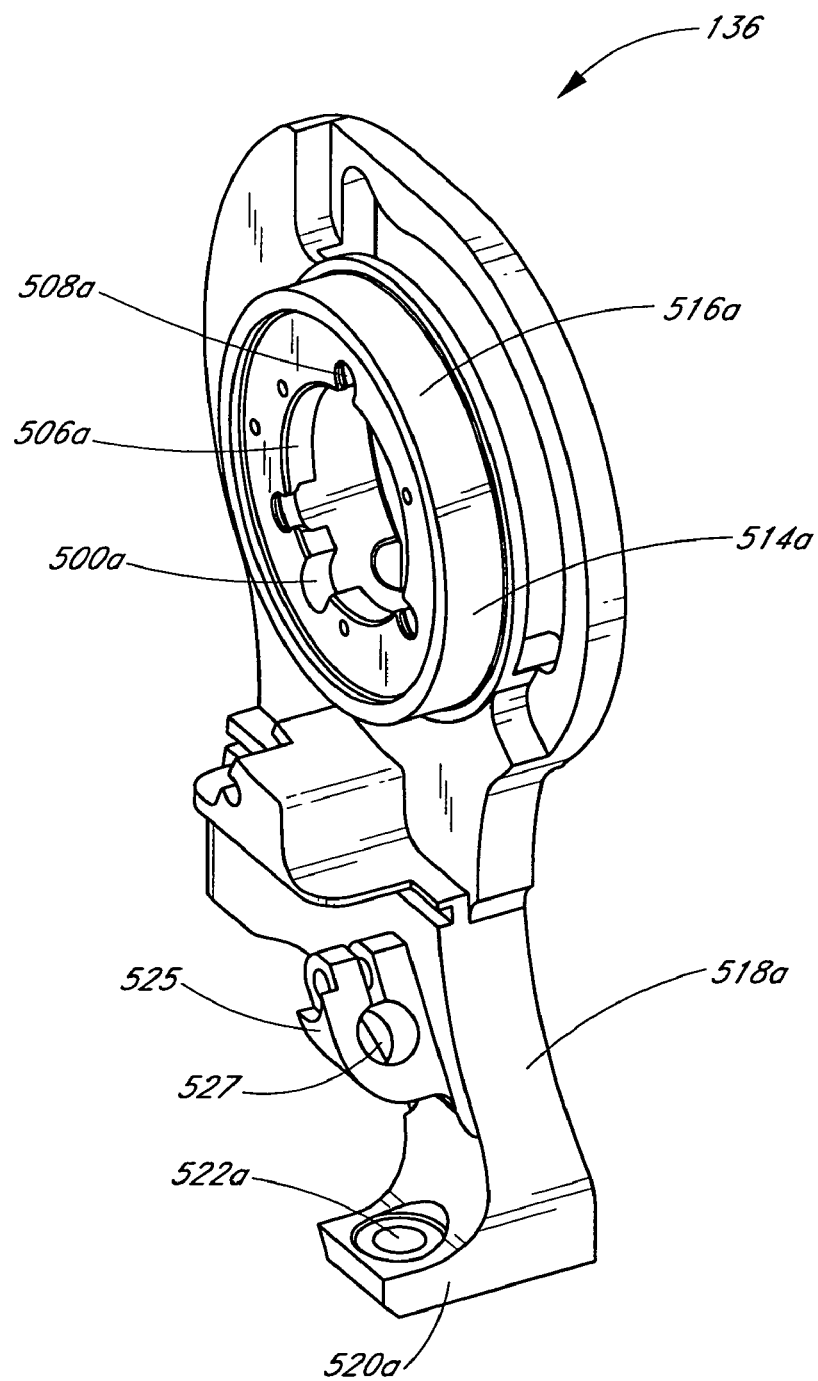
FIG. 67 is a simplified perspective view of a right side mount of the actuator of FIG. 6 illustrating features and advantages in accordance with an embodiment of the invention.
Figure 69:
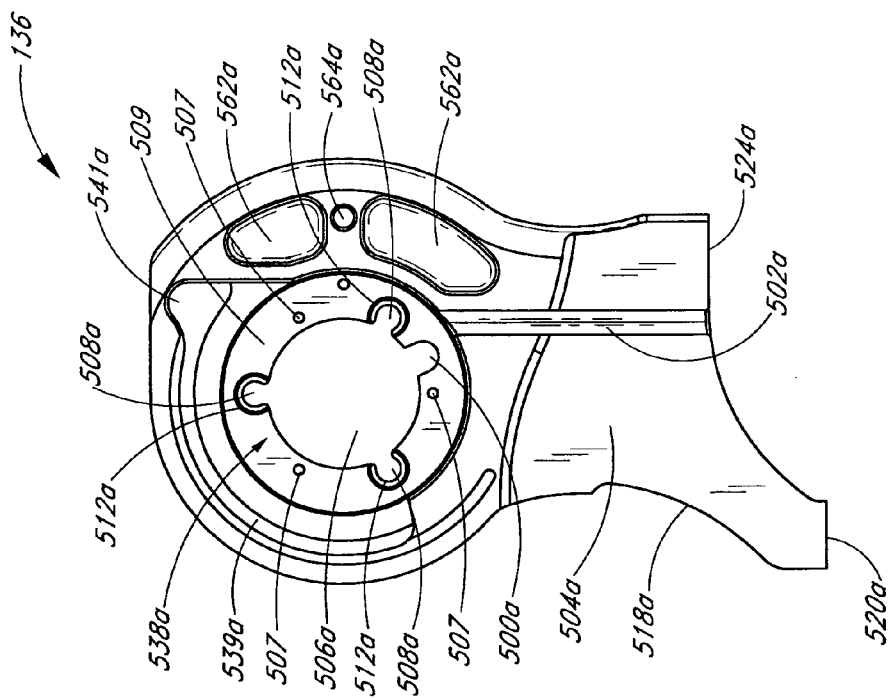
FIG. 69 is a simplified rear (exterior face) view of the right side mount of FIG. 67 illustrating features and advantages in accordance with an embodiment of the invention.
Figure 68:
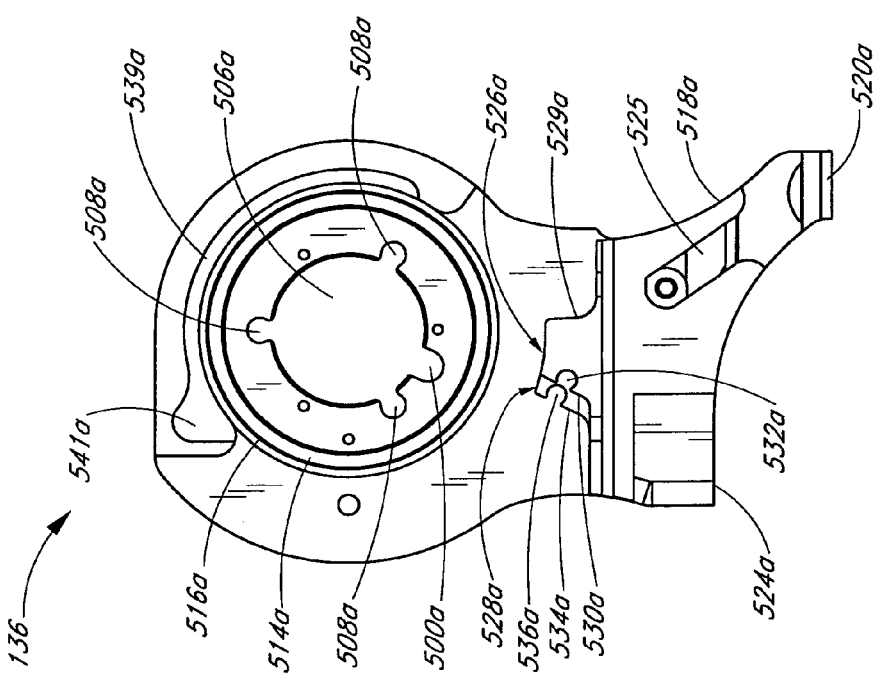
FIG. 68 is a simplified front (interior face) view of the right side mount of FIG. 67 illustrating features and advantages in accordance with an embodiment of the invention.

FIGS. 67–69 show different views of one embodiment of the right side mount 136. The right mount 136 has a notch 500a through which a shielded cable or lead wires of the angle sensing system 154 passes. The right mount 136 has a groove 502a on its exterior surface or side 504a along which this cable runs and connects to the frame and electronics assembly 114.

The right mount 136 has a generally circular through cavity, hole or passage 506a. The cavity 506a is generally aligned with and fits over the shoulders or steps 208a1, 208a2, 208a3 (see, for example, FIG. 13) on the outer surface of the right core side plate 116. In one embodiment, the cavity 506a forms a close tolerance slip fit with the shoulders or steps 208a1, 208a2, 208a3.

In some embodiments, the cavity 506a also receives at least a portion of the angle sensing system 154 and a plurality of threaded holes 507 extend inwardly from side mount surface 509. The holes 507 receive screws or the like to facilitate connection to the angle sensing system 154. In the illustrated embodiment, three holes 507 are provided that are arranged substantially equidistantly and in a circular fashion around the cavity 506a.

The right side mount 136 includes a plurality of generally equidistantly spaced circularly arranged through holes 508a. Each of the through holes 508a receives a respective one of the through rods 158. The holes 508a are generally radially outwardly offset relative to the cavity 506a. In the illustrated embodiment, the holes 508a and holes 507 are alternatingly interspersed and spaced to provide clearance space.

The holes 508a are substantially aligned with the holes 180a, 180b of respective core side plates 116, 118 and the passages 228 of the inner spline 122. The studs or rods 158 secure selected components of the knee actuator 112, such as the core side plates 116, 118, the inner spline 122 and the side mounts 136, 138.

As best seen in FIG. 69, the exteriorly or outwardly facing side of the right mount 136 has a plurality of recessed surfaces 512a with each generally circumscribing or surrounding a respective one of the holes 508a. Each of the recessed surfaces 512a receives a respective one of the cone nuts 160 or the like to secure the through rods 158 in place.

The right mount 136 includes an inwardly facing generally circular or annular ring 514a with a generally circular bearing surface 516a. The ring 514a is received within the cavity 129a of the right bearing 126 (see, for example, FIG. 22). The bearing surface 516a engages the inner bearing surface 131a of the right bearing 126. In one embodiment, the ring portion 514a forms a close tolerance slip fit within the right bearing cavity 129a.

The right mount 136 includes a generally downwardly extending rear support or leg member 518a that connects to the frame and electronics assembly 114. The leg 518a has generally flat foot or seat member 520a with a through hole 522a that receives the bolt 164a (see, for example, FIG. 6) or the like to connect the rear portion of the right mount 136 to the frame and electronics assembly 114.

The right mount 136 has a threaded hole or the like at around 524a that receives a bolt or the like to connect the front portion of the right mount 136 to the frame and electronics assembly 114. The right side mount 136 may include another threaded hole substantially adjacent to the rear through hole 522a that receives a bolt or the like to further secure the connection between the right mount 136 and the frame and electronics assembly 114.

The side mount leg 518a, in one embodiment, includes a mount or support element 525 that supports a battery charging and system programming socket, port or receptacle, as described further below. The support 525 has a mounting hole 527 that receives the socket.

As best seen in FIG. 68, in some embodiments, the right side mount 136 includes a pair of substantially adjacent bumper mounts or supports 526a, 528a that facilitate in providing an extension stop system and shock absorption at substantially full knee extension, as discussed further below. The bumper mount 526a is inwardly offset relative to the bumper mount 528a. Stated differently, the bumper mount 528a is outwardly offset relative to the bumper mount 526a. In modified embodiments, this arrangement may be reversed, as needed or desired.

The bumper mount 526a includes a rearwardly slanting and generally flat surface 530a on which one bumper is seated. The bumper mount 526a has a female slot, recess or cavity 532a that receives a male portion of the bumper to facilitate alignment and connection therebetween.

The bumper mount 528a includes a rearwardly slanting and generally flat surface 534a on which a second bumper is seated. The bumper mount 528a has a female slot, recess or cavity 536a that receives a male portion of the bumper to facilitate alignment and connection therebetween.

In the illustrated embodiment, the right side mount 136 includes an exterior side recessed region or portion 538a and a curved generally C-shaped slot or opening 539a that desirably provides clearance space for the knee angle sensing or measuring assembly or system 154 (see, for example, FIG. 6). The slot 539a may have a widened portion 541a at one closed end that is substantially aligned with the slot 269a (see, for example, FIG. 43) of the outer spline 132 to provide clearance space for assembly.

In the illustrated embodiment, the side mount 136 further includes a pair of relief pockets or cavities 562a that receive portions of a knee cover, as described further below. The side mount 136 has an opening or cavity 564a intermediate the pockets 562a that receives a connector pin or the like that facilitates attachment of the right side cap 156a.

The right mount 136 may include other recesses, holes, passages, slots, notches, contours and the like that can provide clearance space, alignment facilitation, connection features and component access, among other desirable characteristics. Material may be selectively removed at portions of the right mount 136 to advantageously provide device weight reduction while maintaining structural integrity, as needed or desired.

Figure 70:
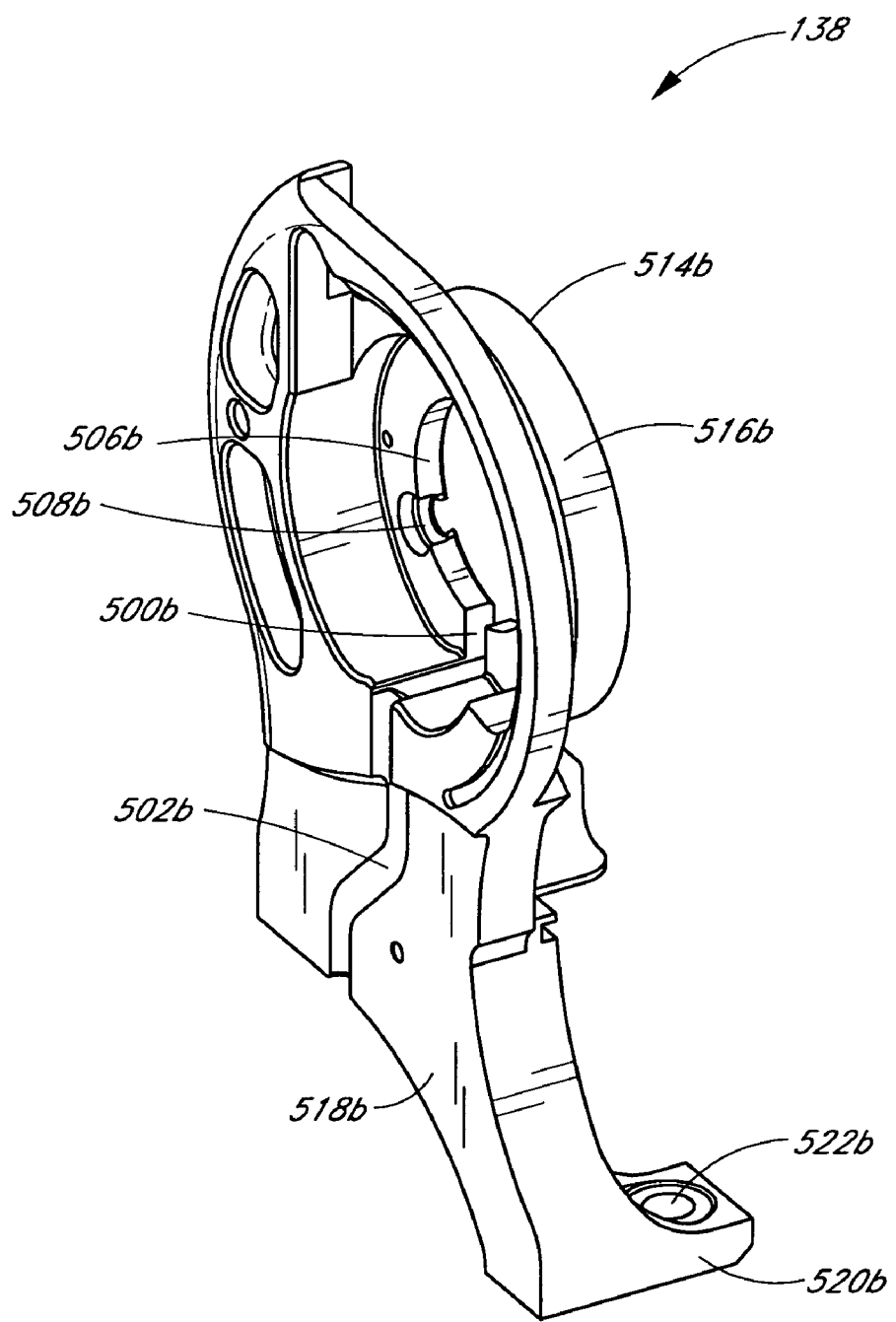
FIG. 70 is a simplified perspective view of a left side mount of the actuator of FIG. 6 illustrating features and advantages in accordance with an embodiment of the invention.
Figure 71:
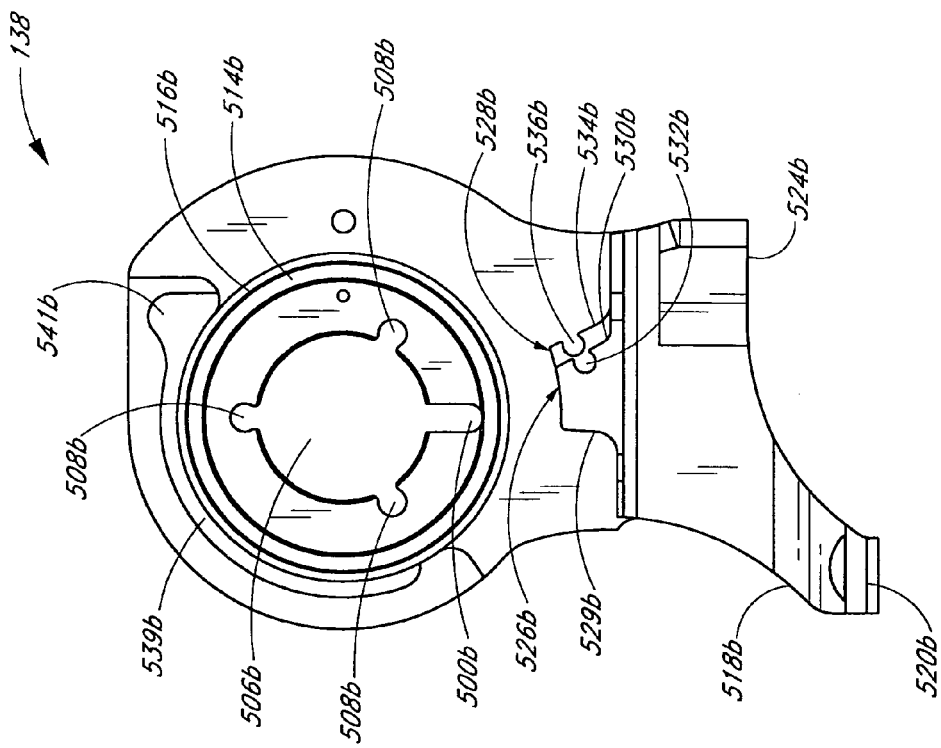
FIG. 71 is a simplified front (interior face) view of the left side mount of FIG. 70 illustrating features and advantages in accordance with an embodiment of the invention.
Figure 72:
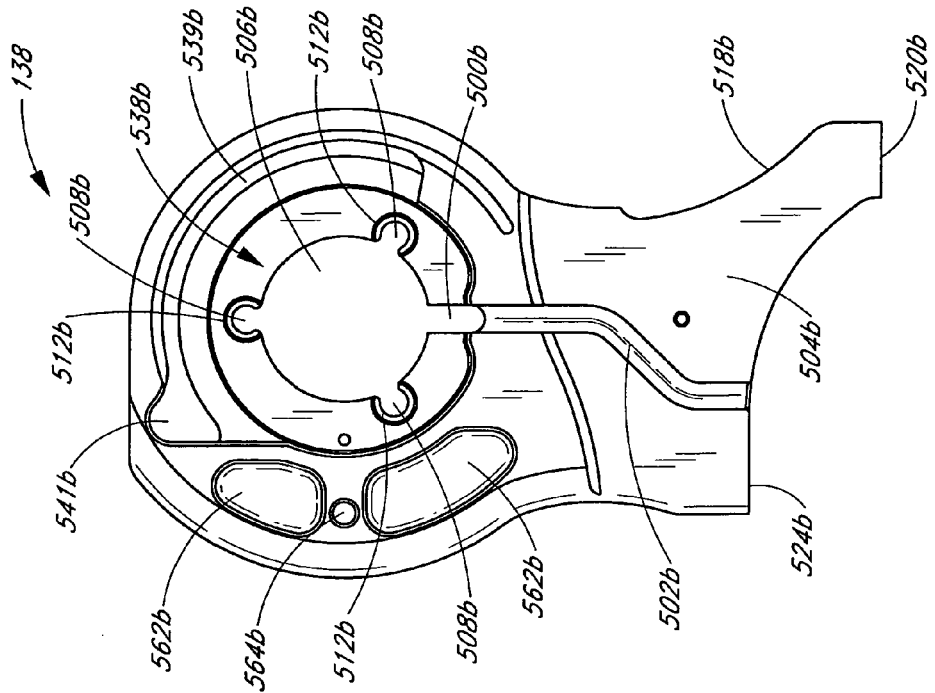
FIG. 72 is a simplified rear (exterior face) view of the left side mount of FIG. 70 illustrating features and advantages in accordance with an embodiment of the invention.

FIGS. 70–72 show different views of one embodiment of the left side mount 138. The left mount 138 has a notch 500b substantially aligned with the notch 212 of the left core side plate 118 through which the shielded cable or lead wires 218 (see, for example, FIG. 23) passes. The left mount 138 has a groove 502b on its exterior surface or side 504b along which the cable 218 runs and connects to the frame and electronics assembly 114. Advantageously, the notch 500b and groove 502b facilitate in keeping the cable 218 in position and prevent undesirable movement.

The left mount 138 has a generally circular through cavity, hole or passage 506b. The cavity 506b is generally aligned with and fits over the shoulders or steps 208b1, 208b2, 208b3, 208b4 (see, for example, FIG. 17) on the outer surface of the left core side plate 118. In one embodiment, the cavity 506b forms a close tolerance slip fit with the shoulders or steps 208b1, 208b2, 208b3.

The left side mount 138 includes a plurality of generally equidistantly spaced circularly arranged through holes 508b. Each of the through holes 508b receives a respective one of the through rods 158. The holes 508b are generally radially outwardly offset relative to the cavity 506b.

The holes 508b are substantially aligned with holes 508a of the right mount, the holes 180a, 180b of respective core side plates 116, 118 and the passages 228 of the inner spline 122. The studs or rods 158 pass through the holes 508b, the holes 508a, the holes 180a, 180b and the passages 228 to secure the core side plates 116, 118, the inner spline 122 and the side mounts 136, 138.

As best seen in FIG. 72, the exteriorly or outwardly facing side of the left mount 138 has a plurality of recessed surfaces 512b with each generally circumscribing or surrounding a respective one of the holes 508b. Each of the recessed surfaces 512b receives a respective one of the cone nuts 160 or the like to secure the through rods 158 in place.

The left mount 138 includes an inwardly facing generally circular or annular ring 514b with a generally circular bearing surface 516b. The ring 514b is received within the cavity 129b of the left bearing 128 (see, for example, FIG. 22). The bearing surface 516b engages the inner bearing surface 131b of the left bearing 128. In one embodiment, the ring portion 514b forms a close tolerance slip fit within the left bearing cavity 129b.

The left mount 138 includes a generally downwardly extending rear support or leg member 518b that connects to the frame and electronics assembly 114. The leg 518b has generally flat foot or seat member 520b with a through hole 522b that receives the bolt 164b (see, for example, FIG. 6) or the like to connect the rear portion of the left mount 138 to the frame and electronics assembly 114.

The left mount 138 has a threaded hole or the like at around 524b that receives a bolt or the like to connect the front portion of the left mount 138 to the frame and electronics assembly 114. The left side mount 138 may include another threaded hole substantially adjacent to the rear through hole 522b that receives a bolt or the like to further secure the connection between the left mount 138 and the frame and electronics assembly 114.

As best seen in FIG. 71, in some embodiments, the left side mount 138 includes a pair of substantially adjacent bumper mounts or supports 526b, 528b that facilitate in providing an extension stop system and shock absorption at substantially full knee extension, as discussed further below. The bumper mount 526b is inwardly offset relative to the bumper mount 528b. Stated differently, the bumper mount 528b is outwardly offset relative to the bumper mount 526b. In modified embodiments, this arrangement may be reversed, as needed or desired.

The bumper mount 526b includes a rearwardly slanting and generally flat surface 530b on which one bumper is seated. The bumper mount 526b has a female slot, recess or cavity 532b that receives a male portion of the bumper to facilitate alignment and connection therebetween.

The bumper mount 528b includes a rearwardly slanting and generally flat surface 534b on which a second bumper is seated. The bumper mount 528b has a female slot, recess or cavity 536b that receives a male portion of the bumper to facilitate alignment and connection therebetween.

In the illustrated embodiment, the left side mount 138 includes an exterior side recessed region or portion 538b and a curved generally C-shaped slot or opening 539b that desirably provide clearance space for the extension assist assembly or system 148 (see, for example, FIG. 6). The slot 539b may have a widened portion 541b at one closed end that is substantially aligned with the slot 269b (see, for example, FIG. 42) of the outer spline 132 to provide clearance space for assembly.

In the illustrated embodiment, the side mount 138 further includes a pair of relief pockets or cavities 562b that receive portions of a knee cover, as described further below. The side mount 138 has an opening or cavity 564b intermediate the pockets 562b that receives a connector pin or the like that facilitates attachment of the left side cap 156b.

The left mount 138 may include other recesses, holes, passages, slots, notches, contours and the like that can provide clearance space, alignment facilitation, connection features and component access, among other desirable characteristics. Material may be selectively removed at portions of the left mount 138 to advantageously provide device weight reduction while maintaining structural integrity, as needed or desired.

In one embodiment, the side mounts 136, 138 fabricated from an aluminum alloy such as anodized 7075-T6 aluminum alloy. In modified embodiments, the side mounts 136, 138 can be efficaciously fabricated from other suitable metals, alloys, plastics, ceramics, among others, as required or desired.

The side mounts 136, 138 are desirably formed by machining. In modified embodiments, the side mounts 136, 138 can be efficaciously fabricated from other suitable techniques, for example, casting, forging, molding, laser processing, among others, as required or desired.

Multi-Stage Bumper System

Embodiments of the invention provide an extension stop system generally comprising the bumper system 150 on the side mounts 136, 138 and the spaced stops 282 (282a, 282b) of the outer spline 132. At substantially full knee extension, the stops 282a, 282b engage or contact the specially designed shock absorbing bumper assembly 150 to prevent further knee rotation. Thus, the extension stop system controls the maximum allowable extension by physically limiting the rotation between the outer side mounts 136, 138 and the outer spline 132, and hence the rotation of the knee.

Figure 73:
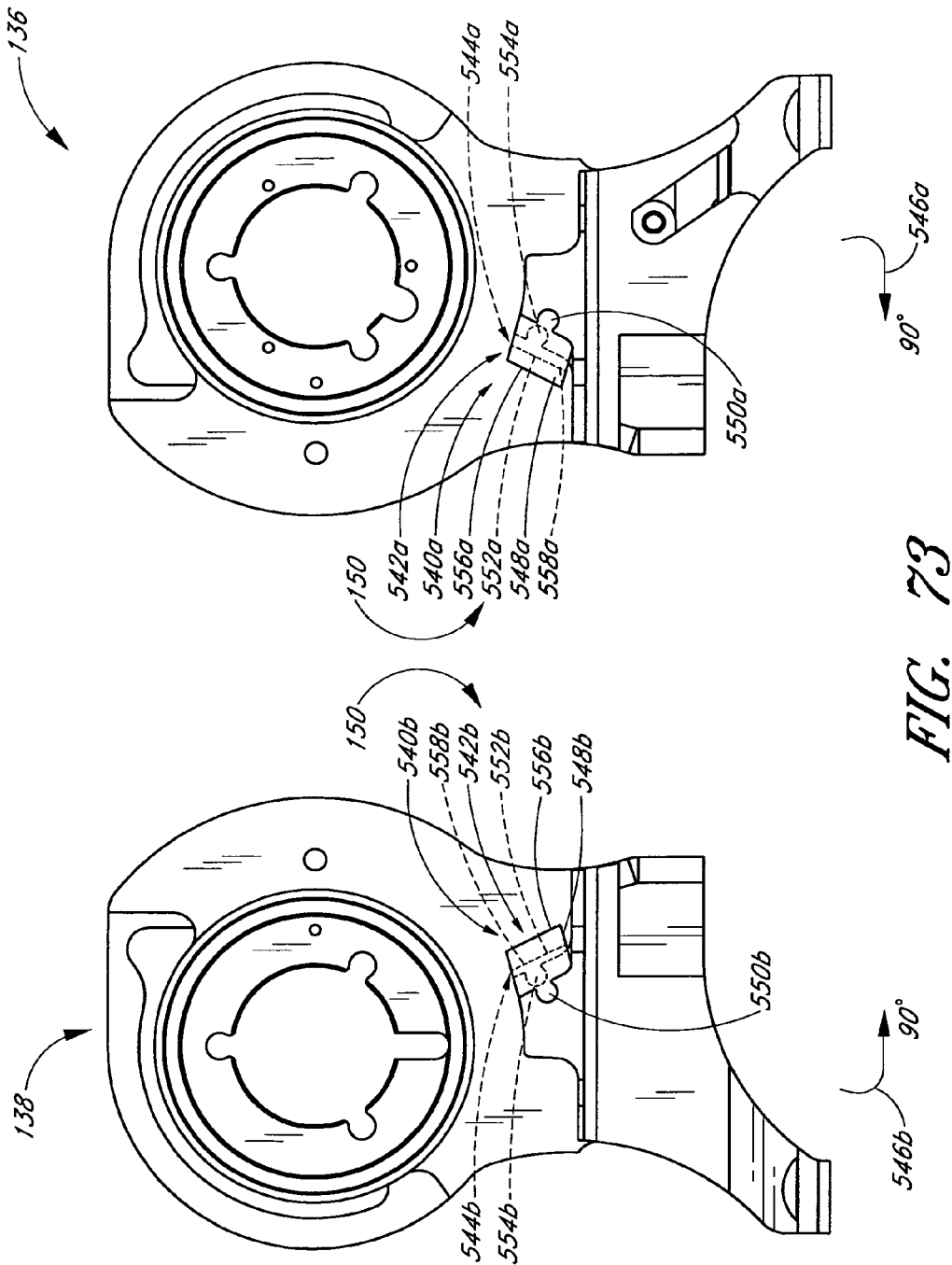
FIG. 73 is a simplified side (interior) view of a shock absorbing multi-stage bumper system of the actuator of FIG. 6 illustrating features and advantages in accordance with an embodiment of the invention.
Figure 74:
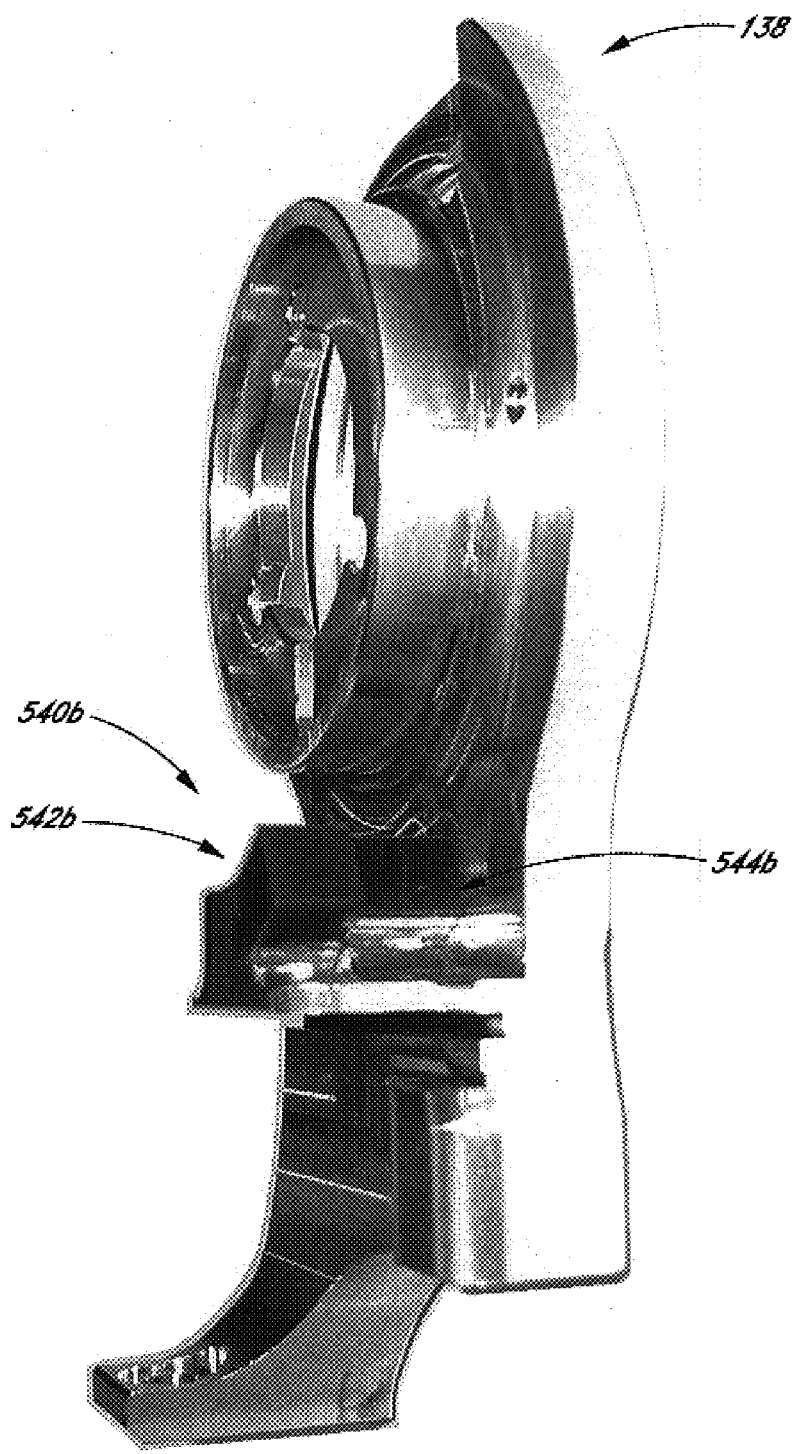
FIG. 74 is a simplified perspective view of one multi-stage bumper assembly of the bumper system of FIG. 73 illustrating features and advantages in accordance with an embodiment of the invention.

FIG. 73 shows one embodiment of the shock absorbing bumper system 150. The bumper system generally comprises two bumper assemblies 540a, 540b with one each on a respective one of the side mounts 136, 138. FIG. 74 shows another view of the bumper assembly 540b mounted on the left side mount 138.

The side mounts 136, 138 shown in FIG. 73 when in assembled form would be rotated by about 90° (as generally shown by arrows 546a, 546b) so that the bumper assemblies 540a, 540b face forwardly and are spaced and aligned with one another and the corresponding stops 282a, 282b. Advantageously, the bumper assemblies 540a, 540b provide a substantially smooth shock absorbing, cushioning and/or dissipating effect when engaged with respective stops 282a, 282b to substantially prevent or mitigate jarring or discomfort to the prosthetic knee wearer.

The right bumper assembly 540a generally comprises a substantially soft and compressible first bumper 542a and an adjacent substantially hard and rigid second bumper 544a. The left bumper assembly 540b generally comprises a substantially soft, resilient and compressible first bumper 542b and an adjacent substantially hard and rigid second bumper 544b.

The bumpers or stops 542a, 544a are attached to respective bumper supports 526a, 528a of the right side mount 136. Thus, the bumper 542a is inwardly offset relative to the bumper 544a. Stated differently, the bumper 544a is outwardly offset relative to the bumper 542a. In modified embodiments, this arrangement may be reversed, as needed or desired.

The bumpers or stops 542b, 544b are attached to respective bumper supports 526b, 528b of the left side mount 138. Thus, the bumper 542b is inwardly offset relative to the bumper 544b. Stated differently, the bumper 544b is outwardly offset relative to the bumper 542b. In modified embodiments, this arrangement may be reversed, as needed or desired.

The flexible bumper 542a includes a generally main body portion or member 548a that engages the outer spline stop 282a at substantially full knee extension and a male locking portion or member 550a that facilitates attachment to the bumper support 526a. The bumper 544a includes a generally main body portion or member 552a that also engages the outer spline stop 282a at substantially full knee extension and a male locking portion or member 554a that facilitates attachment to the bumper support 528a.

The flexible bumper 542b includes a generally main body portion or member 548b that engages the outer spline stop 282b at substantially full knee extension and a male locking portion or member 550b that facilitates attachment to the bumper support 526b. The bumper 544b includes a generally main body portion or member 552b that also engages the outer spline stop 282b at substantially full knee extension and a male locking portion or member 554b that facilitates attachment to the bumper support 528b.

The bumper element 548a has a rear surface that is seated or rests on the generally flat surface 530a of the bumper support 526a of the right side mount 136. In the illustrated embodiment, the bumper element 548a is generally cubical in shape with generally rectangular sides. In modified embodiments, the bumper element 548a may be configured in other suitable polygonal or non-polygonal shapes with efficacy, as needed or desired.

The bumper element 552a has a rear surface that is seated or rests on the generally flat surface 534a of the bumper support 528a of the right side mount 136. In the illustrated embodiment, the bumper element 552a is generally cubical in shape with generally rectangular sides. In modified embodiments, the bumper element 552a may be configured in other suitable polygonal or non-polygonal shapes with efficacy, as needed or desired.

The bumper element 548b has a rear surface that is seated or rests on the generally flat surface 530b of the bumper support 526b of the left side mount 138. In the illustrated embodiment, the bumper element 548b is generally cubical in shape with generally rectangular sides. In modified embodiments, the bumper element 548b may be configured in other suitable polygonal or non-polygonal shapes with efficacy, as needed or desired.

The bumper element 552b has a rear surface that is seated or rests on the generally flat surface 534b of the bumper support 528b of the left side mount 138. In the illustrated embodiment, the bumper element 552b is generally cubical in shape with generally rectangular sides. In modified embodiments, the bumper element 552b may be configured in other suitable polygonal or non-polygonal shapes with efficacy, as needed or desired.

The soft bumper element 548a has a front face or surface 556a and the hard bumper element 552a has a front face or surface 558a that are arranged in a stepped fashion with the surface 556a extending forwardly with respect to the surface 558a. In the illustrated embodiment, the surfaces 556a, 558a are rearwardly slanted or angled such that they make substantially flush contact with the corresponding engaging surface 283a of the stop 282a of the outer spline 132.

The soft bumper element 548b has a front face or surface 556b and the hard bumper element 552b has a front face or surface 558b that are arranged in a stepped fashion with the surface 556b extending forwardly with respect to the surface 558b. In the illustrated embodiment, the surfaces 556b, 558b are rearwardly slanted or angled such that they make substantially flush contact with the corresponding engaging surface 283b of the stop 282b of the outer spline 132.

The male locking bumper element 550a is sized and configured to fit within the slot 532a of the bumper support 526a of the right side mount 136. In the illustrated embodiment, the male locking element 550a is generally cylindrical in shape with a generally circular cross section and a narrowed neck portion that facilitates interlocking within the slot 532a and inhibits undesirable removal or movement. In modified embodiments, other suitable polygonal or non-polygonal interlocking configurations may be efficaciously used, as needed or desired.

The male locking bumper element 554a is sized and configured to fit within the slot 536a of the bumper support 528a of the right side mount 136. In the illustrated embodiment, the male locking element 554a is generally cylindrical in shape with a generally circular cross section and a narrowed neck portion that facilitates interlocking within the slot 536a and inhibits undesirable removal or movement. In modified embodiments, other suitable polygonal or non-polygonal interlocking configurations may be efficaciously used, as needed or desired.

The male locking bumper element 550b is sized and configured to fit within the slot 532b of the bumper support 526b of the left side mount 138. In the illustrated embodiment, the male locking element 550b is generally cylindrical in shape with a generally circular cross section and a narrowed neck portion that facilitates interlocking within the slot 532b and inhibits undesirable removal or movement. In modified embodiments, other suitable polygonal or non-polygonal interlocking configurations may be efficaciously used, as needed or desired.

The male locking bumper element 554b is sized and configured to fit within the slot 536b of the bumper support 528b of the left side mount 138. In the illustrated embodiment, the male locking element 554b is generally cylindrical in shape with a generally circular cross section and a narrowed neck portion that facilitates interlocking within the slot 536b and inhibits undesirable removal or movement. In modified embodiments, other suitable polygonal or non-polygonal interlocking configurations may be efficaciously used, as needed or desired.

The bumpers 542a, 542b comprise a suitably soft, compressible and resilient material to provide the desired shock absorption properties. In one embodiment, the bumpers 542a, 542b comprise urethane such as a thermoplastic urethane (TPU). In modified embodiments, other suitable plastics and the like may be efficaciously utilized, as needed or desired.

In one embodiment, the bumpers 542a, 542b comprise a material having a Shore A hardness of about 90 A durometer. In another embodiment, the bumpers 542a, 542b comprise a material having a Shore A hardness of about 85 A durometer to about 95 A durometer, including all values and sub-ranges therebetween. In yet another embodiment, the bumpers 542a, 542b comprise a material having a Shore A hardness of about 80 A durometer to about 99 A durometer, including all values and sub-ranges therebetween. In modified embodiments, other suitable hardnesses may be efficaciously utilized, as needed or desired.

The bumpers 544a, 544b comprise a suitably hard and substantially rigid material to provide a hard stop for knee extension rotation. In one embodiment, the bumpers 544a, 544b comprise urethane such as a thermoplastic urethane (TPU). In modified embodiments, other suitable plastics and the like may be efficaciously utilized, as needed or desired. The use of urethane or the like advantageously avoids metal (alloy) to metal (alloy) contact and substantially prevents undesirable wear of the stops 282a, 282b.

In one embodiment, the bumpers 544a, 544b comprise a material having a Shore D hardness of about 75 D durometer. In another embodiment, the bumpers 544a, 544b comprise a material having a Shore D hardness of about 70 D durometer to about 80 D durometer, including all values and sub-ranges therebetween. In yet another embodiment, the bumpers 544a, 544b comprise a material having a Shore D hardness of about 60 D durometer to about 99 D durometer, including all values and sub-ranges therebetween. In modified embodiments, other suitable hardnesses may be efficaciously utilized, as needed or desired.

In one embodiment, the soft bumpers 542a, 542b are formed by molding. In modified embodiments, the bumpers 542a, 542b can be efficaciously fabricated from other suitable techniques, for example, casting, forging, machining, laser processing, among others, as required or desired.

In one embodiment, the hard bumpers 544a, 544b are formed by molding. In modified embodiments, the bumpers 544a, 544b can be efficaciously fabricated from other suitable techniques, for example, casting, forging, machining, laser processing, among others, as required or desired.

During assembly of the bumper assemblies 540a, 540b on the respective side mounts 136, 138, in one embodiment, the hard bumpers 544a, 544b are first connected to respective bumper supports 528a, 528b. The male locking bumper elements 552a, 552b are slid into respective slots 536a, 536b to mount the hard bumpers 544a, 544b in place.

Similarly, the soft bumpers 542a, 542b are then connected to respective bumper supports 526a, 526b. The male locking bumper elements 550a, 550b are slid into respective slots 532a, 532b to mount the soft bumpers 542a, 542b in place.

In one embodiment, an adhesive such as Loctite® 495 which is a Loctite® cyanoacrylate ("Super Glue") or the like is used to secure the soft bumpers 542a, 542b to respective bumper supports 526a, 526b. The hard bumpers 544a, 544b are secured without an adhesive since the configuration of the interlocking features 552a, 552b and 532a, 532b and the positioning of the hard bumpers 544a, 544b between respective soft bumpers 542a, 542b and wall portions of respective side mounts 136, 138 prevents any undesirable movement of the hard bumpers 544a, 544b and keeps them in place. In modified embodiments, an adhesive such as Loctite® 495 which is a Loctite® cyanoacrylate ("Super Glue") or the like may be used to secure the hard bumpers 544a, 544b to respective bumper supports 528a, 528b, as needed or desired.

In operation of the extension stop system, at substantially full knee extension, the stops 282 (282a, 282b) contact the respective multi- or two-stage bumper assemblies 540 (540a, 540b). The stops 282a, 282b first contact respective soft bumpers 542a, 542b which are compressed as the knee rotates. The soft bumpers 542a, 542b stop compressing when the stops 282a, 282b contact respective hard bumpers 544a, 544b. This controls the limit of knee extension rotation and stops further knee extension. As the knee flexes, the soft bumpers 542a, 542b expand to substantially their original uncompressed state.

Figure 75:
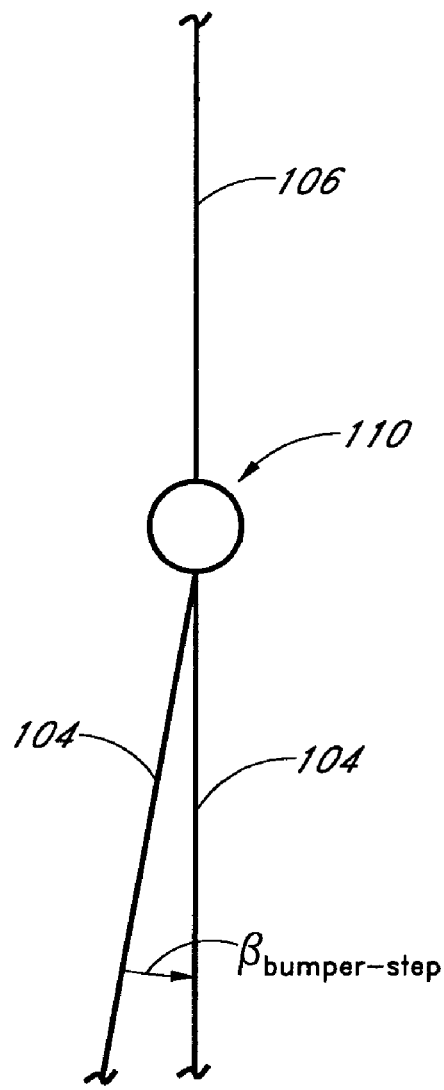
FIG. 75 is a simplified schematic view of knee rotation during operation of the bumper system of FIG. 73 illustrating features and advantages in accordance with an embodiment of the invention.

As schematically shown in FIG. 75, the knee rotation angle corresponding to when the stops 282 first engage the soft bumpers 542 and subsequently engage the hard bumpers 544 is generally given by $\beta_{bumper-step}$. This is due to the stepped configuration of the bumper assemblies 540 of embodiments of the invention.

In one embodiment, the angle $\beta_{bumper-step}$ is about 3°. In another embodiment, the angle $\beta_{bumper-step}$ is in the range from about 2° to about 4°, including all values and sub-ranges therebetween. In yet another embodiment, the angle $\beta_{bumper-step}$ is in the range from about 1° to about 5°, including all values and sub-ranges therebetween. In modified embodiments, $\beta_{bumper-step}$ may be higher or lower, as needed or desired.

Figure 76:
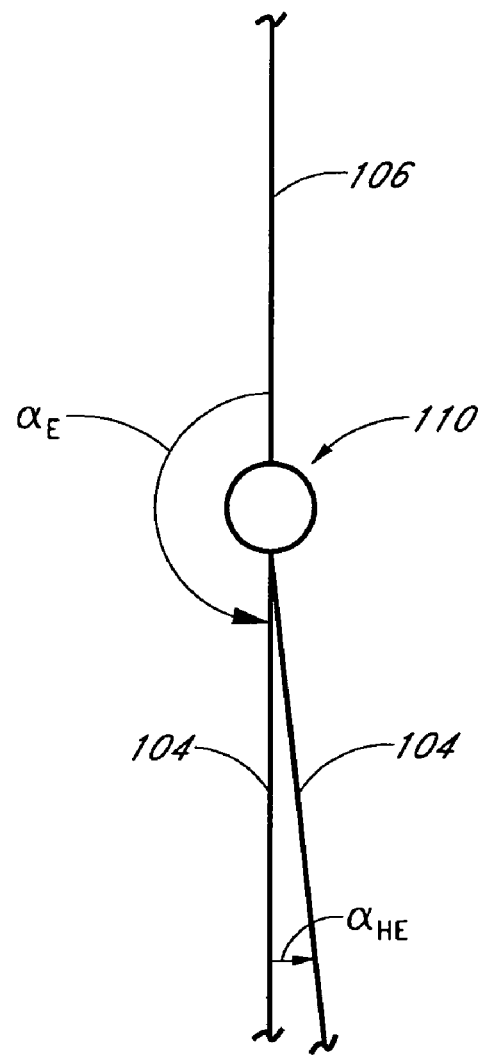
FIG. 76 is a simplified schematic view of knee hyperextension during operation of the bumper system of FIG. 73 illustrating features and advantages in accordance with another embodiment of the invention.

Referring in particular to the schematic drawing of FIG. 76, in one embodiment, the shock absorbing bumper system 150 allows a maximum extension angle which is substantially the same as an anatomical extension angle $\alpha_E$. The extension angle $\alpha_E$ typically is about 180° or close to it.

In another embodiment, the bumper system 150 allows a maximum extension angle which is slightly greater than $\alpha_E$. This allows for a small degree of temporary knee hyperextension. The hyperextension angle is generally denoted by $\alpha_{HE}$ in FIG. 76.

In one embodiment, the hyperextension angle $\alpha_{HE}$ is about 1.5°. In another embodiment, the hyperextension angle OCHE is in the range form about 1° to about 2°, including all values and sub-ranges therebetween. In yet another embodiment, the hyperextension angle $\alpha_{HE}$ is in the range form about 0.5° to about 2.5°, including all values and sub-ranges therebetween. In modified embodiments, $\alpha_{HE}$ may be higher or lower, as needed or desired.

As schematically illustrated in FIGS. 77 and 78, embodiments of the shock absorbing multi-stage bumper system may comprise bumper assemblies 540', 540" having more than two bumpers arranged in a generally side-by-side configuration. The bumper height (or relative operational height) generally varies with the properties of the bumper material, e.g., softness, compressibility, resilience, flexibility, hardness and rigidity.

The bumper assembly 540' of the embodiment of FIG. 77 generally comprises a plurality of bumpers 542a', 542b', 542c', 544a', 544b' and so on. The bumper assembly 540" of the embodiment of FIG. 77 generally comprises a plurality of bumpers 542a", 542b",542c", 544a", 544b", 544c", 544d" and so on. In modified embodiments, the relatively soft bumpers 542', 542" and the relatively hard bumpers 544', 544" may be interspersed in any suitable manner, as needed or desired. For example, but not limited to, in a staggered, repetitive or alternating pattern or spaced from adjacent bumpers.

Referring to FIGS. 77 and 78, in one embodiment, the direction of arrows 560 generally denotes decreasing softness or increasing hardness. In another embodiment, the direction of arrows 560 generally denotes decreasing compressibility or increasing rigidity. In another embodiment, the direction of arrows 560 generally denotes decreasing resilience or flexibility.

Embodiments of the invention also provide a flexion stop system generally comprising a bumper system and one or more stops on the outer spline 132, for example, at 284. In one embodiment, the flexion stop system is generally similar to embodiments of the extension stop system and includes one or more shock absorbing multi-stage bumper assemblies that contact one or more respective stops at generally the maximum allowable knee flexion.

In one embodiment, hard stop 529*a* (FIG. 68) and 529*b* (FIG. 71) on respective side mounts 136, 138 contact one or more stops 284 of the outer spline 132 to control the maximum allowable knee flexion and provide a flexion stop system. In another embodiment, bumpers or bumper assemblies at about 529*a* (FIG. 68) and 529*b* (FIG. 71) on respective side mounts 136, 138 contact one or more stops 284 of the outer spline 132 to control the maximum allowable knee flexion and provide a flexion stop system.

The flexion stop system controls the maximum knee flexion to a predetermined flexion angle $\alpha_F$. This is generally achieved by physically limiting the rotation between the side mounts 136, 138 and the outer spline 132, and hence the rotation of the knee joint.

In one embodiment, the flexion stop system is configured to allow a maximum flexion angle $\alpha_F$ of about 120°. In another embodiment, the flexion stop system of is configured to allow a maximum flexion angle in the range from about 120° to about 140°–150°, including all values and sub-ranges therebetween. In modified embodiments, the maximum flexion angle $\alpha_F$ may be higher or lower, as needed or desired.

Studs and Cone Nuts

As best seen in the exploded view of FIG. 6, the knee actuator 112 comprises the fastening through rods, dowels or studs 158 which are end-threaded to threadably engage associated nuts 160 at each end. In one embodiment, three studs 158 each with two associated nuts 160 are utilized thereby allowing a straightforward assembly and disassembly procedure with a minimum of fasteners. In modified embodiments, other quantities of fastening studs may be utilized, as needed or desired.

The studs or rods 158 pass through the holes 508*b* of the left side mount 138, the holes 508*a* of the right side mount 136, the holes 180*a*, 180*b* of respective core side plates 116, 118 and the passages 228 of the inner spline 122. The studs 158 in combination with the nuts 160 secure the core side plates 116, 118, the inner spline 122 and the side mounts 136, 138 and clamp these components of the knee actuator 112 together.

The fastening studs 158 are desirably press fit within the passages 228. Advantageously, this reduces undesirable mechanical backlash and enhances torque transmission between the inner spline 122 (and rotors 120) and the side mounts 136, 138.

In one embodiment, the fastening studs 158 comprise a magnetic material. In a modified embodiment, the studs 158 comprise a non-magnetic material, such as stainless steel or the like, which may facilitate in substantially isolating the studs 158 from the magnetic path 140 (see, for example, FIG. 4) through the actuator 112 and can improve power efficiency.

The nuts 160 engage the respective end threads of the respective fastening studs 158 to clamp the core side plates 116, 118, the inner spline 122 and the side mounts 136, 138. A suitable adhesive or glue, such as Loctite® threadlocker or the like, can be applied to the end threads to provide a strong coupling between the studs 158 and corresponding nuts 160.

The right side nuts 160 are received in the corresponding recessed surfaces 512*a* (see, for example, FIG. 69) of the right side mount 136. The left side nuts 160 are received in the corresponding recessed surfaces 512*b* (see, for example, FIG. 72) of the left side mount 138.

In one embodiment, the nuts 160 comprise cone nuts. Advantageously, the use of cone nuts improves wear resistance and substantially prevents or reduces undesirable backlash.

The nuts 160 may also comprise lock nuts with self-locking features. In one embodiment, the nuts 160 may each have a torque-off head that shears off when the nuts 160 are tightened to a predetermined or desired torque. The nuts 160 may also have tamper resistant features so that they are not removable with a standard wrench or tool but with a special removal tool, thereby preventing undesirable disassembly.

Extension Assist System

In some embodiments, the prosthetic knee 110 comprises the extension assist assembly or system 148 to help straighten the leg by urging or biasing the leg to extension by applying a controlled torque or force. FIGS. 79 and 80 show different views of one embodiment of the extension assist system 148.

The extension assist system 148 facilitates knee extension and is particularly useful during swing phase extension. During the swing phase, the extension assist system 148 provides an urging force to encourage straightening of the knee or lower limb just before initial contact with a supporting or ground surface.

Though embodiments of the prosthetic knee actuator 112 can provide a low-end torque that is substantially zero or close to zero, thereby permitting substantially free swing phase extension, an extension assist can be advantageous in certain situations. For example, on stairs, the foot position is important on the step and the extension assist system 148 provides the desired momentum so that the foot lands properly on the supporting surface.

The extension assist system 148 is also advantageous when walking or moving at higher speeds. The extension assist system 148 can also advantageously reduce or prevent patient fatigue by providing additional momentum during extension.

The extension assist system 148 is generally mounted in the exterior side recessed region or portion 538*b* (see, for example, FIG. 72) of the left side mount 138. Advantageously, the substantially internally mounted extension assist system 148 provides a reduced knee profile and protection for its components against undesirable side impact or contact. The extension assist system 148 generally comprises an internal spring 570, an inner shield or guard 572 on one side of the spring 570 and an outer shield or guard 574 on an opposed side of the spring 570, a rotatable arm 576, an axle 578 and a bearing 580.

In one embodiment, the spring 570 comprises a torsion or coil spring as shown, for example, in FIGS. 79 and 80. In modified embodiments, other types of springs, resilient, biasing or urging mechanisms, such as bands or the like and other devices capable of suitable energy storage and release may be utilized with efficacy, as needed or desired.

In one embodiment, the spring 570 is pre-loaded, that is, it has a selected pre-load in its rest or non-actuated state. In another embodiment, the spring 570 has a substantially zero pre-load in its rest or non-actuated state. The spring 570, in one analogy, may be though of as being similar to an anatomical ligament.

The torsion spring 570 is generally circular or annular in shape and has a generally central circular or cylindrical cavity, passage or hole 582. The passage 582 has a diameter that is dimensioned and configured so that it fits over the outer diameter of the core mandrel portion 168 (see, for example, FIG. 7).

The spring 570 is generally positioned in the exterior side recessed region or portion 538b of the left side mount 138. The core mandrel portion 168 extends through the left side mount cavity 506b and into the left side mount recessed region 538b.

The spring 570 at its inner free end comprises an inner curved or bent hook, finger or leg 584. The inner finger 584 is received within or locked into the slot, notch or groove 188 of the core mandrel portion 168. In one embodiment, the inner finger 584 has a thickness that forms a press fit into the slot 188 of the core mandrel portion 168.

The spring 570 at its outer free end comprises an outer curved or bent hook, finger or leg 586. The outer finger 586 engages or locks with a portion of the arm 576, as described further below. As also described further below, the outer shield 574 is specially designed to cover a gap or slot 588 of the spring 570. The gap or slot 588 is present because of the spacing between the outermost spring coil and the adjacent spring coil. The gap or slot 588 is proximate to or adjacent the outer arm 586 and receives a portion of the outer shield 574.

The inner spring shield 572 is fitted over the core mandrel portion 168 and positioned interiorly relative to the spring 570. In the illustrated embodiment, the inner shield 572 is in the form of a generally circular annular disk with a cavity or hole 590 that is dimensioned and configured so that it fits over the outer diameter of the core mandrel portion 168.

The bearing 580 is fitted and positioned within the generally circular bore 190 (see, for example, FIG. 7) of the core mandrel portion 168. The bearing 580 comprises an outer bearing surface 592 that is coupled to the bore 190 and a generally circular cavity or hole 594 with an inner bearing surface 596 that is coupled to the axle 578. In one embodiment, Loctite® threadlocker, Loctite® retaining compound or the like is used to provide this coupling between the bearing 580 and the core mandrel portion 168 and the axle 578. The bearing 580 advantageously facilitates rotation of the core mandrel portion 168 and the axle 578 substantially independently of one another.

The outer spring shield 574 generally comprises a support portion or section 620 connected to a main body portion or section 622 positioned exteriorly relative to the spring 570. In the illustrated embodiment, the main body portion 622 is in the form of a generally circular disk.

The shield support portion 620 generally comprises a pair of seats or shoulders 624, 626 that engage the spring 570. The first seat 624 is received within the gap, slot or spring portion 588 and the second seat 626 is positioned generally behind and abuts or engages the spring outer finger 586.

Advantageously, the specially designed outer shield 574 covers the spring gap 588 and prevents dirt and lint from getting between the coils of the spring 570. The shield 574 desirably also acts as a wiper to clean dirt and off of the outside diameter of the spring 570 as it rotates.

The shield main body portion 622 generally comprises a substantially central and circular hole or passage 628 through which the axle 578 extends. The hole 628 is substantially aligned with the bearing hole 594. In the illustrated embodiment, the main body portion 622 includes a curved generally C-shaped slot 630 that forms a radially extending portion or section 632 that is substantially aligned with and abuts or engages a portion of the arm 576. The C-shaped slot 630 desirably keys the shield 574 to the spring arm 576.

In one embodiment, the shield 574 comprises a small bearing standoff boss or land on the side of the shield 574 opposite the slot 630. The boss or land desirably facilitates in ensuring that axial loads are transmitted through the bearing 580 instead of causing rubbing which could adversely affect knee performance.

In one embodiment, the shield 574 comprises Delrin. In modified embodiments, other suitable materials my be used with efficacy, as needed or desired.

The spring arm 576 generally comprises a proximal main body portion or section 634, a medial portion or section 636 and a distal portion or section 638. In the illustrated embodiment, the arm 576 is generally in the form of an angled bar or plate.

The arm proximal portion 634 generally comprises a proximal end 640 with a substantially circular hole or passage 642 through which the axle 578 extends. The proximal portion is substantially aligned with and abuts or engages the outer shield portion 632. The hole 642 is substantially aligned with the outer shield hole 628 and the bearing hole 594.

The arm medial portion 636 is connected to the proximal portion 634 and generally comprises a seat or shoulder portion 644 and a curved or bent hook, finger or leg 646. The arm finger is substantially aligned with the spring outer finger 586. The spring outer finger 586 engages or locks with the arm finger 646.

The arm distal portion 638 is connected to the medial portion 636 and generally comprises an angled portion or section 648 and a distal end 650. The angled portion 648 extends generally interiorly and radially outwardly through the slot or opening 539b (see, for example, FIGS. 71 and 72) of the left side mount 138. The slot 539b desirably provided clearance space for rotation of the angled portion 539b.

The distal end 650 of the spring arm 576 is connected to the outer spline 132. The distal end 650 is dimensioned and configured so that it fits within the slot, cavity or opening 269b (see, for example, FIG. 41) of the outer spline 132. In one embodiment, the distal end 650 is generally rectangular or U-shaped though in modified other suitable shapes may be used, as needed or desired.

The set screw 273 (see, for example, FIG. 6) or the like engages the outer spline threaded hole 271b (see, for example, FIG. 41) and contacts or abuts the spring arm distal end 650 to securely connect it to the outer spline 132. In another embodiment, the distal end 650 may include a threaded hole or the like that engages a connector pin to secure the distal end 650 to the outer spline 132.

The axle, pin, shaft or bar 578 generally comprises a shank portion 652 connected to a head or cap portion 654. The shank 652 extends through the arm hole 642, the outer shield hole 628 and into the bearing hole 594. The head 654 generally abuts the arm proximal end 640.

The shank 652 is coupled to the bearing hole 594 using Loctite® threadlocker or retaining compound. The shank 652 is press fitted in the arm hole 642 and the outer shield hole 628 such that the rotation of the shank 652 (and/or axle 578) generally corresponds to rotation of the arm 576 and the outer shield 574.

The extension assist system 148 operatively couples the spring 570 to both the core mandrel portion 168 and the outer spline 132. This coupling, connection or communication allows substantially independent actuation or tensioning of the spring 570 due to the rotation of the core mandrel portion 168 (and corresponding rotation of the side mount 138) and due to rotation of the outer spline 132.

FIG. 80 shows the prosthetic knee 110 in a substantially fully extended state. The arrows 142a, 142b generally depict the direction of knee rotation or flexion. The arrow 142a denotes the rotation or flexion of the side mount 138 (and hence the core mandrel portion 168) which generally corresponds to rotation of the lower leg pylon 104. The arrow 142b denotes the rotation or flexion of the outer spline 132 which generally corresponds to rotation of the upper leg socket 106.

The rotation of the core mandrel portion 168 in the direction 142a causes rotation of the spring inner finger 584 which is locked with the mandrel portion 168. This tensions or loads the spring 570 which thereby stores energy for subsequent release. The bearing 580 facilitates in the rotation of the mandrel portion 168 substantially independently of the axle 578. During knee extension or rotation in the opposite direction the spring 570 releases the stored energy thereby advantageously facilitating knee extension.

The rotation of the outer spline 132 in the direction 142b causes rotation of the spring arm 576 which is attached at its distal end 650 to the outer spline 132. This causes rotation of the spring outer finger 586 which is locked with or coupled to the arm 576 and this tensions or loads the spring 570 which thereby stores energy for subsequent release. The bearing 580 facilitates in the rotation of the axle 578, which is connected to the spring arm 576, substantially independently of the core mandrel portion 168. During knee extension or rotation in the opposite direction the spring 570 releases the stored energy thereby advantageously facilitating knee extension.

During energy storage, the spring 570 provides some degree of resistance to knee rotation. For example, during swing flexion, it is desirable to reach a certain target swing flexion angle. In this case, to allow the knee to swing substantially freely to reach the target angle, in one embodiment, a compromise or balance is provided for optimal performance.

The total resistance to swing flexion will be due to the actuator torque and the resistance due to the spring 570. In one embodiment, the actuator torque during swing flexion is passive (not electronically controlled, that is, with substantially zero magnetic field). The spring properties may be selected to achieve optimal performance. The passive torque can be manipulated to achieve optimal performance, for example, by adjusting the number of blades 120, 130 and/or the gap therebetween.

The spring 570 desirably has a suitably high fatigue life for enhanced durability. In one embodiment, the spring 570 has a fatigue life of at least one million cycles. In one embodiment, the spring 570 has a fatigue life of at least about 3–4 million cycles. In modified embodiments, other suitable spring fatigue life properties may be utilized with efficacy, as needed or desired.

In one embodiment, the spring 570 has a diameter of about 3.8 cm (1.5 inches). In another embodiment, the spring 570 has a diameter of about 2.5 cm (1 inch) to about 5.1 cm (2 inches), including all values and sub-ranges therebetween. In one embodiment, the spring 570 comprises high carbon spring steel.

To achieve a high fatigue life, for a spring that has to survive an extremely high degree of rotation and, in one embodiment is relatively small and occupies a small space, the spring 570 is specially designed.

In some embodiments, a high fatigue life is achieved by altering the heat treatment of the spring 570 from the standard heat treatment process used by the spring manufacturer and by coating the spring 570 with an antifriction, anti-wear coating. Typically, springs made from high carbon spring steel are quenched and tempered after cold forming in order to achieve the desired strength and toughness of the material.

An analysis of conventional springs that had not performed well during fatigue testing revealed that impurities in the metal would congregate during the quench process causing dislocations in the metal lattice structure where cracks would initiate. To overcome this problem, the temperature of the quench bath is lowered so that the quench occurs in a much shorter time. This way, advantageously, the impurities do not have time to congregate and the metal lattice structure is much more homogeneous, thereby desirably providing a higher fatigue life for the spring 570.

In conventional coil springs of a small size that undergo a high degree of rotation, the friction forces between the spring coils are significant as the spring is loaded up. These friction forces can undesirably cause high wear rates and premature spring failure. In addition, the friction and rubbing between coils causes noise and wasted energy. With a suitable antifriction coating, in one study, the wear of the coated spring 570 over three million cycles was too small to be measured, the energy efficiency of the spring improved from about 80% to about 95%, and the noise was completely eliminated.

The extension assist system 148 of embodiments of the invention can be used to provide a wide range of extension assisting force or torque profiles which may be customized or fine-tuned to the specific needs of a patient. This may include the use of different spring sizes and different spring constants. The spring pre-load may be adjusted or fine-tuned using a tensioning screw or the like.

FIG. 81 shows some embodiments of extension assisting torque profiles as a function of rotation angle with maximum rotation angle being denoted by $\phi_{max}$. In one embodiment, the torque profile is substantially linear as generally denoted by line or curve 656. The torque generally increases with increasing rotation angle. The torsion spring 570, in one embodiment, provides the linear torque profile 656.

In another embodiment, the torque profile is non-linear as generally denoted by line or curve 658. In this case, the torque initially increases with rotation angle and then decreases with the torque reversing direction after a certain point. A suitably mounted extension spring 570' (see FIG. 82), in one embodiment, provides the torque profile 658. The extension spring 570' can be mounted generally across the knee diameter.

One important design parameter is the total energy stored in the extension assist spring. This is generally represented by the area below the torque profile line or curve. Thus, the areas below respective curves 656 and 658 denote the total energy stored in the respective springs. Thus, advantageously, springs with different variable torque profiles but substantially the same total energy storage characteristics may be used, as needed or desired.

In one embodiment, the spring 570 is capable of storing about 1.2 Joules over about 60° of knee flexion. In modified embodiments, the spring may have other suitable energy storing capabilities with efficacy, as needed or desired.

Angle Sensing System

In some embodiments, the prosthetic knee 110 comprises the knee angle sensor system or assembly 154 that measures the knee angle and communicates with the frame and electronics system 114. FIG. 83 shows an exploded perspective view of one embodiment of the knee angle sensor system 154.

The angle sensor system 154 is used to encode the absolute knee angle. The angle sensor system 154 desirably measures the degree to which a single degree-of-freedom knee joint is flexed or extended.

The angle sensor system 154 is generally mounted in the exterior side recessed region or portion 538a of the right side mount 136. Advantageously, the substantially internally mounted angle sensor system 154 provides a reduced knee profile and protection for its components against undesirable side impact or contact. The angle sensor system 154 generally comprises an angle sensor 668 and a rotatable arm 670 connected to the angle sensor 668 by a shaft, axle or pin 674.

A cable or lead wires 672 connect the angle sensor 668 to the frame and electronics assembly 114 for knee control purposes. A suitable connector or the like is provided at one end of the cable 672 to facilitate this interface. The cable 672 is desirably shielded.

The cable 672 passes through the notch 500a of the right side mount 136 and runs along the exterior surface groove 502a of the right side mount 136 (see, for example, FIG. 69) and connects to the frame and electronics assembly 114. Advantageously, the notch 500a and groove 502a facilitate in keeping the cable 672 in position and prevent undesirable movement.

In the illustrated embodiment, the angle sensor 668 generally comprises a substantially cylindrical housing 676 and a plurality of radially outwardly extending wings, mounts or connection members 678. The housing 676 generally comprises an inner portion or section 682 with an inner face or surface 684 and an outer portion or section 686 with an outer face or surface 688.

The inner and outer portions 682, 686 are generally separated by a plane passing through the wings 678. The inner and outer portions 682, 686 of the housing 676 also define a generally cylindrical or circular side, peripheral or circumferential face or surface 690. The housing inner portion 682 is sized and configured so that it fits within or extends into the cavity or recess 506a (see, for example, FIG. 69) of the right side mount 136.

The housing outer portion 686 (and shaft 680) are generally positioned within the recessed region or portion 538a (see, for example, FIG. 69) of the right side mount 136. The shaft 674 extends outwardly from the housing outer face 688 and is mechanically connected to the arm 670.

The wings or mounts 678 extend from the housing surface 690 and facilitate in connecting the angle sensor 668 to the right side mount 136. In the illustrated embodiment, the angle sensor 668 comprises three wings 678, though in modified embodiments fewer or more wings 678 may be efficaciously utilized, as needed or desired.

Each of the wings 678 comprises a through hole or cavity 692 that receive respective screws or the like to connect the angle sensor 668 to the right side mount 136. In the illustrated embodiment, the holes 692 are arranged substantially equidistantly and in a circular fashion around the housing 676.

The wing holes 692 are substantially aligned with the threaded holes 507 (see, for example, FIG. 69) on the right side mount surface 509. Screws, connector pins or the like pass through respective holes 692 and threadably engage respective threaded holes 507 to secure or fasten the angle sensor 668 to the right side mount 136. A suitable adhesive or glue, such as Loctite® threadlocker or the like, can be utilized with the screws to provide a strong coupling between the angle sensor 668 and the right side mount 136.

The wings 678 abut against the surface 509 (see, for example, FIG. 69) of the right side mount 136. In the illustrated embodiment, the wings 678 and nuts 160 associated with the right side mount 136 are alternatingly interspersed and spaced to provide clearance space therebetween.

The shaft 674 has a proximal portion or section 694 and a distal portion or section 696 generally separated at a shoulder or step 698. The shaft 674 is rotatable and its proximal portion 694 extends through the housing 676 and more particularly through the housing outer face 688. The shaft proximal portion 694 connects to the angle sensor's inner componentry, such as electronics and the like, which is used to measure the knee angle.

A notch or groove 700 may be provided proximate the shoulder 698 to facilitate alignment or positioning. In one embodiment, a portion of the proximal section 694 that is proximal to the notch 700 extends into the sensor housing 676.

The shaft distal portion 696 is desirably threaded and connects to the arm 670. The shoulder 698 abuts against the rotatable arm 670 and facilitates in spacing it from the sensor housing 676.

The arm 670 is generally configured in the shape of a substantially flat angled bar and is operatively coupled to the right side mount 136 via the angle sensor 668 and to the outer spline 132. The arm 670 generally comprises a proximal main body portion or section 702, a medial portion or section 704 and a distal portion, section or end 706.

The arm proximal portion 702 has a proximal end 708 with a through hole or cavity 712. The shaft threaded portion 696 extends through the arm hole 712 and a nut 714 (see, for example, FIG. 6) or the like is engaged with the threaded portion 696 to securely connect the shaft 674 and arm 670. A suitable adhesive or glue, such as Loctite® threadlocker or the like, can be utilized with the threaded portion 696 and nut 714 to provide a strong coupling between the shaft 674 and arm 670.

The shaft shoulder 698 abuts against the arm proximal end 708 and spaces the arm proximal portion 702 from the sensor housing 676 and more particularly the housing outer surface 688. The arm proximal portion 702 extends generally radially outwardly and substantially parallel to the housing outer surface 688.

The medial portion 704 generally includes two connected sections or portions 716 and 718 that are angled relative to one another. The first section 716 is adjacent the arm proximal portion 702 and angled relative to it. The second section 718 is adjacent the arm distal end 706 and angled relative to it.

The arm section 716 extends generally radially outwards and laterally or longitudinally inwards. The arm section 716 passes through the curved generally C-shaped slot or opening 539a (see, for example, FIG. 69). The slot 539a desirably provides a rotational angular range of about 180° for the arm 670 (and the arm portion 716 extending through the slot 539a), though typically the maximum knee angle rotation is about 140°–150° and, in one embodiment, about 145°.

The medial second section 718 extends generally radially outwardly. The arm section 718 facilitates in aligning the arm distal end 706 with the slot, cavity or opening 269a (see, for example, FIGS. 43 and 44) of the outer spline 132.

The arm distal end 706 is received within the outer spline slot 269a. The distal end 706 has a through hole or cavity 720 that is substantially aligned with the threaded hole 271a (see, for example, FIG. 44) of the outer spline 132. A screw or the like extends through the hole 720 and is threadably engaged with the hole 271a to secure the arm distal end 706 to the outer spline 132. A suitable adhesive or glue, such as Loctite® threadlocker or the like, can be utilized with the threaded hole 271a and associated screw to provide a strong coupling between the arm 670 and the outer spline 132.

The distal end 706 is sized and configured to fit within the outer spline slot 269a, in one embodiment, in a generally close tolerance fit. In the illustrated embodiment, the distal end 706 is generally rectangular or U-shaped though in modified other suitable shapes may be used, as needed or desired.

The angle sensor system 154 is operatively coupled, connected or communicated with the outer spline 132 and the right side mount 136. The angle sensor system 154 detects and measures the knee rotation angle and transmits it to the frame and electronics assembly 114 for knee control purposes.

The angle sensor system 154 measures the knee rotation angle when the outer spline 132 rotates, the right side mount 136 rotates or both rotate at the same time. As noted above and herein, rotation of the outer spline 132 corresponds to rotation of the outer rotors 130 and rotation of the right mount 136 (and left mount 138) corresponds to rotation of the inner rotors 120, inner spline 122, core rod 113 and core side plates 116, 118.

Rotation of the outer spline 132 causes rotation of the arm 670 which has its distal end 706 fixed to the outer spline 132. The arm portion 716 rotates or moves through the right side mount slot 539a. The rotation of the arm 670 results in rotation of the shaft 674 relative to the angle sensor 668 (and its internal componentry) which is used by the angle sensor 668 to measure the knee rotation angle.

Rotation of the right side mount 136 causes rotation of the angle sensor 668 since the sensor housing 676 is fixed to the right mount 136. The rotation of the angle sensor 668 is relative to the shaft 674 which is used by the angle sensor 668 to measure the knee rotation angle. When both the outer spline 132 and the right mount 136 rotate relative to one another, the angle sensor 668 uses the relative rotational positioning of the shaft 674 to measure the corresponding knee rotation angle.

In some embodiments, the signal from the knee angle sensor 668 is conditioned by amplification, band filtering and differentiation before being transmitted to a processor of the frame and electronics assembly 114. The differentiation is used to determine the rotational or angular velocity of the knee. The knee angular velocity signal further determines whether the knee is flexing or extending.

In one embodiment, the angle sensor 668 comprises a potentiometer. In modified embodiments, other suitable angle sensing devices, for example, optical or magnetic shaft encoders and the like, may be efficaciously used, as needed or desired.

In one embodiment, the angle sensor 668 comprises a 5 kiloOhm (kΩ) precision potentiometer. A five volt power is supplied to one end of the potentiometer while the other end is held at ground. This provides a signal output proportional to a position between 0° and 180°. As indicated above, the maximum knee angle rotation is typically between about 140°–150° and, in one embodiment, is controlled to about 145°. During assembly, the angle sensor system 154 is calibrated.

Frame and Electronics Assembly

FIGS. 84–91 show different views of one embodiment of the frame and electronics assembly 114. The frame and electronics assembly 114 facilitates in monitoring and controlling the operation of the knee actuator 112. The frame and electronics assembly 114 also provides power and communicates with the actuator assembly 112 via electrical signals.

The frame and electronics assembly 114 generally comprises a load cell pylon or frame 800, an electronic controller, control system or unit 802 and a power supply or battery system 804. FIGS. 92–96 show different views of one embodiment of the frame 800.

The frame 800 is connected to the knee actuator 112 and the lower pylon 104 (see, for example, FIG. 2). The frame 800 houses or supports the control system 802 and the battery system 804 and may also facilitate in shielding them and other associated electronic components and the like from the magnetic field generated by the knee actuator 112.

The frame 800 advantageously allows simple connections to foot and shock systems without the use of specialized pylons. Another advantage is the ability to change height or foot rotation without recalibration or system reset. Another benefit is that there is a low contribution to the prosthesis profile and hence this allows for increased number of foot options.

In one embodiment, the frame 800 is fabricated from aluminum or an aluminum alloy. In modified embodiments, other suitable metals, alloys, plastics, ceramics, among others, may be utilized with efficacy, as required or desired.

In the illustrated embodiment, the frame 800 is generally in the form of a three-dimensional rectangular structure. The frame 800 includes a base or distal portion or section 806 that has a plurality of threaded holes 808 (see, for example, FIG. 91) to facilitate connection to a lower leg pylon such as the pylon 104.

FIGS. 97 and 98 show a distal pyramid connector, adapter or stud 812 with through holes 814 aligned with a respective one of the frame holes 808. The pyramid connector 812 connects the prosthetic knee 110 to the pylon 104. Desirably, the pyramid connector 812 allows for proper coupling and alignment between the prosthetic knee 110 (and/or frame 800) and the pylon 104. In modified embodiments, other suitable connectors or the like may be efficaciously used, as needed or desired.

Bolts, screws 816 or the like pass through respective connector holes 814 and threadably engage respective frame holes 808 to attach the pyramid connector 812 to the frame base 806. A suitable adhesive or glue, such as Loctite® threadlocker or the like, can be applied to the threads to provide a strong coupling between the frame 800 and the pyramid connector 812.

In one embodiment, the pyramid connector 812 comprises titanium or a titanium alloy. In another embodiment, the pyramid connector 812 comprises aluminum or a aluminum alloy. In modified embodiments, the pyramid connector 812 can be efficaciously fabricated from other suitable metals, alloys, plastics, ceramics, among others, as required or desired.

The frame 800 includes a front side, portion or section 818 and a rear side, portion or section 820 between which the base 806 extends. In the illustrated embodiment, the right and left sides of the frame are generally open to facilitate, for example, device assembly and provide weight reduction while maintaining structural integrity.

The front side 818 has a support element or member 822 that facilitates in securing the control system 802 to the frame 800. The support element 822 has a through hole 824 that receives a screw or the like, as discussed further below.

The frame 800 includes a medial seat, platform or support element 826 that generally extends between the frame front and rear sides 818, 820. The platform 826 facilitates in supporting the control system 802 and battery system 804 in the frame 800. The support platform 826 has a pair of spaced through holes 828 that receives screws or the like, as described further below The frame 800 at around its top proximal end includes a front mount support 830 and a rear mount support that facilitate in connection to the knee actuator 112 and more particularly to the side mounts 136, 138. In the illustrated embodiment, the front support 830 is generally higher than the rear support 832 and the two are connected by a support element or member 834 that extends therebetween.

The front support 830 includes a pair of spaced through holes 836a, 836b that are aligned with respective threaded holes at respective front portions 524a, 524b (see, for example, FIGS. 68, 69, 71 and 72) of respective right and left side mounts 136, 138. Bolts, screws 838a, 838b or the like pass through respective holes 836a, 836b and threadably engage the respective threaded holes at respective side mount front portions 524a, 524b to connect the fronts of the frame 800 and the side mounts 136, 138.

The rear support 832 includes a pair spaced threaded holes 840a, 840b on either side of the support element 834 which are aligned with respective through holes 522a, 522b (see, for example, FIGS. 67 and 70) on respective feet or seats 520a, 520b of respective right and left side mounts 136, 138. The feet 520a, 520b are seated on the rear support 832. Bolts, screws 164a, 164b (see, for example, FIG. 6) or the like pass through respective holes 522a, 522b and threadably engage respective threaded holes 840a, 840b to connect the rears of the frame 800 and the side mounts 136, 138.

In one embodiment, the rear support 832 further includes another pair of spaced through holes 842a, 842b with one on either side of the holes 840a, 840b. The holes 842a, 842b are aligned with respective threaded holes provided on respective feet 520a, 520b. Screws or the like pass through respective holes 842a, 842b and threadably engage these respective threaded holes at respective side mount rear feet 520a, 520b to further connect and secure the rears of the frame 800 and the side mounts 136, 138.

In one embodiment, a vibrator motor 844 is mounted on the frame 800 at or proximate to the support element 834. The vibrator motor 844 is part of a vibrating warning system and is activated by signals from the control system 802 to alert or draw the attention of the wearer, as described further below.

The front side 818 of the frame 800 includes an aperture, window, cavity or opening 846 in which a front load force sensor 848 (see FIG. 93) is mounted. The frame front side 818 further includes a recess or cavity 850 with a recessed surface 852. An amplifier or signal amplification device 854 (see FIG. 93) is mounted in the recess 850 and is in electrical communication with the force sensor 848.

A passage 856 (see, for example, FIG. 92) through which a lead wire or the like passes connects or interfaces the force sensor 848 and the amplifier 854. An opening or hole 858 (see, for example, FIGS. 86 and 92) in the recessed surface 852 through which a lead wire or the like passes connects or interfaces the amplifier 854 and the control system 802.

In one embodiment, the front force sensor 848 comprises two strain gages 860a, 860b (see FIG. 93) mounted in the frame aperture 846. In modified embodiments, other suitable force or moment measurement sensors or devices may be efficaciously utilized, as needed or desired.

The rear side 818 of the frame 800 includes an aperture, window, cavity or opening 866 in which a rear load force sensor 868 (see FIG. 94) is mounted. The frame rear side 820 further includes a recess or cavity 870 with a recessed surface 872. An amplifier or signal amplification device 874 (see FIG. 94) is mounted in the recess 870 and is in electrical communication with the force sensor 868.

A passage 876 (see, for example, FIG. 92) through which a lead wire or the like passes connects or interfaces the force sensor 868 and the amplifier 874. An opening or hole 878 (see, for example, FIG. 87) in the recessed surface 872 through which a lead wire or the like passes connects or interfaces the amplifier 874 and the control system 802.

In one embodiment, the rear force sensor 868 comprises two strain gages 880a, 880b (see FIG. 94) mounted in the frame aperture 866. In modified embodiments, other suitable force or moment measurement sensors or devices may be efficaciously utilized, as needed or desired.

In one embodiment, the axial force sensors 848, 868 measure the component of force applied to the knee prosthesis 110 from the ground or other supporting surface in a direction substantially along or parallel to a shin longitudinal axis 882 (see, for example, FIG. 2). The force measurement is also used to determine whether the prosthetic foot 102 is on or off the ground or other supporting surface. That is, a zero axial force indicates that the foot 102 is not on the ground, for example, in the swing phase, while a non-zero axial force indicates that the foot 102 is on the ground, for example, in the stance phase.

In one embodiment, the measurements from the force sensors 848, 868 are used by the control system 802 to determine or compute the component of torque applied to the knee prosthesis 110 (and/or knee actuator 112) in substantially the knee rotation direction 142 (see, for example, FIG. 2). The moment measurement is also used to determine whether the applied knee moment is a flexion or extension moment and the direction of movement or knee rotation. For example, typically in normal walking, at heel strike a flexion moment is applied to the knee prosthesis 110, tending to flex the knee joint, and throughout late stance an extension moment is applied, tending to extend the joint.

In one embodiment, there is substantially no cross-talk between the front force sensor 848 and the rear force sensor 868. Advantageously, this provides for accurate measurement and differentiation or distinction between load on the front (toe-end) of the foot 102 and load on the rear (heel-end) of the foot 102.

In one embodiment, the four strain gages 860a, 860b, 880a, 880b are arranged in a wheatstone or standard bridge configuration. They are supplied with 5 volt power and produce an output or approximately 3 mv/v for each pound force of loading. Instrumentation amplifiers 854, 874 condition the bridge output and communicate it to the control system 802.

The frame 800 may include various recesses, windows holes, passages, slots, notches, contours and the like that can provide clearance space, alignment facilitation, connection features and component access, among other desirable characteristics. Material may be selectively removed at portions of the frame 800 to advantageously provide device weight reduction while maintaining structural integrity, as needed or desired.

The control system 802 is mounted within the frame 800. More particularly, in the illustrated embodiment, the control system 800 is generally above the frame base 806 and below the frame platform 826.

In the illustrated embodiment, the control system generally comprises two printed circuit boards (PCBs) 884 and 886. The front and rear circuit boards 884, 886 are spaced from one another and have the electronic control components, for example, a microprocessor, and associated components mounted thereon. In modified embodiments, fewer or more circuit boards or the like may be utilized with efficacy, as needed or desired.

Each of the circuit boards 884, 886 have respective bottom and top mounting holes 888, 890. The bottom holes 884 are engaged by a spacer system or assembly 892 and the top holes 886 are engaged by a mounting system or assembly 894 for securing the circuit boards 884, 886 in place within the frame 800.

The spacer system 892 generally comprises a pair of substantially aligned spacers 896, 898 and a pair of substantially aligned associated screws 902, 904 or the like. The spacer 896 is generally positioned between and abuts the frame support element 822 and the circuit board 884. The spacer 898 is generally positioned between and abuts the two circuit boards 884, 886. The spacers 896, 898 are substantially aligned with circuit board lower holes 888.

The screw 902 passes through the frame support hole 824 (see, for example, FIG. 92), the spacer 896 and the bottom hole 888 of the circuit board 884. The screw 902 is threadably engaged with the spacer 898 and may also threadably engage the spacer 896. The screw 904 passes through the bottom hole 888 of the second circuit board 886 and is threadably engaged with the spacer 898. In this manner, the spacer assembly 892 secures the lower portions of the circuit boards 884, 886 to the frame 800 and spaces the boards 884, 886.

The upper mounting system 894 generally connects the upper portions of the circuit boards 884, 886 and the battery system 804 to the frame platform 826. The mounting system 894 includes a generally flat plate or mount 906 with a pair of spaced holes 908 substantially aligned with respective through holes 828 (see, for example, FIG. 92) of the frame platform 826.

Screws 912 or the like pass through respective frame holes 828 and extend into respective mount holes 908 to secure the mount 906 to the frame platform 826. The screws 912 may threadably engage the holes 908 and/or associated nuts or the like may be used, as needed or desired.

In the illustrated embodiment, the mounting system 894 further comprises a pair of spaced and offset front and rear mounting support elements or members 914 with one each abutting (or adjacent to) respective circuit boards 884, 886. Each of the mounting elements 914 has a respective hole 916 substantially aligned with respective circuit board top holes 890.

Screws 918 or the like pass through respective circuit board holes 890 and extend into respective mount holes 916 to secure respective circuit boards 884, 886 to the mounting system 894 (and thereby frame platform 826). The screws 918 may threadably engage the mounting holes 916 and/or associated nuts or the like may be used, as needed or desired.

In the illustrated embodiment, the mounting system 894 further comprises a pair of spaced and offset right and left side mounting support elements or members 920 which facilitate mounting of the battery system 804 to the frame 800. Each of the mounting elements 920 has a respective hole 922, as described further below.

In one embodiment, the on-board control system 802 comprises a Motorola MC68HC912B32CFU8 microprocessor. The processor, in one embodiment, includes a Motorola HC12 compatible 16 bit processor, 32 Kilobytes flash eeprom, 768 byte eeprom, an 8 channel 10 bit AD converter, a serial peripheral interface (SPI), a serial communications interface (SCI), a programmable timer and pulse accumulators, a programmable pulse width modulator output, Motorola background mode debugging support, and programmable digital input-output (I/O) pins. In one embodiment, 32 Kilobytes of fast static ram are used.

The control system 802 comprises a controller to control the current through the magnetic coil 115 (see, for example, FIG. 6). In one embodiment, the current through the actuator coil 115 is controlled using a UCC3800 pulse width modulator controller.

In one embodiment, the control system 802 can control the coil current in the range from about 0 amperes to about 1.8 amperes in about hundred (100) increments, levels or steps. In modified embodiments, other current ranges and current control resolutions may be efficaciously utilized, as needed or desired.

As noted above, and also discussed further below, some embodiments provide for degaussing or demagnetization of the actuator blades 120, 130. The control system 802 includes a circuit that is designed to allow reversal of the current direction through the coil 115, thereby advantageously eliminating or mitigating undesirable residual magnetism build-up. Software control of this reversal allows demagnetization of the blades 120, 130 prior to situations where low torque is desirable.

In some embodiments, the control system 802 includes a warning system that is activated to alert or draw the attention of the wearer, as described further below. In embodiment, the control system 802 comprises an audible warning system. In another embodiment, the control system 802 comprises a vibrating warning system. In yet another embodiment, both audible and vibrating warning systems are used.

The power or battery system or pack 804 is generally position above and supported by the frame platform 826. The power system 804 provides electrical power to operate the various system components such as the control system 802.

As shown in FIG. 85, the power system 804 generally comprises a battery cell pack having one or more rechargeable batteries, battery cells or power sources 930. Advantageously, the power system 804 (and battery pack) are compact to facilitate in providing an overall compact knee design.

In one embodiment, the power system 804 comprises three batteries 930. In one embodiment, the batteries 930 comprise lithium ion batteries. In modified embodiments, other number of batteries and other suitable of battery types may be efficaciously utilized, as needed or desired.

The power system 804 includes a cover 932 (see, for example, FIG. 85) or the like in which the batteries 930 are housed. In one embodiment, the cover 932 comprises heat shrink or the like. In modified embodiments, other suitable materials may be efficaciously used, as needed or desired.

The power system 804 includes one or more battery separators 934 (see, for example, FIG. 85) with one each between adjacent batteries 930. The separators 934 can comprise a cushioning adhesive material such as tape foam or the like to protect the batteries 930 and hold them in place.

The power system 804 includes a battery mount or support 936 (see, for example, FIG. 85) generally below the batteries 930 on which the batteries 930 are seated. An adhesive or bonding tape 938 or the like may be provided intermediate the batteries 930 and the battery mount 936 to hold the batteries 930 in place.

The battery mount 936 has an upper contoured surface 940 that comprises channels, grooves or the like that facilitate alignment and positioning of the batteries 930 thereon. In the illustrated embodiment, the battery mount 936 comprises a pair of spaced and offset right and left side mounting elements or members 942. The mounting elements 942 extend out of the battery cover 932 and generally flank the frame platform 826 with the power system 804 seated generally thereon.

The mounting elements 942 abut against or are adjacent to respective mounting elements 920 of the mounting assembly 894. Each of the mounting elements 942 has a respective hole 944 aligned with a respective hole 922 of the mounting assembly 894.

Screws or the like pass through respective mounting holes 944 and respective mounting holes 922 to secure the power system 804 to the frame platform 826. The screws may threadably engage the holes 922 and/or the holes 944 and/or associated nuts or the like may be used, as needed or desired.

In one embodiment, the power system 804 produces an unregulated voltage of about 10 volts to about 12.5 volts, including all values and sub-ranges therebetween. The battery voltage, in one embodiment, is used to drive the magnetic coil current directly.

The power system 804 provides other voltages the electronics. These include, but are not limited to, voltage supplies of about 6 volts, about 5 volts, about 3.2 volts and about 2.5 volts.

In the illustrated embodiment, the battery system 804 comprises an internal protection circuit 946. The protection circuit 946 limits current to a predetermined maximum value.

In one embodiment, the protection circuit 946 limits current to about 2 amperes and momentarily shuts down the battery system 804 in the presence of higher current demands for safety purposes. The protection circuitry 946 also prevents overcharge of the battery system 804, for example, from highly discharged states.

The prosthetic knee 110 of embodiments of the invention desirably comprises an on-board battery charger for the power system 804. The input to the charger is, in one embodiment, a supply of about 18 volts and about 2 amperes. Medical grade power supplies may be used to provide the 18 volt source. The on-board charger controls the battery charging functions.

FIGS. 97–100 show different views of one embodiment of a charging, programming and power control panel or display 950 of the prosthetic knee assembly 110 (and/or the frame and electronics assembly 114). The control panel 950 communicates with the knee control system 802 which in turn communicates with the knee actuator 112, power system 804 and other associated electronics.

The control panel 950 is generally mounted on the rear of the prosthetic knee assembly 110 generally around the mechanical connection between the frame 800 and the side mounts 136, 138. More specifically, the control panel 950 is mounted between the rear legs 518a, 518b of respective side mounts 136, 138 and proximate to the frame upper support member 834.

The control panel 950 generally comprises a protective cover or shield 952, a port, socket or receptacle 954 with a protective cover 956, a power switch 958 and charging indicators 960. The control panel 950 may be interfaced with a separate circuit board that connects to the main control system 802.

The cover 952 can be raised to provide access to the port 954 and power switch 958 and then locked back into place. The cover 956 comprises a flexible material and may be transparent or at least partially transparent.

The port 954 is mounted in the cavity 527 of the right mount support 525 (see, for example, FIG. 67). The cover 956 protects the port 954 when it is not in use. The cover 956 can be selectively lifted to expose the port 954 and locked back down in position to shield the port 954. In the illustrated embodiment, the port 954 comprises a six pin socket that interfaces with a compatible plug from a cable or the like.

In one embodiment, the port 954 serves as both a charging port and a programming port. The battery charge is supplied from a suitable power source and the programming interface may be provided by a personal digital assistant (PDA) or the like. In modified embodiments, separate charging and programming ports may be used, as needed or desired.

In one embodiment, the prosthetic knee 110 may is remotely controlled and programmable. In one embodiment, the internet is used for communicating with the prosthetic knee 110, for example, to provide software upgrades or the like.

The power switch 958 is used to turn the prosthetic knee 110 on and off. In the illustrated embodiment, the power switch 958 comprises a sliding on-off switch. In modified embodiments, other suitable power switches such as push-button and the like may be efficaciously utilized, as needed or desired.

The charging indicators 960 show the status of battery charging. The charging indicators 960 may comprise blinking and steadily illuminated lights of different colors, for example, green and red, to indicate the charging status and on-off status.

The battery charging system, in some embodiments, disconnects the power system 804 from the control electronics 802 whenever the charger 954 is connected to a power source or a dummy charge plug is inserted into the charging receptacle 954. Thus, the knee 110 is off when connected to a charging source.

Embodiments of the invention provide convenient knee charging accessories that may be used, for example, at home, office, on the road or in an automobile. These include adapters, cables, plugs, sockets that may be easily connected to a power source (e.g. conventional wall outlet or automobile port) and interfaced with the charging port 954 of the prosthetic knee 110.

In one embodiment, the power or battery system 804 has an about 1,800 Milli-Amp-Hour (mAH) capacity. In another embodiment, the power or battery system 804 has an about 5,400 Milli-Amp-Hour (mAH) capacity.

In one embodiment, the power system or battery pack 804 comprises three battery cells 930 connected in series. In another embodiment, the power system or battery pack 804 comprises three battery cells 930 connected in parallel.

When the power system 804 is substantially fully charged, in one embodiment, the life of the charge is about 24 hours to about 48 hours depending on the level of the activity. The power system 804 desirably has a short charging time from substantially full discharge to substantially full charge. In one embodiment, the charging time is about 2.5 hours. In another embodiment, the charging time is in the range from about two (2) hours to about four (4) hours, including all values and sub-ranges therebetween. Partial usable charges occur much more rapidly.

Shroud

FIGS. 101–105 show different views of one embodiment of a prosthetic knee cover or shroud 1016. FIGS. 106 and 107 show different views of one embodiment of the prosthetic knee assembly 110 including the knee cover 1016. FIG. 108 shows one embodiment of the lower limb prosthetic assembly 100.

In one embodiment, the knee cover 1016 generally comprises an outer flexible skin, sheath, casing or jacket and an internal substantially rigid exoskeleton. The flexible skin carries substantially zero or only a small load that desirably facilitates accurate measurement of the load by the force sensors 848, 868. The substantially rigid exoskeleton which may comprise ribs, sleeves and the like desirably protects the internals of the knee against impact.

In one embodiment, the flexible skin comprises urethane. In modified embodiments, the skin may comprise other suitable flexible plastics or materials with efficacy, as needed or desired.

In one embodiment, the substantially rigid exoskeleton comprises a polycarbonate. In modified embodiments, the exoskeleton may comprise other suitable substantially rigid plastics or materials with efficacy, as needed or desired.

In one embodiment, the knee cover 1016 comprises at least a partially transparent material. In one embodiment, the knee cover 1016 comprises a material that is substantially blue in color.

The knee cover 1016 has a through passage that receives the knee actuator 112 and the frame and electronics assembly 114. The knee cover generally comprises a proximal or upper portion or section 1020 that substantially houses the actuator 112, a distal or lower portion or section 1024 that substantially houses the frame and electronics assembly 114 and a middle or medial section or portion 1022 that substantially houses the connection between the actuator 112 and the assembly 114.

The cover proximal portion 1020 generally comprises a front wall 1026 and a pair of spaced right and left side walls or ears 1028a and 1028b respectively. In the illustrated embodiment, the front wall 1026 is generally curved or semi-circular in shape.

The cover proximal portion 1020 comprises a substantially rigid and central internal ridge, rib or core 1030 that is connected to the front wall 1026. In the illustrated embodiment, the rib 1030 is generally curved or semi-circular in shape and is substantially centrally positioned between the side ears 1028a and 1028b. The rib 1030 advantageously provides clearance space on its sides for rotation or movement of the spaced outer spline stops or fangs 282 (282a, 292b).

Advantageously, the rigid rib 1030 provides support and protection, for example, during kneeling when the knee 110 rests on or contacts a surface. Typically, the rib 1030 is slightly spaced from the outer spline 132 so that it does not interfere with rotation of the outer spline 132. In one embodiment, the rib 1030 is integral with the flexible skin of the knee cover 1016 and comprises the same material as the skin.

The cover proximal portion 1120 has an open top end and rear that allows for attachment between the upper pyramid connector 152 and the stump socket 106 and clearance space for rotation (see, for example, FIGS. 106–108). The outer spline 132 rotates substantially independently of the knee cover 1016 while the rotation of the side mounts 136, 138 is coupled to the knee cover 1016, as described further below.

The knee cover ears 1028a, 1028b fit over respective right and left side caps 156a, 156b which are a part of the rigid exoskeleton that protects against impact. The right cap 156a protects the angle sensor 154 and the left side cap 156b protects the extension assist 148.

Suitably placed grooves of the knee cover 1016 receive respective ribs or the like of the side caps 156 to connect the side caps 156 and the knee cover 1016 (and its proximal portion 1020). In one embodiment, the side cap ribs are substantially rigid. Adhesive or the like can be utilized to further secure this connection.

Locating bosses of the knee cover 1016 that extend inwardly from respective ears 1028a, 1028b are keyed with relief pockets 562a, 562b in the respective side mounts 136, 138. This further secures and aligns the knee cover 1016 (and its proximal portion 1020) with the side mounts 136, 138 and the actuator 112.

Since the knee cover 1016 (and its proximal portion 1020) are connected to the side mounts 136, 138 directly and via the side caps 156, the knee cover 1016 rotates along with the rotation of the side mounts 136, 138. As described further below, the knee cover 1016 is also connected to the frame and electronics assembly 114 which also rotates with the rotation of the side mounts 136, 138. Thus, rotation of the knee cover 1016 generally corresponds to that of the side mounts 136, 138, frame and electronics assembly 114 and the lower pylon 104.

The knee cover medial portion 1022 has a rear opening or open portion or face 1036 that desirably provides access to the control panel 950 (see, for example, FIG. 97). The medial portion has a rear arch portion (or arched edges) 1038 that advantageously provides clearance space for rotation of the stump socket 106 (see, for example, FIG. 108) such that it does not interfere with the control panel 950.

The knee cover distal portion 1024 is generally rectangular in shape. In one embodiment, the distal portion 1024 has an internal reinforcing sleeve or cover 1034 (see, for example, FIG. 105) that receives at least a portion of the frame and actuator assembly 114.

The distal portion 1024 has a distal end opening 1032 with a lip with a groove or the like that receives a lower edge or lip of the sleeve 1034 (see, for example, FIG. 104). Internal ribs or the like an be provided, for example, at the corners of the distal portion 1024 to facilitate connection of the sleeve 1034 therein. Adhesive or the like can be utilized to further secure this connection. These internal ribs not only hold the sleeve 1034 of the rigid exoskeleton in place, they also prevent the sleeve 1034 from banging against the frame 800 and making noise.

Pads or the like can be provided at selected positions between the sleeve 1034 and the frame and electronics assembly 114 for protection and/or mounting purposes. The pads may utilize a pressure sensitive adhesive backing or the like that facilitates attachment to the frame 800. The pads desirably prevent the sleeve 1034 from banging against the frame 800 and making noise.

FIG. 108 shows one knee rotation position where the stump socket 106 contacts a rear upper portion or edge 1040 of the knee cover distal portion 1024. This portion 1040 can include a protective thicker skin, padding, rib or the like to avoid undesirable contact between the socket 106 and the prosthetic knee 110.

Referring in particular to FIG. 106, in one embodiment, the width $W_{106}$, is about 65 mm ($2frax;9;16$ inches) and the width $W_{1062}$ is about 75 mm ($2frax;15;16$ inches). In modified *embodiments*, other suitable dimensions may be efficaciously *used*, as needed or *desired*.

Referring in particular to FIG. 107, in one embodiment, the length $L_{1071}$ is about 65 mm (2*frax*;9;16 *inches*), the length $L_{1072}$ is about 78 mm (3*frax*;1;16 *inches*), the height $H_{1071}$ is about 230 mm (9*frax*;1;16 *inches*), the height $H_{1072}$ is about 197 mm (7¾ *inches*), the height $H_{1073}$ is about 32 mm (1*frax*;3;16 *inches*) to about 33 mm (1*frax*;5;16 *inches*) and the height $H_{1074}$ is about 30 mm (1*frax*;3;16 *inches*). In modified *embodiments*, other suitable dimensions may be efficaciously *used*, as needed or *desired*.

Prosthetic Knee Operation

The prosthetic knee of embodiments of the invention provides high-speed instantly responsive control of knee movement, yet is robust and affordable for the amputee. The prosthetic knee embodiments advantageously provide enhanced security, energy efficiency, comfort, stability and optimized gait dynamics for amputees and simulate and/or closely recreate the dynamics of a natural knee joint.

The pressure control embodiments desirably maintain a zero or near zero pressure within the actuator thereby advantageously providing for long lifetime of use and low maintenance requirements. The dynamic seal embodiments are advantageous in providing reliable sealing and enhanced performance and reliability.

Another advantage is that the actuator weight is located more proximal in the knee thereby desirably providing a light-weight feel during swing phase. Yet another advantage is the ability to provide a low torque production during swing phase, thereby allowing for easy initiation of knee flexion.

During operation, the electromagnet or magnetic coil 114 is actuated, as needed, by a selected or predetermined electrical signal, voltage or current. This generates variable magnetic field that passes through blades 120, 130 and through the MR fluid or film therebetween to generate a variable damping torque (or rotary viscous or frictional resistance) which precisely and accurately controls the rotary motion of the knee joint.

Desirably, the prosthetic knee embodiments a rapid and precise response. Another advantage is that a wide dynamic torque or torsional resistance range can be provided with a small low-end torque.

In one embodiment, the actuator 112 provides a dynamic torque in the range from about 0.5 Newton-meters (N-m) to about 50 N-m, including all values and sub-ranges therebetween. In another embodiment, the actuator 112 provides a dynamic torque in the range from about 0.2 Newton-meters (N-m) to about 100 N-m, including all values and sub-ranges therebetween. In another embodiment, the actuator 112 provides a dynamic torque in the range from about 0.1 Newton-meters (N-m) to about 200 N-m, including all values and sub-ranges therebetween. In modified embodiments, other suitable dynamic torque ranges may be efficaciously provided, as needed or desired.

As noted above, some embodiments provide for degaussing or demagnetization of the actuator blades 120, 130. Advantageously, this allows the knee to "free-up" and desirably creates a low torque ability and wide dynamic torque range. Software control of this reversal allows demagnetization of the blades 120, 130 prior to situations where low torque is desirable.

The operation of the prosthetic knee 110 can be controlled by suitable software and hardware. Some control, degaussing, software and other operational embodiments are disclosed in U.S. patent application Ser. No. 11/077,177, filed Mar. 9, 2005, U.S. Provisional Patent Application No. 60/569,511, filed May 7, 2004, and U.S. Provisional Patent Application No. 60/572,996, filed May 19, 2004, each entitled, CONTROL SYSTEM AND METHOD FOR A PROSTHETIC KNEE, and U.S. Provisional Patent Application No. 60/551,717, filed Mar. 10, 2004, entitled, CONTROL SYSTEM FOR PROSTHETIC KNEE, the entirety of each one of which is hereby incorporated by reference herein and each one of which is considered as part of this application.

Some prosthetic knees and control systems are disclosed in U.S. Pat. No. 6,764,520 B2, issued Jul. 20, 2004, and U.S. Pat. No. 6,610,101 B2, issued Aug. 26, 2003, the entirety of each one of which is hereby incorporated by reference herein.

MR Fluid Loading Procedure

FIGS. 109–125 describe embodiments of methods to assemble the knee actuator 112 and load the magnetorheological fluid 134 therein using a vacuum fill technique. Advantageously, this allows for an efficient (e.g., faster manufacturing speed) loading scheme and substantially uniform distribution of the MR fluid within the small gaps between the inner blades 120 and outer blades 130 which provides more consistent production.

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention.

FIG. 109 shows one embodiment of a high-level flow chart, diagram or method 1120 of assembling at least a portion of the actuator 112 and loading MR fluid therein. It should be understood that any of the acts or steps disclosed, taught or suggested herein can each comprise a plurality of further acts or steps.

The method 1120 generally comprises acts or steps 1122, 1124, 1126 and 1128. The act 1122 generally comprises assembling at least a portion of the actuator 112, the act 1124 generally comprises preparing the actuator for loading of the MR fluid, the act 1126 generally comprises preparing the MR fluid for loading and the act 1128 generally comprises loading the MR fluid in the actuator 112. Each of these is discussed in further detail below.

FIG. 110 shows one embodiment of the act, step or method 1122 of assembling the actuator 112 in further detail in a flow chart or diagram format. The act 1122 generally comprises acts or steps 1130, 1132 and 1134. The act 1130 generally comprises assembling an outer spline assembly, the act 1132 generally comprises assembling a cartridge assembly and the act 1134 generally comprises assembling the outer spline assembly, the cartridge assembly and other actuator components. Each of these is discussed in further detail below.

FIG. 111 shows one embodiment of the act, step or method 1130 of assembling the outer spline assembly in further detail in a flow chart or diagram format. The act 1130 generally comprises acts or steps 1136 and 1138. The act 1136 generally comprises installing the diaphragm assembly 146 (see, for example, FIG. 6) and the act 1138 generally comprises installing the pyramid connector 152 (see, for example, FIG. 6). The diaphragm assembly 146 and pyramid connector 152 are installed with the outer spline 132 to form the outer spline assembly.

In one embodiment, the diaphragm assembly 146 is installed within the cavity 450 (see, for example, FIG. 66) of the pyramid connector 152 which is then attached to the top portion 270 (see, for example, FIG. 41) of the outer spline 132. In another embodiment, the diaphragm assembly 146 is installed within the top portion cavity 272 (see, for example, FIG. 41) of the outer spline 132 and the pyramid connector 152 is then attached to the outer spline top portion 270.

FIG. 112 shows one embodiment of the act, step or method 1132 of assembling the cartridge assembly in further detail in a flow chart or diagram format. The act 1132 generally comprises acts or steps 1140, 1142, 1144, 1146, 1148, 1150 and 1152. Each of these is discussed further below.

The act 1140 generally comprises installing the right core side 116 on the core rod 113 (see, for example, FIG. 6). The cavity 178a (see, for example, FIG. 13) of the right core side 116 is fitted substantially over the core portion end 170 (see, for example, FIG. 7).

The act 1142 generally comprises installing the coil 115 (see, for example, FIG. 6) over the core rod 113. The cavity 216 (see, for example, FIG. 23) of the coil 115 is fitted substantially over the core portion 166 (see, for example, FIG. 7) of the core rod 113.

The act 1144 generally comprises installing the through rods 158 on the inner spline 122 (see, for example, FIG. 6). The rods 158 are fitted through the passages 228 (see, for example, FIG. 28) of the inner spline 122.

The act 1146 generally comprises installing the O-rings 182 (see, for example, FIG. 6) on the inner spline 122. The right O-ring 182a is mounted in or on the inner spline groove or flange 232a and the left O-ring 182b is mounted in or on the inner spline groove or flange 232b (see, for example, FIG. 29).

The act 1148 generally comprises forming a set of inner blades 120 and outer blades 130 (see, for example, FIG. 6). A predetermined number of inner blades 120 and outer blades 130 is used to form the set. In one embodiment, the inner blades 120 and outer blades 130 are alternatingly interspersed.

The act 1150 generally comprises installing the inner blades 120 and outer blades 130 on the inner spline 130. More particularly, the inner blades 120 are fitted on the inner spline 130 with the inner blade teeth 238 (see, for example, FIG. 33) engaged with corresponding inner spline grooves 226 (see, for example, FIG. 28). The outer blades 130 are fitted within the outer spline 132, as described above and further below.

The act 1152 generally comprises installing the left core side 118 (see, for example, FIG. 6) on the core rod 113. The cavity 178b (see, for example, FIG. 17) of the left core side 118 is fitted substantially over the core portion end 172 (see, for example, FIG. 7). This substantially completes the assembly of the cartridge assembly.

FIG. 113 shows one embodiment of the act, step or method 1134 of assembling the outer spline assembly, the cartridge assembly and other actuator components in further detail in a flow chart or diagram format. The act 1134 generally comprises acts or steps 1154, 1156 (1156a, 1156b), 1158 (1158a, 1158b), 1160 (1160a, 1160b), 1162, 1164 and 1166. Each of these is discussed further below.

The act 1154 generally comprises installing the cartridge assembly in the outer spline 132. The outer blades 130 are fitted within the outer spline 132 with the outer blade teeth 248 (see, for example, FIG. 37) engaged with corresponding outer spline grooves 260 (see, for example, FIG. 41).

The act 1156a generally comprises installing the right dynamic seal 162a (see, for example, FIG. 6). The dynamic seal 162a is fitted between the right core side 116 and the outer spline 132.

The act 1156b generally comprises installing the left dynamic seal 162b (see, for example, FIG. 6). The dynamic seal 162b is fitted between the left core side 118 and the outer spline 132.

The act 1158a generally comprises installing the right bearing 126 (see, for example, FIG. 22) in the outer spline 132. The act 1158b generally comprises installing the left bearing 128 (see, for example, FIG. 22) in the outer spline 132.

The act 1160a generally comprises installing the right side mount 136 (see, for example, FIG. 6). The right side mount 136 is communicated with the right bearing 126.

The act 1160b generally comprises installing the left side mount 138 (see, for example, FIG. 6). The left side mount 138 is communicated with the left bearing 128.

The act 1162 generally comprises installing the nuts 160 (see, for example, FIG. 6) on respective through rods 158. The nuts 160 are tightened to clamp the inner spline 122, right core side 116, left core side 118, right side mount 136 and left side mount 138 to one another. The nuts 160 may initially be only partially tightened and then further tightened at a later assembly stage, as needed or desired.

The act 1164 generally comprises installing the angle sensing system 154 (see, for example, FIG. 6). The angle sensor 668 is mounted on the right side mount 136 and the arm 670 is connected to the sensor 668 and the outer spline 132.

The act 1166 generally comprises pressure testing the actuator 112 to check the seal integrity. An air pump or the like is connected to the outer spline chamber 258 (see, for example, FIG. 45) via the threaded port or hole 280 and the chamber 258 is pressurized to a predetermined pressure (e.g., 20 psi) for a predetermined time.

In one embodiment, the actuator 112 (e.g., outer spline 132 and side mounts 136, 138) is rotated during at least part of the pressure test. The pressure is monitored to confirm the seal integrity.

FIG. 114 shows one embodiment of the act, step or method 1124 of preparing the actuator 112 for MR fluid loading in further detail in a flow chart or diagram format. FIG. 115 shows one embodiment of a set-up or system to perform at least a portion of the act 1124.

The act 1124 generally comprises acts or steps 1168, 1170, 1172, 1174 and 1176. Each of these is discussed further below.

The act 1168 generally comprises attaching a pyramid tool or holder 1320 to the pyramid connector 152. The pyramid tool 1320 desirably allows the actuator 112 to be seated on a surface in a desired orientation.

The act 1170 generally comprises pressure testing the actuator 112. The act 1170 may be skipped if pressure testing has been recently performed in act 1166 (see FIG. 113). But, in some cases, for example, if the dry (without MR fluid) actuator has been kept in storage for a certain period, it is desirable to repeat the pressure testing in act 1170.

The act 1172 generally comprises weighing the dry actuator 112 and recording its weight. The pyramid tool 1320 may be used to seat the actuator 112 on a suitable weighing scale 1322 or the like.

The act 1174 generally comprises attaching a holding fixture 1324 to the actuator 112. The holding fixture 1324 allows the actuator to be mounted in a vacuum system, as described further below.

The act 1176 generally comprises attaching a funnel 1326 or the like to the actuator. The funnel 1326 is threadably attached to the threaded port or hole 280 of the outer spline 132 such that the funnel is substantially vertical to facilitate addition of the MR fluid, as described further below.

FIG. 116 shows one embodiment of the act, step or method 1126 of preparing the MR fluid for loading in further detail in a flow chart or diagram format. FIG. 117 shows one embodiment of a set-up or system to perform at least a portion of the act 1126.

The act 1126 generally comprises acts or steps 1180, 1182, 1184, 1186, 1188, 1190, 1192, 1194, 1196 and 1198. Each of these is discussed further below.

The act 1180 generally comprises placing the MR fluid in a container or receptacle 1330. A predetermined quantity of the MR fluid is added to the container 1330.

The act 1182 generally comprises stirring the MR fluid. A spatula or the like is used to stir the MR fluid, breaking up any visible clumps, so that the MR fluid has a substantially uniform consistency.

The act 1184 generally comprises placing the MR fluid container 1330 under a stirrer 1334 within a vacuum chamber 1332. The act 1186 generally comprises sealing the vacuum chamber 1332, for example, by using a bell jar or the like.

The act 1188 generally comprises drawing or applying a vacuum or partial vacuum. The vacuum or partial vacuum is applied (for example, by utilizing a pump, suction device or the like) for a predetermined time and pressure in the vacuum chamber 1332. The vacuum advantageously facilitates in degassing the MR fluid by extracting residual dissolved air or other gases in the MR fluid.

In one embodiment, the vacuum or partial vacuum is applied at about 29.4 inches mercury ("Hg) for about 30 minutes. In another embodiment, the vacuum or partial vacuum is applied at about 28 inches mercury ("Hg) for about 30 minutes. In yet another embodiment, the vacuum or partial vacuum is applied at about 28 inches mercury ("Hg) to about 29.4 inches mercury ("Hg) for about 30 minutes. The difference between this vacuum creating pressure value and the atmospheric or ambient pressure is the actual pressure in the vacuum chamber 1332. The vacuum creating pressure may also be considered a suction pressure. In modified embodiments, other suitable vacuum creating or suction pressures and times may be efficaciously utilized, as needed or desired.

The act 1190 generally comprises turning on the stirrer 1334 to stir the MR fluid in the container 1330 which is under the vacuum or partial vacuum. The stirring of the MR fluid is maintained for a predetermined time and/or until no bubbles are visible and further facilitates in degassing the MR fluid. In one embodiment, the stirrer 1334 is used to stir the MR fluid for about 30 minutes.

The act 1192 generally comprises turning of the stirrer 1334. The act 1194 generally comprises turning off the vacuum and slowly releasing the vacuum. The act 1196 generally comprises unsealing the vacuum chamber 1332. The act 1198 generally comprises removing the MR fluid container 1330 from the vacuum chamber 1332.

FIG. 118 shows one embodiment of the act, step or method 1128 of loading the MR fluid in the actuator 112 in further detail in a flow chart or diagram format. The act 1128 generally comprises acts or steps 1220, 1222, 1224 and 1226. Each of these is discussed further below.

FIG. 119 shows one embodiment of the act, step or method 1220 of adding the MR fluid to the funnel 1326 in further detail in a flow chart or diagram format. FIG. 120 shows one embodiment of a set-up or system to perform at least a portion of the act 1220.

The act 1220 generally comprises acts or steps 1230, 1232 and 1234. Each of these is discussed further below.

The act 1230 generally comprises pouring the MR fluid into the funnel 1326 attached to the actuator 112 on the weighing scale 1322. A suitable pipette 1340 or the like is used to transfer the prepared MR fluid from the container 1330 to the funnel 1326.

The act 1232 generally comprises monitoring the reading of the weighing scale 1322. The act 1234 generally comprises filling an appropriate and/or predetermined MR fluid weight (and/or volume) in the actuator 112 and recording the weight. In one embodiment, an extra quantity (e.g., one gram) of MR fluid is added to compensate for any fluid remaining in the funnel.

FIG. 121 shows one embodiment of the act, step or method 1222 of applying a, vacuum or partial vacuum in further detail in a flow chart or diagram format. FIG. 122 shows one embodiment of a set-up or system to perform at least a portion of the act 1222. FIG. 123 shows one embodiment of a set-up or system generally comprising a vacuum table 1360 to perform at least a portion of the act 1222.

The act 1222 generally comprises acts or steps 1240, 1242, 1244, 1246 and 1248. Each of these is discussed further below.

The act 1240 generally comprises placing the actuator 112 in the vacuum chamber 1332. The pyramid tool 1320 is used to seat the actuator 112 and the funnel 1326 is oriented to be substantially vertical.

The act 1242 generally comprises connecting the holding fixture 1324 to an agitator system 1350. The agitator system 1350 generally comprises a mechanical agitator 1352 (e.g. air motor) connected to the holding fixture 1324 and driven by an actuator 1356 which, in one embodiment, controls the opening and closing of one or more valves associated with the actuation of the mechanical agitator 1352 (e.g. air motor). Cables or hydraulic/pneumatic lines connect the agitator 1352 and the actuator 1356. The holding fixture 1324 is bolted to the agitator 1352.

The act 1244 generally comprises sealing the vacuum chamber 1332, for example, by using a bell jar or the like. The act 1246 generally comprises drawing or applying a vacuum or partial vacuum. The vacuum is slowly applied (for example, by utilizing a pump, suction device or the like) for a predetermined time and pressure. This pressure is desirably chosen or selected such that it does not cause undesirable vaporization of the MR fluid but is appropriate to facilitate MR fluid loading.

In one embodiment, the vacuum or partial vacuum is applied at about 28 inches mercury ("Hg) for about 30 seconds. In another embodiment, the vacuum or partial vacuum is applied at about 29.4 inches mercury ("Hg) for about 30 seconds. In yet another embodiment, the vacuum or partial vacuum is applied at about 28 inches mercury ("Hg) to about 29.4 inches mercury ("Hg) for about 30 seconds. The difference between this vacuum creating pressure value and the atmospheric or ambient pressure is the actual pressure in the vacuum chamber 1332. The vacuum creating pressure may also be considered a suction pressure. In modified embodiments, other suitable vacuum creating or suction pressures and times may be efficaciously utilized, as needed or desired.

The vacuum advantageously creates a suction effect that draws MR fluid into the actuator 112 (outer spline 132) and desirably distributes it substantially uniformly in the gaps between the blades 120 and 130. Stated differently, the vacuum pulls air out of the chamber 144 by bubbling through the MR fluid.

The act 1248 generally comprises agitating the actuator 112. The agitator 1352 is actuated to rotate, for example, cyclically in a back and forth manner, the actuator 112. The agitation is performed periodically, for example, at a frequency of few times a minute.

Advantageously, this further facilitates in drawing the MR fluid into the actuator 112 as the fluid mixes or distributes as air bubbles out. In one embodiment, the actuator 112 is agitated for about 30 seconds. In modified embodiments, other suitable agitation times may be used with efficacy, as needed or desired. In one embodiment, the actuator agitation is synchronized with the application of vacuum or partial vacuum, for example, by applying the vacuum or partial vacuum and performing the actuator agitation over substantially the same time period. In one embodiment, the agitation frequency is about 10 times/minute or about 0.17 Hertz (Hz).

FIG. 124 shows one embodiment of the act, step or method 1224 of feeding nitrogen in further detail in a flow chart or diagram format. The act 1224 generally comprises acts or steps 1260, 1262, 1264, 1266 and 1268. Each of these is discussed further below.

The act 1260 generally comprises feeding nitrogen into the vacuum chamber 1332. In modified embodiments, other suitable inert, compressible gases may be efficaciously utilized, as needed or desired. In another embodiment, air is used.

The act 1262 generally comprises releasing the vacuum in the vacuum chamber 1332 as the nitrogen is fed to release the vacuum and facilitate in pushing the MR fluid down and into the chamber 144. In one embodiment, the vacuum is released slowly at about 2" Hg per 10 seconds.

The act 1264 generally comprises further agitating the actuator 112 to facilitate in forcing the MR fluid down and into the chamber 144. Advantageously, the nitrogen (inert, compressible gas) occupies the unfilled space within the actuator 112 (chamber 144) and facilitates in controlling undesirable pressure build-up, as discussed in further detail above.

The act 1266 generally comprises turning off the nitrogen supply once the vacuum has been released and the pressure has returned to substantially ambient conditions. The act 1268 generally comprises unsealing the vacuum chamber 1332. The cycle of vacuum filling, agitating and supplying an inert gas may be repeated more than once, as needed or desired.

The vacuum table 1360 (FIG. 123) may include a pressure gauge 1358 to monitor the pressure and various valves and the like to direct and control the flow paths. These may include a nitrogen feed valve 1362, a pressure release valve 1364, a pressure regulator 1366 associated with the actuator 1356 of the agitator 1352 (e.g. air motor), among others.

FIG. 125 shows one embodiment of the act, step or method 1226 of substantially completing the MR fluid loading procedure in further detail in a flow chart or diagram format. The act 1226 generally comprises acts or steps 1280, 1282, 1284, 1286 and 1288. Each of these is discussed further below.

The act 1280 generally comprises disconnecting the holding fixture 1324 from the agitator 1352. The act 1282 generally comprises removing the actuator 112 from the vacuum chamber 1332. The act 1284 generally comprises removing the fixture 1324 and the funnel 1326 from the actuator 112. The act 1286 generally comprises placing the actuator 112 on the weighing scale 1322 and recording the weight. Care is taken in handling the actuator 112 (for example, by avoiding tipping it) so that the nitrogen head in the chamber 144 is not released.

The actuator 112 can be pressure tested to check the seal integrity once the MR fluid has been loaded therein. An air pump or the like is connected to the outer spline chamber 258 (see, for example, FIG. 45) via the threaded port or hole 280 and the chamber 258 is pressurized to a predetermined pressure (e.g., 20 psi) for a predetermined time. Nitrogen or other inert gas that has been loaded into the actuator 112 may be used for the pressure test instead of air, as needed or desired.

The act 1288 generally comprises capping the threaded port or hole 280 of the outer spline 132 with a suitable threaded screw or plug. In one embodiment, a M6 3 mm set screw is used. A suitable adhesive or glue, such as Loctite® threadlocker or the like, can be applied to the threads to provide a strong coupling. In one embodiment, a torque of about 2.5 N-m is applied to the set screw.

In one embodiment, the actuator 112 contains volume of about 5 milliliter (mL) of MR fluid. In another embodiment, the actuator 112 contains a volume in the range from about 4 mL to about 6 mL of MR fluid, including all values and sub-ranges therebetween. In yet another embodiment, the actuator 112 contains a volume in the range from about 2 mL to about 8 mL of MR fluid, including all values and sub-ranges therebetween. In yet another embodiment, the actuator 112 contains a volume in the range from about 1 mL to about 10 mL of MR fluid, including all values and sub-ranges therebetween. In modified embodiment, other suitable volumes of MR fluid may be efficaciously utilized, as needed or desired.

Magnetorheological Fluid

In some embodiments, the magnetorheological fluid comprises a plurality of iron, ferrous or magnetic particles suspended in fluid. These suspended particles form torque producing chains in response to an applied magnetic (energy) field. Thus, the magnetorheological (MR) fluid undergoes a rheology or viscosity change or variation which is dependent on the magnitude of the applied magnetic field. In turn, this variation in the bulk fluid viscosity determines the magnitude of the shearing force/stress or torque generated, and hence the level of damping or braking provided. Typically, the bulk viscosity of the MR fluid increases with increasing strength of the applied field. By controlling the magnitude of this magnetic field, the rotary motion of the artificial limb is rapidly and precisely adjusted and/or controlled, for example, to control the flexion and extension during swing and stance phases to provide a more natural and safe ambulation for the amputee.

The magnetorheological fluid used in conjunction with embodiments of the invention can comprise a wide variety of MR fluids or magnetically controlled or controllable mediums. Some embodiments of suitable MR fluids are disclosed in U.S. patent application Ser. No. 10/722,313, filed Nov. 25, 2003, which corresponds to U.S. Patent Application Publication No. 2004/0217324 A1, published Nov. 4, 2004, and U.S. Provisional Patent Application No. 60/467,722, filed May 2, 2003, both entitled MAGNETORHEOLOGICAL FLUID COMPOSITIONS AND PROSTHETIC KNEES UTILIZING SAME, the entirety of each one of which is hereby incorporated by reference herein and each one of which is considered as part of this application.

Embodiments of the invention can efficaciously utilize other field responsive (FR) fluids and mediums. In one embodiment, an electrorheological (ER) fluid is used whose rheology can be changed by an electric (energy) field. Thus, the electrorheological (ER) fluid undergoes a rheology or viscosity change or variation which is dependent on the magnitude of the applied electric field. Other suitable electronically or electrically controlled or controllable mediums may be efficaciously utilized, as needed or desired.

Embodiments of the invention and the concepts disclosed, taught or suggested herein can be used in conjunction with other types of prosthetic knees, control systems and other prosthetic devices and joints including ankles, feet, hips, elbows and wrists. Some embodiments of a prosthetic ankle, foot unit and control system are disclosed in U.S. Provisional Patent Application No. 60/544,259, filed Feb. 12, 2004, entitled LOWER LIMB PROSTHESIS WITH ANKLE-MOTION-CONTROLLED FOOT, U.S. Provisional Patent Application No. 60/588,232, filed Jul. 15, 2004, entitled PROSTHETIC OR ORTHOTIC SYSTEM WITH ANKLE-MOTION-CONTROLLED FOOT, and U.S. patent application Ser. No. 11/056,344, filed Feb. 11, 2005, entitled SYSTEM AND METHOD FOR MOTION-CONTROLLED FOOT UNIT, the entirety of each one of which is hereby incorporated by reference herein and each one of which is considered as part of this application.

Embodiments of the invention and the concepts disclosed, taught or suggested herein can be used in conjunction with orthotic devices for bracing and/or supporting joints and muscles. The orthotic devices can be attached to the limb of a patient and can brace joints including knees, ankles, feet, hips, elbows and wrists. Embodiments of the invention and the concepts disclosed, taught or suggested herein can be used in conjunction with other muscle assist devices or muscle replacement devices and the like.

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention.

From the foregoing description, it will be appreciated that novel approaches relating to prosthetic devices, pressure control and handling of slurries and fluids have been disclosed. While the components, techniques and aspects of the invention have been described with a certain degree of particularity, it is manifest that many changes may be made in the specific designs, constructions and methodology herein above described without departing from the spirit and scope of this disclosure.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A method of loading a magnetorheological fluid in a prosthetic knee, comprising:
   providing a prosthetic knee actuator comprising a plurality of first blades and second blades with gaps therebetween in a chamber of an outer housing with at least one of said plurality of first blades and said plurality of second blades being rotatable;
   providing a magnetorheological fluid in a channel that is in fluid communication with said chamber; and
   applying a vacuum over said prosthetic knee actuator and said channel to force said fluid into said chamber.

2. The method of claim 1, wherein after forcing said fluid into said chamber said fluid is substantially uniformly distributed in said gaps between said blades.

3. The method of claim 1, wherein providing a prosthetic knee actuator comprises providing an actuator that is capable of shearing said fluid in said gaps between said blades.

4. The method of claim 1, wherein said gaps have a size of about 18 µm (0.0007 inches).

5. The method of claim 1, wherein providing a magnetorheological fluid comprises providing a magnetorheological fluid having a volume in the range from about 1 mL to about 10 mL.

6. The method of claim 1, wherein prior to providing a magnetorheological fluid said method comprises applying a vacuum to said fluid to substantially degas said fluid.

7. The method of claim 6, wherein applying a vacuum to said fluid comprises applying a vacuum at about 29.4 inches mercury.

8. The method of claim 6, wherein applying a vacuum to said fluid comprises applying a vacuum for about 30 minutes.

9. The method of claim 1, wherein applying a vacuum comprises applying a vacuum at about 28 inches mercury.

10. The method of claim 1, wherein said method further comprises agitating said prosthetic knee actuator to facilitate settling of said fluid.

11. The method of claim 10, wherein agitating said prosthetic knee actuator comprises agitating said prosthetic knee actuator while said prosthetic knee actuator is under vacuum.

12. The method of claim 11, wherein agitating said prosthetic knee actuator comprises rotating said prosthetic knee actuator in a back and forth manner.

13. The method of claim 1, wherein said method further comprises feeding a substantially inert gas into said vacuum and releasing said vacuum to further force said fluid into said gaps and allow said gas to occupy a portion of said chamber.

14. The method of claim 13, wherein releasing said vacuum comprises releasing said vacuum at a rate of about 2 inches mercury per 10 seconds.

15. The method of claim 13, wherein feeding a substantially inert gas comprises feeding nitrogen.

16. The method of claim 1, wherein said method further comprises capping a fill hole of said outer housing to sealingly contain said fluid in said chamber.

17. The method of claim 16, wherein prior to capping a fill hole said method comprises pressure testing said prosthetic knee actuator with said fluid therein.

18. The method of claim 1, wherein prior to providing a magnetorheological fluid said method comprises pressure testing said prosthetic knee actuator.

* * * * *

UNITED STATES PATENT AND TRADEMARK OFFICE
CERTIFICATE OF CORRECTION

PATENT NO.      : 7,198,071 B2
APPLICATION NO. : 11/124610
DATED           : April 3, 2007
INVENTOR(S)     : Charles R. Bisbee, III et al.

It is certified that error appears in the above-identified patent and that said Letters Patent is hereby corrected as shown below:

Title Pg, Item (56) Ref. Cited on page 3, column 1 (Other Publications), lines 14-15, please delete "Instrumnetation Engineeris" and insert -- Instrumentation Engineers --, therefor.

Title Pg, Item (56) Ref. Cited on page 3, column 2 (Other Publications), line 43, please delete "199701_018.asp" and insert -- 1997_01_018.asp --, therefor.

At column 3, line 32, delete "View" and insert -- view --, therefor.

At column 11, line 18, after "invention" delete "van" and insert -- can --, therefor.

At column 30, line 49, delete "6Al -4V" and insert -- 6Al-4V --, therefor. (Consider Space)

At column 33, line 34, before "outer" delete "a" and insert -- an --, therefor.

At column 35, line 67, after "about" delete "cm" and insert -- 5 cm --, therefor.

At column 44, line 47, after "pressure" insert -- . --.

At column 44, line 61, before "aluminum" delete "a" and insert -- an --, therefor.

At column 52, line 38, delete "OCHE" and insert -- $\alpha_{HE}$ --, therefor.

At column 52, line 57, delete "542b",542c"" and insert -- 542b", 542c" --, therefor. (Consider Space)

At column 56, line 14, delete "my" and insert -- may --, therefor.

At column 62, line 55, before "aluminum" delete "a" and insert -- an --, therefor.

UNITED STATES PATENT AND TRADEMARK OFFICE
CERTIFICATE OF CORRECTION

PATENT NO. : 7,198,071 B2
APPLICATION NO. : 11/124610
DATED : April 3, 2007
INVENTOR(S) : Charles R. Bisbee, III et al.

It is certified that error appears in the above-identified patent and that said Letters Patent is hereby corrected as shown below:

At column 63, line 9, after "below" insert -- . --.

At column 70, line 45, after "like" delete "an" and insert -- can --, therefor.

At column 70, line 66, after "width" delete "$W_{106}$," and insert -- $W_{0161}$ --, therefor.

At column 70, line 66, delete "(2frax;9;16 *inches*)" and insert -- (2-9/16 inches) --, therefor.

At column 70, line 67, delete "(2frax;15;16 *inches*). I*n*" and insert -- (2-15/16 inches). In --, therefor.

At column 71, lines 1-2, delete "fied *embodiments*, other suitable dimensions may be efficaciously *used*, as needed or *desired*." and insert -- fied embodiments, other suitable dimensions may be efficaciously used, as needed or desired. --, therefor.

At column 71, lines 3-11, please delete the entire paragraph:

"Referring in particular to FIG. 107, in one embodiment, the length $L_{1071}$ is about 65 mm (2frax;9;16 *inches*), the length $L_{1072}$ is about 78 mm (3frax;1;16 *inches*), the height $H_{1071}$ is about 230 mm (9frax;1;16 *inches*), the height $H_{1072}$ is about 197 mm (7 3/4 *inches*), the height $H_{1073}$ is about 32 mm (1frax;3;16 *inches*) to about 33 mm (1frax;5;16 *inches*) and the height $H_{1074}$ is about 30 mm (1frax;3;16 *inches*). I*n* modified *embodiments*, other suitable dimensions may be efficaciously *used*, as needed or *desired*."

UNITED STATES PATENT AND TRADEMARK OFFICE
CERTIFICATE OF CORRECTION

| | |
|---|---|
| PATENT NO. | : 7,198,071 B2 |
| APPLICATION NO. | : 11/124610 |
| DATED | : April 3, 2007 |
| INVENTOR(S) | : Charles R. Bisbee, III et al. |

It is certified that error appears in the above-identified patent and that said Letters Patent is hereby corrected as shown below:

and insert:

-- Referring in particular to FIG. 107, in one embodiment, the length $L_{1071}$ is about 65 mm (2-9/16 inches), the length $L_{1072}$ is about 78 mm (3-1/16 inches), the height $H_{1071}$ is about 230 mm (9-1/16 inches), the height $H_{1072}$ is about 197 mm (7-3/4 inches), the height $H_{1073}$ is about 32 mm (1-3/16 inches) to about 33 mm (1-5/16 inches) and the height $H_{1074}$ is about 30 mm (1-3/16 inches). In modified embodiments, other suitable dimensions may be efficaciously used, as needed or desired. --, therefor.

Signed and Sealed this

Seventeenth Day of March, 2009

JOHN DOLL
*Acting Director of the United States Patent and Trademark Office*